US007317140B2

(12) United States Patent
Mittendorf et al.

(10) Patent No.: US 7,317,140 B2
(45) Date of Patent: Jan. 8, 2008

(54) SUGAR AND LIPID METABOLISM REGULATORS IN PLANTS II

(75) Inventors: Volker Mittendorf, Durham, NC (US); Heiko Haertel, Durham, NC (US); Petra Cirpus, Mannheim (DE)

(73) Assignee: BASF Plant Science GMBH (DE)

(*) Notice: Subject to any disclaimer, the term of this patent is extended or adjusted under 35 U.S.C. 154(b) by 227 days.

(21) Appl. No.: 10/171,404

(22) Filed: Jun. 4, 2002

(65) Prior Publication Data
US 2003/0177529 A1    Sep. 18, 2003

Related U.S. Application Data

(60) Provisional application No. 60/295,680, filed on Jun. 4, 2001.

(51) Int. Cl.
*A01H 5/00* (2006.01)
*C12N 15/82* (2006.01)
(52) U.S. Cl. .................. 800/281; 800/298; 435/468
(58) Field of Classification Search ............. 800/278, 800/281, 284, 298, 306, 312, 320, 314; 536/23.1, 536/23.2, 23.6
See application file for complete search history.

(56) References Cited

U.S. PATENT DOCUMENTS

| 5,444,166 | A | 8/1995 | Ecker et al. |
| 5,602,322 | A | 2/1997 | Ecker et al. ............. 800/205 |
| 5,955,650 | A | 9/1999 | Hitz |
| 6,084,164 | A | 7/2000 | Bidney et al. |
| 6,995,253 | B1 | 2/2006 | Innes et al. |

FOREIGN PATENT DOCUMENTS

| WO | WO 94/29467 | 12/1994 |
| WO | WO 00/61771 | 10/2000 |
| WO | WO 00/66750 | 11/2000 |
| WO | WO 01/26459 A2 | 4/2001 |
| WO | WO 02/022675 A3 | 3/2002 |
| WO | WO 02/074977 | 9/2002 |

OTHER PUBLICATIONS

Arenas-Huertero, et al. 2000, "Analysis of *Arabidopsis* glucose insensitive mutants, gin5 and gin6, reveals a central role of the plant hormone ABA in the regulation of plant vegetative development by sugar", Genes Dev. 14:2085-2096.
Beaudoin, et al. 2000, "Interactions between Abscisic Acid and Ethylene Signaling Cascades", Plant Cell 2000:1103-1115.
Brenner, 1976, "Regulatory Function of Δ6 Desaturase—Key Enzyme of Polyunsaturated Fatty Acid Synthesis", Adv. Exp. Med. Biol. 83:85-101.
Browse, et al. 1986, "Fluxes through the prokaryotic and eukaryotic pathways of lipid syntesis in the '16:3' plant *Arabidopsis thaliana*", Biochemical J. 235:25-31.

Cahoon, et al. 1992, "Expression of a coriander desaturase results in petroselinic acid production in transgenic tobacco", Proc. Natl. Acad. Sci. USA 89:11184-11188.
Cohen, 1992, "Signal integration at the level of protein kinases, protein phosphatases and their substrates", Trends Biochem. Sci. 17:408-413.
Colon-Carmona, et al. 2000, "Aux/IAA Proteins Are Phosphorylated by Phytochrome in Vitro" Plant Physiol. 124:1728-1738.
Frentzen, 1998, "Acyltransferases from basic science to modified seed oils", Lipids 100:161-166.
Höfgen, et al. 1990, "Biochemical and Genetic Analysis of Different Patatin Isoforms Expressed in Various Organs of Potato (*Solanum tuberosum*)", Plant Sci. 66:221-230.
Kang & Rawsthorne, 1994, "Starch and fatty acid synthesis in plastids from developing embryos of oilseed rape (*Brassica napus* L.)", Plant J. 6:795-805.
Kuo, et al. 1996, "Okadaic Acid, a Protein Phosphatase Inhibitor; Blocks Calcium Changes, Gene Expression. and Cell Death Induced by Gibberellin in Wheat Aleurone Cells", Plant Cell. 8:259-269.
Millar, et al. 2000, "All fatty acids are not equal: discrimination in plant membrane lipids", Trends in Plant Science 5:95-101.
Ogas, et al. 1997, "Cellular Differentiation Regulated by Gibberellin in the *Arabidopsis thaliana* pickle Mutant", Science 277:91-94.
Ogas, et al. 1999, "PICKLE is a CHD3 chromatin-remodeling factor that regulates the transition from embryonic to vegetative development in *Arabidopsis*", Proc. Natl. Acad. Sci. USA 96:13839-13844.
Ohlrogge & Browse, 1995, "Lipid Biosynthesis", Plant Cell 7:957-970.
Plaxton, 1996, "The Organization and Regulation of Plant Glycolysis", Annu. Rev. Plant Physiol. Plant Mol. Biol. 47:185-214.
Ritchie & Gilroy, 1998, "Calcium-Dependent Protein Phosphorylation May Mediate the Gibberellic Acid Response in Barley Aleurone", Plant Physiol. 116:765-776.
Shanklin & Cahoon, 1998, "Desaturation and Related Modifications of Fatty Acids", Annu. Rev. Plant Physiol. Plant Mol. Biol. 49:611-641.
Töpfer, et al. 1995, "Modification of Plant Lipid Synthesis," Science 268:681-686.
Van de Loo, et al. 1995, "An oleate 12-hydroxylase from *Ricinus communis* L. is a fatty acyl desaturase homolog", Proc. Natl. Acad. Sci. USA 92:6743-6747.
Van de Loo, et al. 1993, "Unusual Fatty Acids" in Lipid Metabolism in Plants, pp. 91-126, TS Moore Jr., CRC Press.
Voelker, 1996, "Plant ACYl-ACP Thioesterases: Chain-Length Determining Enzymes in Plant Fatty Acid Biosynthesis", Genetic Engineering Ed.:Setlow 18:111-133.

*Primary Examiner*—Elizabeth F. McElwain
(74) *Attorney, Agent, or Firm*—Connolly Bove Lodge & Hutz LLP

(57) ABSTRACT

Isolated nucleic acids and proteins associated with lipid and sugar metabolism regulation are provided. In particular, lipid metabolism proteins (LMP) and encoding nucleic acids originating from *Arabidopsis thaliana* are provided. The nucleic acids and proteins are used in methods of producing transgenic plants and modulating levels of seed storage compounds. Preferably, the seed storage compounds are lipids, fatty acids, starches or seed storage proteins.

17 Claims, 29 Drawing Sheets

OTHER PUBLICATIONS

Zhou, et al. 1998, "Glucose and ethylene signal transduction crosstalk revealed by an *Arabidopsis* glucose-insensitve mutant", Proc. Natl. Acad. Sci. USA 95:10294-10299.

Yamada et al., Database GenEMBL, Accession AY074284, Apr. 26, 2002.

Asamizu et al., Database EST, Accession AV523321, Sep. 1, 2000.

Database N Geneseq. Accession AAC48649, Oct. 18, 2000.

Buhr, T., et al., 2002, "Ribozyme termination of RNA transcripts down-regulate seed fatty acid genes in transgenic soybean", The Plant Journal, 30(2):155-163.

Ohlrogge, J., et al., 2000, "Fatty acid synthesis: from CO2 to functional genomics", Biochem. Society Transactions 28(6):567-573.

Vysotskaia et al., Nov. 1, 1998, Database Accession No. 080743.

Figure 1A

SEQ ID NO:1, Nucleotide sequence of the open reading frame of pk002b

ATGGTTCGTCCTGGATTCATTATGCGGCCGCCTGGTACAATCGGTGCTGTTCAAC
TAGCACCACGACCCCTTATTCCAGGAATGCCTGGTCTCCGTCCTGTAATGCCTCCT
ATGGTTAGACCGGCTTCTCTTCCTTTTGTAACACCTGCAGAAAAGCCCCAGACCA
CAATTTACATTGGCAAGATAGCTACCGTGGAAAATGACTTTATGATGTCTATTCT
TGAGTTTTGTGGCCATGTCAAAAGCTGTTTACGTGCGGAAGATCCTACCACCAAG
AAACCTAAAGGTTTTGGATTCTATGAATTTGAATCAGCTGAAGGGATTCTCCGCG
CAATACGCCTGCTGACCCAACGTACTATAGATGGACAAGAGCTTTTGGTGAATGT
TAATCAAGCAACAAAGGAGTATTTGCTAAAATATGTTGAGAAGAAAATAGAGAC
TGCAAAGAAAGCCAAGGAAAGTCAAGGAACCAAAGAGAACCAAGCTGAAGGTC
CTGAGAGTGAGCAAGACAAGCTTGAGAGTGCTGATAATGAGACAGGGAAGGAT
GGAGAATCGAAGATTAAAGAAACATCGATATTGCGAATTCTGCTGTCCTAACT
GATGAAGAAGGGAAGCAGACAGAGAGGCTATGGAAAAGATTGAAACTGCTAT
TGAAGAAAGGTTAAAGTCCAACCCTTTGCCTCCTCCACCACCACCACCTGCTGAT
GGTTCAGGCATGGAATTTGCTTTCAAATCTAAGGATGGTGACTCCAACACTGACG
TAGCTAGGAGTGATGCCGCAGCAAATGATGTTGAGACTTCTGGAGAACACAATA
GGCCTGACACAAGCTCACCTGATTGGAGTAAGAGAAATGACCGAAGAGGCAGAG
AAAGAGGTGAGAAGGAGCAAGAAATGGATAGATACGAGAGGGAGGCTGAAAGA
GAACGGTCAAGGAAAGAGAGAGAGCAAAGGAGGAAACTTGAGGATGCAGAGCG
TGCTTACCAGACTCGTCTTCGACAATGGGAACGAAGAGAAAGAGAAAAGGAGAA
GGAACGACAGTACGAGAAGGAGAAAGAGAAAGAGAAAGAGCGCAAGAGGAAA
AAGGAAATCCGCTATGAGGAAGAAGAGGAAGAAGACGATGATGATTCAAGAAG
AAGATGGCATAGGGCTGCATTAGATGAGAGAAGAAGACGACAACTAAGAGAAA
AGGAGGATGACTTAGCTGATAGATTGAAAGAAGAGGAAGAGGTTGCTGAGGCG
AAGAGGAGTGCCGAGGAGCAAAATTTGCAGCAACAGCAATTAGATGCCTTAAGA
ATCCTATCGGGACAGGCAGCTATTGGAAGCGAAACGGTTCAGACATCACCTATT
GAAAATGATCACAAGGCAACTCTCCAAACTGTCGGTGAATCTGCCAATGAGCAC
CATGCAGCAGATTTTGAAGAAATGGTTCTGGTAATGAATCGATGGCTATCGATA
ATAATAGTGGATCAGAGGCACATGCTCCCTCAAAGAAATTAGGATTTGGGCTTGT
GGGATCCGGAAAGCGAACTTCTGTGCCTTCTGTTTTCTATGAGGAGGATGAAGAT
GAAGCACGTAAGGCTAAAAAGATGAAACCTTTGGTTCCTATAGATTACTCAACC
GAGGAACAAGAGGCTGTGGCCCATGGTGGCTCAGGGAATACACCACCTCATTTG
GCTTTAGCCGCTGAATTTGCAAAACGAATTTCGAGTACCAATCCCAAGGAAGAG

Figure 1A Continued

ACGATAGAAACCGAAAAACAAAGGAGCAGACGTTCTCATGATAAGGCAAGCCA
CCGGGACAGGGAAAGGGAAAGGGAAAGGGACAGGGACAGGGATAGAGTCAGG
GACCGAGGTGACGGGCATAGTGGTCCCACCAAAGACGCCAAAGAGTCTGGAAAA
GCAAAGATAATTGATACTAAGTTTCTGGATGCGAAACAATTGATAGATACAATCC
CAAAGACAAAGGAAGATTTATTTTCTTACGAGATAAACTGGGCTATGTATGACA
AGCACCAAGTGCACGAAAGAATGAGACCATGGATCTCAAAGAAAATTATGGAGT
TTCTCGGAGAAGAGGAAGCCACTCTGGTAGATTTCATCGTGTCAAACACTCAACA
ACACGTGCAGGCGTCTCAGATGCTTGAGCTGTTGCAATCAATTCTAGACGAAGAA
GCTGAGATGTTTGTGCTGAAGATGTGGAGAACGCTCATCTTTGAGATCAAGCGGG
TTGAAGCTGGAGTCCCGGTAAAATCCAAAGCCTGA

Figure 1B

SEQ ID NO:2, Amino acid sequence of the open reading frame of pk002b

MVRPGFIMRPPGTIGAVQLAPRPLIPGMPGLRPVMPPMVRPASLPFVTPAEKPQTTIYI
GKIATVENDFMMSILEFCGHVKSCLRAEDPTTKKPKGFGFYEFESAEGILRAIRLLTQ
RTIDGQELLVNVNQATKEYLLKYVEKKIETAKKAKESQGTKENQAEGPESEQDKLES
ADNETGKDGESKIKENIDIANSAVLTDEEREADREAMEKIETAIEERLKSNPLPPPPPP
PADGSGMEFAFKSKDGDSNTDVARSDAAANDVETSGEHNRPDTSSPDWSKRNDRR
GRERGEKEQEMDRYEREAERERSRKEREQRRKLEDAERAYQTRLRQWERREREKE
KERQYEKEKEKEKERKRKKEIRYEEEEEEDDDDSRRRWHRAALDERRRRQLREKED
DLADRLKEEEEVAEAKRSAEEQNLQQQQLDALRILSGQAAIGSETVQTSPIENDHKA
TLQTVGESANEHHAADFEENGSGNESMAIDNNSGSEAHAPSKKLGFGLVGSGKRTS
VPSVFYEEDEDEARKAKKMKPLVPIDYSTEEQEAVAHGGSGNTPPHLALAAEFAKRI
SSTNPKEETIETEKQRSRRSHDKASHRDRERERERDRDRDRVRDRGDGHSGPTKDAK
ESGKAKIIDTKFLDAKQLIDTIPKTKEDLFSYEINWAMYDKHQVHERMRPWISKKIME
FLGEEEATLVDFIVSNTQQHVQASQMLELLQSILDEEAEMFVLKMWRTLIFEIKRVEA
GVPVKSKA

Figure 2A

SEQ ID NO:3, Nucleotide sequence of the open reading frame of pk020b

GTGCTGAAAAAGAAGAAACCCATACTTACTGACGAGCATTTCGTAGATGGTCGG
TTTGGTTCGATGTTCCAAAATCCGGACTTCCAAATTGATAAGGACTCATATGAAT

Figure 2A Continued

ATGGTGTCCTACACCCTGTTGCTTCTTCGAAGAAGCAACCTTCTCTGTTAGATGA
ACACTTTGAAGCTGTATCAGATGATGACGAGAACAGTGATTCTGATGCATCACAG
CCTTCAGATGACGAGGCCGACGATGGAGACGCAACTAGGCCAAGCAAGAAAGC
GAGAACTCCGAAGTTGTATGAAGTGAAAGATGAGCGGCATGCCGCAGCTTATCA
CAACCGCACTTCACTGGCTAAAGAAGATAGTCTTCCTATGGGCGAGCGTGTCAAG
GCTATAGAGAACCGGCGTGGCAACTTTGGAGGCTCGAAAGATATCAAATTCGGT
CCTGGAGGATCACGGGAGTTTTCTTTCAAGGCGAGAGGGTCATCAAAGTACAAA
GAAGATAGAGACGATGAGTATGAAGATGGGCAAAGAAACAAGAGGAGAGGAGT
TCAGTCTCTTGGACTGAAATCAACAAATATTAGAGGCGGTTTCAGAGGTAGAGG
AGGTGGTGGTTTTAGAGGGAGAGGAGGCGGCGGTTCCCGGGGAAAAGGTGGCCG
TGGTGGTGGGCGTGGAAGAGGCCGGCAATGA

Figure 2B

SEQ ID NO:4, Amino acid sequence of the open reading frame of pk020b

VLKKKKPILTDEHFVDGRFGSMFQNPDFQIDKDSYEYGVLHPVASSKKQPSLLDEHF
EAVSDDDENSDSDASQPSDDEADDGDATRPSKKARTPKLYEVKDERHAAAYHNRTS
LAKEDSLPMGERVKAIENRRGNFGGSKDIKFGPGGSREFSFKARGSSKYKEDRDDEY
EDGQRNKRRGVQSLGLKSTNIRGGFRGRGGGGFRGRGGGGSRGKGGRGGGRGRGR
Q

Figure 3A

SEQ ID NO:5, Nucleotide sequence of the open reading frame of pk033

ATGGAGCAGATGATATTCATTAGAAAAGACGACAAAGTAGAGGTTTTTCTGAA
GAAGAAGAGTTAAAAGGGTCTTATTACAGAGCGATTCTGGAAGATAATCCAACG
AAATCAGGACACAATAAGCTTAAAGTTCGTTACTTGACGCAGCTCAATGAACAC
CGTTTGGCTCCTTTAACGGAATTCGTCGATCAGAGGTTCATTCGTCCTGTCCCGTC
GGAGGATGTGAACGACGGCGTCGTTTTTGTAGAAGGCTTGATGGTCGACGCTTAT
CTCAAAGATGGGTGGTGGACTGGTGTGGTGGTAAAAACAATGGAGGATGAGAAG
TTTTTGGTTTACTTCGATTGCCCACCAGACATTATTCAGTTTGAGAAAAGAAATT
GAGGGTTCATCTTGATTGGACCGGCTTCAAATGGATCCGACCTGATAATAAGGAA
TTGGTCAAGTCTGTTTTAGTTGCGGGACAATGGTGGAATTGAGATTTGATTGTG
CTTGGATTCCGGTAATTGTCATTAAGGAGTTGGAGAAGGACAAGAGGTTTCTTGT

Figure 3A Continued

CAAGTACTGGAATAAGTCCTATAGCTGCCGGGAATCGAAAAATTTAATTGTTGAT
TCCCTAAGACTAAGGCCTATGCAGCCTCCTTTATCTGTTGGAAAGTATGAATTGC
TGGATCATGTAGAGGCGTTTAGTGGTTTTGAATGGCGTCAAGGTGTGGTCAGGGG
AATTGTCTTTGAGGGAAGGTACATGGTAAGTTTCGGGGCAACAAAGGAGGCATC
GCAATTTAATCACTCTGATATTAGGCCTCCAATGGAGTGGGAAGATGGAGTTTGG
CATAAAAGAACAAAGCCAAAACGCCAGAAAGAAACTTCTTTAGACGGCAACAG
AAATGTGCAGACAAAGGAACCACCGGGAAATGAGATGGCTGATGATGTGAAAA
AAGAATCTGGTTTACCTATAACCCTGGGGGTAACTGCAACAAAGAACAAAACCC
AAGGAAAGGTATCCCCTGTGCCAATGAAGAATGGCTTTGGAAATGAGTCAACTC
GAGAGAAGATGCCTGAGGAGCCTAAGATCAAATATTATACTCGAAAGAGGAAAA
GAGGAGGTCTAAAGCTCAATTCATACATCAATAAGACTGTGTTATCCTCGGATCG
GACCCCCAATGTGGTGAAGAATTCTGCTTCTAATGCTGAGGAAAACCATGCAAA
ACACACAATAATGGTTTTGCCTTTTGCAAAGAAGTCACCGGTCTGGAAGACTTAT
GAATCACTGGAGGTCTTCAAAAGTGTATCACACAGTCTTCATTTCAGCCCATTGT
TTGAGACTAAGCAAGATTTCCGTGAAGGGTATGCAATAGGTATGATGGTGACTTA
TTTTGGGTTACTGGAGAAATTTAAAGATCTTGAAGCCGACGTTCCTGTAAGCCAA
CTAAATAGCCTTAAAGATTCATTTTCGGAGCTCGAGAAACATGGCTTCAATGTTA
CAACTCCATTATCACGGATCGACAAGCTGTCAGCACTCAAAGATAGACAACTAT
ATATAATGGAGGAACTAAAAGGTTTTGACAAGGAGATGACAAATGAATTTAGCA
AGGCTAAACAAGAGTTTGATGACATGGAACAAAAGATTCTTGAGGTGAAACACA
AGATTATCGAGCTGCAGAGGCAAGAAGCTGCTCTAAAAGAACAAAAGGAAGCA
GAAAAAGAACAGAAAGATGCAGCCTGGAAAAAGATATGTCAGATGGAGTCATG
CGCAAAAGATCTCAATGTAGAGCTTGAAGATGTGGAGTTTGAGTTTGAGACAATT
TTGTCGGCTCCTTGGTAA

Figure 3B

SEQ ID NO:6, Amino acid sequence of the open reading frame of pk033

MEQMIFIRKDDKVEVFSEEEELKGSYYRAILEDNPTKSGHNKLKVRYLTQLNEHRLA
PLTEFVDQRFIRPVPSEDVNDGVVFVEGLMVDAYLKDGWWTGVVVKTMEDEKFLV
YFDCPPDIIQFEKKKLRVHLDWTGFKWIRPDNKELVKSVFSCGTMVELRFDCAWIPVI
VIKELEKDKRFLVKYWNKSYSCRESKNLIVDSLRLRPMQPPLSVGKYELLDHVEAFS
GFEWRQGVVRGIVFEGRYMVSFGATKEASQFNHSDIRPPMEWEDGVWHKRTKPKR
QKETSLDGNRNVQTKEPPGNEMADDVKKESGLPITLGVTATKNKTQGKVSPVPMKN

Figure 3B Continued

GFGNESTREKMPEEPKIKYYTRKRKRGGLKLNSYINKTVLSSDRTPNVVKNSASNAE
ENHAKHTIMVLPFAKKSPVWKTYESLEVFKSVSHSLHFSPLFETKQDFREGYAIGMM
VTYFGLLEKFKDLEADVPVSQLNSLKDSFSELEKHGFNVTTPLSRIDKLSALKDRQLY
IMEELKGFDKEMTNEFSKAKQEFDDMEQKILEVKHKIIELQRQEAALKEQKEAEKEQ
KDAAWKKICQMESCAKDLNVELEDVEFEFETILSAPW

Figure 4A

SEQ ID NO:7, Nucleotide sequence of the open reading frame of pk037

ATGGCTATGGTAGATGAACCGTTGTATCCCATTGCTGTGCTTATAGATGAGCTTA
AGAATGATGATATTCAGCTTCGTTTGAACTCGATCCGTCGCTTATCTACTATAGCT
CGTGCTCTTGGAGAGGAGCGTACAAGGAAGGAGTTAATCCCTTTTTTGAGTGAGA
ATAGTGACGATGACGATGAGGTGCTTCTTGCAATGGCTGAGGAGTTAGGAGTTTT
TATTCCGTTTGTTGGAGGAATTGAGTTTGCGCATGTTCTTCTTCCTCCTTTGGAAT
CTCTATGTACTGTTGAAGAGACTTGTGTGAGAGGAAAAGCTGTGGAATCGCTTTG
TAAGATTGGATCTCAGATGAAAGAGAATGATCTTGTTAATCTTTTGTTCCTCTTG
TGAAGAGGTTAGCGGGTGGTGAATGGTTTGCAGCAAGAGTTTCTGCATGTGGTAT
ATTTCATGTTGCATACCAAGGTTGCACTGATGTTTTGAAGACTGAGTTACGGGCT
ACTTATAGCCAGTTGTGCAAAGATGATATGCCAATGGTGCGAAGAGCTGCTGCAT
CTAACCTGGGGAAATTTGCTACAACTGTCGAGTCTACCTTTTTGATTGCTGAGAT
CATGACTATGTTCGATGATCTTACTAAAGATGACCAAGATTCTGTGAGACTATTG
GCTGTTGAAGGGTGTGCAGCTCTTGGAAAGTTGTTGGAACCTCAGGATTGTGTTG
CACGCATTTTACCTGTTATTGTTAATTTCTCTCAGGATAAATCTTGGAGGGTGCGC
TACATGGTTGCAAATCAGCTATATGAACTTTGTAAGGCAGTGGGTCCTGATTGCA
CGAGGACGGATTTGGTTCCAGCATATGTAAGATTGCTAAGGGACAATGAGGCTG
AAGTGCGAATAGCAGCAGCGGGAAAAGTGACCAAGTTCTGTCGGCTTTTGAATC
CAGAGCTTGCGATTCAGCACATCCTTCCTTGTGTGAAGGAATTATCATCGGATTC
TTCTCAACATGTCCGCTCTGCTCTAGCTTCAGTAATAATGGGGATGGCTCCTATCC
TTGGGAAGGACTCAACCATTGAGCATCTGTTACCAATTTTTCTTTCCCTTTTGAAA
GATGAATTTCCTGATGTGCGCCTTAACATCATAAGCAAGTTAGATCAAGTCAACC
AGGTTATTGGAATTGATCTACTATCTCAATCCTTGTTACCGGCCATTGTAGAACTT
GCTGAGGATCGGCACTGGAGAGTCCGACTTGCAATAATAGAGTATGTTCCACTGT
TGGCCAGCCAGTTAGGTATAGGATTTTTCGATTACAAGCTCGGAGCCCTTTGCAT

Figure 4A Continued

GCAATGGCTGCAAGACAAGGTCTACTCTATCCGCGAAGCTGCAGCTGCAGCAAA
CAACCTAAAGCGCCTCGCAGAGGAGTTTGGTCCTGAATGGGCAATGCAGCACTT
AGTTCCCCAGGTATTGGACATGGTCAACAATCCGCACTACCTACACAGGATGATG
GTTCTACGCGCAATATCTCTCATGGCGCCTGTAATGGGATCAGAAATCACATGCT
CTAAGTTTCTTCCTGTGGTTGTTGAAGCATCAAAAGACAGAGTTCCAAACATCAA
GTTCAACGTTGCCAAACTTCTGCAATCCCTCATCCCCATAGTCGACCAATCAGTG
GTGGACAAAACAATCCGTCAGTGTTTGGTGGACCTGAGCGAAGACCCTGATGTT
GATGTTCGTTATTTGCAAATCAAGCACTTAATTCCATCGATGGTTCCACAGCAG
CACAATCCTGA

Figure 4B

SEQ ID NO:8, Amino acid sequence of the open reading frame of pk037

MAMVDEPLYPIAVLIDELKNDDIQLRLNSIRRLSTIARALGEERTRKELIPFLSENSDD
DDEVLLAMAEELGVFIPFVGGIEFAHVLLPPLESLCTVEETCVRGKAVESLCKIGSQM
KENDLVESFVPLVKRLAGGEWFAARVSACGIFHVAYQGCTDVLKTELRATYSQLCK
DDMPMVRRAAASNLGKFATTVESTFLIAEIMTMFDDLTKDDQDSVRLLAVEGCAAL
GKLLEPQDCVARILPVIVNFSQDKSWRVRYMVANQLYELCKAVGPDCTRTDLVPAY
VRLLRDNEAEVRIAAAGKVTKFCRLLNPELAIQHILPCVKELSSDSSQHVRSALASVI
MGMAPILGKDSTIEHLLPIFLSLLKDEFPDVRLNIISKLDQVNQVIGIDLLSQSLLPAIVE
LAEDRHWRVRLAIIEYVPLLASQLGIGFFDYKLGALCMQWLQDKVYSIREAAAAAN
NLKRLAEEFGPEWAMQHLVPQVLDMVNNPHYLHRMMVLRAISLMAPVMGSEITCS
KFLPVVVEASKDRVPNIKFNVAKLLQSLIPIVDQSVVDKTIRQCLVDLSEDPDVDVRY
FANQALNSIDGSTAAQS

Figure 5A

SEQ ID NO:9, Nucleotide sequence of the open reading frame of pk038

ATGACCACGTTATTCCTCCTTATTGCTCTATTCATCACAACCATCCTCAACCCAAC
AAGTGGAGAATCAGTAGGTGTATGCTATGGAATGATGGGGAACAACCTTCCTTCT
CAATCAGACACAATCGCTCTCTTTAGACAAAACAACATCCGACGTGTTAGACTCT
ACGATCCAAACCAAGCCGCTTTAAACGCTCTTAGAAACACGGGTATCGAAGTCA
TCATCGGCGTTCCAAACACCGATCTTCGTTCACTCACTAACCCTTCTTCCGCTAGA
TCATGGCTCCAAAACAACGTCCTCAACTATTACCCCGCCGTTAGCTTCAAGTACA

Figure 5A Continued

TCGCCGTAGGTAACGAAGTATCTCCGTCGAACGGCGGTGATGTTGTGCTCCCTGC
CATGCGTAACGTTTACGATGCTCTAAGAGGTGCAAATCTTCAAGATCGTATTAAA
GTTTCTACCGCCATTGATATGACTTTGATTGGAAACTCTTTCCCTCCTTCCTCCGG
AGAGTTTCGTGGTGACGTTAGATGGTATATCGATCCCGTCATCGGGTTTCTTACG
AGTACGAACTCAGCGTTACTAGCCAACATCTATCCTTACTTCAGCTACGTTGACA
ATCCACGTGACATATCTCTCTTACGCTCTCTTCACTTCTCCTTCCGTCGTCGTAT
GGGACGGCTCTCGTGGCTACCAAAACCTCTTTGACGCTTTACTTGACGTTGTTTAC
TCTGCCGTTGAACGCTCAGGCGGTGGATCTCTCCCAGTGGTTGTTTCCGAGAGCG
GATGGCCTTCTAACGGTGGAAACGCCGCGAGTTTCGATAACGCGCGAGCTTTTA
CACGAATCTTGCGTCGCGTGTGAGAGAGAACAGAGGAACACCGAAGAGACCTGG
AAGAGGAGTGGAAACGTATTTGTTCGCTATGTTTGATGAGAATCAAAAGAGTCCT
GAGATCGAGAAGAATTTTGGTTTGTTTTTTCCTAATAAACAACCAAAATTTCCGA
TCACATTCTCTGCCGCGAGAGACGGTACGGCGGTTGAGTGA

Figure 5B

SEQ ID NO:10, Amino acid sequence of the open reading frame of pk038

MTTLFLLIALFITTILNPTSGESVGVCYGMMGNNLPSQSDTIALFRQNNIRRVRLYDPN
QAALNALRNTGIEVIIGVPNTDLRSLTNPSSARSWLQNNVLNYYPAVSFKYIAVGNE
VSPSNGGDVVLPAMRNVYDALRGANLQDRIKVSTAIDMTLIGNSFPPSSGEFRGDVR
WYIDPVIGFLTSTNSALLANIYPYFSYVDNPRDISLSYALFTSPSVVVWDGSRGYQNL
FDALLDVVYSAVERSGGGSLPVVVSESGWPSNGGNAASFDNARAFYTNLASRVREN
RGTPKRPGRGVETYLFAMFDENQKSPEIEKNFGLFFPNKQPKFPITFSAARDGTAVE

Figure 6A

SEQ ID NO:11, Nucleotide sequence of the open reading frame of pk042a

GTGTCCATCACTGGAAAGGGAGTGAAAGCCACCGTTAAAGGTAGAGAGATTATG
GTGGGGAACAAGAATCTGATGAATGATCATAAAGTTATTATTCCAGATGATGCTG
AAGAGTTGCTAGCTGACTCTGAAGATATGGCCCAGACCGGAATTCTTGTCTCCAT
AAACAGTGAACTGATTGGAGTTTTGTCTGTTTCGGATCCTCTAAAACCGAGTGCT
CGAGAAGCCATCTCCATTCTAAAATCCATGAATATCAAAAGCATCATGGTAACTG
GTGGCAACTGGGGAACAGCAAACTCAATTGCTAGAGAAGTCGGTATCGACTCTG

Figure 6A Continued

TTATCGCAGAAGCTAAACCTGAGCAAAAAGCAGAGAAAGTCAAGGAATTACAGG
CTGCGGGACATGTTGTGGCAATGGTAGGTGACGGAATCAATGACTCACCGGCTCT
CGTGGCAGCGGATGTAGGTATGGCGATAGGTGCAGGAACAGACATTGCTATAGA
AGCAGCGGATATAGTTCTGATGGAAAGCAACTTAGAAGATGTGATCACAGCCAT
TGATCTTTCAAGGAAAACGTTCTCAAGAATCCGTCTCAACTACGTATGGGCTCTC
GGGTATAACCTCATGGGGATACCGATCGCTGCGGGAGTGCTTTTCCCAGGGACAC
GTTTCAGGTTGCCTCCATGGATTGCAGGTGCTGCAATGGCTGCTTCTTCTGTTAGT
GTTGTGTGTTGCTCTCTCTTGCTTAAGAACTACAAGCGACCTAAGAAGCTTGATC
ATCTGGAGATTCGGGAGATTCAGGTGGAGCGAGTTTAA

Figure 6B

SEQ ID NO:12, Amino acid sequence of the open reading frame of pk042a

VSITGKGVKATVKGREIMVGNKNLMNDHKVIIPDDAEELLADSEDMAQTGILVSINS
ELIGVLSVSDPLKPSAREAISILKSMNIKSIMVTGGNWGTANSIAREVGIDSVIAEAKPE
QKAEKVKELQAAGHVVAMVGDGINDSPALVAADVGMAIGAGTDIAIEAADIVLMES
NLEDVITAIDLSRKTFSRIRLNYVWALGYNLMGIPIAAGVLFPGTRFRLPPWIAGAAM
AASSVSVVCCSLLLKNYKRPKKLDHLEIREIQVERV

Figure 7A

SEQ ID NO:13, Nucleotide sequence of the open reading frame of pk053b

GTGGCCATGGAAGGAGAATTTCAGGATGAGCTTGTGGTTGTTGGAGATGGAGTG
GATTCAGCTTCTTTGATTATGGCCTTAAGGAAGAAAGCATGTCATGTCACTCTTG
AGACTCTTGAAGAAGTGAAGAAGCCACAGGTCGAAGAGAAGTCTATTACACCGC
ATTGCTGCATAGCTCAATGTCCTGTGGTTAGCAATGAGCAGCCAAGGCCTGAGGT
TTATAGAATAGTGCATGATTCTTATGGTCCAACCACTGGGTGCTTAGTTATGTAA

Figure 7B

SEQ ID NO:14, Amino acid sequence of the open reading frame of pk053b

VAMEGEFQDELVVVGDGVDSASLIMALRKKACHVTLETLEEVKKPQVEEKSITPHC
CIAQCPVVSNEQPRPEVYRIVHDSYGPTTGCLVM

Figure 8A

SEQ ID NO:15, Nucleotide sequence of the open reading frame of pk060

ATGGTCTTGATTACTAAGATGTCTCTCTCTTTCTACATCATTCATCTTCTCATTTTC
TCCTTGATTTCCACTTGTGTTGTCTCCAACCAGGCCGAGGATAATCTTCTTCAAGG
CCTAAACAGCTACCGAACTGCTCAAAGAGTTCCTCCATTTGCCAAGAATGAGAA
GGCTGATTGTGTGGCTGATGAGATCGCCGACAAGCTCGAAGATCAGCCATGCAC
AAACCACACCACAGCGAGCACGGTTACTCCTGGCTCGGTACCTCCACGGCTGAC
GAACTACCAGGACATTCTCTCTGAATGCAAAATCGACCCAAACACTACCCGTGAC
GGATTGATCTTACCTGTCTGTATCCCTAACCGGATCCCGACTTTGGCTTTAACTAA
TTACACCCAAACTGGTTATGCTCGGTATCTTAATGATTCGAGGTATGTCGGGGCT
GGTGTTGGGTCGGAGAAAGAGTGGATGGTGGTTGTATTGACGACAAGTACTCCA
GGTGGAAGCTTTACAGCTGGTGTTGCTGCTGGCAAGGCGACGTCTGTGAGAGTA
ATGGCTGGTTTAGGGCTAATGGGGTTGTTGTTTAGTTGCCTTGTGCTCTTCTGA

Figure 8B

SEQ ID NO:16, Amino acid sequence of the open reading frame of pk060

MVLITKMSLSFYIIHLLIFSLISTCVVSNQAEDNLLQGLNSYRTAQRVPPFAKNEKADC
VADEIADKLEDQPCTNHTTASTVTPGSVPPRLTNYQDILSECKIDPNTTRDGLILPVCI
PNRIPTLALTNYTQTGYARYLNDSRYVGAGVGSEKEWMVVVLTTSTPGGSFTAGVA
AGKATSVRVMAGLGLMGLLFSCLVLF

Figure 9A

SEQ ID NO:17, Nucleotide sequence of the open reading frame of pk063b

ATGGAGAAAGTGACCAACTCAGACTTGAAATCCTCTGTTGATGGTGGCGTTGTTG
ATGTGTATGGAGAAGATTCAGCCACCATTGAGCACAACATAACTCCTTGGTCTCT
CTCTGTTTCTAGTGGATATTCATTGCTGAGAGATCCTCGCTACAACAAAGGACTT
GCTTTCACTGAGAAAGAGAGAGACACTCATTACTTGCGTGGTCTTCTCCCTCCAG
TTGTTCTTGATCAAAAGCTTCAGGAGAAGAGGCTGTTAACAATATCCGACAATA
TCAATTCCCATTACAAAGTACATGGCTCTGACAGAACTTCAGGAAAGAAACGA
GAGACTGTTTTACGAGCTATTGATAGATAATGTTGAGGAGCTACTTCCTATTGTTT
ATACTCCAACTGTTGGTGAAGCTTGTCAGAAATTTGGAAGTATTTTCAGGCGACC
TCAGGGTTTATTCATCAGTTTAAAAGACAAGGGAAAGATTCTAGATGTGTTAAAG

Figure 9A Continued

AACTGGCCTGAAAGGAACATACAGGTTATTGTTGTTACTGACGGTGAAAGGATTT
TAGGATTAGGAGATCTTGGATGTCAGGGGATGGGTATACCGGTTGGTAAGTTGG
CGTTATATTCAGCACTTGGAGGTGTTCGTCCTTCAGCGTGTTTACCTGTCACCATT
GATGTGGGAACAAACAATGAGAAACTGTTGAATGATGAGTTCTACATAGGACTC
AGGCAAAAGAGAGCAACGGGACAGGAATATAGTGAACTCTTGAATGAATTCATG
AGTGCTGTGAAACAGAACTATGGTGAAAAGTTCTTATTCAGTTTGAAGATTTTG
CTAATCATAATGCCTTTGAGTTGCTTGCAAAATACAGCGATACTCATCTCGTCTTC
AACGATGATATACAGGGGACAGCATCAGTTGTTTTAGCAGGATTAGTTTCCGCAC
AGAAGTTAACGAATAGCCCACTTGCAGAGCATACCTTCCTCTTTCTTGGTGCTGG
TGAAGCTGGAACTGGAATAGCAGAACTCATAGCTCTCTATATGTCAAAACAGAT
GAATGCTTCGGTAGAGGAAAGCCGCAAGAAAATCTGGCTTGTTGATTCCAAGGG
ATTGATTGTTAACTCCCGCAAAGATTCACTTCAAGACTTTAAGAAACCATGGGCT
CATGAACATGAACCAGTCAAAGACCTCTTAGGTGCTATCAAGGCAATAAAACCG
ACTGTTCTGATTGGATCTTCTGGCGTTGGACGGTCTTTTACAAAAGAAGTGATAG
AAGCCATGTCCTCCATTAATGAGAGACCACTGATAATGGCTCTCTCTAACCCCAC
AACACAATCTGAATGTACAGCCGAAGAAGCTTATACTTGGAGTAAGGGCCGTGC
CATTTTTGCTAGTGGAAGCCCTTTTGATCCAGTTGAGTATGAAGGAAAGGTGTTT
GTATCTACACAGGCGAACAATGCGTACATATTCCCGGGCTTTGGACTTGGTTTGG
TTATCTCTGGAGCAATACGGGTACATGACGATATGCTTCTAGCTGCTGCTGAGGC
ATTAGCTGGACAAGTAAGCAAAGAGAACTATGAGAAAGGAATGATATATCCTTC
ATTCTCTTCCATCCGGAAAATATCAGCTCAGATTGCAGCCAATGTAGCAACTAAG
GCGTATGAACTAGGATTGGCAGGGCGGCTTCCACGGCCGAAAGATATTGTCAAA
TGTGCAGAGAGTAGCATGTACAGCCCCACATACCGTCTCTACCGTTGA

Figure 9B

SEQ ID NO:18, Amino acid sequence of the open reading frame of pk063b

MEKVTNSDLKSSVDGGVVDVYGEDSATIEHNITPWSLSVSSGYSLLRDPRYNKGLAF
TEKERDTHYLRGLLPPVVLDQKLQEKRLLNNIRQYQFPLQKYMALTELQERNERLFY
ELLIDNVEELLPIVYTPTVGEACQKFGSIFRRPQGLFISLKDKGKILDVLKNWPERNIQ
VIVVTDGERILGLGDLGCQGMGIPVGKLALYSALGGVRPSACLPVTIDVGTNNEKLL
NDEFYIGLRQKRATGQEYSELLNEFMSAVKQNYGEKVLIQFEDFANHNAFELLAKYS
DTHLVFNDDIQGTASVVLAGLVSAQKLTNSPLAEHTFLFLGAGEAGTGIAELIALYM
SKQMNASVEESRKKIWLVDSKGLIVNSRKDSLQDFKKPWAHEHEPVKDLLGAIKAIK

Figure 9B Continued

PTVLIGSSGVGRSFTKEVIEAMSSINERPLIMALSNPTTQSECTAEEAYTWSKGRAIFA
SGSPFDPVEYEGKVFVSTQANNAYIFPGFGLGLVISGAIRVHDDMLLAAAEALAGQV
SKENYEKGMIYPSFSSIRKISAQIAANVATKAYELGLAGRLPRPKDIVKCAESSMYSPT
YRLYR

Figure 10A

SEQ ID NO:19, Nucleotide sequence of the open reading frame of pk064

ATGGCGTCAGACAAACAAAAGGCGGAGAGAGCCGAGGTTGCGGCGAGGCTAGC
GGCTGAGGACTTGCATGACATTAACAAATCCGGTGGTGCTGATGTCACAATGTAT
AAGGTGACGGAGAGAACAACTGAACATCCACCGGAGCAAGATAGGCCCGGTGT
GATAGGTTCAGTGTTCAGGGCTGTCCAAGGAACGTATGAGCATGCGAGAGACGC
TGTAGTTGGAAAAACCCACGAAGCGGCTGAGTCTACCAAAGAAGGAGCTCAGAT
AGCTTCAGAGAAAGCGGTTGGAGCAAAGGACGCAACCGTCGAGAAAGCTAAGG
AAACCGCTGATTATACTGCGGAGAAGGTGGGTGAGTATAAAGACTATACGGTTG
ATAAAGCTAAAGAGGCTAAGGACACAACTGCAGAGAAGGCGAAGGAGACTGCT
AATTATACTGCGGATAAGGCGGTGGAAGCAAAGGATAAGACGGCGGAGAAGAT
TGGTGAGTACAAAGACTATGCGGTGGATAAGGCAGTAGAAGCTAAAGATAAGAC
AGCGGAGAAGGCGAAGGAGACTTCGAATTATACGGCGGATAAGGCTAAAGAGG
CTAAGGACAAGACGGCTGAGAAGGTTGGTGAGTATAAGGATTACACGGTGGACA
AGGCCGTGGAAGCTAGGGATTACACAGCGGAGAAGGCTATTGAAGCAAAGGAT
AAGACAGCTGAGAAGACTGGAGAGTATAAGGACTATACGGTGGAGAAGGCGAC
GGAGGGGAAAGATGTTACGGTGAGTAAGCTAGGAGAGCTGAAGGATAGTGCCGT
TGAGACAGCGAAGAGAGCTATGGGTTTCTTGTCGGGGAAGACAGAGGAGGCCAA
AGGAAAAGCTGTGGAGACCAAAGATACTGCCAAGGAAAACATGGAGAAAGCTG
GAGAAGTAACAAGACAAAAGATGGAGGAAATGAGATTGGAAGGTAAAGAGCTC
AAAGAAGAAGCTGGAGCAAAAGCCCAAGAGGCATCTCAAAAGACTAGGGAGAG
TACTGAGTCGGGAGCTCAAAAAGCCGAAGAGACCAAAGATTCTCCTGCCGTGAG
GGGAAATGAAGCGAAAGGGACTATTTTTGGTGCATTAGGGAATGTAACGGAAGC
AATAAAGAGCAAACTGACAATGCCATCAGACATTGTGGAGGAAACACGCGCGGC
ACGTGAGCATGGAGGGACGGGTAGGACTGTGGTTGAAGTCAAGGTCGAGGATTC
AAAGCCGGGTAAGGTGGCGACTTCACTGAAGGCGTCGGATCAAATGACCGGTCA

Figure 10A Continued

AACATTCAACGACGTTGGACGGATGGATGATGATGCTCGGAAAGATAAGGGAAA
GCTGTGA

Figure 10B

SEQ ID NO:20, Amino acid sequence of the open reading frame of pk064

MASDKQKAERAEVAARLAAEDLHDINKSGGADVTMYKVTERTTEHPPEQDRPGVIG
SVFRAVQGTYEHARDAVVGKTHEAAESTKEGAQIASEKAVGAKDATVEKAKETAD
YTAEKVGEYKDYTVDKAKEAKDTTAEKAKETANYTADKAVEAKDKTAEKIGEYK
DYAVDKAVEAKDKTAEKAKETSNYTADKAKEAKDKTAEKVGEYKDYTVDKAVEA
RDYTAEKAIEAKDKTAEKTGEYKDYTVEKATEGKDVTVSKLGELKDSAVETAKRA
MGFLSGKTEEAKGKAVETKDTAKENMEKAGEVTRQKMEEMRLEGKELKEEAGAK
AQEASQKTRESTESGAQKAEETKDSPAVRGNEAKGTIFGALGNVTEAIKSKLTMPSDI
VEETRAAREHGGTGRTVVEVKVEDSKPGKVATSLKASDQMTGQTFNDVGRMDDD
ARKDKGKL

Figure 11A

SEQ ID NO:21, Nucleotide sequence of the open reading frame of pk073

ATGCTCTCTGACGCCGGGGGTGGTTCCGATTGCCGGCGTCGGGACTTATCAACTC
CCATCAACCTTCATGTGTTCTATATAAGCTTTATCTTCATTGAATCTTCCTCCGTT
ATCTCAAATCTCTCAAAATATCTAAATCTCCTTTTTTATGTGAGCTTCTTCACTGA
AAGTTTTCTTTGTGACGGAAGAGTATATCGATGCTCTATTGGCTCCGATCTGACTC
AGATCTTGGATGCATCTCTGTCTTCGAACCCAAAACAAGAAAATTCACAACAGTC
CAACAGCTCCTCTTCTCAAACATCAGAGCAAGACTTCATCAACTTATCAAAAAGC
TCTAGATCTGGACTAGCACCAACACCACCTTTGGTTTCTTCTCACCGGTTTTCGTT
GATGGCAGGAGTATCTCTTGGACCATCAGATGTGCTTCTTCCGCTGGGAACGTCG
ACGGCACACGACGAGCTCAAACGCTGGCAATGGTCACCCTATATGATTCACAGT
CGCCCATCATTCCAATTCTTCAGAATGACGGAGGCGCTTTCCTTATCCCGACAAC
ATCAACCCTAG

Figure 11B

SEQ ID NO:22; Amino acid sequence of the open reading frame of pk073

MLSDAGGGSDCRRRDLSTPINLHVFYISFIFIESSSVISNLSKYLNLLFYVSFFTESFLCD
GRVYRCSIGSDLTQILDASLSSNPKQENSQQSNSSSSQTSEQDFINLSKSSRSGLAPTPP
LVSSHRFSLMAGVSLGPSDVLLPLGTSTAHDELKRWQWSPYMIHSRPSFQFFRMTEA
LSLSRQHQP

Figure 12A

SEQ ID NO:23, Nucleotide sequence of the open reading frame of pk082

ATGGAAGGTGGAGCTGCTCTCTACAATCCTCGAACTGTCGAAGAAGTTTTCAAGG
ATTTCAAAGGTCGTCGTACTGCCATTGTCAAAGCTCTCACCACCGATGTTCAAGA
GTTTTACCAACAATGTGACCCTGAGAAGGAGAATCTTTGCTTGTATGGGTTACCG
AATGAAGAATGGGAAGTGAATTTACCAGCTGAAGAAGTGCCTCCTGAGTTACCA
GAGCCAGCTCTTGGTATTAACTTTGCTAGGGATGGGCTCTCTGAAAAGGAATGGC
TTTCGCTTGTTGCTATTCACAGTGACGCTTGGTTACTGTCTGTCTCGTTTTACTTTG
GCTCAAGGTTTTCTTTCCACAAGGAAGAGAGGAAGCGTTTGTTCAACATGATCAA
TGATGTTCCTACTATATTTGAAGTAGTGACTGGAATGGCTAAAGCAAAGGACAA
GTCATCTGCTGCAAATCAAAACGGAAACAAATCCAAGTCTAACTCTAAAGTTAG
AACTTCAGGGGGAAAAAGCTCAAAGACCAAGCAGCCAAAAGAGGAGGACGAAG
AAATAGATGAAGATGATGAGGATGACCACGGGGAAACCCTTTGTGGAGCCTGTG
GAGACAGTGATGGTGCTGATGAATTCTGGATCTGCTGTGACCTTTGTGAGAAGTG
GTTCCATGGCAAGTGTGTGAAGATCACTCCAGCTAGAGCTGAGCATATCAAACA
ATACAAGTGCCCTTCATGCAGCAACAAAAGAGCTCGAGCTTAA

Figure 12B

SEQ ID NO:24, Amino acid sequence of the open reading frame of pk082

MEGGAALYNPRTVEEVFKDFKGRRTAIVKALTTDVQEFYQQCDPEKENLCLYGLPN
EEWEVNLPAEEVPPELPEPALGINFARDGLSEKEWLSLVAIHSDAWLLSVSFYFGSRF
SFHKEERKRLFNMINDVPTIFEVVTGMAKAKDKSSAANQNGNKSKSNSKVRTSGGK
SSKTKQPKEEDEEIDEDDEDDHGETLCGACGDSDGADEFWICCDLCEKWFHGKCVK
ITPARAEHIKQYKCPSCSNKRARA

Figure 13A

SEQ ID NO:25, Nucleotide sequence of the open reading frame of pk084a

ATGGGGTCATCACAGTCTTCGCAATTACTCGATGAAGAAGAAGAAGAAGAT
GAAGCAGAGAGCGAAGGTGAAGAAGTAGAAGAAGAAGAAGATGAAGCAGAGA
GCGAATTGAATAACAGAAGAATCGAGCTGGATAATCTCTTGGTCAAGAAAGTTC
TCGAGCAAGAGCCTGAGATGCTTCCTTGTCACGCCTCTGCTTCTCCACTCTCTCCT
CAGCTCTCTTCTCTTGGAACTCCTCGAATCGGACCTTCCATTAAAGTCTGGGATCC
TTACAACGTCCTCGCGCCACCTCCTCCTTCTTCTCCGCCTCTTTTCTCTCGTATCTC
CTCCGCCGCGGAACACGATCGCTCCGCCGTGACGGAAGTCTATTTCATCAGCCAC
GGCGAGTGTGATCTCAATCTCAGGCCTGATCTGATTGGAGGTAGATGCCACGTGG
CTACTCTCACACCCAACGGGAAACGTCAGGCGAGAGCTCTAGCCGTATTTTTAAA
CTCTGAAGGTGTTCGATTCACCTCCGTCTTCTCTTCGCCTCTGGATCGAGCTAGAT
CCATGGCTGTTTCTGTTTGCCAGGAAATGAATTTTCCTGAGGAGCATTTGCAAGT
CTCGGATGCTGTGGTTGAGATGAGTTTAGGGGACTGGGAAAGCTGTCATCGGTCA
GAGATTTACACACCTGAAACTCTAAGTTTAATAGAAAGATGCCAACCTGATTTCT
CAGCTCCATCTGGTGAATCACTCAGACAAGTAGAGTTTCGGATGGTTCAGTTTCT
GAATGGGACAGTCTCAGGACTTTCGGAGAAGCTCAGGTCAGAACTTCTTCCATCT
ACACAGCACACAAATTCCAGAGGGTTCTCGTTAGCTACTTCTATTCATCGCCCAA
TTCTTACAAGGAAGAAATCTGGGAAGAGCCGGTTTCAGGTGATGAATGCAACTG
GTGATCACGAGGGTAGTGAAGAGATATTTAGTAATCACAATGATGAACAACACC
TAGGTGATATAAACATCAAGAGTTCTTCTTCTCAACTCTCAACCTGCATTGGAGT
TTTCACTCACTCTTTACCTATAAAGTGTCTTCTTACCGGTATCCTTGGATGCAGCC
CGGTAATGACACATAAGATCTGTGTGGAGGATTCCTCTGTGACCGTATTACAGCA
TTCGTGGAAAACCGGGTGGCAGGTAAAGCGGTTAAATGACACCGCTCATCTTAG
ACTGTTGTAG

Figure 13B

SEQ ID NO:26, Amino acid sequence of the open reading frame of pk084a

MGSSQSSQLLDEEEEEEDEAESEGEEVEEEEDEAESELNNRRIELDNLLVKKVLEQEP
EMLPCHASASPLSPQLSSLGTPRIGPSIKVWDPYNVLAPPPPSSPPLFSRISSAAEHDRS
AVTEVYFISHGECDLNLRPDLIGGRCHVATLTPNGKRQARALAVFLNSEGVRFTSVFS
SPLDRARSMAVSVCQEMNFPEEHLQVSDAVVEMSLGDWESCHRSEIYTPETLSLIER
CQPDFSAPSGESLRQVEFRMVQFLNGTVSGLSEKLRSELLPSTQHTNSRGFSLATSIHR

Figure 13B Continued

PILTRKKSGKSRFQVMNATGDHEGSEEIFSNHNDEQHLGDINIKSSSSQLSTCIGVFTH
SLPIKCLLTGILGCSPVMTHKICVEDSSVTVLQHSWKTGWQVKRLNDTAHLRLL

Figure 14A

SEQ ID NO:27, Nucleotide sequence of the open reading frame of pk086

ATGCTAGATCACAGTGAAAAGGTCTTATTGGTTGATTCAGAAACCATGAAAACA
AGAGCTGAAGATATGATCGAACAGAACAACACTAGTGTTAACGACAAGAAGAA
GACTTGTGCTGATTGTGGAACCAGTAAAACTCCTCTTTGGCGTGGTGGTCCTGTT
GGTCCAAAGTCGTTGTGTAACGCGTGTGGGATCAGAAACAGAAGAAGAGAAGA
GGAGGAACAGAAGATAATAAGAAATTAAAGAAATCGAGTTCTGGCGGCGGAAA
CCGTAAATTTGGTGAATCGTTAAAACAGAGTTTGATGGATTTGGGGATAAGGAA
GAGATCAACGGTGGAGAAGCAACGACAGAAGCTTGGTGAAGAAGAACAAGCCG
CTGTGTTACTCATGGCTCTTTCTTATGGCTCTGTTTACGCTTAG

Figure 14B

SEQ ID NO:28, Amino acid sequence of the open reading frame of pk086

MLDHSEKVLLVDSETMKTRAEDMIEQNNTSVNDKKKTCADCGTSKTPLWRGGPVG
PKSLCNACGIRNRKKRRGGTEDNKKLKKSSSGGGNRKFGESLKQSLMDLGIRKRSTV
EKQRQKLGEEEQAAVLLMALSYGSVYA

Figure 15A

SEQ ID NO:29, Nucleotide sequence of the open reading frame of pk088b

ATGGCAACACACTCTTCCTTCACCGCAACAACACCTCTCTTTCTCATCGTTCTTCT
ATCCCTATCCTCCGTCTCAGTTCTCGGCGCATCTCACCACCACGCAACGGCGCCG
GCTCCGTCTGTAGACTGTTCGACTCTCATACTCAACATGGCTGACTGTTTATCCTT
CGTTTCGAGCGGAGGCACGGTGGCGAAACCGGAAGGTACATGTTGCTCTGGTCTT
AAGACGGTGCTTAAAGCTGACTCTCAGTGTCTATGTGAAGCGTTTAAGAGCAGTG
CTTCTCTTGGAGTTACTTTGAATATCACTAAGGCTTCTACTCTTCCCGCCGCATGC
AAGCTTCACGCTCCTTCTATCGCTACTTGTGGATGTCTTGCTCCAGGAGTAGCTGC
TGCTGGACCTGAGACAGCCGGATTTCTAGCTCCAAATCCTTCTTCAGGGAACGAT

Figure 15A Continued

GGATCTTCTTTGATTCCGACCTCGTTCACAACTGTACTCAGTGCCGTACTGTTCGT
TTTGTTCTTCTCTAGTGCGTAA

Figure 15B

SEQ ID NO:30, Amino acid sequence of the open reading frame of pk088b

MATHSSFTATTPLFLIVLLSLSSVSVLGASHHHATAPAPSVDCSTLILNMADCLSFVSS
GGTVAKPEGTCCSGLKTVLKADSQCLCEAFKSSASLGVTLNITKASTLPAACKLHAP
SIATCGLSVAPSTAPGLAPGVAAAGPETAGFLAPNPSSGNDGSSLIPTSFTTVLSAVLF
VLFFSSA

Figure 16A

SEQ ID NO:31, Nucleotide sequence of the open reading frame of pk095

ATGGACCCTTTAGCTTCCCAACATCAACACAACCATCTGGAAGATAATAACCAAA
CCCTAACCCATAATAATCCTCAATCCGATTCCACCACCGACTCATCAACTTCCTCC
GCTCAACGCAAACGCAAAGGCAAAGGTGGTCCGGACAACTCCAAGTTCCGTTAC
CGTGGCGTTCGACAAAGAAGCTGGGGCAAATGGGTCGCCGAGATCCGAGAGCCA
CGTAAGCGCACTCGCAAGTGGCTTGGTACTTTCGCAACCGCCGAAGACGCCGCA
CGTGCCTACGACCGGGCTGCCGTTTACCTATACGGGTCACGTGCTCAGCTCAACT
TAACCCCTTCGTCTCCTTCCTCCGTCTCTTCCTCTTCCTCCTCCGTCTCCGCCGCTT
CTTCTCCTTCCACCTCCTCTTCCTCCACTCAAACCCTAAGACCTCTCCTCCCTCGC
CCCGCCGCCGCCACCGTAGGAGGAGGAGCCAACTTTGGTCCGTACGGTATCCCTT
TTAACAACAACATCTTCCTTAATGGTGGGACCTCTATGTTATGCCCTAGTTATGGT
TTTTTCCCTCAACAACAACAACAACAAAATCAGATGGTCCAGATGGGACAATTCC
AACACCAACAGTATCAGAATCTTCATTCTAATACTAACAATAACAAGATTTCTGA
CATCGAGCTCACTGATGTTCCGGTAACTAATTCGACTTCGTTTCATCATGAGGTG
GCGTTAGGGCAGGAACAAGGAGGAAGTGGGTGTAATAATAATAGTTCGATGGAG
GATTTGAACTCTCTAGCTGGTTCGGTGGGTTCGAGTCTATCAATAACTCATCCAC
CGCCGTTGGTTGATCCGGTATGTTCTATGGGTCTGGATCCGGGTTATATGGTTGG
AGATGGATCTTCGACCATTTGGCCTTTTGGAGGAGAAGAAGAATATAGTCATAAT
TGGGGGAGTATTTGGGATTTTATTGATCCATCTTGGGGGAATTCTATTAA

Figure 16B

SEQ ID NO:32, Amino acid sequence of the open reading frame of pk095

MDPLASQHQHNHLEDNNQTLTHNNPQSDSTTDSSTSSAQRKRKGKGGPDNSKFRYR
GVRQRSWGKWVAEIREPRKRTRKWLGTFATAEDAARAYDRAAVYLYGSRAQLNLT
PSSPSSVSSSSSSVSAASSPSTSSSSTQTLRPLLPRPAAATVGGGANFGPYGIPFNNNIFL
NGGTSMLCPSYGFFPQQQQQQNQMVQMGQFQHQQYQNLHSNTNNNKISDIELTDV
PVTNSTSFHHEVALGQEQGGSGCNNNSSMEDLNSLAGSVGSSLSITHPPPLVDPVCS
MGLDPGYMVGDGSSTIWPFGGEEEYSHNWGSIWDFIDPILGEFY

Figure 17A

SEQ ID NO:33, Nucleotide sequence of the open reading frame of pk096

ATGGTTAAAGAAATAGCTTCTTGGTTATTGATACTATCAATGGTGGTGTTTGTTTC
TCCGGTTTTAGCTATAAACGGCGGTGGTTATCCACGATGTAACTGCGAAGACGAA
GGAAACAGTTCTGGAGTACAGAGAACATTCTAGAAACTCAAAGAGTAAGCGAT
TTCTTAATCGCAGTAGCTTATTTCTCAATCCCTATTGAGTTACTTTACTTCGTGAG
TTGTTCCAATGTTCCATTCAAATGGGTTCTCTTTGAGTTTATCGCCTTCATTGTTCT
TTGTGGTATGACTCATCTTCTTCATGGTTGGACTTACTCTGCTCATCCATTTAGAT
TAATGATGGCGTTTACTGTTTTCAAGATGTTGACTGCTTTAGTCTCTTGTGCTACT
GCGATTACGCTTATTACTTTGATTCCTCTGCTTTTGAAAGTTAAAGTTAGAGAGTT
TATGCTTAAGAAGAAAGCTCATGAGCTTGGTCGTGAAGTTGGTTTGATTTTGATT
AAGAAAGAGACTGGCTTTCATGTTCGTATGCTTACTCAAGAGATTCGTAAGTCTT
TGGATCGTCATACGATTCTTTATACTACTTTGGTTGAGCTTTCGAAGACTTTAGGG
TTGCAGAATTTTGCGGTTTGGATGCCGAATGACGGTGGAACGGAGATGGATTTGA
CTCATGAGTTGAGAGGGAGAGGTGGTTATGGTGGTTGTTCTGTTTCTATGGAGGA
TTTGGATGTTGTTAGGATTAGGGAGAGTGATGAAGTGAATGTGTTGAGTGTTGAC
TCGTCCATTGCTCGAGCTAGTGGTGGTGGTGGGGATGTTAGTGAGATTGGTGCCG
TGGCTGCTATTAGAATGCCGATGCTTCGTGTTTCGGATTTTAATGGAGAGCTAAG
TTATGCGATACTTGTTTGTGTTTTACCGGGCGGGACGCCTCGGGATTGGACTTATC
AGGAGATTGAGATTGTTAAAGTTGTGGCGGATCAAGTAACCGTTGCGTTAGATCA
TGCAGCGGTTCTTGAAGAGTCTCAGCTTATGAGGGAGAAGCTGGCGGAACAGAA
CAGGGCGTTGCAGATGGCGAAGAGAGACGCGTTGAGAGCGAGCCAAGCGAGGA
ATGCGTTTCAGAAAACGATGAGCGAAGGGATGAGGCGTCCTATGCATTCGATAC
TCGGTCTTTTGTCGATGATTCAGGACGAGAAGTTGAGTGACGAGCAGAAAATGA

Figure 17A Continued

TTGTTGATACGATGGTTAAAACAGGGAATGTTATGTCGAATTTGGTGGGGGACTC
TATGGATGTGCCTGACGGTAGATTTGGTACGGAGATGAAACCATTTAGTCTGCAT
CGTACGATCCATGAAGCAGCTTGTATGGCGAGATGTTTGTGTCTATGCAATGGAA
TTAGGTTCTTGGTTGACGCGGAGAAGTCTCTACCTGATAATGTAGTAGGTGATGA
AAGAAGGGTCTTTCAAGTGATACTTCATATAGTTGGTAGTTTAGTAAAGCCTAGA
AAACGTCAAGAAGGATCTTCATTGATGTTTAAGGTTTTGAAAGAAAGAGGAAGC
TTGGATAGGAGTGATCATAGATGGGCTGCTTGGAGATCACCGGCTTCTTCAGCAG
ATGGAGATGTGTATATAAGATTTGAAATGAATGTAGAGAATGATGATTCAAGTTC
TCAATCATTTGCTTCTGTTTCCTCCAGAGATCAAGAAGTTGGTGATGTTAGATTCT
CCGGCGGCTATGGGTTAGGACAAGATCTAAGCTTTGGTGTTTGTAAGAAAGTGGT
GCAGTTGATTCATGGGAATATCTCGGTGGTCCCTGGCTCGGATGGTTCACCGGAG
ACCATGTCGTTGCTCCCTCGGTTCGACGTAGACCCTCCATATCTGTCCATGGATC
CAGCGAGTCGCCAGCTCCTGACCACCACGCTCACCCACATTCGAATTCTCTGTTA
CGTGGCTTACAAGTTTTATTGGTAGACACCAACGATTCGAACCGGGCAGTTACAC
GTAAACTCTTAGAGAAACTCGGGTGCGATGTAACCGCGGTTTCCTCTGGATTCGA
TTGCCTTACCGCCATTGCTCCCGGCTCGTCCTCGCCTTCTACTTCGTTTCAAGTGG
TGGTGCTTGATCTTCAAATGGCAGAGATGGACGGTTATGAAGTGGCCATGAGGA
TCAGGAGTCGATCTTGGCCGTTGATTGTGGCGACGACAGTGGGCTTGGATGAAG
AAATGTGGGACAAGTGTGCACAGATTGGAATCAATGGAGTTGTGAGAAAGCCAG
TGGTGTTAAGAGCTATGGAGAGTGAGCTCCGAAGAGTATTGTTGCAAGCTGACC
AACTTCTCTAA

Figure 17B

SEQ ID NO:34, Amino acid sequence of the open reading frame of pk096

MVKEIASWLLILSMVVFVSPVLAINGGGYPRCNCEDEGNSFWSTENILETQRVSDFLI
AVAYFSIPIELLYFVSCSNVPFKWVLFEFIAFIVLCGMTHLLHGWTYSAHPFRLMMAF
TVFKMLTALVSCATAITLITLIPLLLKVKVREFMLKKKAHELGREVGLILIKKETGFH
VRMLTQEIRKSLDRHTILYTTLVELSKTLGLQNFAVWMPNDGGTEMDLTHELRGRG
GYGGCSVSMEDLDVVRIRESDEVNVLSVDSSIARASGGGGDVSEIGAVAAIRMPMLR
VSDFNGELSYAILVCVLPGGTPRDWTYQEIEIVKVVADQVTVALDHAAVLEESQLM
REKLAEQNRALQMAKRDALRASQARNAFQKTMSEGMRRPMHSILGLLSMIQDEKLS
DEQKMIVDTMVKTGNVMSNLVGDSMDVPDGRFGTEMKPFSLHRTIHEAACMARCL
CLCNGIRFLVDAEKSLPDNVVGDERRVFQVILHIVGSLVKPRKRQEGSSLMFKVLKE

Figure 17B Continued

RGSLDRSDHRWAAWRSPASSADGDVYIRFEMNVENDDSSSQSFASVSSRDQEVGDV
RFSGGYGLGQDLSFGVCKKVVQLIHGNISVVPGSDGSPETMSLLPRFRRRPSISVHGS
SESPAPDHHAHPHSNSLLRGLQVLLVDTNDSNRAVTRKLLEKLGCDVTAVSSGFDCL
TAIAPGSSSPSTSFQVVVLDLQMAEMDGYEVAMRIRSRSWPLIVATTVGLDEEMWD
KCAQIGINGVVRKPVVLRAMESELRRVLLQADQLL

Figure 18A

SEQ ID NO:35, Nucleotide sequence of the open reading frame of pk097a

ATGGAAGTCTGCAATTGTATTGAACCGCAATGGCCAGCGGATGAATTGTTAATGA
AATACCAATACATCTCCGATTTCTTCATTGCGATTGCGTATTTTCGATTCCTCTT
GAGTTGATTTACTTTGTGAAGAAATCAGCCGTGTTTCCGTATAGATGGGTACTTG
TTCAGTTTGGTGCTTTTATCGTTCTTTGTGGAGCAACTCATCTTATTAACTTATGG
ACTTTCACTACGCATTCGAGAACCGTGGCGCTTGTGATGACTACCGCGAAGGTGT
TAACCGCTGTTGTCTCGTGTGCTACTGCGTTGATGCTTGTTCATATTATTCCTGAT
CTTTTGAGTGTTAAGACTCGGGAGCTTTTCTTGAAAAATAAAGCTGCTGAGCTCG
ATAGAGAAATGGGATTGATTCGAACTCAGGAAGAAACCGGAAGGCATGTGAGA
ATGTTGACTCATGAGATTAGAAGCACTTTAGATAGACATACTATTTTAAAGACTA
CACTTGTTGAGCTTGGTAGGACATTAGCTTTGGAGGAGTGTGCATTGTGGATGCC
TACTAGAACTGGGTTAGAGCTACAGCTTTCTTATACACTTCGTCATCAACATCCC
GTGGAGTATACGGTTCCTATTCAATTACCGGTGATTAACCAAGTGTTTGGTACTA
GTAGGGCTGTAAAAATATCTCCTAATTCTCCTGTGGCTAGGTTGAGACCTGTTTCT
GGGAAATATATGCTAGGGGAGGTGGTCGCTGTGAGGGTTCCGCTTCTCCACCTTT
CTAATTTTCAGATTAATGACTGGCCTGAGCTTTCAACAAAGAGATATGCTTTGAT
GGTTTTGATGCTTCCTTCAGATAGTGCAAGGCAATGGCATGTCCATGAGTTGGAA
CTCGTTGAAGTCGTCGCTGATCAGGTGGCTGTAGCTCTCTCACATGCTGCGATCC
TAGAAGAGTCGATGCGAGCTAGGGACCTTCTCATGGAGCAGAATGTTGCTCTTGA
TCTAGCTAGACGAGAAGCAGAAACAGCAATCCGTGCCCGCAATGATTTCCTAGC
GGTTATGAACCATGAAATGCGAACACCGATGCATGCGATTATTGCACTCTCTTCC
TTACTCCAAGAAACGGAACTAACCCCTGAACAAAGACTGATGGTGGAAACAATA
CTTAAAAGTAGTAACCTTTTGGCAACTTTGATGAATGATGTCTTAGATCTTTCAA
GGTTAGAAGATGGAAGTCTTCAACTTGAACTTGGGACATTCAATCTTCATACATT
ATTTAGAGAGGTCCTCAATCTGATAAAGCCTATAGCGGTTGTTAAGAAATTACCC

Figure 18A Continued

ATCACACTAAATCTTGCACCAGATTTGCCAGAATTTGTTGTTGGGGATGAGAAAC
GGCTAATGCAGATAATATTAAATATAGTTGGTAATGCTGTGAAATTCTCCAAACA
AGGTAGTATCTCCGTAACCGCTCTTGTCACCAAGTCAGACACGAGCTGCTGAC
TTTTTTGTCGTGCCAACTGGGAGTCATTTCTACTTGAGAGTGAAGGTAAAAGACT
CTGGAGCAGGAATAAATCCTCAAGACATTCCAAAGATTTTCACTAAATTTGCTCA
AACACAATCTTTAGCGACGAGAAGCTCGGGTGGTAGTGGGCTTGGCCTCGCCATC
TCCAAGAGGTTTGTGAATCTGATGGAGGGTAACATTTGGATTGAGAGCGATGGTC
TTGGAAAAGGATGCACGGCTATCTTTGATGTTAAACTTGGGATCTCAGAACGTTC
AAACGAATCTAAACAGTCGGGCATACCGAAAGTTCCAGCCATTCCCCGACATTC
AAATTTCACTGGACTTAAGGTTCTTGTCATGGATGAGAACGGGGTAAGTAGAATG
GTGACGAAGGGACTTCTTGTACACCTTGGGTGCGAAGTGACCACGGTGAGTTCA
AACGAGGAGTGTCTCCGAGTTGTGTCCCATGAGCACAAAGTGGTCTTCATGGACG
TGTGCATGCCCGGGGTCGAAAACTACCAAATCGCTCTCCGTATTCACGAGAAATT
CACAAAACAACGCCACCAACGGCCACTACTTGTGGCACTCAGTGGTAACACTGA
CAAATCCACAAAAGAGAAATGCATGAGCTTTGGTCTAGACGGTGTGTTGCTCAA
ACCCGTATCACTAGACAACATAAGAGATGTTCTGTCTGATCTTCTCGAGCCCCGG
GTACTGTACGAGGGCATGTAA

Figure 18B

SEQ ID NO:36, Amino acid sequence of the open reading frame of pk097a

MEVCNCIEPQWPADELLMKYQYISDFFIAIAYFSIPLELIYFVKKSAVFPYRWVLVQF
GAFIVLCGATHLINLWTFTTHSRTVALVMTTAKVLTAVVSCATALMLVHIIPDLLSV
KTRELFLKNKAAELDREMGLIRTQEETGRHVRMLTHEIRSTLDRHTILKTTLVELGRT
LALEECALWMPTRTGLELQLSYTLRHQHPVEYTVPIQLPVINQVFGTSRAVKISPNSP
VARLRPVSGKYMLGEVVAVRVPLLHLSNFQINDWPELSTKRYALMVLMLPSDSARQ
WHVHELELVEVVADQVAVALSHAAILEESMRARDLLMEQNVALDLARREAETAIR
ARNDFLAVMNHEMRTPMHAIIALSSLLQETELTPEQRLMVETILKSSNLLATLMNDV
LDLSRLEDGSLQLELGTFNLHTLFREVLNLIKPIAVVKKLPITLNLAPDLPEFVVGDEK
RLMQIILNIVGNAVKFSKQGSISVTALVTKSDTRAADFFVVPTGSHFYLRVKVKDSGA
GINPQDIPKIFTKFAQTQSLATRSSGGSGLGLAISKRFVNLMEGNIWIESDGLGKGCTA
IFDVKLGISERSNESKQSGIPKVPAIPRHSNFTGLKVLVMDENGVSRMVTKGLLVHLG
CEVTTVSSNEECLRVVSHEHKVVFMDVCMPGVENYQIALRIHEKFTKQRHQRPLLV
ALSGNTDKSTKEKCMSFGLDGVLLKPVSLDNIRDVLSDLLEPRVLYEGM

Figure 18C

SEQ ID NO:37, Nucleotide sequence of the open reading frame of pk097b

ATGGAAGTCTGCAATTGTATTGAACCGCAATGGCCAGCGGATGAATTGTTAATGA
AATACCAATACATCTCCGATTTCTTCATTGCGATTGCGTATTTTCGATTCCTCTT
GAGTTGATTTACTTTGTGAAGAAATCAGCCGTGTTTCCGTATAGATGGGTACTTG
TTCAGTTTGGTGCTTTTATCGTTCTTTGTGGAGCAACTCATCTTATTAACTTATGG
ACTTTCACTACGCATTCGAGAACCGTGGCGCTTGTGATGACTACCGCGAAGGTGT
TAACCGCTGTTGTCTCGTGTGCTACTGCGTTGATGCTTGTTCATATTATTCCTGAT
CTTTTGAGTGTTAAGACTCGGGAGCTTTCTTGAAAAATAAAGCTGCTGAGCTCG
ATAGAGAAATGGGATTGATTCGAACTCAGGAAGAAACCGGAAGGCATGTGAGA
ATGTTGACTCATGAGATTAGAAGCACTTTAGATAGACATACTATTTTAAAGACTA
CACTTGTTGAGCTTGGTAGGACATTAGCTTTGGAGGAGTGTGCATTGTGGATGCC
TACTAGAACTGGGTTAGAGCTACAGCTTTCTTATACACTTCGTCATCAACATCCC
GTGGAGTATACGGTTCCTATTCAATTACCGGTGATTAACCAAGTGTTTGGTACTA
GTAGGGCTGTAAAAATATCTCCTAATTCTCCTGTGGCTAGGTTGAGACCTGTTTCT
GGGAAATATATGCTAGGGGAGGTGGTCGCTGTGAGGGTTCCGCTTCTCCACCTTT
CTAATTTTCAGATTAATGACTGGCCTGAGCTTTCAACAAAGAGATATGCTTTGAT
GGTTTTGATGCTTCCTTCAGATAGTGCAAGGCAATGGCATGTCGATGAGTTGGAA
CTCGTTGAAGTCGTCGCTGATCAGGTGGCTGTAGCTCTCTCACATGCTGCGATCC
TAGAAGAGTCGATGCGAGCTAGGGACCTTCTCATGGAGCAGAATGTTGCTCTTGA
TCTAGCTAGACGAGAAGCAGAAACAGCAATCCGTGCCCGCAATGATTTCCTAGC
GGTTATGAACCATGAAATGCGAACACCGATGCATGCGATTATTGCACTCTCTTCC
TTACTCCAAGAAACGGAACTAACCCCTGAACAAAGACTGATGGTGGAAACAATA
CTTAAAAGTAGTAACCTTTTGGCAACTTTGATGAATGATGTCTTAGATCTTTCAA
GGTTAGAAGATGGAAGTCTTCAACTTGAACTTGGGACATTCAATCTTCATACATT
ATTTAGAGAGGTCCTCAATCTGATAAAGCCTATAGCGGTTGTTAAGAAATTACCC
ATCACACTAAATCTTGCACCAGATTTGCCAGAATTTGTTGTTGGGGATGAGAAAC
GGCTAATGCAGATAATATTAAATATAGTTGGTAATGCTGTGAAATTCTCCAAACA
AGGTAGTATCTCCGTAACCGCTCTTGTCACCAAGTCAGACACACGAGCTGCTGAC
TTTTTTGTCGTGCCAACTGGGAGTCATTTCTACTTGAGAGTGAAGGTAAAAGACT
CTGGAGCAGGAATAAATCCTCAAGACATTCCAAAGATTTTCACTAAATTTGCTCA
AACACAATCTTTAGCGACGAGAAGCTCGGGTGGTAGTGGGCTTGGCCTCGCCATC
TCCAAGAGGTTTGTGAATCTGATGGAGGGTAACATTTGGATTGAGAGCGATGGTC
TTGGAAAAGGATGCACGGCTATCTTTGATGTTAAACTTGGGATCTCAGAACGTTC

Figure 18C Continued

AAACGAATCTAAACAGTCGGGCATACCGAAAGTTCCAGCCATTCCCCGACATTC
AAATTTCACTGGACTTAAGGTTCTTGTCATGGATGAGAACGGGGTAAGTAGAATG
GTGACGAAGGGACTTCTTGTACACCTTGGGTGCGAAGTGACCACGGTGAGTTCA
AACGAGGAGTGTCTCCGAGTTGTGTCCCATGAGCACAAAGTGGTCTTCATGGACG
TGTGCATGCCCGGGGTCGAAAACTACCAAATCGCTCTCCGTATTCACGAGAAATT
CACAAAACAACGCCACCAACGGCCACTACTTGTGGCACTCAGTGGTAACACTGA
CAAATCCACAAAAGAGAAATGCATGAGCTTTGGTCTAGACGTGTGTTGCTCAAA
CCCGTATCACTAG

Figure 18D

SEQ ID NO:38, Amino acid sequence of the open reading frame of pk097b

MEVCNCIEPQWPADELLMKYQYISDFFIAIAYFSIPLELIYFVKKSAVFPYRWVLVQF
GAFIVLCGATHLINLWTFTTHSRTVALVMTTAKVLTAVVSCATALMLVHIIPDLLSV
KTRELFLKNKAAELDREMGLIRTQEETGRHVRMLTHEIRSTLDRHTILKTTLVELGRT
LALEECALWMPTRTGLELQLSYTLRHQHPVEYTVPIQLPVINQVFGTSRAVKISPNSP
VARLRPVSGKYMLGEVVAVRVPLLHLSNFQINDWPELSTKRYALMVLMLPSDSARQ
WHVDELELVEVVADQVAVALSHAAILEESMRARDLLMEQNVALDLARREAETAIR
ARNDFLAVMNHEMRTPMHAIIALSSLLQETELTPEQRLMVETILKSSNLLATLMNDV
LDLSRLEDGSLQLELGTFNLHTLFREVLNLIKPIAVVKKLPITLNLAPDLPEFVVGDEK
RLMQIILNIVGNAVKFSKQGSISVTALVTKSDTRAADFFVVPTGSHFYLRVKVKDSGA
GINPQDIPKIFTKFAQTQSLATRSSGGSGLGLAISKRFVNLMEGNIWIESDGLGKGCTA
IFDVKLGISERSNESKQSGIPKVPAIPRHSNFTGLKVLVMDENGVSRMVTKGLLVHLG
CEVTTVSSNEECLRVVSHEHKVVFMDVCMPGVENYQIALRIHEKFTKQRHQRPLLV
ALSGNTDKSTKEKCMSFGLDVCCSNPYH

Figure 19A

SEQ ID NO:39, Nucleotide sequence of the open reading frame of pk098

ATGATGGGCAGTGTCGAGCTGAATCTGAGGGAGACTGAGCTGTGTCTTGGTCTTC
CCGGTGGAGATACAGTGGCTCCGGTAACCGGAAACAAGAGAGGGTTCTCAGAGA
CGGTTGATCTGAAGCTAAATCTGAATAATGAGCCTGCAAACAAGGAAGGATCTA
CGACTCATGACGTCGTGACTTTTGATTCCAAGGAGAAGAGTGCTTGTCCTAAAGA
TCCAGCCAAACCTCCGGCCAAGGCACAAGTTGTGGGATGGCCACCGGTGAGATC

Figure 19A Continued

ATACCGGAAGAACGTGATGGTTTCCTGCCAAAAATCAAGCGGTGGCCCGGAGGC
GGCGGCGTTCGTGAAGGTATCAATGGACGGAGCACCGTACTTGAGGAAAATCGA
TTTGAGGATGTATAAAAGCTACGATGAGCTTTCTAATGCTTTGTCCAACATGTTC
AGCTCTTTTACCATGGGCAAACATGGAGGAGAAGAAGGAATGATAGACTTCATG
AATGAGAGGAAATTGATGGATTTGGTGAATAGCTGGGACTATGTTCCCTCTTATG
AAGACAAAGACGGTGATTGGATGCTCGTCGGCGACGTTCCTTGGCCAATGTTCGT
CGATACATGCAAGCGTTTACGTCTCATGAAAGGATCGGATGCCATTGGTCTCGCT
CCGAGGGCGATGGAGAAGTGCAAGAGCAGAGCTTGA

Figure 19B

SEQ ID NO:40, Amino acid sequence of the open reading frame of pk098

MMGSVELNLRETELCLGLPGGDTVAPVTGNKRGFSETVDLKLNLNNEPANKEGSTT
HDVVTFDSKEKSACPKDPAKPPAKAQVVGWPPVRSYRKNVMVSCQKSSGGPEAAA
FVKVSMDGAPYLRKIDLRMYKSYDELSNALSNMFSSFTMGKHGGEEGMIDFMNER
KLMDLVNSWDYVPSYEDKDGDWMLVGDVPWPMFVDTCKRLRLMKGSDAIGLAPR
AMEKCKSRA

Figure 20A

SEQ ID NO:41, Nucleotide sequence of the open reading frame of pk099

ATGATCGGCCAACTTATGAACCTCAAGGCCACGGAGCTCTGTCTCGGCCTCCCCG
GCGGCGCTGAAGCAGTTGAGAGTCCTGCCAAATCGGCGGTGGGAAGCAAGAGAG
GCTTCTCCGAAACCGTTGATCTCATGCTCAATCTTCAATCTAACAAAGAAGGCTC
CGTTGATCTCAAAAACGTTTCTGCTGTTCCCAAGGAGAAGACTACCCTTAAAGAT
CCTTCTAAGCCTCCTGCTAAAGCACAAGTGGTGGGATGGCCACCTGTGAGGAACT
ACAGGAAGAACATGATGACTCAGCAGAAGACCAGTAGTGGTGCGGAGGAGGCC
AGCAGTGAGAAGGCCGGGAACTTTGGTGGAGGAGCAGCCGGAGCCGGCTTGGTG
AAGGTCTCCATGGACGGTGCTCCATATCTGAGGAAAGTTGACCTCAAGATGTACA
AAAGCTACCAGGATCTTTCTGATGCATTGGCCAAAATGTTCAGCTCCTTTACTAT
GGGAAACTATGGAGCACAAGGAATGATAGATTTCATGAACGAGAGCAAGCTAAT
GAATCTGCTGAATAGCTCTGAGTATGTGCCAAGCTACGAGGACAAAGATGGTGA
CTGGATGCTCGTTGGCGATGTCCCATGGGAAATGTTTGTCGAGTCTTGCAAACGT

Figure 20A Continued

TTGCGCATTATGAAGGGATCTGAAGCAGTTGGACTTGCTCCGAGAGCAATGGAG
AAGTACTGCAAGAACAGATCTTGA

Figure 20B

SEQ ID NO:42, Amino acid sequence of the open reading frame of pk099

MIGQLMNLKATELCLGLPGGAEAVESPAKSAVGSKRGFSETVDLMLNLQSNKEGSV
DLKNVSAVPKEKTTLKDPSKPPAKAQVVGWPPVRNYRKNMMTQQKTSSGAEEASS
EKAGNFGGGAAGAGLVKVSMDGAPYLRKVDLKMYKSYQDLSDALAKMFSSFTMG
NYGAQGMIDFMNESKLMNLLNSSEYVPSYEDKDGDWMLVGDVPWEMFVESCKRL
RIMKGSEAVGLAPRAMEKYCKNRS

Figure 21A

SEQ ID NO:43, Nucleotide sequence of the open reading frame of pk100

ATGAAAAGCTTGCATGTGGCGGCCAACGCCGGAGATCTGGCTGAGGATTGTGGA
ATACTCGGTGGAGACGCTGATGATACTGTTTTGATGGATGGAATTGATGAAGTTG
GTAGAGAGATCTGGTTAGATGACCATGGAGGAGATAATAATCATGTTCATGGTC
ATCAAGATGATGATTTGATTGTTCATCATGACCCTTCAATCTTCTATGGAGATCTC
CCAACGCTTCCTGATTTCCCATGCATGTCGTCTTCATCATCGTCTTCAACATCTCC
AGCTCCTGTCAACGCAATCGTCTCCTCAGCCTCTTCTTCTTCGGCAGCTTCTTCCT
CCACTTCCTCAGCTGCTTCTTGGGCTATATTGAGATCAGATGGAGAAGATCCGAC
TCCAAACCAAAACCAATACGCATCAGGAAACTGTGACGACTCTTCTGGTGCATTG
CAATCCACAGCTTCCATGGAGATTCCATTAGACAGCAGTCAAGGTTTTGGTTGCG
GCGAAGGCGGTGGTGATTGCATTGATATGATGGAGACTTTCGGGTACATGGATCT
ACTTGATAGCAACGAGTTCTTTGACACCTCAGCTATATTTAGCCAAGACGACGAC
ACGCAAAACCCTAACTTGATGGACCAAACCCTTGAGAGACAAGAAGACCAGGTC
GTTGTTCCGATGTTGGAGAATAACAGTGGTGGAGACATGCAAATGATGAATTCTT
CCTTGGAACAGGACGATGATCTCGCTGCTGTGTTTTGGAGTGGCTAAAGAACAA
CAAGGAGACTGTGTCGGCTGAGGATTTGAGGAAAGTAAAGATAAAGAAAGCTAC
GATTGAATCAGCGGCAAGAAGACTAGGCGGTGGTAAAGAAGCGATGAAGCAGC
TTTTAAAGCTGATTCTTGAATGGGTCCAAACTAATCACTTACAAAGAAGACGCAC
CACCACCACCACCACCAACCTCTCTTATCAACAATCATTCCAACAAGATCCATTT
CAAAACCCTAACCCTAATAACAACAACCTAATCCCACCGTCCGACCAAACCTGTT

Figure 21A Continued

TCTCACCTTCAACATGGGTTCCTCCACCACCACAACAACAAGCTTTTGTCTCGGA
CCCGGGTTTTGGATACATGCCTGCTCCAAACTATCCGCCACAGCCAGAGTTCCTT
CCTTTACTTGAATCTCCACCGTCATGGCCACCACCACCACAGTCTGGTCCCATGC
CACATCAACAATTCCCCATGCCGCCAACCTCGCAGTATAATCAATTTGGAGATCC
AACAGGTTTCAATGGATACAACATGAATCCGTACCAATATCCTTATGTTCCTGCA
GGACAAATGAGAGATCAGAGATTACTCCGTTTGTGTTCCTCAGCAACTAAAGAG
GCAAGAAAGAAACGGATGGCGAGACAGAGGAGGTTCTTGTCTCATCACCACAGA
CATAACAACAACAACAACAACAACAATAATCAGCAGAACCAAACCCAAATCGG
AGAAACCTGTGCCGCGGTGGCTCCACAACTTAACCCCGTGGCCACAACCGCCAC
GGGAGGGACCTGGATGTATTGGCCTAATGTCCCGGCAGTGCCGCCTCAATTACCG
CCAGTGATGGAGACTCAGTTACCCACCATGGACCGAGCTGGCTCAGCTTCTGCTA
TGCCACGTCAGCAGGTGGTACCAGATCGCCGGCAGGGATGGAAACCAGAAAAGA
ATTTGCGGTTCTCTTGCAGAAAGTCTTGAAGCAAAGCGACGTGGGTAACCTCGG
AAGGATCGTTTTGCCAAAAAAGAAGCTGAGACACACTTGCCGGAGCTAGAGGC
AAGAGACGGCATCTCTCTGGCCATGGAAGACATCGGAACCTCTCGTGTTTGGAAC
ATGCGCTACAGGTTTTGGCCTAACAACAAAAGCAGGATGTATCTCCTCGAGAAC
ACCGGCGATTTTGTGAAAACCAATGGGCTCCAAGAAGGTGATTTCATAGTCATAT
ACTCCGACGTCAAATTGATACGAGGGGTTAAAGTAAGACAACCGAGCGGACAAA
AGCCGGAGGCTCCACCGTCGTCAGCAGCTACGAAGAGACAAAACAAGTCGCAAA
GGAACATAAACAATAACTCTCCGTCGGCGAATGTGGTGGTCGCTTCACCAACTTC
TCAAACTGTTAAATGA

Figure 21B

SEQ ID NO:44, Amino acid sequence of the open reading frame of pk100

MKSLHVAANAGDLAEDCGILGGDADDTVLMDGIDEVGREIWLDDHGGDNNHVHG
HQDDDLIVHHDPSIFYGDLPTLPDFPCMSSSSSSSTSPAPVNAIVSSASSSSAASSSTSS
AASWAILRSDGEDPTPNQNQYASGNCDDSSGALQSTASMEIPLDSSQGFGCGEGGGD
CIDMMETFGYMDLLDSNEFFDTSAIFSQDDDTQNPNLMDQTLERQEDQVVVPMLEN
NSGGDMQMMNSSLEQDDDLAAVFLEWLKNNKETVSAEDLRKVKIKKATIESAARR
LGGGKEAMKQLLKLILEWVQTNHLQRRRTTTTTTNLSYQQSFQQDPFQNPNPNNNN
LIPPSDQTCFSPSTWVPPPPQQQAFVSDPGFGYMPAPNYPPQPEFLPLLESPPSWPPPP
QSGPMPHQQFPMPPTSQYNQFGDPTGFNGYNMNPYQYPYVPAGQMRDQRLLRLCS
SATKEARKKRMARQRRFLSHHHRHNNNNNNNNNQQNQTQIGETCAAVAPQLNPVA

Figure 21B Continued

TTATGGTWMYWPNVPAVPPQLPPVMETQLPTMDRAGSASAMPRQQVVPDRRQGW
KPEKNLRFLLQKVLKQSDVGNLGRIVLPKKEAETHLPELEARDGISLAMEDIGTSRV
WNMRYRFWPNNKSRMYLLENTGDFVKTNGLQEGDFIVIYSDVKLIRGVKVRQPSGQ
KPEAPPSSAATKRQNKSQRNINNNSPSANVVVASPTSQTVK

Figure 22A

SEQ ID NO:45, Nucleotide sequence of the open reading frame of pk105

ATGGAGGAAGTATCTCCGGCGATCGCAGGTCCTTTCAGGCCATTCTCCGAAACCC
AGATGGATTTCACCGGGATCAGATTGGGTAAAGGTTACTGCAATAACCAATACTC
AAATCAAGATTCCGAGAACGGAGATCTAATGGTTTCGTTACCGGAGACTTCATCA
TGCTCTGTTTCTGGGTCACATGGTTCTGAATCTAGGAAAGTTTTGATTTCTCGGAT
CAATTCTCCTAATTTAAACATGAAGGAATCAGCAGCTGCTGATATAGTCGTCGTT
GATATCTCCGCCGGAGATGAGATCAACGGCTCAGATGTTACTAGCGAGAAGAAG
ATGATCAGCAGAACAGAGAGTAGGAGTTTGTTTGAATTCAAGAGTGTGCCTTTGT
ATGGTTTCACTTCGATTTGTGGAAGAAGACCAGAGATGGAAGATGCTGTTTCGAC
TATACCAAGATTCCTTCAATCTTCTTCTGGTTCCATGTTAGATGGTCGGTTTGATC
CTCAATCCGCCGCTCATTTCTTCGGTGTTTACGACGGCCATGGCGGTTCTCAGGTA
GCGAACTATTGTAGAGAGAGGATGCATTTGGCTTTGGCGGAGGAGATAGCTAAG
GAGAAACCGATGCTCTGCGATGGTGATACGTGGCTGGAGAAGTGGAAGAAAGCT
CTTTTCAACTCGTTCCTGAGAGTTGACTCGGAGATTGAGTCAGTTGCGCCGGAGA
CGGTTGGGTCAACGTCGGTGGTTGCCGTTGTTTTCCCGTCTCACATCTTCGTCGCT
AACTGCGGTGACTCTAGAGCCGTTCTTTGCCGCGGCAAAACTGCACTTCCATTAT
CCGTTGACCATAAACCGGATAGAGAAGATGAAGCTGCGAGGATTGAAGCCGCAG
GAGGGAAAGTGATTCAGTGGAATGGAGCTCGTGTTTTCGGTGTTCTCGCCATGTC
GAGATCCATTGGCGATAGATACTTGAAACCATCCATCATTCCTGATCCGGAAGTG
ACGGCTGTGAAGAGAGTAAAAGAAGATGATTGTCTGATTTTGGCGAGTGACGGG
GTTTGGGATGTAATGACGGATGAAGAAGCGTGTGAGATGGCAAGGAAGCGGATT
CTCTTGTGGCACAAGAAAAACGCGGTGGCTGGGGATGCATCGTTGCTCGCGGAT
GAGCGGAGAAAGGAAGGGAAAGATCCTGCGGCGATGTCCGCGGCTGAGTATTTG
TCAAAGCTGGCGATACAGAGAGGAAGCAAAGACAACATAAGTGTGGTGGTGGTT
GATTTGAAGCCTCGGAGGAAACTCAAGAGCAAACCCTTGAACTGA

Figure 22B

SEQ ID NO:46, Amino acid sequence of the open reading frame of pk105

MEEVSPAIAGPFRPFSETQMDFTGIRLGKGYCNNQYSNQDSENGDLMVSLPETSSCS
VSGSHGSESRKVLISRINSPNLNMKESAAADIVVVDISAGDEINGSDVTSEKKMISRTE
SRSLFEFKSVPLYGFTSICGRRPEMEDAVSTIPRFLQSSSGSMLDGRFDPQSAAHFFGV
YDGHGGSQVANYCRERMHLALAEEIAKEKPMLCDGDTWLEKWKKALFNSFLRVDS
EIESVAPETVGSTSVVAVVFPSHIFVANCGDSRAVLCRGKTALPLSVDHKPDREDEAA
RIEAAGGKVIQWNGARVFGVLAMSRSIGDRYLKPSIIPDPEVTAVKRVKEDDCLILAS
DGVWDVMTDEEACEMARKRILLWHKKNAVAGDASLLADERRKEGKDPAAMSAAE
YLSKLAIQRGSKDNISVVVVDLKPRRKLKSKPLN

Figure 23A

SEQ ID NO:47, Nucleotide sequence of the open reading frame of pk107

ATGGAAATGCCCGGTAGAAGATCTAATTACACTTTGCTTAGTCAATTTTCTGACG
ATCAGGTGTCAGTTTCCGTCACCGGAGCTCCTCCGCCTCACTATGATTCCTTGTCG
AGCGAAAACAGGAGCAACCATAACAGCGGGAACACCGGGAAAGCTAAGGCGGA
GAGAGGCGGATTTGATTGGGATCCTAGCGGTGGTGGTGGTGGTGATCATAGGTT
GAATAATCAACCGAATCGGGTTGGGAATAATATGTATGCTTCGTCTCTAGGGTTG
CAAAGGCAATCCAGTGGGAGTAGTTTCGGTGAGAGCTCTTTGTCTGGGGATTATT
ACATGCCTACGCTTTCTGCGGCGGCTAACGAGATCGAATCTGTTGGATTTCCTCA
AGATGATGGGTTTAGGCTTGGATTTGGTGGTGGTGGAGGAGATTTGAGGATACA
GATGGCGGCGGACTCCGCTGGAGGGTCTTCATCTGGGAAGAGCTGGGCGCAGCA
GACGGAGGAGAGTTATCAGCTGCAGCTTGCATTGGCGTTAAGGCTTTCGTCGGAG
GCTACTTGTGCCGACGATCCGAACTTTCTGGATCCTGTACCGGACGAGTCTGCTT
TACGGACTTCGCCAAGTTCAGCCGAAACCGTTTCACATCGTTTCTGGGTTAATGG
CTGCTTATCGTACTATGATAAAGTTCCTGATGGGTTTTATATGATGAATGGTCTGG
ATCCCTATATTTGGACCTTATGCATCGACCTGCATGAAAGTGGTCGCATCCCTTC
AATTGAATCATTAAGAGCTGTTGATTCTGGTGTTGATTCTTCGCTTGAAGCGATC
ATAGTTGATAGGCGTAGTGATCCAGCCTTCAAGGAACTTCACAATAGAGTCCACG
ACATATCTTGTAGCTGCATTACCACAAAAGAGGTTGTTGATCAGCTGGCAAAGCT
TATCTGCAATCGTATGGGGGGTCCAGTTATCATGGGGGAAGATGAGTTGGTTCCC
ATGTGGAAGGAGTGCATTGATGGTCTAAAAGAAATCTTTAAAGTGGTGGTTCCCA
TAGGTAGCCTCTCTGTTGGACTCTGCAGACATCGAGCTTTACTCTTCAAAGTACT

Figure 23A Continued

GGCTGACATAATTGATTTACCCTGTCGAATTGCCAAAGGATGTAAATATTGTAAT
AGAGACGATGCCGCTTCGTGCCTTGTCAGGTTTGGGCTTGATAGGGAGTACCTGG
TTGATTTAGTAGGAAAGCCAGGTCACTTATGGGAGCCTGATTCCTTGCTAAATGG
TCCTTCATCTATCTCAATTTCTTCTCCTCTGCGGTTTCCACGACCAAAGCCAGTTG
AACCCGCAGTCGATTTTAGGTTACTAGCCAAACAATATTTCTCCGATAGCCAGTC
TCTTAATCTTGTTTTCGATCCTGCATCAGATGATATGGGATTCTCAATGTTTCATA
GGCAATATGATAATCCGGGTGGAGAGAATGACGCATTGGCAGAAAATGGTGGTG
GGTCTTTGCCACCCAGTGCTAATATGCCTCCACAGAACATGATGCGTGCGTCAAA
TCAAATTGAAGCAGCACCTATGAATGCCCCACCAATCAGTCAGCCAGTTCCAAAC
AGGGCAAATAGGGAACTTGGACTTGATGGTGATGATATGGACATCCCGTGGTGT
GATCTTAATATAAAAGAAAAGATTGGAGCAGGTTCCTTTGGCACTGTCCACCGTG
CTGAGTGGCATGGCTCGGATGTTGCTGTGAAAATTCTCATGGAGCAAGACTTCCA
TGCTGAGCGTGTTAATGAGTTCTTAAGAGAGGTTGCGATAATGAAACGCCTTCGC
CACCCTAACATTGTTCTCTTCATGGGTGCGGTCACTCAACCTCCAAATTTGTCAAT
AGTGACAGAATATTTGTCAAGAGGTAGTTTATACAGACTTTTGCATAAAAGTGGA
GCAAGGGAGCAATTAGATGAGAGACGTCGCCTGAGTATGGCTTATGATGTGGCT
AAGGGAATGAATTATCTTCACAATCGCAATCCTCCAATTGTGCATAGAGATCTAA
AATCTCCAAACTTATTGGTTGACAAAAAATATACAGTCAAGGTTTGTGATTTTGG
TCTCTCGCGATTGAAGGCCAGCACGTTTCTTTCCTCGAAGTCAGCAGCTGGAACC
CCCGAGTGGATGGCACCAGAAGTCCTGCGAGATGAGCCGTCTAATGAAAAGTCA
GATGTGTACAGCTTCGGGGTCATCTTGTGGGAGCTTGCTACATTGCAACAACCAT
GGGGTAACTTAAATCCGGCTCAGGTTGTAGCTGCGGTTGGTTTCAAGTGTAAACG
GCTGGAGATCCCGCGTAATCTGAATCCTCAGGTTGCAGCCATAATCGAGGGTTGT
TGGACCAATGAGCCATGGAAGCGTCCATCATTTGCAACTATAATGGACTTGCTAA
GACCATTGATCAAATCAGCGGTTCCTCCGCCCAACCGCTCGGATTTGTAA

Figure 23B

SEQ ID NO:48, Amino acid sequence of the open reading frame of pk107

MEMPGRRSNYTLLSQFSDDQVSVSVTGAPPPHYDSLSSENRSNHNSGNTGKAKAER
GGFDWDPSGGGGGDHRLNNQPNRVGNNMYASSLGLQRQSSGSSFGESSLSGDYYM
PTLSAAANEIESVGFPQDDGFRLGFGGGGGDLRIQMAADSAGGSSSGKSWAQQTEES
YQLQLALALRLSSEATCADDPNFLDPVPDESALRTSPSSAETVSHRFWVNGCLSYYD
KVPDGFYMMNGLDPYIWTLCIDLHESGRIPSIESLRAVDSGVDSSLEAIIVDRRSDPAF

Figure 23B Continued

KELHNRVHDISCSCITTKEVVDQLAKLICNRMGGPVIMGEDELVPMWKECIDGLKEI
FKVVVPIGSLSVGLCRHRALLFKVLADIIDLPCRIAKGCKYCNRDDAASCLVRFGLDR
EYLVDLVGKPGHLWEPDSLLNGPSSISISSPLRFPRPKPVEPAVDFRLLAKQYFSDSQS
LNLVFDPASDDMGFSMFHRQYDNPGGENDALAENGGGSLPPSANMPPQNMMRASN
QIEAAPMNAPPISQPVPNRANRELGLDGDDMDIPWCDLNIKEKIGAGSFGTVHRAEW
HGSDVAVKILMEQDFHAERVNEFLREVAIMKRLRHPNIVLFMGAVTQPPNLSIVTEY
LSRGSLYRLLHKSGAREQLDERRRLSMAYDVAKGMNYLHNRNPPIVHRDLKSPNLL
VDKKYTVKVCDFGLSRLKASTFLSSKSAAGTPEWMAPEVLRDEPSNEKSDVYSFGVI
LWELATLQQPWGNLNPAQVVAAVGFKCKRLEIPRNLNPQVAAIIEGCWTNEPWKRP
SFATIMDLLRPLIKSAVPPPNRSDL

SEQUENCE LISTING

<160> NUMBER OF SEQ ID NOS: 99

<210> SEQ ID NO 1
<211> LENGTH: 2253
<212> TYPE: DNA
<213> ORGANISM: Arabidopsis thaliana

<400> SEQUENCE: 1

```
atggttcgtc ctggattcat tatgcggccg cctggtacaa tcggtgctgt tcaactagca      60
ccacgacccc ttattccagg aatgcctggt ctccgtcctg taatgcctcc tatggttaga     120
ccggcttctc ttcctttgt aacacctgca gaaaagcccc agaccacaat ttacattggc      180
aagatagcta ccgtggaaaa tgactttatg atgtctattc ttgagttttg tggccatgtc     240
aaaagctgtt tacgtgcgga agatcctacc accaagaaac ctaaaggttt tggattctat     300
gaatttgaat cagctgaagg gattctccgc gcaatacgcc tgctgaccca acgtactata     360
gatggacaag agcttttggt gaatgttaat caagcaacaa aggagtattt gctaaaatat     420
gttgagaaga aaatagagac tgcaaagaaa gccaaggaaa gtcaaggaac caaagagaac     480
caagctgaag gtcctgagag tgagcaagac aagcttgaga gtgctgataa tgagacaggg     540
aaggatggag aatcgaagat taaagaaaac atcgatattg cgaattctgc tgtcctaact     600
gatgaagaaa gggaagcaga cagagaggct atggaaaaga ttgaaactgc tattgaagaa     660
aggttaaagt ccaacccttt gcctcctcca ccaccaccac ctgctgatgg ttcaggcatg     720
gaatttgctt tcaaatctaa ggatggtgac tccaacactg acgtagctag gagtgatgcc     780
gcagcaaatg atgttgagac ttctggagaa cacaataggc ctgacacaag ctcacctgat     840
tggagtaaga gaaatgaccg aagaggcaga gaaagaggtg agaaggagca agaaatggat     900
agatacgaga gggaggctga agagaacgg tcaaggaaag agagagagca aaggaggaaa     960
cttgaggatg cagagcgtgc ttaccagact cgtcttcgac aatgggaacg aagagaaaga    1020
gaaaaggaga aggaacgaca gtacgagaag gagaaagaga aagagaaaga gcgcaagagg    1080
aaaaaggaaa tccgctatga ggaagaagag gaagaagacg atgatgattc aagaagaaga    1140
tggcataggg ctgcattaga tgagagaaga agacgacaac taagagaaaa ggaggatgac    1200
ttagctgata gattgaaaga agaggaagag gttgctgagg cgaagaggag tgccgaggag    1260
caaaatttgc agcaacagca attagatgcc ttaagaatcc tatcgggaca ggcagctatt    1320
ggaagcgaaa cggttcagac atcacctatt gaaaatgatc acaaggcaac tctccaaact    1380
```

-continued

```
gtcggtgaat ctgccaatga gcaccatgca gcagattttg aagaaaatgg ttctggtaat    1440
gaatcgatgg ctatcgataa taatagtgga tcagaggcac atgctccctc aaagaaatta    1500
ggatttgggc ttgtgggatc cggaaagcga acttctgtgc cttctgtttt ctatgaggag    1560
gatgaagatg aagcacgtaa ggctaaaaag atgaaacctt tggttcctat agattactca    1620
accgaggaac aagaggctgt ggcccatggt ggctcaggga atacaccacc tcatttggct    1680
ttagccgctg aatttgcaaa acgaatttcg agtaccaatc ccaaggaaga gacgatagaa    1740
accgaaaaac aaaggagcag acgttctcat gataaggcaa gccaccggga caggaaagg     1800
gaagggaaa gggacaggga caggatagga gtcagggacc gaggtgacgg gcatagtggt     1860
cccaccaaag acgccaaaga gtctggaaaa gcaagataaa ttgatactaa gtttctggat    1920
gcgaaacaat tgatagatac aatcccaaag acaaggaaga atttatttc ttacgagata     1980
aactgggcta tgtatgacaa gcaccaagtg cacgaaagaa tgagaccatg gatctcaaag    2040
aaaattatgg agtttctcgg agaagaggaa gccactctgg tagatttcat cgtgtcaaac    2100
actcaacaac acgtgcaggc gtctcagatg cttgagctgt tgcaatcaat tctagacgaa    2160
gaagctgaga tgtttgtgct gaagatgtgg agaacgctca tctttgagat caagcgggtt    2220
gaagctggag tcccggtaaa atccaaagcc tga                                 2253
```

```
<210> SEQ ID NO 2
<211> LENGTH: 750
<212> TYPE: PRT
<213> ORGANISM: Arabidopsis thaliana

<400> SEQUENCE: 2
```

```
Met Val Arg Pro Gly Phe Ile Met Arg Pro Gly Thr Ile Gly Ala
  1               5                  10                  15

Val Gln Leu Ala Pro Arg Pro Leu Ile Pro Gly Met Pro Gly Leu Arg
                 20                  25                  30

Pro Val Met Pro Pro Met Val Arg Pro Ala Ser Leu Pro Phe Val Thr
             35                  40                  45

Pro Ala Glu Lys Pro Gln Thr Thr Ile Tyr Ile Gly Lys Ile Ala Thr
         50                  55                  60

Val Glu Asn Asp Phe Met Met Ser Ile Leu Glu Phe Cys Gly His Val
 65                  70                  75                  80

Lys Ser Cys Leu Arg Ala Glu Asp Pro Thr Thr Lys Lys Pro Lys Gly
                 85                  90                  95

Phe Gly Phe Tyr Glu Phe Glu Ser Ala Glu Gly Ile Leu Arg Ala Ile
            100                 105                 110

Arg Leu Leu Thr Gln Arg Thr Ile Asp Gly Gln Glu Leu Leu Val Asn
        115                 120                 125

Val Asn Gln Ala Thr Lys Glu Tyr Leu Leu Lys Tyr Val Glu Lys Lys
    130                 135                 140

Ile Glu Thr Ala Lys Lys Ala Lys Glu Ser Gln Gly Thr Lys Glu Asn
145                 150                 155                 160

Gln Ala Glu Gly Pro Glu Ser Glu Gln Asp Lys Leu Glu Ser Ala Asp
                165                 170                 175

Asn Glu Thr Gly Lys Asp Gly Glu Ser Lys Ile Lys Glu Asn Ile Asp
            180                 185                 190

Ile Ala Asn Ser Ala Val Leu Thr Asp Glu Glu Arg Glu Ala Asp Arg
        195                 200                 205

Glu Ala Met Glu Lys Ile Glu Thr Ala Ile Glu Glu Arg Leu Lys Ser
    210                 215                 220
```

```
Asn Pro Leu Pro Pro Pro Pro Pro Pro Ala Asp Gly Ser Gly Met
225                 230                 235                 240

Glu Phe Ala Phe Lys Ser Lys Asp Gly Asp Ser Asn Thr Asp Val Ala
            245                 250                 255

Arg Ser Asp Ala Ala Ala Asn Asp Val Glu Thr Ser Gly Glu His Asn
        260                 265                 270

Arg Pro Asp Thr Ser Ser Pro Asp Trp Ser Lys Arg Asn Asp Arg Arg
    275                 280                 285

Gly Arg Glu Arg Gly Glu Lys Glu Gln Glu Met Asp Arg Tyr Glu Arg
290                 295                 300

Glu Ala Glu Arg Glu Arg Ser Arg Lys Glu Arg Gln Arg Arg Lys
305                 310                 315                 320

Leu Glu Asp Ala Glu Arg Ala Tyr Gln Thr Arg Leu Arg Gln Trp Glu
            325                 330                 335

Arg Arg Glu Arg Glu Lys Glu Lys Glu Arg Gln Tyr Glu Lys Glu Lys
        340                 345                 350

Glu Lys Glu Lys Glu Arg Lys Arg Lys Lys Glu Ile Arg Tyr Glu Glu
        355                 360                 365

Glu Glu Glu Glu Asp Asp Asp Ser Arg Arg Arg Trp His Arg Ala
370                 375                 380

Ala Leu Asp Glu Arg Arg Arg Gln Leu Arg Glu Lys Glu Asp Asp
385                 390                 395                 400

Leu Ala Asp Arg Leu Lys Glu Glu Glu Val Ala Glu Ala Lys Arg
            405                 410                 415

Ser Ala Glu Glu Gln Asn Leu Gln Gln Gln Gln Leu Asp Ala Leu Arg
        420                 425                 430

Ile Leu Ser Gly Gln Ala Ala Ile Gly Ser Glu Thr Val Gln Thr Ser
        435                 440                 445

Pro Ile Glu Asn Asp His Lys Ala Thr Leu Gln Thr Val Gly Glu Ser
    450                 455                 460

Ala Asn Glu His His Ala Ala Asp Phe Glu Glu Asn Gly Ser Gly Asn
465                 470                 475                 480

Glu Ser Met Ala Ile Asp Asn Asn Ser Gly Ser Glu Ala His Ala Pro
            485                 490                 495

Ser Lys Lys Leu Gly Phe Gly Leu Val Gly Ser Gly Lys Arg Thr Ser
        500                 505                 510

Val Pro Ser Val Phe Tyr Glu Glu Asp Glu Asp Glu Ala Arg Lys Ala
        515                 520                 525

Lys Lys Met Lys Pro Leu Val Pro Ile Asp Tyr Ser Thr Glu Glu Gln
    530                 535                 540

Glu Ala Val Ala His Gly Gly Ser Gly Asn Thr Pro Pro His Leu Ala
545                 550                 555                 560

Leu Ala Ala Glu Phe Ala Lys Arg Ile Ser Ser Thr Asn Pro Lys Glu
            565                 570                 575

Glu Thr Ile Glu Thr Glu Lys Gln Arg Ser Arg Arg Ser His Asp Lys
        580                 585                 590

Ala Ser His Arg Asp Arg Glu Arg Glu Arg Arg Asp Arg Asp Arg
        595                 600                 605

Asp Arg Val Arg Asp Arg Gly Asp Gly His Ser Gly Pro Thr Lys Asp
    610                 615                 620

Ala Lys Glu Ser Gly Lys Ala Lys Ile Ile Asp Thr Lys Phe Leu Asp
625                 630                 635                 640
```

```
Ala Lys Gln Leu Ile Asp Thr Ile Pro Lys Thr Lys Glu Asp Leu Phe
                645                 650                 655

Ser Tyr Glu Ile Asn Trp Ala Met Tyr Asp Lys His Gln Val His Glu
            660                 665                 670

Arg Met Arg Pro Trp Ile Ser Lys Lys Ile Met Glu Phe Leu Gly Glu
        675                 680                 685

Glu Glu Ala Thr Leu Val Asp Phe Ile Val Ser Asn Thr Gln Gln His
    690                 695                 700

Val Gln Ala Ser Gln Met Leu Glu Leu Leu Gln Ser Ile Leu Asp Glu
705                 710                 715                 720

Glu Ala Glu Met Phe Val Leu Lys Met Trp Arg Thr Leu Ile Phe Glu
                725                 730                 735

Ile Lys Arg Val Glu Ala Gly Val Pro Val Lys Ser Lys Ala
            740                 745                 750

<210> SEQ ID NO 3
<211> LENGTH: 681
<212> TYPE: DNA
<213> ORGANISM: Arabidopsis thaliana

<400> SEQUENCE: 3
gtgctgaaaa agaagaaacc catacttact gacgagcatt tcgtagatgg tcggtttggt      60
tcgatgttcc aaaatccgga cttccaaatt gataaggact catatgaata tggtgtccta     120
caccctgttg cttcttcgaa gaagcaacct tctctgttag atgaacactt tgaagctgta     180
tcagatgatg acgagaacag tgattctgat gcatcacagc cttcagatga cgaggccgac     240
gatggagacg caactaggcc aagcaagaaa gcgagaactc cgaagttgta tgaagtgaaa     300
gatgagcggc atgccgcagc ttatcacaac cgcacttcac tggctaaaga agatagtctt     360
cctatgggcg agcgtgtcaa ggctatagag aaccggcgtg gcaactttgg aggctcgaaa     420
gatatcaaat tcggtcctgg aggatcacgg gagttttctt tcaaggcgag agggtcatca     480
aagtacaaag aagatagaga cgatgagtat gaagatgggc aaagaaacaa gaggagagga     540
gttcagtctc ttggactgaa atcaacaaat attagaggcg gtttcagagg tagaggaggt     600
ggtggtttta gagggagagg aggcggcggt tcccggggaa aaggtggccg tggtggtggg     660
cgtggaagag gccggcaatg a                                              681

<210> SEQ ID NO 4
<211> LENGTH: 226
<212> TYPE: PRT
<213> ORGANISM: Arabidopsis thaliana

<400> SEQUENCE: 4

Val Leu Lys Lys Lys Pro Ile Leu Thr Asp Glu His Phe Val Asp
  1               5                  10                  15

Gly Arg Phe Gly Ser Met Phe Gln Asn Pro Asp Phe Gln Ile Asp Lys
             20                  25                  30

Asp Ser Tyr Glu Tyr Gly Val Leu His Pro Val Ala Ser Ser Lys Lys
         35                  40                  45

Gln Pro Ser Leu Leu Asp Glu His Phe Glu Ala Val Ser Asp Asp
     50                  55                  60

Glu Asn Ser Asp Ser Asp Ala Ser Gln Pro Ser Asp Glu Ala Asp
 65                  70                  75                  80

Asp Gly Asp Ala Thr Arg Pro Ser Lys Lys Ala Arg Thr Pro Lys Leu
                 85                  90                  95
```

```
Tyr Glu Val Lys Asp Glu Arg His Ala Ala Tyr His Asn Arg Thr
             100                 105                 110

Ser Leu Ala Lys Glu Asp Ser Leu Pro Met Gly Glu Arg Val Lys Ala
         115                 120                 125

Ile Glu Asn Arg Arg Gly Asn Phe Gly Gly Ser Lys Asp Ile Lys Phe
     130                 135                 140

Gly Pro Gly Gly Ser Arg Glu Phe Ser Phe Lys Ala Arg Gly Ser Ser
145                 150                 155                 160

Lys Tyr Lys Glu Asp Arg Asp Glu Tyr Glu Asp Gly Gln Arg Asn
                 165                 170                 175

Lys Arg Arg Gly Val Gln Ser Leu Gly Leu Lys Ser Thr Asn Ile Arg
             180                 185                 190

Gly Gly Phe Arg Gly Arg Gly Gly Gly Phe Arg Gly Arg Gly Gly
             195                 200                 205

Gly Gly Ser Arg Gly Lys Gly Gly Arg Gly Gly Arg Gly Arg Gly
     210                 215                 220

Arg Gln
225

<210> SEQ ID NO 5
<211> LENGTH: 1815
<212> TYPE: DNA
<213> ORGANISM: Arabidopsis thaliana

<400> SEQUENCE: 5
atggagcaga tgatattcat tagaaaagac gacaaagtag aggttttttc tgaagaagaa        60
gagttaaaag ggtcttatta cagagcgatt ctggaagata tccaacgaa atcaggacac       120 aataagctta agttcgtta cttgacgcag ctcaatgaac accgtttggc tcctttaacg       180
gaattcgtcg atcagaggtt cattcgtcct gtcccgtcgg aggatgtgaa cgacggcgtc       240 gttttttgtag aaggcttgat ggtcgacgct tatctcaaag atgggtggtg gactggtgtg       300
gtggtaaaaa caatggagga tgagaagttt ttggtttact tcgattgccc accagacatt       360
attcagtttg agaaaaagaa attgagggtt catcttgatt ggaccggctt caaatggatc       420
cgacctgata taaggaatt ggtcaagtct gttttttagtt gcgggacaat ggtggaattg       480
agatttgatt gtgcttggat tccggtaatt gtcattaagg agttggagaa ggacaagagg       540
tttcttgtca agtactggaa taagtcctat agctgccggg aatcgaaaaa tttaattgtt       600
gattccctaa gactaaggcc tatgcagcct cctttatctg ttggaaagta tgaattgctg       660
gatcatgtag aggcgtttag tggttttgaa tggcgtcaag tgtggtcag gggaattgtc       720 tttgagggaa ggtacatggt aagtttcggg gcaacaaagg aggcatcgca atttaatcac       780
tctgatatta ggcctccaat ggagtgggaa gatggagttt ggcataaaag aacaaagcca       840
aaacgccaga agaaacttc tttagacggc aacagaaatg tgcagacaaa ggaaccaccg       900
ggaaatgaga tggctgatga tgtgaaaaaa gaatctggtt tacctataac cctgggggta       960
actgcaacaa agaacaaaac ccaaggaaag gtatcccctg tgccaatgaa gaatggcttt      1020
ggaaatgagt caactcgaga gaagatgcct gaggagccta agatcaaata ttatactcga      1080
aagaggaaaa gaggaggtct aaagctcaat tcatacatca ataagactgt gttatcctcg      1140
gatcggaccc ccaatgtggt gaagaattct gcttctaatg ctgaggaaaa ccatgcaaaa      1200
cacacaataa tggttttgcc ttttgcaaag aagtcaccgg tctggaagac ttatgaatca      1260
ctggaggtct tcaaaagtgt atcacacagt cttcatttca gcccattgtt tgagactaag      1320
```

-continued

```
caagatttcc gtgaagggta tgcaataggt atgatggtga cttatttttgg gttactggag   1380 aaatttaaag atcttgaagc cgacgttcct gtaagccaac taaatagcct taaagattca   1440
ttttcggagc tcgagaaaca tggcttcaat gttacaactc cattatcacg gatcgacaag   1500
ctgtcagcac tcaaagatag acaactatat ataatggagg aactaaaagg ttttgacaag   1560
gagatgacaa atgaatttag caaggctaaa caagagtttg atgacatgga acaaaagatt   1620
cttgaggtga acacaagat tatcgagctg cagaggcaag aagctgctct aaaagaacaa   1680
aaggaagcag aaaagaaca gaaagatgca gcctggaaaa agatatgtca gatggagtca   1740
tgcgcaaaag atctcaatgt agagcttgaa gatgtggagt ttgagtttga dacaattttg   1800
tcggctcctt ggtaa                                                    1815
```

<210> SEQ ID NO 6
<211> LENGTH: 604
<212> TYPE: PRT
<213> ORGANISM: Arabidopsis thaliana

<400> SEQUENCE: 6

```
Met Glu Gln Met Ile Phe Ile Arg Lys Asp Asp Lys Val Glu Val Phe
 1               5                  10                  15

Ser Glu Glu Glu Leu Lys Gly Ser Tyr Tyr Arg Ala Ile Leu Glu
            20                  25                  30

Asp Asn Pro Thr Lys Ser Gly His Asn Lys Leu Lys Val Arg Tyr Leu
        35                  40                  45

Thr Gln Leu Asn Glu His Arg Leu Ala Pro Leu Thr Glu Phe Val Asp
    50                  55                  60

Gln Arg Phe Ile Arg Pro Val Pro Ser Glu Asp Val Asn Asp Gly Val
65                  70                  75                  80

Val Phe Val Glu Gly Leu Met Val Asp Ala Tyr Leu Lys Asp Gly Trp
                85                  90                  95

Trp Thr Gly Val Val Lys Thr Met Glu Asp Glu Lys Phe Leu Val
            100                 105                 110

Tyr Phe Asp Cys Pro Pro Asp Ile Ile Gln Phe Glu Lys Lys Lys Leu
        115                 120                 125

Arg Val His Leu Asp Trp Thr Gly Phe Lys Trp Ile Arg Pro Asp Asn
    130                 135                 140

Lys Glu Leu Val Lys Ser Val Phe Ser Cys Gly Thr Met Val Glu Leu
145                 150                 155                 160

Arg Phe Asp Cys Ala Trp Ile Pro Val Ile Val Ile Lys Glu Leu Glu
                165                 170                 175

Lys Asp Lys Arg Phe Leu Val Lys Tyr Trp Asn Lys Ser Tyr Ser Cys
            180                 185                 190

Arg Glu Ser Lys Asn Leu Ile Val Asp Ser Leu Arg Leu Arg Pro Met
        195                 200                 205

Gln Pro Pro Leu Ser Val Gly Lys Tyr Glu Leu Leu Asp His Val Glu
    210                 215                 220

Ala Phe Ser Gly Phe Glu Trp Arg Gln Gly Val Val Arg Gly Ile Val
225                 230                 235                 240

Phe Glu Gly Arg Tyr Met Val Ser Phe Gly Ala Thr Lys Glu Ala Ser
                245                 250                 255

Gln Phe Asn His Ser Asp Ile Arg Pro Pro Met Glu Trp Glu Asp Gly
            260                 265                 270

Val Trp His Lys Arg Thr Lys Pro Lys Arg Gln Lys Glu Thr Ser Leu
        275                 280                 285
```

```
Asp Gly Asn Arg Asn Val Gln Thr Lys Glu Pro Pro Gly Asn Glu Met
    290                 295                 300

Ala Asp Asp Val Lys Lys Glu Ser Gly Leu Pro Ile Thr Leu Gly Val
305                 310                 315                 320

Thr Ala Thr Lys Asn Lys Thr Gln Gly Lys Val Ser Pro Val Pro Met
                325                 330                 335

Lys Asn Gly Phe Gly Asn Glu Ser Thr Arg Glu Lys Met Pro Glu Glu
            340                 345                 350

Pro Lys Ile Lys Tyr Tyr Thr Arg Lys Arg Lys Arg Gly Gly Leu Lys
        355                 360                 365

Leu Asn Ser Tyr Ile Asn Lys Thr Val Leu Ser Ser Asp Arg Thr Pro
    370                 375                 380

Asn Val Val Lys Asn Ser Ala Ser Asn Ala Glu Glu Asn His Ala Lys
385                 390                 395                 400

His Thr Ile Met Val Leu Pro Phe Ala Lys Lys Ser Pro Val Trp Lys
                405                 410                 415

Thr Tyr Glu Ser Leu Glu Val Phe Lys Ser Val Ser His Ser Leu His
            420                 425                 430

Phe Ser Pro Leu Phe Glu Thr Lys Gln Asp Phe Arg Glu Gly Tyr Ala
        435                 440                 445

Ile Gly Met Met Val Thr Tyr Phe Gly Leu Leu Glu Lys Phe Lys Asp
    450                 455                 460

Leu Glu Ala Asp Val Pro Val Ser Gln Leu Asn Ser Leu Lys Asp Ser
465                 470                 475                 480

Phe Ser Glu Leu Glu Lys His Gly Phe Asn Val Thr Thr Pro Leu Ser
                485                 490                 495

Arg Ile Asp Lys Leu Ser Ala Leu Lys Asp Arg Gln Leu Tyr Ile Met
            500                 505                 510

Glu Glu Leu Lys Gly Phe Asp Lys Glu Met Thr Asn Glu Phe Ser Lys
        515                 520                 525

Ala Lys Gln Glu Phe Asp Asp Met Glu Gln Lys Ile Leu Glu Val Lys
530                 535                 540

His Lys Ile Ile Glu Leu Gln Arg Gln Glu Ala Ala Leu Lys Glu Gln
545                 550                 555                 560

Lys Glu Ala Glu Lys Glu Gln Lys Asp Ala Ala Trp Lys Lys Ile Cys
                565                 570                 575

Gln Met Glu Ser Cys Ala Lys Asp Leu Asn Val Glu Leu Glu Asp Val
            580                 585                 590

Glu Phe Glu Phe Glu Thr Ile Leu Ser Ala Pro Trp
        595                 600

<210> SEQ ID NO 7
<211> LENGTH: 1773
<212> TYPE: DNA
<213> ORGANISM: Arabidopsis thaliana

<400> SEQUENCE: 7
atggctatgg tagatgaacc gttgtatccc attgctgtgc ttatagatga gcttaagaat      60
gatgatattc agcttcgttt gaactcgatc cgtcgcttat ctactatagc tcgtgctctt     120
ggagaggagc gtacaaggaa ggagttaatc cctttttga gtgagaatag tgacgatgac     180
gatgaggtgc ttcttgcaat ggctgaggag ttaggagttt ttattccgtt tgttggagga     240
attgagtttg cgcatgttct tcttcctcct ttggaatctc tatgtactgt tgaagagact     300
```

```
tgtgtgagag gaaaagctgt ggaatcgctt tgtaagattg gatctcagat gaaagagaat    360
gatcttgttg aatcttttgt tcctcttgtg aagaggttag cgggtggtga atggtttgca    420
gcaagagttt ctgcatgtgg tatatttcat gttgcatacc aaggttgcac tgatgttttg    480
aagactgagt tacgggctac ttatagccag ttgtgcaaag atgatatgcc aatggtgcga    540
agagctgctg catctaacct ggggaaattt gctacaactg tcgagtctac cttttttgatt   600
gctgagatca tgactatgtt cgatgatctt actaaagatg accaagattc tgtgagacta    660
ttggctgttg aagggtgtgc agctcttgga agttgttggg aacctcagga ttgtgttgca    720
cgcattttac ctgttattgt taatttctct caggataaat cttggagggt gcgctacatg    780
gttgcaaatc agctatatga actttgtaag gcagtgggtc ctgattgcac gaggacggat    840
ttggttccag catatgtaag attgctaagg acaatgagg ctgaagtgcg aatagcagca     900
gcgggaaaag tgaccaagtt ctgtcggctt ttgaatccag agcttgcgat tcagcacatc    960
cttcctgtg tgaaggaatt atcatcggat tcttctcaac atgtccgctc tgctctagct    1020
tcagtaataa tggggatggc tcctatcctt gggaaggact caaccattga gcatctgtta   1080
ccaatttttc tttcccttt gaaagatgaa tttcctgatg tgcgccttaa catcataagc     1140
aagttagatc aagtcaacca ggttattgga attgatctac tatctcaatc cttgttaccg   1200
gccattgtag aacttgctga ggatcggcac tggagagtcc gacttgcaat aatagagtat   1260
gttccactgt tggccagcca gttaggtata ggattttttcg attacaagct cggagccctt   1320
tgcatgcaat ggctgcaaga caaggtctac tctatccgcg aagctgcagc tgcagcaaac   1380
aacctaaagc gcctcgcaga ggagtttggt cctgaatggg caatgcagca cttagttccc   1440
caggtattgg acatggtcaa caatccgcac tacctacaca ggatgatggt tctacgcgca   1500
atatctctca tggcgcctgt aatgggatca gaaatcacat gctctaagtt tcttcctgtg   1560
gttgttgaag catcaaaaga cagagttcca aacatcaagt tcaacgttgc caaacttctg   1620
caatccctca tccccatagt cgaccaatca gtggtggaca aaacaatccg tcagtgtttg   1680
gtggacctga gcgaagaccc tgatgttgat gttcgttatt ttgcaaatca agcacttaat   1740
tccatcgatg gttccacagc agcacaatcc tga                                1773
```

<210> SEQ ID NO 8
<211> LENGTH: 590
<212> TYPE: PRT
<213> ORGANISM: Arabidopsis thaliana

<400> SEQUENCE: 8

```
Met Ala Met Val Asp Glu Pro Leu Tyr Pro Ile Ala Val Leu Ile Asp
 1               5                  10                  15

Glu Leu Lys Asn Asp Asp Ile Gln Leu Arg Leu Asn Ser Ile Arg Arg
            20                  25                  30

Leu Ser Thr Ile Ala Arg Ala Leu Gly Glu Glu Arg Thr Arg Lys Glu
        35                  40                  45

Leu Ile Pro Phe Leu Ser Glu Asn Ser Asp Asp Asp Glu Val Leu
    50                  55                  60

Leu Ala Met Ala Glu Glu Leu Gly Val Phe Ile Pro Phe Val Gly Gly
65                  70                  75                  80

Ile Glu Phe Ala His Val Leu Leu Pro Leu Glu Ser Leu Cys Thr
                85                  90                  95

Val Glu Glu Thr Cys Val Arg Gly Lys Ala Val Glu Ser Leu Cys Lys
            100                 105                 110
```

-continued

```
Ile Gly Ser Gln Met Lys Glu Asn Asp Leu Val Glu Ser Phe Val Pro
        115                 120                 125
Leu Val Lys Arg Leu Ala Gly Gly Glu Trp Phe Ala Ala Arg Val Ser
        130                 135                 140
Ala Cys Gly Ile Phe His Val Ala Tyr Gln Gly Cys Thr Asp Val Leu
145                 150                 155                 160
Lys Thr Glu Leu Arg Ala Thr Tyr Ser Gln Leu Cys Lys Asp Asp Met
                165                 170                 175
Pro Met Val Arg Arg Ala Ala Ser Asn Leu Gly Lys Phe Ala Thr
                180                 185                 190
Thr Val Glu Ser Thr Phe Leu Ile Ala Glu Ile Met Thr Met Phe Asp
        195                 200                 205
Asp Leu Thr Lys Asp Asp Gln Asp Ser Val Arg Leu Leu Ala Val Glu
        210                 215                 220
Gly Cys Ala Ala Leu Gly Lys Leu Leu Glu Pro Gln Asp Cys Val Ala
225                 230                 235                 240
Arg Ile Leu Pro Val Ile Val Asn Phe Ser Gln Asp Lys Ser Trp Arg
                245                 250                 255
Val Arg Tyr Met Val Ala Asn Gln Leu Tyr Glu Leu Cys Lys Ala Val
                260                 265                 270
Gly Pro Asp Cys Thr Arg Thr Asp Leu Val Pro Ala Tyr Val Arg Leu
        275                 280                 285
Leu Arg Asp Asn Glu Ala Glu Val Arg Ile Ala Ala Ala Gly Lys Val
        290                 295                 300
Thr Lys Phe Cys Arg Leu Leu Asn Pro Glu Leu Ala Ile Gln His Ile
305                 310                 315                 320
Leu Pro Cys Val Lys Glu Leu Ser Ser Asp Ser Ser Gln His Val Arg
                325                 330                 335
Ser Ala Leu Ala Ser Val Ile Met Gly Met Ala Pro Ile Leu Gly Lys
                340                 345                 350
Asp Ser Thr Ile Glu His Leu Leu Pro Ile Phe Leu Ser Leu Leu Lys
        355                 360                 365
Asp Glu Phe Pro Asp Val Arg Leu Asn Ile Ile Ser Lys Leu Asp Gln
        370                 375                 380
Val Asn Gln Val Ile Gly Ile Asp Leu Leu Ser Gln Ser Leu Leu Pro
385                 390                 395                 400
Ala Ile Val Glu Leu Ala Glu Asp Arg His Trp Arg Val Arg Leu Ala
                405                 410                 415
Ile Ile Glu Tyr Val Pro Leu Leu Ala Ser Gln Leu Gly Ile Gly Phe
                420                 425                 430
Phe Asp Tyr Lys Leu Gly Ala Leu Cys Met Gln Trp Leu Gln Asp Lys
        435                 440                 445
Val Tyr Ser Ile Arg Glu Ala Ala Ala Ala Asn Asn Leu Lys Arg
        450                 455                 460
Leu Ala Glu Glu Phe Gly Pro Glu Trp Ala Met Gln His Leu Val Pro
465                 470                 475                 480
Gln Val Leu Asp Met Val Asn Asn Pro His Tyr Leu His Arg Met Met
                485                 490                 495
Val Leu Arg Ala Ile Ser Leu Met Ala Pro Val Met Gly Ser Glu Ile
                500                 505                 510
Thr Cys Ser Lys Phe Leu Pro Val Val Glu Ala Ser Lys Asp Arg
        515                 520                 525
Val Pro Asn Ile Lys Phe Asn Val Ala Lys Leu Leu Gln Ser Leu Ile
```

```
            530               535               540
Pro Ile Val Asp Gln Ser Val Val Asp Lys Thr Ile Arg Gln Cys Leu
545               550               555               560

Val Asp Leu Ser Glu Asp Pro Asp Val Asp Val Arg Tyr Phe Ala Asn
              565               570               575

Gln Ala Leu Asn Ser Ile Asp Gly Ser Thr Ala Ala Gln Ser
              580               585               590
```

<210> SEQ ID NO 9
<211> LENGTH: 1035
<212> TYPE: DNA
<213> ORGANISM: Arabidopsis thaliana

<400> SEQUENCE: 9

```
atgaccacgt tattcctcct tattgctcta ttcatcacaa ccatcctcaa cccaacaagt     60
ggagaatcag taggtgtatg ctatggaatg atggggaaca accttccttc tcaatcagac   120
acaatcgctc tctttagaca aacaacatc cgacgtgtta gactctacga tccaaaccaa    180
gccgctttaa acgctcttag aaacacgggt atcgaagtca tcatcggcgt tccaaacacc   240
gatcttcgtt cactcactaa cccttcttcc gctagatcat ggctccaaaa caacgtcctc   300
aactattacc ccgccgttag cttcaagtac atcgccgtag gtaacgaagt atctccgtcg   360
aacggcggtg atgttgtgct ccctgccatg cgtaacgttt acgatgctct aagaggtgca   420
aatcttcaag atcgtattaa agtttctacc gccattgata tgactttgat tggaaactct   480
ttccctcctt cctccggaga gtttcgtggt gacgttagat ggtatatcga tcccgtcatc   540
gggtttctta cgagtacgaa ctcagcgtta ctagccaaca tctatcctta cttcagctac   600
gttgacaatc cacgtgacat atctctctct tacgctctct tcacttctcc ttccgtcgtc   660
gtatgggacg gctctcgtgg ctaccaaaac ctctttgacg ctttacttga cgttgtttac   720
tctgccgttg aacgctcagg cggtggatct ctcccagtgg ttgtttccga gagcggatgg   780
ccttctaacg gtggaaacgc cgcgagtttc gataacgcgc gagctttta cacgaatctt   840
gcgtcgcgtg tgagagagaa cagaggaaca ccgaagagac ctggaagagg agtggaaacg   900
tatttgttcg ctatgtttga tgagaatcaa aagagtcctg agatcgagaa gaattttggt   960
ttgttttttc ctaataaaca accaaaattt ccgatcacat tctctgccgc gagagacggt  1020
acggcggttg agtga                                                   1035
```

<210> SEQ ID NO 10
<211> LENGTH: 344
<212> TYPE: PRT
<213> ORGANISM: Arabidopsis thaliana

<400> SEQUENCE: 10

```
Met Thr Thr Leu Phe Leu Leu Ile Ala Leu Phe Ile Thr Thr Ile Leu
  1               5                  10                  15

Asn Pro Thr Ser Gly Glu Ser Val Gly Val Cys Tyr Gly Met Met Gly
              20                  25                  30

Asn Asn Leu Pro Ser Gln Ser Asp Thr Ile Ala Leu Phe Arg Gln Asn
          35                  40                  45

Asn Ile Arg Arg Val Arg Leu Tyr Asp Pro Asn Gln Ala Ala Leu Asn
      50                  55                  60

Ala Leu Arg Asn Thr Gly Ile Glu Val Ile Ile Gly Val Pro Asn Thr
 65                  70                  75                  80

Asp Leu Arg Ser Leu Thr Asn Pro Ser Ser Ala Arg Ser Trp Leu Gln
```

```
                85                  90                  95
Asn Asn Val Leu Asn Tyr Tyr Pro Ala Val Ser Phe Lys Tyr Ile Ala
            100                 105                 110

Val Gly Asn Glu Val Ser Pro Ser Asn Gly Gly Asp Val Val Leu Pro
            115                 120                 125

Ala Met Arg Asn Val Tyr Asp Ala Leu Arg Gly Ala Asn Leu Gln Asp
        130                 135                 140

Arg Ile Lys Val Ser Thr Ala Ile Asp Met Thr Leu Ile Gly Asn Ser
145                 150                 155                 160

Phe Pro Pro Ser Ser Gly Glu Phe Arg Gly Asp Val Arg Trp Tyr Ile
                165                 170                 175

Asp Pro Val Ile Gly Phe Leu Thr Ser Thr Asn Ser Ala Leu Leu Ala
            180                 185                 190

Asn Ile Tyr Pro Tyr Phe Ser Tyr Val Asp Asn Pro Arg Asp Ile Ser
        195                 200                 205

Leu Ser Tyr Ala Leu Phe Thr Ser Pro Ser Val Val Trp Asp Gly
210                 215                 220

Ser Arg Gly Tyr Gln Asn Leu Phe Asp Ala Leu Leu Asp Val Val Tyr
225                 230                 235                 240

Ser Ala Val Glu Arg Ser Gly Gly Ser Leu Pro Val Val Ser
                245                 250                 255

Glu Ser Gly Trp Pro Ser Asn Gly Gly Asn Ala Ala Ser Phe Asp Asn
                260                 265                 270

Ala Arg Ala Phe Tyr Thr Asn Leu Ala Ser Arg Val Arg Glu Asn Arg
            275                 280                 285

Gly Thr Pro Lys Arg Pro Gly Arg Gly Val Glu Thr Tyr Leu Phe Ala
        290                 295                 300

Met Phe Asp Glu Asn Gln Lys Ser Pro Glu Ile Glu Lys Asn Phe Gly
305                 310                 315                 320

Leu Phe Phe Pro Asn Lys Gln Pro Lys Phe Pro Ile Thr Phe Ser Ala
                325                 330                 335

Ala Arg Asp Gly Thr Ala Val Glu
            340

<210> SEQ ID NO 11
<211> LENGTH: 804
<212> TYPE: DNA
<213> ORGANISM: Arabidopsis thaliana

<400> SEQUENCE: 11
gtgtccatca ctggaaaggg agtgaaagcc accgttaaag gtagagagat tatggtgggg      60
aacaagaatc tgatgaatga tcataaagtt attattccag atgatgctga agagttgcta     120
gctgactctg aagatatggc ccagaccgga attcttgtct ccataaacag tgaactgatt     180
ggagttttgt ctgtttcgga tcctctaaaa ccgagtgctc gagaagccat ctccattcta     240
aaatccatga atatcaaaag catcatggta actggtggca actggggaac agcaaactca     300
attgctagag aagtcggtat cgactctgtt atcgcagaag ctaaacctga gcaaaaagca     360
gagaaagtca aggaattaca ggctgcggga catgttgtgg caatggtagg tgacggaatc     420
aatgactcac cggctctcgt ggcagcggat gtaggtatgg cgataggtgc aggaacagac     480
attgctatag aagcagcgga tatagttctg atggaaagca acttagaaga tgtgatcaca     540
gccattgatc tttcaaggaa aacgttctca agaatccgtc tcaactacgt atgggctctc     600
ggtataaacc tcatggggat accgatcgct gcgggagtgc ttttcccagg gacacgtttc     660
```

```
aggttgcctc catgattgca aggtgctgca atggctgctt cttctgttag tgttgtgtgt    720
tgctctctct tgcttaagaa ctacaagcga cctaagaagc ttgatcatct ggagattcgg    780
gagattcagg tggagcgagt ttaa                                           804
```

<210> SEQ ID NO 12
<211> LENGTH: 267
<212> TYPE: PRT
<213> ORGANISM: Arabidopsis thaliana

<400> SEQUENCE: 12

```
Val Ser Ile Thr Gly Lys Gly Val Lys Ala Thr Val Lys Gly Arg Glu
 1               5                  10                  15

Ile Met Val Gly Asn Lys Asn Leu Met Asn Asp His Lys Val Ile Ile
                20                  25                  30

Pro Asp Asp Ala Glu Glu Leu Leu Ala Asp Ser Glu Asp Met Ala Gln
        35                  40                  45

Thr Gly Ile Leu Val Ser Ile Asn Ser Glu Leu Ile Gly Val Leu Ser
    50                  55                  60

Val Ser Asp Pro Leu Lys Pro Ser Ala Arg Glu Ala Ile Ser Ile Leu
65                  70                  75                  80

Lys Ser Met Asn Ile Lys Ser Ile Met Val Thr Gly Gly Asn Trp Gly
                85                  90                  95

Thr Ala Asn Ser Ile Ala Arg Glu Val Gly Ile Asp Ser Val Ile Ala
                100                 105                 110

Glu Ala Lys Pro Glu Gln Lys Ala Glu Lys Val Lys Glu Leu Gln Ala
        115                 120                 125

Ala Gly His Val Val Ala Met Val Gly Asp Gly Ile Asn Asp Ser Pro
    130                 135                 140

Ala Leu Val Ala Ala Asp Val Gly Met Ala Ile Gly Ala Gly Thr Asp
145                 150                 155                 160

Ile Ala Ile Glu Ala Ala Asp Ile Val Leu Met Glu Ser Asn Leu Glu
                165                 170                 175

Asp Val Ile Thr Ala Ile Asp Leu Ser Arg Lys Thr Phe Ser Arg Ile
                180                 185                 190

Arg Leu Asn Tyr Val Trp Ala Leu Gly Tyr Asn Leu Met Gly Ile Pro
        195                 200                 205

Ile Ala Ala Gly Val Leu Phe Pro Gly Thr Arg Phe Arg Leu Pro Pro
    210                 215                 220

Trp Ile Ala Gly Ala Ala Met Ala Ala Ser Ser Val Ser Val Val Cys
225                 230                 235                 240

Cys Ser Leu Leu Leu Lys Asn Tyr Lys Arg Pro Lys Lys Leu Asp His
                245                 250                 255

Leu Glu Ile Arg Glu Ile Gln Val Glu Arg Val
                260                 265
```

<210> SEQ ID NO 13
<211> LENGTH: 273
<212> TYPE: DNA
<213> ORGANISM: Arabidopsis thaliana

<400> SEQUENCE: 13

```
gtggccatgg aaggagaatt tcaggatgag cttgtggttg ttggagatgg agtggattca    60
gcttctttga ttatggcctt aaggaagaaa gcatgtcatg tcactcttga gactcttgaa   120
gaagtgaaga agccacaggt cgaagagaag tctattacac cgcattgctg catagctcaa   180
```

```
tgtcctgtgg ttagcaatga gcagccaagg cctgaggttt atagaatagt gcatgattct      240
tatggtccaa ccactgggtg cttagttatg taa                                   273
```

<210> SEQ ID NO 14
<211> LENGTH: 90
<212> TYPE: PRT
<213> ORGANISM: Arabidopsis thaliana

<400> SEQUENCE: 14

```
Val Ala Met Glu Gly Glu Phe Gln Asp Glu Leu Val Val Val Gly Asp
  1               5                  10                  15

Gly Val Asp Ser Ala Ser Leu Ile Met Ala Leu Arg Lys Lys Ala Cys
                 20                  25                  30

His Val Thr Leu Glu Thr Leu Glu Glu Val Lys Lys Pro Gln Val Glu
             35                  40                  45

Glu Lys Ser Ile Thr Pro His Cys Cys Ile Ala Gln Cys Pro Val Val
         50                  55                  60

Ser Asn Glu Gln Pro Arg Pro Glu Val Tyr Arg Ile Val His Asp Ser
 65                  70                  75                  80

Tyr Gly Pro Thr Thr Gly Cys Leu Val Met
                 85                  90
```

<210> SEQ ID NO 15
<211> LENGTH: 603
<212> TYPE: DNA
<213> ORGANISM: Arabidopsis thaliana

<400> SEQUENCE: 15

```
atggtcttga ttactaagat gtctctctct ttctacatca ttcatcttct cattttctcc       60
ttgatttcca cttgtgttgt ctccaaccag gccgaggata atcttcttca aggcctaaac      120
agctaccgaa ctgctcaaag agttcctcca tttgccaaga atgagaaggc tgattgtgtg      180
gctgatgaga tcgccgacaa gctcgaagat cagccatgca caaccacac cacagcgagc       240 acggttactc ctggctcggt acctccacgg ctgacgaact accaggacat tctctctgaa      300
tgcaaaatcg acccaaacac tacccgtgac ggattgatct tacctgtctg tatccctaac      360
cggatcccga ctttggcttt aactaattac acccaaactg ttatgctcg gtatcttaat      420 gattcgaggt atgtcggggc tggtgttggg tcggagaaag agtggatggt ggttgtattg      480
acgacaagta ctccaggtgg aagctttaca gctggtgttg ctgctggcaa ggcgacgtct      540
gtgagagtaa tggctggttt agggctaatg gggttgttgt ttagttgcct tgtgctcttc      600
tga                                                                    603
```

<210> SEQ ID NO 16
<211> LENGTH: 200
<212> TYPE: PRT
<213> ORGANISM: Arabidopsis thaliana

<400> SEQUENCE: 16

```
Met Val Leu Ile Thr Lys Met Ser Leu Ser Phe Tyr Ile Ile His Leu
  1               5                  10                  15

Leu Ile Phe Ser Leu Ile Ser Thr Cys Val Val Ser Asn Gln Ala Glu
                 20                  25                  30

Asp Asn Leu Leu Gln Gly Leu Asn Ser Tyr Arg Thr Ala Gln Arg Val
             35                  40                  45

Pro Pro Phe Ala Lys Asn Glu Lys Ala Asp Cys Val Ala Asp Glu Ile
```

```
         50                  55                  60
Ala Asp Lys Leu Glu Asp Gln Pro Cys Thr Asn His Thr Thr Ala Ser
 65                  70                  75                  80

Thr Val Thr Pro Gly Ser Val Pro Pro Arg Leu Thr Asn Tyr Gln Asp
                 85                  90                  95

Ile Leu Ser Glu Cys Lys Ile Asp Pro Asn Thr Thr Arg Asp Gly Leu
            100                 105                 110

Ile Leu Pro Val Cys Ile Pro Asn Arg Ile Pro Thr Leu Ala Leu Thr
        115                 120                 125

Asn Tyr Thr Gln Thr Gly Tyr Ala Arg Tyr Leu Asn Asp Ser Arg Tyr
130                 135                 140

Val Gly Ala Gly Val Gly Ser Glu Lys Glu Trp Met Val Val Leu
145                 150                 155                 160

Thr Thr Ser Thr Pro Gly Gly Ser Phe Thr Ala Gly Val Ala Ala Gly
                165                 170                 175

Lys Ala Thr Ser Val Arg Val Met Ala Gly Leu Gly Leu Met Gly Leu
            180                 185                 190

Leu Phe Ser Cys Leu Val Leu Phe
        195                 200

<210> SEQ ID NO 17
<211> LENGTH: 1746
<212> TYPE: DNA
<213> ORGANISM: Arabidopsis thaliana

<400> SEQUENCE: 17
atggagaaag tgaccaactc agacttgaaa tcctctgttg atggtggcgt tgttgatgtg    60
tatggagaag attcagccac cattgagcac aacataactc cttggtctct ctctgtttct   120
agtggatatt cattgctgag agatcctcgc tacaacaaag gacttgcttt cactgagaaa   180
gagagagaca ctcattactt gcgtggtctt ctccctccag ttgttcttga tcaaaagctt   240
caggagaaga ggctgttgaa caatatccga caatatcaat tcccattaca aaagtacatg   300
gctctgacag aacttcagga agaaacgag agactgtttt acgagctatt gatagataat   360
gttgaggagc tacttcctat tgtttatact ccaactgttg gtgaagcttg tcagaaattt   420
ggaagtattt caggcgacc tcagggttta ttcatcagtt taaaagacaa gggaaagatt   480
ctagatgtgt taaagaactg gcctgaaagg aacatacagg ttattgttgt tactgacggt   540
gaaaggattt taggattagg agatcttgga tgtcagggga tgggtatacc ggttggtaag   600
ttggcgttat attcagcact tggaggtgtt cgtccttcag cgtgtttacc tgtcaccatt   660
gatgtgggaa caaacaatga gaaactgttg aatgatgagt tctacatagg actcaggcaa   720
aagagagcaa cgggacagga atatagtgaa ctcttgaatg aattcatgag tgctgtgaaa   780
cagaactatg gtgaaaaagt tcttattcag tttgaagatt ttgctaatca taatgccttt   840
gagttgcttg caaaatacag cgatactcat ctcgtcttca acgatgatat acagggggaca   900
gcatcagttg ttttagcagg attagtttcc gcacagaagt taacgaatag cccacttgca   960
gagcataccct tcctctttct tggtgctggt gaagctggaa ctggaatagc agaactcata  1020
gctctctata tgtcaaaaca gatgaatgct tcggtagagg aaagccgcaa gaaaatctgg  1080
cttgttgatt ccaagggatt gattgttaac tcccgcaaag attcacttca agactttaag  1140
aaaccatggg ctcatgaaca tgaaccagtc aaagacctct taggtgctat caaggcaata  1200
aaaccgactg ttctgattgg atcttctggc gttggacggt cttttacaaa agaagtgata  1260
```

-continued

```
gaagccatgt cctccattaa tgagagacca ctgataatgg ctctctctaa ccccacaaca   1320
caatctgaat gtacagccga agaagcttat acttggagta agggccgtgc cattttttgct  1380 agtggaagcc cttttgatcc agttgagtat gaaggaaagg tgtttgtatc tacacaggcg   1440
aacaatgcgt acatattccc gggctttgga cttggtttgg ttatctctgg agcaatacgg   1500
gtacatgacg atatgcttct agctgctgct gaggcattag ctggacaagt aagcaaagag   1560
aactatgaga aggaatgat atatccttca ttctcttcca tccggaaaat atcagctcag    1620
attgcagcca atgtagcaac taaggcgtat gaactaggat tggcagggcg gcttccacgg   1680
ccgaaagata ttgtcaaatg tgcagagagt agcatgtaca gccccacata ccgtctctac   1740
cgttga                                                              1746
```

<210> SEQ ID NO 18
<211> LENGTH: 581
<212> TYPE: PRT
<213> ORGANISM: Arabidopsis thaliana

<400> SEQUENCE: 18

| Met | Glu | Lys | Val | Thr | Asn | Ser | Asp | Leu | Lys | Ser | Ser | Val | Asp | Gly | Gly |
|---|---|---|---|---|---|---|---|---|---|---|---|---|---|---|---|
| 1 | | | | 5 | | | | | 10 | | | | | 15 | |

Val Val Asp Val Tyr Gly Glu Asp Ser Ala Thr Ile Glu His Asn Ile
            20                  25                  30

Thr Pro Trp Ser Leu Ser Val Ser Ser Gly Tyr Ser Leu Leu Arg Asp
        35                  40                  45

Pro Arg Tyr Asn Lys Gly Leu Ala Phe Thr Glu Lys Glu Arg Asp Thr
    50                  55                  60

His Tyr Leu Arg Gly Leu Leu Pro Pro Val Val Leu Asp Gln Lys Leu
65                  70                  75                  80

Gln Glu Lys Arg Leu Leu Asn Asn Ile Arg Gln Tyr Gln Phe Pro Leu
                85                  90                  95

Gln Lys Tyr Met Ala Leu Thr Glu Gln Glu Arg Asn Glu Arg Leu
            100                 105                 110

Phe Tyr Glu Leu Leu Ile Asp Asn Val Glu Glu Leu Leu Pro Ile Val
        115                 120                 125

Tyr Thr Pro Thr Val Gly Glu Ala Cys Gln Lys Phe Gly Ser Ile Phe
    130                 135                 140

Arg Arg Pro Gln Gly Leu Phe Ile Ser Leu Lys Asp Lys Gly Lys Ile
145                 150                 155                 160

Leu Asp Val Leu Lys Asn Trp Pro Glu Arg Asn Ile Gln Val Ile Val
                165                 170                 175

Val Thr Asp Gly Glu Arg Ile Leu Gly Leu Gly Asp Leu Gly Cys Gln
            180                 185                 190

Gly Met Gly Ile Pro Val Gly Lys Leu Ala Leu Tyr Ser Ala Leu Gly
        195                 200                 205

Gly Val Arg Pro Ser Ala Cys Leu Pro Val Thr Ile Asp Val Gly Thr
    210                 215                 220

Asn Asn Glu Lys Leu Leu Asn Asp Glu Phe Tyr Ile Gly Leu Arg Gln
225                 230                 235                 240

Lys Arg Ala Thr Gly Gln Glu Tyr Ser Glu Leu Leu Asn Glu Phe Met
                245                 250                 255

Ser Ala Val Lys Gln Asn Tyr Gly Glu Lys Val Leu Ile Gln Phe Glu
            260                 265                 270

Asp Phe Ala Asn His Asn Ala Phe Glu Leu Leu Ala Lys Tyr Ser Asp
        275                 280                 285

```
Thr His Leu Val Phe Asn Asp Asp Ile Gln Gly Thr Ala Ser Val Val
        290                 295                 300
Leu Ala Gly Leu Val Ser Ala Gln Lys Leu Thr Asn Ser Pro Leu Ala
305                 310                 315                 320
Glu His Thr Phe Leu Phe Leu Gly Ala Gly Glu Ala Gly Thr Gly Ile
                325                 330                 335
Ala Glu Leu Ile Ala Leu Tyr Met Ser Lys Gln Met Asn Ala Ser Val
            340                 345                 350
Glu Glu Ser Arg Lys Lys Ile Trp Leu Val Asp Ser Lys Gly Leu Ile
        355                 360                 365
Val Asn Ser Arg Lys Asp Ser Leu Gln Asp Phe Lys Lys Pro Trp Ala
370                 375                 380
His Glu His Glu Pro Val Lys Asp Leu Leu Gly Ala Ile Lys Ala Ile
385                 390                 395                 400
Lys Pro Thr Val Leu Ile Gly Ser Ser Val Gly Arg Ser Phe Thr
                405                 410                 415
Lys Glu Val Ile Glu Ala Met Ser Ser Ile Asn Glu Arg Pro Leu Ile
            420                 425                 430
Met Ala Leu Ser Asn Pro Thr Thr Gln Ser Glu Cys Thr Ala Glu Glu
        435                 440                 445
Ala Tyr Thr Trp Ser Lys Gly Arg Ala Ile Phe Ala Ser Gly Ser Pro
    450                 455                 460
Phe Asp Pro Val Glu Tyr Glu Gly Lys Val Phe Val Ser Thr Gln Ala
465                 470                 475                 480
Asn Asn Ala Tyr Ile Phe Pro Gly Phe Gly Leu Gly Leu Val Ile Ser
                485                 490                 495
Gly Ala Ile Arg Val His Asp Asp Met Leu Ala Ala Ala Glu Ala
            500                 505                 510
Leu Ala Gly Gln Val Ser Lys Glu Asn Tyr Glu Lys Gly Met Ile Tyr
        515                 520                 525
Pro Ser Phe Ser Ser Ile Arg Lys Ile Ser Ala Gln Ile Ala Ala Asn
    530                 535                 540
Val Ala Thr Lys Ala Tyr Glu Leu Gly Leu Ala Gly Arg Leu Pro Arg
545                 550                 555                 560
Pro Lys Asp Ile Val Lys Cys Ala Glu Ser Ser Met Tyr Ser Pro Thr
                565                 570                 575
Tyr Arg Leu Tyr Arg
            580

<210> SEQ ID NO 19
<211> LENGTH: 1347
<212> TYPE: DNA
<213> ORGANISM: Arabidopsis thaliana

<400> SEQUENCE: 19
atggcgtcag acaaacaaaa ggcggagaga gccgaggttg cggcgaggct agcggctgag      60
gacttgcatg acattaacaa atccggtggt gctgatgtca aatgtataa ggtgacggag     120 agaacaactg aacatccacc ggagcaagat aggcccggtg tgataggttc agtgttcagg     180
gctgtccaag gaacgtatga gcatgcgaga gacgctgtag ttggaaaaac ccacgaagcg     240
gctgagtcta ccaaagaagg agctcagata gcttcagaga aagcggttgg agcaaaggac     300
gcaaccgtcg agaaagctaa ggaaccgct gattatactg cggagaaggt gggtgagtat     360
aaagactata cggttgataa agctaaagag gctaaggaca caactgcaga gaaggcgaag     420
```

-continued

```
gagactgcta attatactgc ggataaggcg gtggaagcaa aggataagac ggcggagaag    480
attggtgagt acaaagacta tgcggtggat aaggcagtag aagctaaaga taagacagcg    540
gagaaggcga aggagacttc gaattatacg gcggataagg ctaaagaggc taaggacaag    600
acggctgaga aggttggtga gtataaggat tacacggtgg acaaggccgt ggaagctagg    660
gattacacag cggagaaggc tattgaagca aaggataaga cagctgagaa gactggagag    720
tataaggact atacggtgga gaaggcgacg gaggggaaag atgttacggt gagtaagcta    780
ggagagctga aggatagtgc cgttgagaca gcgaagagag ctatgggttt cttgtcgggg    840
aagacagagg aggccaaagg aaaagctgtg gagaccaaag atactgccaa ggaaaacatg    900
gagaaagctg agaagtaaca agacaaaag atggaggaaa tgagattgga aggtaaagag    960
ctcaaagaag aagctggagc aaaagcccaa gaggcatctc aaaagactag ggagagtact   1020
gagtcgggag ctcaaaaagc cgaagagacc aaagattctc ctgccgtgag gggaaatgaa   1080
gcgaagggaa ctattttttgg tgcattaggg aatgtaacgg aagcaataaa gagcaaactg   1140
acaatgccat cagacattgt ggaggaaaca cgcgcggcac gtgagcatgg agggacgggt   1200
aggactgtgg ttgaagtcaa ggtcgaggat tcaaagccgg gtaaggtggc gacttcactg   1260
aaggcgtcgg atcaaatgac cggtcaaaca ttcaacgacg ttggacggat ggatgatgat   1320
gctcggaaag ataagggaaa gctgtga                                       1347
```

<210> SEQ ID NO 20
<211> LENGTH: 448
<212> TYPE: PRT
<213> ORGANISM: Arabidopsis thaliana

<400> SEQUENCE: 20

```
Met Ala Ser Asp Lys Gln Lys Ala Glu Arg Ala Glu Val Ala Ala Arg
  1               5                  10                  15

Leu Ala Ala Glu Asp Leu His Asp Ile Asn Lys Ser Gly Gly Ala Asp
                 20                  25                  30

Val Thr Met Tyr Lys Val Thr Glu Arg Thr Thr Glu His Pro Pro Glu
             35                  40                  45

Gln Asp Arg Pro Gly Val Ile Gly Ser Val Phe Arg Ala Val Gln Gly
         50                  55                  60

Thr Tyr Glu His Ala Arg Asp Ala Val Val Gly Lys Thr His Glu Ala
 65                  70                  75                  80

Ala Glu Ser Thr Lys Glu Gly Ala Gln Ile Ala Ser Glu Lys Ala Val
                 85                  90                  95

Gly Ala Lys Asp Ala Thr Val Glu Lys Ala Lys Glu Thr Ala Asp Tyr
                100                 105                 110

Thr Ala Glu Lys Val Gly Glu Tyr Lys Asp Tyr Thr Val Asp Lys Ala
            115                 120                 125

Lys Glu Ala Lys Asp Thr Thr Ala Glu Lys Ala Lys Glu Thr Ala Asn
        130                 135                 140

Tyr Thr Ala Asp Lys Ala Val Glu Ala Lys Asp Lys Thr Ala Glu Lys
145                 150                 155                 160

Ile Gly Glu Tyr Lys Asp Tyr Ala Val Asp Lys Ala Val Glu Ala Lys
                165                 170                 175

Asp Lys Thr Ala Glu Lys Ala Lys Glu Thr Ser Asn Tyr Thr Ala Asp
            180                 185                 190

Lys Ala Lys Glu Ala Lys Asp Lys Thr Ala Glu Lys Val Gly Glu Tyr
        195                 200                 205
```

```
Lys Asp Tyr Thr Val Asp Lys Ala Val Glu Ala Arg Asp Tyr Thr Ala
        210                 215                 220
Glu Lys Ala Ile Glu Ala Lys Asp Lys Thr Ala Glu Lys Thr Gly Glu
225                 230                 235                 240
Tyr Lys Asp Tyr Thr Val Glu Lys Ala Thr Glu Gly Lys Asp Val Thr
                245                 250                 255
Val Ser Lys Leu Gly Glu Leu Lys Asp Ser Ala Val Glu Thr Ala Lys
            260                 265                 270
Arg Ala Met Gly Phe Leu Ser Gly Lys Thr Glu Glu Ala Lys Gly Lys
        275                 280                 285
Ala Val Glu Thr Lys Asp Thr Ala Lys Glu Asn Met Glu Lys Ala Gly
    290                 295                 300
Glu Val Thr Arg Gln Lys Met Glu Glu Met Arg Leu Glu Gly Lys Glu
305                 310                 315                 320
Leu Lys Glu Glu Ala Gly Ala Lys Ala Gln Glu Ala Ser Gln Lys Thr
                325                 330                 335
Arg Glu Ser Thr Glu Ser Gly Ala Gln Lys Ala Glu Glu Thr Lys Asp
            340                 345                 350
Ser Pro Ala Val Arg Gly Asn Glu Ala Lys Gly Thr Ile Phe Gly Ala
        355                 360                 365
Leu Gly Asn Val Thr Glu Ala Ile Lys Ser Lys Leu Thr Met Pro Ser
    370                 375                 380
Asp Ile Val Glu Glu Thr Arg Ala Ala Arg Glu His Gly Gly Thr Gly
385                 390                 395                 400
Arg Thr Val Val Glu Val Lys Val Glu Asp Ser Lys Pro Gly Lys Val
                405                 410                 415
Ala Thr Ser Leu Lys Ala Ser Asp Gln Met Thr Gly Gln Thr Phe Asn
            420                 425                 430
Asp Val Gly Arg Met Asp Asp Ala Arg Lys Asp Lys Gly Lys Leu
        435                 440                 445

<210> SEQ ID NO 21
<211> LENGTH: 564
<212> TYPE: DNA
<213> ORGANISM: Arabidopsis thaliana

<400> SEQUENCE: 21
atgctctctg acgccggggg tggttccgat tgccggcgtc gggacttatc aactcccatc      60
aaccttcatg tgttctatat aagctttatc ttcattgaat cttcctccgt tatctcaaat     120
ctctcaaaat atctaaatct ccttttttat gtgagcttct tcactgaaag ttttctttgt     180
gacggaagag tatatcgatg ctctattggc tccgatctga ctcagatctt ggatgcatct     240
ctgtcttcga acccaaaaca agaaaattca aacagtccaa cagctcctc ttctcaaaca      300
tcagagcaag acttcatcaa cttatcaaaa agctctagat ctggactagc accaacacca     360
cctttggttt cttctcaccg gttttcgttg atggcaggag tatctcttgg accatcagat     420
gtgcttcttc cgctgggaac gtcgacggca cacgacgagc tcaaacgctg caatggtca      480
ccctatatga ttcacagtcg cccatcattc caattcttca gaatgacgga ggcgctttcc    540
ttatcccgac aacatcaacc ctag                                            564

<210> SEQ ID NO 22
<211> LENGTH: 187
<212> TYPE: PRT
<213> ORGANISM: Arabidopsis thaliana
```

<400> SEQUENCE: 22

| | | | | | | | | | | | | | | | |
|---|---|---|---|---|---|---|---|---|---|---|---|---|---|---|---|
|Met|Leu|Ser|Asp|Ala|Gly|Gly|Ser|Asp|Cys|Arg|Arg|Arg|Asp|Leu|
|1| | | |5| | | |10| | | | |15| |
|Ser|Thr|Pro|Ile|Asn|Leu|His|Val|Phe|Tyr|Ile|Ser|Phe|Ile|Phe|Ile|
| | | | |20| | | |25| | | | |30| | |
|Glu|Ser|Ser|Ser|Val|Ile|Ser|Asn|Leu|Ser|Lys|Tyr|Leu|Asn|Leu|Leu|
| | | |35| | | | |40| | | | |45| | |
|Phe|Tyr|Val|Ser|Phe|Phe|Thr|Glu|Ser|Phe|Leu|Cys|Asp|Gly|Arg|Val|
| | |50| | | | |55| | | | |60| | | |
|Tyr|Arg|Cys|Ser|Ile|Gly|Ser|Asp|Leu|Thr|Gln|Ile|Leu|Asp|Ala|Ser|
|65| | | | |70| | | | |75| | | | |80|
|Leu|Ser|Ser|Asn|Pro|Lys|Gln|Glu|Asn|Ser|Gln|Gln|Ser|Asn|Ser|Ser|
| | | | |85| | | | |90| | | | |95| |
|Ser|Ser|Gln|Thr|Ser|Glu|Gln|Asp|Phe|Ile|Asn|Leu|Ser|Lys|Ser|Ser|
| | | |100| | | | |105| | | | |110| | |
|Arg|Ser|Gly|Leu|Ala|Pro|Thr|Pro|Pro|Leu|Val|Ser|Ser|His|Arg|Phe|
| | |115| | | | |120| | | | |125| | | |
|Ser|Leu|Met|Ala|Gly|Val|Ser|Leu|Gly|Pro|Ser|Asp|Val|Leu|Leu|Pro|
| |130| | | | |135| | | | |140| | | | |
|Leu|Gly|Thr|Ser|Thr|Ala|His|Asp|Glu|Leu|Lys|Arg|Trp|Gln|Trp|Ser|
|145| | | | |150| | | | |155| | | | |160|
|Pro|Tyr|Met|Ile|His|Ser|Arg|Pro|Ser|Phe|Gln|Phe|Phe|Arg|Met|Thr|
| | | | |165| | | | |170| | | | |175| |
|Glu|Ala|Leu|Ser|Leu|Ser|Arg|Gln|His|Gln|Pro| | | | | |
| | | |180| | | | |185| | | | | | | |

<210> SEQ ID NO 23
<211> LENGTH: 753
<212> TYPE: DNA
<213> ORGANISM: Arabidopsis thaliana

<400> SEQUENCE: 23

```
atggaaggtg gagctgctct ctacaatcct cgaactgtcg aagaagtttt caaggatttc      60
aaaggtcgtc gtactgccat tgtcaaagct ctcaccaccg atgttcaaga gttttaccaa     120
caatgtgacc ctgagaagga gaatctttgc ttgtatgggt taccgaatga agaatgggaa     180
gtgaatttac cagctgaaga agtgcctcct gagttaccag agccagctct tggtattaac     240
tttgctaggg atgggctctc tgaaaaggaa tggcttttcg cttgttgctat tcacagtgac     300
gcttggttac tgtctgtctc gttttacttt ggctcaaggt tttcttttcca caaggaagag     360
aggaagcgtt tgttcaacat gatcaatgat gttcctacta tatttgaagt agtgactgga     420
atggctaaag caaggacaa gtcatctgct gcaaatcaaa acggaaacaa atccaagtct     480
aactctaaag ttagaacttc aggggggaaa agctcaaaga ccaagcagcc aaaagaggag     540
gacgaagaaa tagatgaaga tgatgaggat gaccacgggg aaacccttg tggagcctgt     600
ggagacagtg atggtgctga tgaattctgg atctgctgtg acctttgtga aagtggttc     660
catggcaagt gtgtgaagat cactccagct agagctgagc atatcaaaca atacaagtgc     720
ccttcatgca gcaacaaaag agctcgagct taa                                  753
```

<210> SEQ ID NO 24
<211> LENGTH: 250
<212> TYPE: PRT
<213> ORGANISM: Arabidopsis thaliana

<400> SEQUENCE: 24

```
Met Glu Gly Gly Ala Ala Leu Tyr Asn Pro Arg Thr Val Glu Val
 1               5                  10                  15

Phe Lys Asp Phe Lys Gly Arg Arg Thr Ala Ile Val Lys Ala Leu Thr
             20                  25                  30

Thr Asp Val Gln Glu Phe Tyr Gln Gln Cys Asp Pro Glu Lys Glu Asn
         35                  40                  45

Leu Cys Leu Tyr Gly Leu Pro Asn Glu Glu Trp Glu Val Asn Leu Pro
     50                  55                  60

Ala Glu Glu Val Pro Pro Glu Leu Pro Glu Pro Ala Leu Gly Ile Asn
 65                  70                  75                  80

Phe Ala Arg Asp Gly Leu Ser Glu Lys Glu Trp Leu Ser Leu Val Ala
                 85                  90                  95

Ile His Ser Asp Ala Trp Leu Leu Ser Val Ser Phe Tyr Phe Gly Ser
             100                 105                 110

Arg Phe Ser Phe His Lys Glu Arg Lys Arg Leu Phe Asn Met Ile
         115                 120                 125

Asn Asp Val Pro Thr Ile Phe Glu Val Val Thr Gly Met Ala Lys Ala
 130                 135                 140

Lys Asp Lys Ser Ser Ala Ala Asn Gln Asn Gly Asn Lys Ser Lys Ser
145                 150                 155                 160

Asn Ser Lys Val Arg Thr Ser Gly Gly Lys Ser Lys Thr Lys Gln
             165                 170                 175

Pro Lys Glu Glu Asp Glu Ile Asp Glu Asp Glu Asp His
         180                 185                 190

Gly Glu Thr Leu Cys Gly Ala Cys Gly Asp Ser Asp Gly Ala Asp Glu
             195                 200                 205

Phe Trp Ile Cys Cys Asp Leu Cys Glu Lys Trp Phe His Gly Lys Cys
 210                 215                 220

Val Lys Ile Thr Pro Ala Arg Ala Glu His Ile Lys Gln Tyr Lys Cys
225                 230                 235                 240

Pro Ser Cys Ser Asn Lys Arg Ala Arg Ala
             245                 250
```

<210> SEQ ID NO 25
<211> LENGTH: 1218
<212> TYPE: DNA
<213> ORGANISM: Arabidopsis thaliana

<400> SEQUENCE: 25

```
atgggtcat cacagtcttc gcaattactc gatgaagaag aagaagaaga agatgaagca      60
gagagcgaag gtgaagaagt agaagaagaa gaagatgaag cagagagcga attgaataac    120
agaagaatcg agctggataa tctcttggtc aagaaagttc tcgagcaaga gcctgagatg    180
cttccttgtc acgcctctgc ttctccactc tctcctcagc tctcttctct tggaactcct    240
cgaatcggac cttccattaa agtctgggat ccttacaacg tcctcgcgcc acctcctcct    300
tcttctccgc ctcttttctc tcgtatctcc tccgccgcgg aacacgatcg ctccgccgtg    360
acggaagtct atttcatcag ccacggcgag tgtgatctca atctcaggcc tgatctgatt    420
ggaggtagat gccacgtggc tactctcaca cccaacggga aacgtcaggc gagagctcta    480
gccgtatttt taaactctga aggtgttcga ttcacctccg tcttctcttc gcctctggat    540
cgagctagat ccatggctgt ttctgtttgc caggaaatga attttcctga ggagcatttg    600
caagtctcgg atgctgtggt tgagatgagt ttaggggact gggaaagctg tcatcggtca    660
```

```
gagatttaca cacctgaaac tctaagttta atagaaagat gccaacctga tttctcagct      720
ccatctggtg aatcactcag acaagtagag tttcggatgg ttcagtttct gaatgggaca      780
gtctcaggac tttcggagaa gctcaggtca gaacttcttc catctacaca gcacacaaat      840
tccagagggt tctcgttagc tacttctatt catcgcccaa ttcttacaag gaagaaatct      900
gggaagagcc ggtttcaggt gatgaatgca actggtgatc acgagggtag tgaagagata      960
tttagtaatc acaatgatga acaacaccta ggtgatataa acatcaagag ttcttcttct     1020
caactctcaa cctgcattgg agttttcact cactctttac ctataaagtg tcttcttacc     1080
ggtatccttg gatgcagccc ggtaatgaca cataagatct gtgtggagga ttcctctgtg     1140
accgtattac agcattcgtg gaaaaccggg tggcaggtaa agcggttaaa tgacaccgct     1200
catcttagac tgttgtag                                                   1218
```

<210> SEQ ID NO 26
<211> LENGTH: 405
<212> TYPE: PRT
<213> ORGANISM: Arabidopsis thaliana

<400> SEQUENCE: 26

```
Met Gly Ser Ser Gln Ser Ser Gln Leu Leu Asp Glu Glu Glu Glu
 1               5                  10                  15

Glu Asp Glu Ala Glu Ser Glu Gly Glu Val Glu Glu Glu Asp
            20                  25                  30

Glu Ala Glu Ser Glu Leu Asn Asn Arg Arg Ile Glu Leu Asp Asn Leu
        35                  40                  45

Leu Val Lys Lys Val Leu Glu Gln Glu Pro Glu Met Leu Pro Cys His
    50                  55                  60

Ala Ser Ala Ser Pro Leu Ser Pro Gln Leu Ser Ser Leu Gly Thr Pro
65                  70                  75                  80

Arg Ile Gly Pro Ser Ile Lys Val Trp Asp Pro Tyr Asn Val Leu Ala
                85                  90                  95

Pro Pro Pro Pro Ser Ser Pro Leu Phe Ser Arg Ile Ser Ser Ala
            100                 105                 110

Ala Glu His Asp Arg Ser Ala Val Thr Glu Val Tyr Phe Ile Ser His
        115                 120                 125

Gly Glu Cys Asp Leu Asn Leu Arg Pro Asp Leu Ile Gly Gly Arg Cys
    130                 135                 140

His Val Ala Thr Leu Thr Pro Asn Gly Lys Arg Gln Ala Arg Ala Leu
145                 150                 155                 160

Ala Val Phe Leu Asn Ser Glu Gly Val Arg Phe Thr Ser Val Phe Ser
                165                 170                 175

Ser Pro Leu Asp Arg Ala Arg Ser Met Ala Val Ser Val Cys Gln Glu
            180                 185                 190

Met Asn Phe Pro Glu Glu His Leu Gln Val Ser Asp Ala Val Val Glu
        195                 200                 205

Met Ser Leu Gly Asp Trp Glu Ser Cys His Arg Ser Glu Ile Tyr Thr
    210                 215                 220

Pro Glu Thr Leu Ser Leu Ile Glu Arg Cys Gln Pro Asp Phe Ser Ala
225                 230                 235                 240

Pro Ser Gly Glu Ser Leu Arg Gln Val Glu Phe Arg Met Val Gln Phe
                245                 250                 255

Leu Asn Gly Thr Val Ser Gly Leu Ser Glu Lys Leu Arg Ser Glu Leu
            260                 265                 270
```

```
Leu Pro Ser Thr Gln His Thr Asn Ser Arg Gly Phe Ser Leu Ala Thr
        275                 280                 285

Ser Ile His Arg Pro Ile Leu Thr Arg Lys Lys Ser Gly Lys Ser Arg
        290                 295                 300

Phe Gln Val Met Asn Ala Thr Gly Asp His Glu Gly Ser Glu Glu Ile
305                 310                 315                 320

Phe Ser Asn His Asn Asp Glu Gln His Leu Gly Asp Ile Asn Ile Lys
                325                 330                 335

Ser Ser Ser Ser Gln Leu Ser Thr Cys Ile Gly Val Phe Thr His Ser
            340                 345                 350

Leu Pro Ile Lys Cys Leu Leu Thr Gly Ile Leu Gly Cys Ser Pro Val
        355                 360                 365

Met Thr His Lys Ile Cys Val Glu Asp Ser Ser Val Thr Val Leu Gln
        370                 375                 380

His Ser Trp Lys Thr Gly Trp Gln Val Lys Arg Leu Asn Asp Thr Ala
385                 390                 395                 400

His Leu Arg Leu Leu
            405

<210> SEQ ID NO 27
<211> LENGTH: 420
<212> TYPE: DNA
<213> ORGANISM: Arabidopsis thaliana

<400> SEQUENCE: 27
atgctagatc acagtgaaaa ggtcttattg gttgattcag aaaccatgaa acaagagct     60 gaagatatga tcgaacagaa caacactagt gttaacgaca agaagaagac ttgtgctgat    120
tgtggaacca gtaaaactcc tctttggcgt ggtggtcctg ttggtccaaa gtcgttgtgt    180
aacgcgtgtg ggatcagaaa cagaaagaag agaagaggag aaacagaaga taataagaaa    240
ttaaagaaat cgagttctgg cggcggaaac cgtaaatttg gtgaatcgtt aaaacagagt    300
ttgatggatt tggggataag gaagagatca acggtggaga agcaacgaca gaagcttggt    360
gaagaagaac aagccgctgt gttactcatg gctctttctt atggctctgt ttacgcttag    420

<210> SEQ ID NO 28
<211> LENGTH: 139
<212> TYPE: PRT
<213> ORGANISM: Arabidopsis thaliana

<400> SEQUENCE: 28

Met Leu Asp His Ser Glu Lys Val Leu Leu Val Asp Ser Glu Thr Met
1               5                   10                  15

Lys Thr Arg Ala Glu Asp Met Ile Glu Gln Asn Asn Thr Ser Val Asn
            20                  25                  30

Asp Lys Lys Lys Thr Cys Ala Asp Cys Gly Thr Ser Lys Thr Pro Leu
        35                  40                  45

Trp Arg Gly Gly Pro Val Gly Pro Lys Ser Leu Cys Asn Ala Cys Gly
    50                  55                  60

Ile Arg Asn Arg Lys Lys Arg Arg Gly Gly Thr Glu Asp Asn Lys Lys
65                  70                  75                  80

Leu Lys Lys Ser Ser Ser Gly Gly Gly Asn Arg Lys Phe Gly Glu Ser
                85                  90                  95

Leu Lys Gln Ser Leu Met Asp Leu Gly Ile Arg Lys Arg Ser Thr Val
            100                 105                 110
```

```
Glu Lys Gln Arg Gln Lys Leu Gly Glu Glu Glu Gln Ala Ala Val Leu
        115                 120                 125

Leu Met Ala Leu Ser Tyr Gly Ser Val Tyr Ala
        130                 135

<210> SEQ ID NO 29
<211> LENGTH: 522
<212> TYPE: DNA
<213> ORGANISM: Arabidopsis thaliana

<400> SEQUENCE: 29
atggcaacac actcttcctt caccgcaaca acacctctct ttctcatcgt tcttctatcc       60
ctatcctccg tctcagttct cggcgcatct caccaccacg caacggcgcc ggctccgtct      120
gtagactgtt cgactctcat actcaacatg gctgactgtt tatccttcgt ttcgagcgga      180
ggcacggtgg cgaaaccgga aggtacatgt tgctctggtc ttaagacggt gcttaaagct      240
gactctcagt gtctatgtga agcgtttaag agcagtgctt ctcttggagt tactttgaat      300
atcactaagg cttctactct tcccgccgca tgcaagcttc acgctccttc tatcgctact      360
tgtggatgtc ttgctccagg agtagctgct gctggacctg agacagccgg atttctagct      420
ccaaatcctt cttcagggaa cgatggatct tctttgattc cgacctcgtt cacaactgta      480
ctcagtgccg tactgttcgt tttgttcttc tctagtgcgt aa                         522

<210> SEQ ID NO 30
<211> LENGTH: 182
<212> TYPE: PRT
<213> ORGANISM: Arabidopsis thaliana

<400> SEQUENCE: 30

Met Ala Thr His Ser Ser Phe Thr Ala Thr Thr Pro Leu Phe Leu Ile
  1               5                  10                  15

Val Leu Leu Ser Leu Ser Ser Val Ser Val Leu Gly Ala Ser His His
             20                  25                  30

His Ala Thr Ala Pro Ala Pro Ser Val Asp Cys Ser Thr Leu Ile Leu
         35                  40                  45

Asn Met Ala Asp Cys Leu Ser Phe Val Ser Ser Gly Thr Val Ala
     50                  55                  60

Lys Pro Glu Gly Thr Cys Cys Ser Gly Leu Lys Thr Val Leu Lys Ala
 65                  70                  75                  80

Asp Ser Gln Cys Leu Cys Glu Ala Phe Lys Ser Ser Ala Ser Leu Gly
                 85                  90                  95

Val Thr Leu Asn Ile Thr Lys Ala Ser Thr Leu Pro Ala Ala Cys Lys
            100                 105                 110

Leu His Ala Pro Ser Ile Ala Thr Cys Gly Leu Ser Val Ala Pro Ser
        115                 120                 125

Thr Ala Pro Gly Leu Ala Pro Gly Val Ala Ala Gly Pro Glu Thr
        130                 135                 140

Ala Gly Phe Leu Ala Pro Asn Pro Ser Ser Gly Asn Asp Gly Ser Ser
145                 150                 155                 160

Leu Ile Pro Thr Ser Phe Thr Thr Val Leu Ser Ala Val Leu Phe Val
                165                 170                 175

Leu Phe Phe Ser Ser Ala
            180

<210> SEQ ID NO 31
<211> LENGTH: 987
```

-continued

```
<212> TYPE: DNA
<213> ORGANISM: Arabidopsis thaliana

<400> SEQUENCE: 31 atggacccctt tagcttccca acatcaacac aaccatctgg aagataataa ccaaacccta      60
acccataata atcctcaatc cgattccacc accgactcat caacttcctc cgctcaacgc     120
aaacgcaaag gcaaaggtgg tccggacaac tccaagttcc gttaccgtgg cgttcgacaa     180
agaagctggg gcaaatgggt cgccgagatc cgagagccac gtaagcgcac tcgcaagtgg     240
cttggtactt tcgcaaccgc cgaagacgcc gcacgtgcct acgaccgggc tgccgtttac     300
ctatacgggt cacgtgctca gctcaactta acccccttcgt ctccttcctc cgtctcttcc     360
tcttcctcct ccgtctccgc cgcttcttct ccttccacct cctcttcctc cactcaaacc     420
ctaagacctc tcctccctcg ccccgccgcc gccaccgtag gaggaggagc caactttggt     480
ccgtacggta tcccttttaa caacaacatc ttccttaatg gtgggacctc tatgttatgc     540
cctagttatg gttttttccc tcaacaacaa caacaacaaa atcagatggt ccagatggga     600
caattccaac accaacagta tcagaatctt cattctaata ctaacaataa caagatttct     660
gacatcgagc tcactgatgt tccggtaact aattcgactt cgtttcatca tgaggtggcg     720
ttagggcagg aacaaggagg aagtgggtgt aataataata gttcgatgga ggatttgaac     780
tctctagctg gttcggtggg ttcgagtcta tcaataactc atccaccgcc gttggttgat     840
ccggtatgtt ctatgggtct ggatccgggt tatatggttg agatggatc ttcgaccatt     900 tggccttttg gaggagaaga agaatatagt cataattggg ggagtatttg ggatttatt     960 gatcccatct tgggggaatt ctattaa                                          987

<210> SEQ ID NO 32
<211> LENGTH: 328
<212> TYPE: PRT
<213> ORGANISM: Arabidopsis thaliana

<400> SEQUENCE: 32

Met Asp Pro Leu Ala Ser Gln His Gln His Asn His Leu Glu Asp Asn
  1               5                  10                  15

Asn Gln Thr Leu Thr His Asn Asn Pro Gln Ser Asp Ser Thr Thr Asp
              20                  25                  30

Ser Ser Thr Ser Ser Ala Gln Arg Lys Arg Gly Lys Gly Gly Pro
          35                  40                  45

Asp Asn Ser Lys Phe Arg Tyr Arg Gly Val Arg Gln Arg Ser Trp Gly
      50                  55                  60

Lys Trp Val Ala Glu Ile Arg Glu Pro Arg Lys Arg Thr Arg Lys Trp
 65                  70                  75                  80

Leu Gly Thr Phe Ala Thr Ala Glu Asp Ala Ala Arg Ala Tyr Asp Arg
                  85                  90                  95

Ala Ala Val Tyr Leu Tyr Gly Ser Arg Ala Gln Leu Asn Leu Thr Pro
             100                 105                 110

Ser Ser Pro Ser Ser Val Ser Ser Ser Ser Val Ser Ala Ala
         115                 120                 125

Ser Ser Pro Ser Thr Ser Ser Ser Thr Gln Thr Leu Arg Pro Leu
     130                 135                 140

Leu Pro Arg Pro Ala Ala Ala Thr Val Gly Gly Ala Asn Phe Gly
145                 150                 155                 160

Pro Tyr Gly Ile Pro Phe Asn Asn Asn Ile Phe Leu Asn Gly Gly Thr
                 165                 170                 175
```

```
Ser Met Leu Cys Pro Ser Tyr Gly Phe Phe Pro Gln Gln Gln Gln
            180                 185                 190
Gln Asn Gln Met Val Gln Met Gly Gln Phe Gln His Gln Gln Tyr Gln
        195                 200                 205
Asn Leu His Ser Asn Thr Asn Asn Lys Ile Ser Asp Ile Glu Leu
    210                 215                 220
Thr Asp Val Pro Val Thr Asn Ser Thr Ser Phe His His Glu Val Ala
225                 230                 235                 240
Leu Gly Gln Glu Gln Gly Gly Ser Gly Cys Asn Asn Asn Ser Ser Met
                245                 250                 255
Glu Asp Leu Asn Ser Leu Ala Gly Ser Val Gly Ser Ser Leu Ser Ile
            260                 265                 270
Thr His Pro Pro Pro Leu Val Asp Pro Val Cys Ser Met Gly Leu Asp
        275                 280                 285
Pro Gly Tyr Met Val Gly Asp Gly Ser Ser Thr Ile Trp Pro Phe Gly
    290                 295                 300
Gly Glu Glu Glu Tyr Ser His Asn Trp Gly Ser Ile Trp Asp Phe Ile
305                 310                 315                 320
Asp Pro Ile Leu Gly Glu Phe Tyr
                325
```

<210> SEQ ID NO 33
<211> LENGTH: 2322
<212> TYPE: DNA
<213> ORGANISM: Arabidopsis thaliana

<400> SEQUENCE: 33

| | |
|---|---:|
| atggttaaag aaatagcttc ttggttattg atactatcaa tggtggtgtt tgtttctccg | 60 |
| gttttagcta taaacggcgg tggttatcca cgatgtaact gcgaagacga aggaaacagt | 120 |
| ttctggagta cagagaacat tctagaaact caaagagtaa gcgatttctt aatcgcagta | 180 |
| gcttatttct caatccctat tgagttactt tacttcgtga gttgttccaa tgttccattc | 240 |
| aaatggggttc tctttgagtt tatcgccttc attgttcttt gtggtatgac tcatcttctt | 300 |
| catggttgga cttactctgc tcatccattt agattaatga tggcgtttac tgttttcaag | 360 |
| atgttgactg ctttagtctc ttgtgctact gcgattacgc ttattacttt gattcctctg | 420 |
| cttttgaaag ttaaagttag agagtttatg cttaagaaga aagctcatga gcttggtcgt | 480 |
| gaagttggtt tgattttgat taagaaagag actggctttc atgttcgtat gcttactcaa | 540 |
| gagattcgta agtctttgga tcgtcatacg attctttata ctactttggt tgagctttcg | 600 |
| aagactttag ggttgcagaa ttttgcggtt tggatgccga atgacggtgg aacggagatg | 660 |
| gatttgactc atgagttgag agggagaggt ggttatggtg gttgttctgt ttctatggag | 720 |
| gatttggatg ttgttaggat tagggagagt gatgaagtga atgtgttgag tgttgactcg | 780 |
| tccattgctc gagctagtgg tggtggtggg gatgttagtg agattggtgc cgtggctgct | 840 |
| attagaatgc cgatgcttcg tgtttcggat tttaatggag agctaagtta tgcgatactt | 900 |
| gtttgtgttt taccgggcgg gacgcctcgg gattggactt atcaggagat tgagattgtt | 960 |
| aaagttgtgg cggatcaagt aaccgttgcg ttagatcatg cagcggttct tgaagagtct | 1020 |
| cagcttatga gggagaagct ggcggaacag aacagggcgt tgcagatggc gaagagagac | 1080 |
| gcgttgagag cgagccaagc gaggaatgcg tttcagaaaa cgatgagcga agggatgagg | 1140 |
| cgtcctatgc attcgatact cggtcttttg tcgatgattc aggacgagaa gttgagtgac | 1200 |

-continued

```
gagcagaaaa tgattgttga tacgatggtt aaaacaggga atgttatgtc gaatttggtg    1260
ggggactcta tggatgtgcc tgacggtaga tttggtacgg agatgaaacc atttagtctg    1320
catcgtacga tccatgaagc agcttgtatg gcgagatgtt tgtgtctatg caatggaatt    1380
aggttcttgg ttgacgcgga gaagtctcta cctgataatg tagtaggtga tgaaagaagg    1440
gtctttcaag tgatacttca tatagttggt agtttagtaa agcctagaaa acgtcaagaa    1500
ggatcttcat tgatgtttaa ggttttgaaa gaaagaggaa gcttggatag gagtgatcat    1560
agatgggctg cttggagatc accggcttct tcagcagatg gagatgtgta tataagattt    1620
gaaatgaatg tagagaatga tgattcaagt tctcaatcat ttgcttctgt ttcctccaga    1680
gatcaagaag ttggtgatgt tagattctcc ggcggctatg ggttaggaca agatctaagc    1740
tttggtgttt gtaagaaagt ggtgcagttg attcatggga atatctcggt ggtccctggc    1800
tcggatggtt caccggagac catgtcgttg ctccctcggt ttcgacgtag accctccata    1860
tctgtccatg gatccagcga gtcgccagct cctgaccacc acgctcaccc acattcgaat    1920
tctctgttac gtggcttaca agttttattg gtagacacca acgattcgaa ccgggcagtt    1980
acacgtaaac tcttagagaa actcgggtgc gatgtaaccg cggtttcctc tggattcgat    2040
tgccttaccg ccattgctcc cggctcgtcc tcgccttcta cttcgtttca gtggtggtg    2100 cttgatcttc aaatggcaga gatggacggt tatgaagtgg ccatgaggat caggagtcga    2160
tcttggccgt tgattgtggc gacgacagtg ggcttggatg aagaaatgtg ggacaagtgt    2220
gcacagattg gaatcaatgg agttgtgaga aagccagtgg tgttaagagc tatggagagt    2280
gagctccgaa gagtattgtt gcaagctgac caacttctct aa                      2322
```

<210> SEQ ID NO 34
<211> LENGTH: 773
<212> TYPE: PRT
<213> ORGANISM: Arabidopsis thaliana

<400> SEQUENCE: 34

```
Met Val Lys Glu Ile Ala Ser Trp Leu Leu Ile Leu Ser Met Val Val
  1               5                  10                  15

Phe Val Ser Pro Val Leu Ala Ile Asn Gly Gly Tyr Pro Arg Cys
                 20                  25                  30

Asn Cys Glu Asp Glu Gly Asn Ser Phe Trp Ser Thr Glu Asn Ile Leu
             35                  40                  45

Glu Thr Gln Arg Val Ser Asp Phe Leu Ile Ala Val Ala Tyr Phe Ser
         50                  55                  60

Ile Pro Ile Glu Leu Leu Tyr Phe Val Ser Cys Ser Asn Val Pro Phe
 65                  70                  75                  80

Lys Trp Val Leu Phe Glu Phe Ile Ala Phe Ile Val Leu Cys Gly Met
                 85                  90                  95

Thr His Leu Leu His Gly Trp Thr Tyr Ser Ala His Pro Phe Arg Leu
            100                 105                 110

Met Met Ala Phe Thr Val Phe Lys Met Leu Thr Ala Leu Val Ser Cys
        115                 120                 125

Ala Thr Ala Ile Thr Leu Ile Thr Leu Ile Pro Leu Leu Leu Lys Val
    130                 135                 140

Lys Val Arg Glu Phe Met Leu Lys Lys Lys Ala His Glu Leu Gly Arg
145                 150                 155                 160

Glu Val Gly Leu Ile Leu Ile Lys Lys Glu Thr Gly Phe His Val Arg
                165                 170                 175
```

-continued

```
Met Leu Thr Gln Glu Ile Arg Lys Ser Leu Asp Arg His Thr Ile Leu
            180                 185                 190

Tyr Thr Thr Leu Val Glu Leu Ser Lys Thr Leu Gly Leu Gln Asn Phe
        195                 200                 205

Ala Val Trp Met Pro Asn Asp Gly Gly Thr Glu Met Asp Leu Thr His
    210                 215                 220

Glu Leu Arg Gly Arg Gly Gly Tyr Gly Gly Cys Ser Val Ser Met Glu
225                 230                 235                 240

Asp Leu Asp Val Val Arg Ile Arg Glu Ser Asp Val Asn Val Leu
            245                 250                 255

Ser Val Asp Ser Ser Ile Ala Arg Ala Ser Gly Gly Gly Asp Val
            260                 265                 270

Ser Glu Ile Gly Ala Val Ala Ala Ile Arg Met Pro Met Leu Arg Val
            275                 280                 285

Ser Asp Phe Asn Gly Glu Leu Ser Tyr Ala Ile Leu Val Cys Val Leu
290                 295                 300

Pro Gly Gly Thr Pro Arg Asp Trp Thr Tyr Gln Ile Glu Ile Val
305                 310                 315                 320

Lys Val Val Ala Asp Gln Val Thr Val Ala Leu Asp His Ala Ala Val
                325                 330                 335

Leu Glu Glu Ser Gln Leu Met Arg Glu Lys Leu Ala Glu Gln Asn Arg
            340                 345                 350

Ala Leu Gln Met Ala Lys Arg Asp Ala Leu Arg Ala Ser Gln Ala Arg
                355                 360                 365

Asn Ala Phe Gln Lys Thr Met Ser Glu Gly Met Arg Arg Pro Met His
            370                 375                 380

Ser Ile Leu Gly Leu Leu Ser Met Ile Gln Asp Glu Lys Leu Ser Asp
385                 390                 395                 400

Glu Gln Lys Met Ile Val Asp Thr Met Val Lys Thr Gly Asn Val Met
                405                 410                 415

Ser Asn Leu Val Gly Asp Ser Met Asp Val Pro Asp Gly Arg Phe Gly
            420                 425                 430

Thr Glu Met Lys Pro Phe Ser Leu His Arg Thr Ile His Glu Ala Ala
            435                 440                 445

Cys Met Ala Arg Cys Leu Cys Leu Cys Asn Gly Ile Arg Phe Leu Val
    450                 455                 460

Asp Ala Glu Lys Ser Leu Pro Asp Asn Val Val Gly Asp Glu Arg Arg
465                 470                 475                 480

Val Phe Gln Val Ile Leu His Ile Val Gly Ser Leu Val Lys Pro Arg
                485                 490                 495

Lys Arg Gln Glu Gly Ser Ser Leu Met Phe Lys Val Leu Lys Glu Arg
            500                 505                 510

Gly Ser Leu Asp Arg Ser Asp His Arg Trp Ala Ala Trp Arg Ser Pro
            515                 520                 525

Ala Ser Ser Ala Asp Gly Asp Val Tyr Ile Arg Phe Glu Met Asn Val
            530                 535                 540

Glu Asn Asp Asp Ser Ser Gln Ser Phe Ala Ser Val Ser Ser Arg
545                 550                 555                 560

Asp Gln Glu Val Gly Asp Val Arg Phe Ser Gly Gly Tyr Gly Leu Gly
                565                 570                 575

Gln Asp Leu Ser Phe Gly Val Cys Lys Lys Val Val Gln Leu Ile His
            580                 585                 590

Gly Asn Ile Ser Val Val Pro Gly Ser Asp Gly Ser Pro Glu Thr Met
```

```
                    595                 600                 605
Ser Leu Leu Pro Arg Phe Arg Arg Pro Ser Ile Ser Val His Gly
    610                 615                 620

Ser Ser Glu Ser Pro Ala Pro Asp His His Ala His Pro His Ser Asn
625                 630                 635                 640

Ser Leu Leu Arg Gly Leu Gln Val Leu Leu Val Asp Thr Asn Asp Ser
                645                 650                 655

Asn Arg Ala Val Thr Arg Lys Leu Leu Glu Lys Leu Gly Cys Asp Val
                660                 665                 670

Thr Ala Val Ser Ser Gly Phe Asp Cys Leu Thr Ala Ile Ala Pro Gly
            675                 680                 685

Ser Ser Ser Pro Ser Thr Ser Phe Gln Val Val Leu Asp Leu Gln
690                 695                 700

Met Ala Glu Met Asp Gly Tyr Glu Val Ala Met Arg Ile Arg Ser Arg
705                 710                 715                 720

Ser Trp Pro Leu Ile Val Ala Thr Thr Val Gly Leu Asp Glu Glu Met
                725                 730                 735

Trp Asp Lys Cys Ala Gln Ile Gly Ile Asn Gly Val Val Arg Lys Pro
            740                 745                 750

Val Val Leu Arg Ala Met Glu Ser Glu Leu Arg Arg Val Leu Leu Gln
                755                 760                 765

Ala Asp Gln Leu Leu
    770

<210> SEQ ID NO 35
<211> LENGTH: 2217
<212> TYPE: DNA
<213> ORGANISM: Arabidopsis thaliana

<400> SEQUENCE: 35
atggaagtct gcaattgtat tgaaccgcaa tggccagcgg atgaattgtt aatgaaatac      60
caatacatct ccgatttctt cattgcgatt gcgtattttt cgattcctct tgagttgatt     120
tactttgtga agaaatcagc cgtgtttccg tatagatggg tacttgttca gtttggtgct     180
tttatcgttc tttgtggagc aactcatctt attaacttat ggactttcac tacgcattcg     240
agaaccgtgg cgcttgtgat gactaccgcg aaggtgttaa ccgctgttgt ctcgtgtgct     300
actgcgttga tgcttgttca tattattcct gatcttttga gtgttaagac tcgggagctt     360
ttcttgaaaa ataaagctgc tgagctcgat agagaaatgg gattgattcg aactcaggaa     420
gaaaccggaa ggcatgtgag aatgttgact catgagatta aagcacttt agatagacat     480 actatttaa agactacact tgttgagctt ggtaggacat agctttgga ggagtgtgca     540 ttgtggatgc tactagaac tgggttagag ctacagcttt cttatacact tcgtcatcaa     600
catcccgtgg agtatacggt tcctattcaa ttaccggtga ttaaccaagt gtttggtact     660
agtagggctg taaaaatatc tcctaattct cctgtggcta ggttgagacc tgtttctggg     720
aaatatatgc taggggaggt ggtcgctgtg agggttccgc ttctccacct ttctaatttt     780
cagattaatg actggcctga gctttcaaca agagatatg ctttgatggt tttgatgctt     840
ccttcagata gtgcaaggca atggcatgtc catgagttgg aactcgttga agtcgtcgct     900
gatcaggtgg ctgtagctct ctcacatgct gcgatcctag aagagtcgat gcgagctagg     960
gaccttctca tggagcagaa tgttgctctc gatctagcta gacgagaagc agaaacagca    1020
atccgtgccc gcaatgattt cctagcggtt atgaaccatg aaatgcgaac accgatgcat    1080
```

-continued

```
gcgattattg cactctcttc cttactccaa gaaacggaac taaccoctga acaaagactg    1140 atggtggaaa caatacttaa aagtagtaac cttttggcaa ctttgatgaa tgatgtctta    1200
gatctttcaa ggttagaaga tggaagtctt caacttgaac ttgggacatt caatcttcat    1260
acattattta gagaggtcct caatctgata aagcctatag cggttgttaa gaaattaccc    1320
atcacactaa atcttgcacc agatttgcca gaatttgttg ttggggatga aaacggcta    1380 atgcagataa tattaaatat agttggtaat gctgtgaaat ctccaaaaca aggtagtatc    1440
tccgtaaccg ctcttgtcac caagtcagac acacgagctg ctgactttt tgtcgtgcca    1500 actgggagtc atttctactt gagagtgaag gtaaaagact ctggagcagg aataaatcct    1560
caagacattc caaagatttt cactaaattt gctcaaacac aatctttagc gacgagaagc    1620
tcgggtggta gtgggcttgg cctcgccatc tccaagaggt tgtgaatct gatggagggt     1680 aacatttgga ttgagagcga tggtcttgga aaaggatgca cggctatctt tgatgttaaa    1740
cttgggatct cagaacgttc aaacgaatct aaacagtcgg gcataccgaa agttccagcc    1800
attccccgac attcaaattt cactggactt aaggttcttg tcatggatga aacggggta    1860 agtagaatgg tgacgaaggg acttcttgta caccttgggt gcgaagtgac cacggtgagt    1920
tcaaacgagg agtgtctccg agttgtgtcc catgagcaca aagtggtctt catggacgtg    1980
tgcatgcccg gggtcgaaaa ctaccaaatc gctctccgta ttcacagaaa attcacaaaa    2040
caacgccacc aacggccact acttgtggca ctcagtggta acactgacaa atccacaaaa    2100
gagaaatgca tgagctttgg tctagacggt gtgttgctca aacccgtatc actagacaac    2160
ataagagatg ttctgtctga tcttctcgag ccccgggtac tgtacgaggg catgtaa     2217
```

<210> SEQ ID NO 36
<211> LENGTH: 738
<212> TYPE: PRT
<213> ORGANISM: Arabidopsis thaliana

<400> SEQUENCE: 36

```
Met Glu Val Cys Asn Cys Ile Glu Pro Gln Trp Pro Ala Asp Glu Leu
  1               5                  10                  15

Leu Met Lys Tyr Gln Tyr Ile Ser Asp Phe Phe Ile Ala Ile Ala Tyr
             20                  25                  30

Phe Ser Ile Pro Leu Glu Leu Ile Tyr Phe Val Lys Lys Ser Ala Val
         35                  40                  45

Phe Pro Tyr Arg Trp Val Leu Val Gln Phe Gly Ala Phe Ile Val Leu
     50                  55                  60

Cys Gly Ala Thr His Leu Ile Asn Leu Trp Thr Phe Thr Thr His Ser
 65                  70                  75                  80

Arg Thr Val Ala Leu Val Met Thr Thr Ala Lys Val Leu Thr Ala Val
                 85                  90                  95

Val Ser Cys Ala Thr Ala Leu Met Leu Val His Ile Ile Pro Asp Leu
            100                 105                 110

Leu Ser Val Lys Thr Arg Glu Leu Phe Leu Lys Asn Lys Ala Ala Glu
        115                 120                 125

Leu Asp Arg Glu Met Gly Leu Ile Arg Thr Gln Glu Glu Thr Gly Arg
    130                 135                 140

His Val Arg Met Leu Thr His Glu Ile Arg Ser Thr Leu Asp Arg His
145                 150                 155                 160

Thr Ile Leu Lys Thr Thr Leu Val Glu Leu Gly Arg Thr Leu Ala Leu
                165                 170                 175
```

-continued

```
Glu Glu Cys Ala Leu Trp Met Pro Thr Arg Thr Gly Leu Glu Leu Gln
            180                 185                 190

Leu Ser Tyr Thr Leu Arg His Gln His Pro Val Glu Tyr Thr Val Pro
        195                 200                 205

Ile Gln Leu Pro Val Ile Asn Gln Val Phe Gly Thr Ser Arg Ala Val
    210                 215                 220

Lys Ile Ser Pro Asn Ser Pro Val Ala Arg Leu Arg Pro Val Ser Gly
225                 230                 235                 240

Lys Tyr Met Leu Gly Glu Val Ala Val Arg Val Pro Leu Leu His
            245                 250                 255

Leu Ser Asn Phe Gln Ile Asn Asp Trp Pro Glu Leu Ser Thr Lys Arg
            260                 265                 270

Tyr Ala Leu Met Val Leu Met Leu Pro Ser Asp Ser Ala Arg Gln Trp
        275                 280                 285

His Val His Glu Leu Glu Leu Val Glu Val Val Ala Asp Gln Val Ala
        290                 295                 300

Val Ala Leu Ser His Ala Ala Ile Leu Glu Glu Ser Met Arg Ala Arg
305                 310                 315                 320

Asp Leu Leu Met Glu Gln Asn Val Ala Leu Asp Leu Ala Arg Arg Glu
            325                 330                 335

Ala Glu Thr Ala Ile Arg Ala Arg Asn Asp Phe Leu Ala Val Met Asn
        340                 345                 350

His Glu Met Arg Thr Pro Met His Ala Ile Ile Ala Leu Ser Ser Leu
        355                 360                 365

Leu Gln Glu Thr Glu Leu Thr Pro Glu Gln Arg Leu Met Val Glu Thr
370                 375                 380

Ile Leu Lys Ser Ser Asn Leu Leu Ala Thr Leu Met Asn Asp Val Leu
385                 390                 395                 400

Asp Leu Ser Arg Leu Glu Asp Gly Ser Leu Gln Leu Glu Leu Gly Thr
            405                 410                 415

Phe Asn Leu His Thr Leu Phe Arg Glu Val Leu Asn Leu Ile Lys Pro
        420                 425                 430

Ile Ala Val Val Lys Lys Leu Pro Ile Thr Leu Asn Leu Ala Pro Asp
        435                 440                 445

Leu Pro Glu Phe Val Val Gly Asp Glu Lys Arg Leu Met Gln Ile Ile
450                 455                 460

Leu Asn Ile Val Gly Asn Ala Val Lys Phe Ser Lys Gln Gly Ser Ile
465                 470                 475                 480

Ser Val Thr Ala Leu Val Thr Lys Ser Asp Thr Arg Ala Ala Asp Phe
            485                 490                 495

Phe Val Val Pro Thr Gly Ser His Phe Tyr Leu Arg Val Lys Val Lys
            500                 505                 510

Asp Ser Gly Ala Gly Ile Asn Pro Gln Asp Ile Pro Lys Ile Phe Thr
            515                 520                 525

Lys Phe Ala Gln Thr Gln Ser Leu Ala Thr Arg Ser Ser Gly Gly Ser
        530                 535                 540

Gly Leu Gly Leu Ala Ile Ser Lys Arg Phe Val Asn Leu Met Glu Gly
545                 550                 555                 560

Asn Ile Trp Ile Glu Ser Asp Gly Leu Gly Lys Gly Cys Thr Ala Ile
            565                 570                 575

Phe Asp Val Lys Leu Gly Ile Ser Glu Arg Ser Asn Glu Ser Lys Gln
            580                 585                 590

Ser Gly Ile Pro Lys Val Pro Ala Ile Pro Arg His Ser Asn Phe Thr
```

-continued

```
                   595                 600                 605
Gly Leu Lys Val Leu Val Met Asp Glu Asn Gly Val Ser Arg Met Val
        610                 615                 620
Thr Lys Gly Leu Leu Val His Leu Gly Cys Glu Val Thr Thr Val Ser
625                 630                 635                 640
Ser Asn Glu Glu Cys Leu Arg Val Val Ser His Glu His Lys Val Val
                645                 650                 655
Phe Met Asp Val Cys Met Pro Gly Val Glu Asn Tyr Gln Ile Ala Leu
            660                 665                 670
Arg Ile His Glu Lys Phe Thr Lys Gln Arg His Gln Arg Pro Leu Leu
        675                 680                 685
Val Ala Leu Ser Gly Asn Thr Asp Lys Ser Thr Lys Glu Lys Cys Met
    690                 695                 700
Ser Phe Gly Leu Asp Gly Val Leu Leu Lys Pro Val Ser Leu Asp Asn
705                 710                 715                 720
Ile Arg Asp Val Leu Ser Asp Leu Leu Glu Pro Arg Val Leu Tyr Glu
                725                 730                 735
Gly Met
```

<210> SEQ ID NO 37
<211> LENGTH: 2154
<212> TYPE: DNA
<213> ORGANISM: Arabidopsis thaliana

<400> SEQUENCE: 37

```
atggaagtct gcaattgtat tgaaccgcaa tggccagcgg atgaattgtt aatgaaatac    60
caatacatct ccgatttctt cattgcgatt gcgtattttt cgattcctct tgagttgatt   120
tactttgtga agaaatcagc cgtgtttccg tatagatggg tacttgttca gtttggtgct   180
tttatcgttc tttgtggagc aactcatctt attaacttat ggactttcac tacgcattcg   240
agaaccgtgg cgcttgtgat gactaccgcg aaggtgttaa ccgctgttgt ctcgtgtgct   300
actgcgttga tgcttgttca tattattcct gatcttttga gtgttaagac tcgggagctt   360
ttcttgaaaa ataaagctgc tgagctcgat agagaaatgg gattgattcg aactcaggaa   420
gaaaccggaa ggcatgtgag aatgttgact catgagatta gaagcacttt agatagacat   480
actattttaa agactacact tgttgagctt ggtaggacat tagctttgga ggagtgtgca   540
ttgtggatgc ctactagaac tgggttagag ctacagcttt cttatacact tcgtcatcaa   600
catcccgtgg agtatacggt tcctattcaa ttaccggtga ttaaccaagt gtttggtact   660
agtagggctg taaaaatatc tcctaattct cctgtggcta ggttgagacc tgtttctggg   720
aaatatatgc taggggaggt ggtcgctgtg agggttccgc ttctccacct ttctaatttt   780
cagattaatg actggcctga gctttcaaca aagagatatg ctttgatggt tttgatgctt   840
ccttcagata gtgcaaggca atggcatgtc gatgagttgg aactcgttga agtcgtcgct   900
gatcaggtgg ctgtagctct ctcacatgct gcgatcctag aagagtcgat gcgagctagg   960
gaccttctca tggagcagaa tgttgctctt gatctagcta cgagaagc agaaacagca  1020
atccgtgccc gcaatgattt cctagcggtt atgaaccatg aaatgcgaac accgatgcat  1080
gcgattattg cactctcttc cttactccaa gaaacggaac taccccctga caaagactg  1140
atggtggaaa caatacttaa agtagtaac cttttggcaa ctttgatgaa tgatgtctta  1200
gatctttcaa ggttagaaga tggaagtctt caacttgaac ttgggacatt caatcttcat  1260
acattattta gagaggtcct caatctgata aagcctatag cggttgttaa gaaattaccc  1320
```

```
atcacactaa atcttgcacc agatttgcca gaatttgttg ttggggatga gaaacggcta    1380
atgcagataa tattaaatat agttggtaat gctgtgaaat tctccaaaca aggtagtatc    1440
tccgtaaccg ctcttgtcac caagtcagac acacgagctg ctgactttt tgtcgtgcca     1500 actgggagtc atttctactt gagagtgaag gtaaaagact ctggagcagg aataaatcct    1560
caagacattc caaagatttt cactaaattt gctcaaacac aatctttagc gacgagaagc    1620
tcgggtggta gtgggcttgg cctcgccatc tccaagaggt ttgtgaatct gatggagggt    1680
aacatttgga ttgagagcga tggtcttgga aaaggatgca cggctatctt tgatgttaaa    1740
cttgggatct cagaacgttc aaacgaatct aaacagtcgg gcataccgaa agttccagcc    1800
attccccgac attcaaattt cactggactt aaggttcttg tcatggatga aacggggta    1860 agtagaatgg tgacgaaggg acttcttgta caccttgggt gcgaagtgac cacggtgagt    1920
tcaaacgagg agtgtctccg agttgtgtcc catgagcaca aagtggtctt catgacgtg    1980 tgcatgcccg gggtcgaaaa ctaccaaatc gctctccgta ttcacgagaa attcacaaaa    2040
caacgccacc aacggccact acttgtggca ctcagtggta acactgacaa atccacaaaa    2100
gagaaatgca tgagctttgg tctagacgtg tgttgctcaa acccgtatca ctag          2154
```

<210> SEQ ID NO 38
<211> LENGTH: 717
<212> TYPE: PRT
<213> ORGANISM: Arabidopsis thaliana

<400> SEQUENCE: 38

```
Met Glu Val Cys Asn Cys Ile Glu Pro Gln Trp Pro Ala Asp Glu Leu
  1               5                  10                  15

Leu Met Lys Tyr Gln Tyr Ile Ser Asp Phe Ile Ala Ile Ala Tyr
             20                  25                  30

Phe Ser Ile Pro Leu Glu Leu Ile Tyr Phe Val Lys Lys Ser Ala Val
         35                  40                  45

Phe Pro Tyr Arg Trp Val Leu Val Gln Phe Gly Ala Phe Ile Val Leu
     50                  55                  60

Cys Gly Ala Thr His Leu Ile Asn Leu Trp Thr Phe Thr Thr His Ser
 65                  70                  75                  80

Arg Thr Val Ala Leu Val Met Thr Thr Ala Lys Val Leu Thr Ala Val
                 85                  90                  95

Val Ser Cys Ala Thr Ala Leu Met Leu Val His Ile Ile Pro Asp Leu
            100                 105                 110

Leu Ser Val Lys Thr Arg Glu Leu Phe Leu Lys Asn Lys Ala Ala Glu
        115                 120                 125

Leu Asp Arg Glu Met Gly Leu Ile Arg Thr Gln Glu Glu Thr Gly Arg
    130                 135                 140

His Val Arg Met Leu Thr His Glu Ile Arg Ser Thr Leu Asp Arg His
145                 150                 155                 160

Thr Ile Leu Lys Thr Thr Leu Val Glu Leu Gly Arg Thr Leu Ala Leu
                165                 170                 175

Glu Glu Cys Ala Leu Trp Met Pro Thr Arg Thr Gly Leu Glu Leu Gln
            180                 185                 190

Leu Ser Tyr Thr Leu Arg His Gln His Pro Val Glu Tyr Thr Val Pro
        195                 200                 205

Ile Gln Leu Pro Val Ile Asn Gln Val Phe Gly Thr Ser Arg Ala Val
    210                 215                 220
```

-continued

```
Lys Ile Ser Pro Asn Ser Pro Val Ala Arg Leu Arg Pro Val Ser Gly
225                 230                 235                 240

Lys Tyr Met Leu Gly Glu Val Val Ala Val Arg Val Pro Leu Leu His
            245                 250                 255

Leu Ser Asn Phe Gln Ile Asn Asp Trp Pro Glu Leu Ser Thr Lys Arg
            260                 265                 270

Tyr Ala Leu Met Val Leu Met Leu Pro Ser Asp Ser Ala Arg Gln Trp
            275                 280                 285

His Val Asp Glu Leu Glu Leu Val Glu Val Val Ala Asp Gln Val Ala
    290                 295                 300

Val Ala Leu Ser His Ala Ala Ile Leu Glu Glu Ser Met Arg Ala Arg
305                 310                 315                 320

Asp Leu Leu Met Glu Gln Asn Val Ala Leu Asp Leu Ala Arg Arg Glu
                325                 330                 335

Ala Glu Thr Ala Ile Arg Ala Arg Asn Asp Phe Leu Ala Val Met Asn
            340                 345                 350

His Glu Met Arg Thr Pro Met His Ala Ile Ile Ala Leu Ser Ser Leu
        355                 360                 365

Leu Gln Glu Thr Glu Leu Thr Pro Glu Gln Arg Leu Met Val Glu Thr
    370                 375                 380

Ile Leu Lys Ser Ser Asn Leu Leu Ala Thr Leu Met Asn Asp Val Leu
385                 390                 395                 400

Asp Leu Ser Arg Leu Glu Asp Gly Ser Leu Gln Leu Glu Leu Gly Thr
                405                 410                 415

Phe Asn Leu His Thr Leu Phe Arg Glu Val Leu Asn Leu Ile Lys Pro
            420                 425                 430

Ile Ala Val Val Lys Lys Leu Pro Ile Thr Leu Asn Leu Ala Pro Asp
            435                 440                 445

Leu Pro Glu Phe Val Val Gly Asp Glu Lys Arg Leu Met Gln Ile Ile
    450                 455                 460

Leu Asn Ile Val Gly Asn Ala Val Lys Phe Ser Lys Gln Gly Ser Ile
465                 470                 475                 480

Ser Val Thr Ala Leu Val Thr Lys Ser Asp Thr Arg Ala Ala Asp Phe
                485                 490                 495

Phe Val Val Pro Thr Gly Ser His Phe Tyr Leu Arg Val Lys Val Lys
            500                 505                 510

Asp Ser Gly Ala Gly Ile Asn Pro Gln Asp Ile Pro Lys Ile Phe Thr
    515                 520                 525

Lys Phe Ala Gln Thr Gln Ser Leu Ala Thr Arg Ser Ser Gly Gly Ser
    530                 535                 540

Gly Leu Gly Leu Ala Ile Ser Lys Arg Phe Val Asn Leu Met Glu Gly
545                 550                 555                 560

Asn Ile Trp Ile Glu Ser Asp Gly Leu Gly Lys Gly Cys Thr Ala Ile
                565                 570                 575

Phe Asp Val Lys Leu Gly Ile Ser Glu Arg Ser Asn Glu Ser Lys Gln
            580                 585                 590

Ser Gly Ile Pro Lys Val Pro Ala Ile Pro Arg His Ser Asn Phe Thr
        595                 600                 605

Gly Leu Lys Val Leu Val Met Asp Glu Asn Gly Val Ser Arg Met Val
    610                 615                 620

Thr Lys Gly Leu Leu Val His Leu Gly Cys Glu Val Thr Thr Val Ser
625                 630                 635                 640

Ser Asn Glu Glu Cys Leu Arg Val Val Ser His Glu His Lys Val Val
```

```
                  645                 650                 655
Phe Met Asp Val Cys Met Pro Gly Val Glu Asn Tyr Gln Ile Ala Leu
            660                 665                 670
Arg Ile His Glu Lys Phe Thr Lys Gln Arg His Gln Arg Pro Leu Leu
            675                 680                 685
Val Ala Leu Ser Gly Asn Thr Asp Lys Ser Thr Lys Glu Lys Cys Met
            690                 695                 700
Ser Phe Gly Leu Asp Val Cys Cys Ser Asn Pro Tyr His
705                 710                 715
```

<210> SEQ ID NO 39
<211> LENGTH: 690
<212> TYPE: DNA
<213> ORGANISM: Arabidopsis thaliana

<400> SEQUENCE: 39

```
atgatgggca gtgtcgagct gaatctgagg gagactgagc tgtgtcttgg tcttcccggt    60
ggagatacag tggctccggt aaccggaaac aagagagggt tctcagagac ggttgatctg   120
aagctaaatc tgaataatga gcctgcaaac aaggaaggat ctacgactca tgacgtcgtg   180
acttttgatt ccaaggagaa gagtgcttgt cctaaagatc agccaaaacc tccggccaag   240
gcacaagttg tgggatggcc accggtgaga tcataccgga agaacgtgat ggtttcctgc   300
caaaaatcaa gcggtggccc ggaggcggcg gcgttcgtga aggtatcaat ggacggagca   360
ccgtacttga ggaaaatcga tttgaggatg tataaaagct acgatgagct ttctaatgct   420
ttgtccaaca tgttcagctc ttttaccatg gcaaacatg gaggagaaga aggaatgata   480
gacttcatga atgagaggaa attgatggat ttggtgaata gctgggacta tgttccctct   540
tatgaagaca agacggtga ttggatgctc gtcggcgacg ttccttggcc aatgttcgtc   600
gatacatgca agcgtttacg tctcatgaaa ggatcggatg ccattggtct cgctccgagg   660
gcgatggaga agtgcaagag cagagcttga                                    690
```

<210> SEQ ID NO 40
<211> LENGTH: 229
<212> TYPE: PRT
<213> ORGANISM: Arabidopsis thaliana

<400> SEQUENCE: 40

```
Met Met Gly Ser Val Glu Leu Asn Leu Arg Glu Thr Glu Leu Cys Leu
 1               5                  10                  15
Gly Leu Pro Gly Gly Asp Thr Val Ala Pro Val Thr Gly Asn Lys Arg
            20                  25                  30
Gly Phe Ser Glu Thr Val Asp Leu Lys Leu Asn Leu Asn Asn Glu Pro
        35                  40                  45
Ala Asn Lys Glu Gly Ser Thr Thr His Asp Val Thr Phe Asp Ser
     50                  55                  60
Lys Glu Lys Ser Ala Cys Pro Lys Asp Pro Lys Pro Ala Lys
 65                  70                  75                  80
Ala Gln Val Val Gly Trp Pro Pro Val Arg Ser Tyr Arg Lys Asn Val
                85                  90                  95
Met Val Ser Cys Gln Lys Ser Ser Gly Gly Pro Glu Ala Ala Phe
               100                 105                 110
Val Lys Val Ser Met Asp Gly Ala Pro Tyr Leu Arg Lys Ile Asp Leu
           115                 120                 125
Arg Met Tyr Lys Ser Tyr Asp Glu Leu Ser Asn Ala Leu Ser Asn Met
```

```
            130                 135                 140
Phe Ser Ser Phe Thr Met Gly Lys His Gly Glu Glu Gly Met Ile
145                 150                 155                 160

Asp Phe Met Asn Glu Arg Lys Leu Met Asp Leu Val Asn Ser Trp Asp
                165                 170                 175

Tyr Val Pro Ser Tyr Glu Asp Lys Asp Gly Asp Trp Met Leu Val Gly
            180                 185                 190

Asp Val Pro Trp Pro Met Phe Val Asp Thr Cys Lys Arg Leu Arg Leu
            195                 200                 205

Met Lys Gly Ser Asp Ala Ile Gly Leu Ala Pro Arg Ala Met Glu Lys
        210                 215                 220

Cys Lys Ser Arg Ala
225

<210> SEQ ID NO 41
<211> LENGTH: 732
<212> TYPE: DNA
<213> ORGANISM: Arabidopsis thaliana

<400> SEQUENCE: 41
atgatcggcc aacttatgaa cctcaaggcc acggagctct gtctcggcct cccggcggc        60 gctgaagcag ttgagagtcc tgccaaatcg gcggtgggaa gcaagagagg cttctccgaa     120
accgttgatc tcatgctcaa tcttcaatct aacaaagaag gctccgttga tctcaaaaac      180
gtttctgctg ttcccaagga gaagactacc cttaaagatc cttctaagcc tcctgctaaa     240
gcacaagtgg tgggatggcc acctgtgagg aactacagga gaacatgat gactcagcag      300 aagaccagta gtggtgcgga ggaggccagc agtgagaagg ccgggaactt ggtggagga     360 gcagccggag ccggcttggt gaaggtctcc atggacggtg ctccatatct gaggaaagtt    420
gacctcaaga tgtacaaaag ctaccaggat ctttctgatg cattggccaa aatgttcagc    480
tcctttacta tgggaaacta tggagcacaa ggaatgatag atttcatgaa cgagagcaag    540
ctaatgaatc tgctgaatag ctctgagtat gtgccaagct acgaggacaa agatggtgac    600
tggatgctcg ttggcgatgt cccatgggaa atgtttgtcg agtcttgcaa acgtttgcgc    660
attatgaagg gatctgaagc agttggactt gctccgagag caatggagaa gtactgcaag    720
aacagatctt ga                                                         732

<210> SEQ ID NO 42
<211> LENGTH: 243
<212> TYPE: PRT
<213> ORGANISM: Arabidopsis thaliana

<400> SEQUENCE: 42

Met Ile Gly Gln Leu Met Asn Leu Lys Ala Thr Glu Leu Cys Leu Gly
  1               5                  10                  15

Leu Pro Gly Gly Ala Glu Ala Val Glu Ser Pro Ala Lys Ser Ala Val
                20                  25                  30

Gly Ser Lys Arg Gly Phe Ser Glu Thr Val Asp Leu Met Leu Asn Leu
            35                  40                  45

Gln Ser Asn Lys Glu Gly Ser Val Asp Leu Lys Asn Val Ser Ala Val
        50                  55                  60

Pro Lys Glu Lys Thr Thr Leu Lys Asp Pro Ser Lys Pro Pro Ala Lys
 65                  70                  75                  80

Ala Gln Val Val Gly Trp Pro Pro Val Arg Asn Tyr Arg Lys Asn Met
                85                  90                  95
```

```
Met Thr Gln Gln Lys Thr Ser Ser Gly Ala Glu Glu Ala Ser Ser Glu
            100                 105                 110

Lys Ala Gly Asn Phe Gly Gly Gly Ala Ala Gly Ala Gly Leu Val Lys
        115                 120                 125

Val Ser Met Asp Gly Ala Pro Tyr Leu Arg Lys Val Asp Leu Lys Met
    130                 135                 140

Tyr Lys Ser Tyr Gln Asp Leu Ser Asp Ala Leu Ala Lys Met Phe Ser
145                 150                 155                 160

Ser Phe Thr Met Gly Asn Tyr Gly Ala Gln Gly Met Ile Asp Phe Met
                165                 170                 175

Asn Glu Ser Lys Leu Met Asn Leu Leu Asn Ser Ser Glu Tyr Val Pro
            180                 185                 190

Ser Tyr Glu Asp Lys Asp Gly Asp Trp Met Leu Val Gly Asp Val Pro
        195                 200                 205

Trp Glu Met Phe Val Glu Ser Cys Lys Arg Leu Arg Ile Met Lys Gly
    210                 215                 220

Ser Glu Ala Val Gly Leu Ala Pro Arg Ala Met Glu Lys Tyr Cys Lys
225                 230                 235                 240

Asn Arg Ser

<210> SEQ ID NO 43
<211> LENGTH: 2148
<212> TYPE: DNA
<213> ORGANISM: Arabidopsis thaliana

<400> SEQUENCE: 43
atgaaaagct tgcatgtggc ggccaacgcc ggagatctgg ctgaggattg tggaatactc      60
ggtggagacg ctgatgatac tgttttgatg gatggaattg atgaagttgg tagagagatc     120
tggttagatg accatggagg agataataat catgttcatg gtcatcaaga tgatgatttg     180
attgttcatc atgacccttc aatcttctat ggagatctcc caacgcttcc tgatttccca     240
tgcatgtcgt cttcatcatc gtcttcaaca tctccagctc ctgtcaacgc aatcgtctcc     300
tcagcctctt cttcttcggc agcttcttcc tccacttcct cagctgcttc ttgggctata     360
ttgagatcag atggagaaga tccgactcca aaccaaaacc aatacgcatc aggaaactgt     420
gacgactctt ctggtgcatt gcaatccaca gcttccatgg agattccatt agacagcagt     480
caaggttttg ttgcggcga aggcggtggt gattgcattg atatgatgga gactttcggg     540
tacatggatc tacttgatag caacgagttc tttgacacct cagctatatt tagccaagac     600
gacgacacgc aaaaccctaa cttgatggac caaacccttg agagacaaga agaccaggtc     660
gttgttccga tgttggagaa taacagtggt ggagacatgc aaatgatgaa ttcttccttg     720
gaacaggacg atgatctcgc tgctgtgttt ttggagtggc taaagaacaa caaggagact     780
gtgtcggctg aggatttgag gaagtaaag ataagaaag ctacgattga atcagcggca     840
agaagactag gcggtggtaa gaagcgatga agcagcttt taaagctgat tcttgaatgg     900
gtccaaacta atcacttaca agaagacgc accaccacca ccaccaccaa cctctcttat     960
caacaatcat tccaacaaga tccatttcaa accctaacc ctaataacaa caacctaatc    1020
ccaccgtccg accaaacctg tttctcacct tcaacatggg ttcctccacc accacaacaa    1080
caagcttttg tctcggaccc gggttttgga tacatgcctg ctccaaacta tccgccacag    1140
ccagagttcc ttcctttact tgaatctcca ccgtcatggc caccaccacc acagtctggt    1200
cccatgccac atcaacaatt ccccatgccg ccaacctcgc agtataatca atttggagat    1260
```

```
ccaacaggtt tcaatggata caacatgaat ccgtaccaat atccttatgt tcctgcagga    1320
caaatgagag atcagagatt actccgtttg tgttcctcag caactaaaga ggcaagaaag    1380
aaacggatgg cgagacagag gaggttcttg tctcatcacc acagacataa caacaacaac    1440
aacaacaaca ataatcagca gaaccaaacc caaatcggag aaacctgtgc cgcggtggct    1500
ccacaactta accccgtggc cacaaccgcc acgggaggga cctggatgta ttggcctaat    1560
gtcccggcag tgccgcctca attaccgcca gtgatggaga ctcagttacc caccatggac    1620
cgagctggct cagcttctgc tatgccacgt cagcaggtgg taccagatcg ccggcaggga    1680
tggaaaccag aaaagaattt gcggtttctc ttgcagaaag tcttgaagca aagcgacgtg    1740
ggtaacctcg gaaggatcgt tttgccaaaa aagaagctg agacacactt gccggagcta    1800
gaggcaagag acggcatctc tctggccatg gaagacatcg gaacctctcg tgtttggaac    1860
atgcgctaca ggttttggcc taacaacaaa agcaggatgt atctcctcga gaacaccggc    1920
gattttgtga aaccaatgg gctccaagaa ggtgatttca tagtcatata ctccgacgtc    1980
aaattgatac gagggttaa agtaagacaa ccgagcggac aaaagccgga ggctccaccg    2040
tcgtcagcag ctacgaagag acaaaacaag tcgcaaagga acataaacaa taactctccg    2100
tcggcgaatg tggtggtcgc ttcaccaact tctcaaactg ttaaatga               2148

<210> SEQ ID NO 44
<211> LENGTH: 715
<212> TYPE: PRT
<213> ORGANISM: Arabidopsis thaliana

<400> SEQUENCE: 44

Met Lys Ser Leu His Val Ala Ala Asn Ala Gly Asp Leu Ala Glu Asp
  1               5                  10                  15

Cys Gly Ile Leu Gly Gly Asp Ala Asp Asp Thr Val Leu Met Asp Gly
                 20                  25                  30

Ile Asp Glu Val Gly Arg Glu Ile Trp Leu Asp Asp His Gly Gly Asp
             35                  40                  45

Asn Asn His Val His Gly His Gln Asp Asp Asp Leu Ile Val His His
         50                  55                  60

Asp Pro Ser Ile Phe Tyr Gly Asp Leu Pro Thr Leu Pro Asp Phe Pro
 65                  70                  75                  80

Cys Met Ser Ser Ser Ser Ser Ser Thr Ser Pro Ala Pro Val Asn
                 85                  90                  95

Ala Ile Val Ser Ser Ala Ser Ser Ser Ala Ala Ser Ser Ser Thr
                100                 105                 110

Ser Ser Ala Ala Ser Trp Ala Ile Leu Arg Ser Asp Gly Glu Asp Pro
            115                 120                 125

Thr Pro Asn Gln Asn Gln Tyr Ala Ser Gly Asn Cys Asp Asp Ser Ser
        130                 135                 140

Gly Ala Leu Gln Ser Thr Ala Ser Met Glu Ile Pro Leu Asp Ser Ser
145                 150                 155                 160

Gln Gly Phe Gly Cys Gly Glu Gly Gly Gly Asp Cys Ile Asp Met Met
                165                 170                 175

Glu Thr Phe Gly Tyr Met Asp Leu Leu Asp Ser Asn Glu Phe Phe Asp
            180                 185                 190

Thr Ser Ala Ile Phe Ser Gln Asp Asp Thr Gln Asn Pro Asn Leu
        195                 200                 205

Met Asp Gln Thr Leu Glu Arg Gln Glu Asp Gln Val Val Val Pro Met
```

```
                210                 215                 220
Leu Glu Asn Asn Ser Gly Gly Asp Met Gln Met Met Asn Ser Ser Leu
225                 230                 235                 240

Glu Gln Asp Asp Asp Leu Ala Ala Val Phe Leu Glu Trp Leu Lys Asn
                245                 250                 255

Asn Lys Glu Thr Val Ser Ala Glu Asp Leu Arg Lys Val Lys Ile Lys
                260                 265                 270

Lys Ala Thr Ile Glu Ser Ala Ala Arg Arg Leu Gly Gly Lys Glu
                275                 280                 285

Ala Met Lys Gln Leu Leu Lys Leu Ile Leu Glu Trp Val Gln Thr Asn
290                 295                 300

His Leu Gln Arg Arg Arg Thr Thr Thr Thr Thr Asn Leu Ser Tyr
305                 310                 315                 320

Gln Gln Ser Phe Gln Gln Asp Pro Phe Gln Asn Pro Asn Pro Asn Asn
                325                 330                 335

Asn Asn Leu Ile Pro Pro Ser Asp Gln Thr Cys Phe Ser Pro Ser Thr
                340                 345                 350

Trp Val Pro Pro Pro Gln Gln Gln Ala Phe Val Ser Asp Pro Gly
                355                 360                 365

Phe Gly Tyr Met Pro Ala Pro Asn Tyr Pro Pro Gln Pro Glu Phe Leu
370                 375                 380

Pro Leu Leu Glu Ser Pro Ser Trp Pro Pro Pro Gln Ser Gly
385                 390                 395                 400

Pro Met Pro His Gln Gln Phe Pro Met Pro Pro Thr Ser Gln Tyr Asn
                405                 410                 415

Gln Phe Gly Asp Pro Thr Gly Phe Asn Gly Tyr Asn Met Asn Pro Tyr
                420                 425                 430

Gln Tyr Pro Tyr Val Pro Ala Gly Gln Met Arg Asp Gln Arg Leu Leu
                435                 440                 445

Arg Leu Cys Ser Ser Ala Thr Lys Glu Ala Arg Lys Lys Arg Met Ala
                450                 455                 460

Arg Gln Arg Arg Phe Leu Ser His His His Arg His Asn Asn Asn Asn
465                 470                 475                 480

Asn Asn Asn Asn Asn Gln Gln Asn Gln Thr Gln Ile Gly Glu Thr Cys
                485                 490                 495

Ala Ala Val Ala Pro Gln Leu Asn Pro Val Ala Thr Ala Thr Gly
                500                 505                 510

Gly Thr Trp Met Tyr Trp Pro Asn Val Pro Ala Val Pro Pro Gln Leu
                515                 520                 525

Pro Pro Val Met Glu Thr Gln Leu Pro Thr Met Asp Arg Ala Gly Ser
530                 535                 540

Ala Ser Ala Met Pro Arg Gln Gln Val Val Pro Asp Arg Arg Gln Gly
545                 550                 555                 560

Trp Lys Pro Glu Lys Asn Leu Arg Phe Leu Gln Lys Val Leu Lys
                565                 570                 575

Gln Ser Asp Val Gly Asn Leu Gly Arg Ile Val Leu Pro Lys Lys Glu
                580                 585                 590

Ala Glu Thr His Leu Pro Glu Leu Glu Ala Arg Asp Gly Ile Ser Leu
                595                 600                 605

Ala Met Glu Asp Ile Gly Thr Ser Arg Val Trp Asn Met Arg Tyr Arg
                610                 615                 620

Phe Trp Pro Asn Asn Lys Ser Arg Met Tyr Leu Leu Glu Asn Thr Gly
625                 630                 635                 640
```

-continued

```
Asp Phe Val Lys Thr Asn Gly Leu Gln Glu Gly Asp Phe Ile Val Ile
                645                 650                 655
Tyr Ser Asp Val Lys Leu Ile Arg Gly Val Lys Val Arg Gln Pro Ser
            660                 665                 670
Gly Gln Lys Pro Glu Ala Pro Pro Ser Ser Ala Ala Thr Lys Arg Gln
        675                 680                 685
Asn Lys Ser Gln Arg Asn Ile Asn Asn Asn Ser Pro Ser Ala Asn Val
    690                 695                 700
Val Val Ala Ser Pro Thr Ser Gln Thr Val Lys
705                 710                 715

<210> SEQ ID NO 45
<211> LENGTH: 1305
<212> TYPE: DNA
<213> ORGANISM: Arabidopsis thaliana

<400> SEQUENCE: 45
atggaggaag tatctccggc gatcgcaggt cctttcaggc cattctccga aacccagatg      60
gatttcaccg ggatcagatt gggtaaaggt tactgcaata accaatactc aaatcaagat     120
tccgagaacg gagatctaat ggtttcgtta ccggagactt catcatgctc tgtttctggg     180
tcacatggtt ctgaatctag gaaagttttg atttctcgga tcaattctcc taatttaaac     240
atgaaggaat cagcagctgc tgatatagtc gtcgttgata tctccgccgg agatgagatc     300
aacggctcag atgttactag cgagaagaag atgatcagca aacagagag taggagtttg     360 tttgaattca agagtgtgcc tttgtatggt ttcacttcga tttgtggaag aagaccagag     420
atggaagatg ctgtttcgac tataccaaga ttccttcaat cttcttctgg ttccatgtta     480
gatggtcggt tgatcctca atccgccgct catttcttcg gtgtttacga cggccatggc     540
ggttctcagg tagcgaacta ttgtagagag aggatgcatt tggctttggc ggaggagata     600
gctaaggaga aaccgatgct ctgcgatggt gatacgtggc tggagaagtg aagaaaagct     660 ctttttcaact cgttcctgag agttgactcg gagattgagt cagttgcgcc ggagacggtt     720
gggtcaacgt cggtggttgc cgttgttttc ccgtctcaca tcttcgtcgc taactgcggt     780
gactctagag ccgttctttg ccgcggcaaa actgcacttc cattatccgt tgaccataaa     840
ccggatagag aagatgaagc tgcgaggatt gaagccgcag gagggaaagt gattcagtgg     900
aatggagctc gtgttttcgg tgttctcgcc atgtcgagat ccattggcga tagatacttg     960
aaaccatcca tcattcctga tccggaagtg acggctgtga agagagtaaa agaagatgat    1020
tgtctgattt tggcgagtga cggggtttgg gatgtaatga cggatgaaga agcgtgtgag    1080
atggcaagga agcggattct cttgtggcac aagaaaaacg cggtggctgg ggatgcatcg    1140
ttgctcgcgg atgagcggag aaaggaaggg aaagatcctg cggcgatgtc cgcggctgag    1200
tatttgtcaa agctggcgat acagagagga agcaaagaca cataagtgt ggtggtggtt    1260 gatttgaagc ctcggaggaa actcaagagc aaacccttga actga                  1305

<210> SEQ ID NO 46
<211> LENGTH: 434
<212> TYPE: PRT
<213> ORGANISM: Arabidopsis thaliana

<400> SEQUENCE: 46

Met Glu Glu Val Ser Pro Ala Ile Ala Gly Pro Phe Arg Pro Phe Ser
  1               5                  10                  15
```

-continued

```
Glu Thr Gln Met Asp Phe Thr Gly Ile Arg Leu Gly Lys Gly Tyr Cys
             20                  25                  30
Asn Asn Gln Tyr Ser Asn Gln Asp Ser Glu Asn Gly Asp Leu Met Val
         35                  40                  45
Ser Leu Pro Glu Thr Ser Ser Cys Ser Val Ser Gly Ser His Gly Ser
     50                  55                  60
Glu Ser Arg Lys Val Leu Ile Ser Arg Ile Asn Ser Pro Asn Leu Asn
 65                  70                  75                  80
Met Lys Glu Ser Ala Ala Asp Ile Val Val Asp Ile Ser Ala
                 85                  90                  95
Gly Asp Glu Ile Asn Gly Ser Asp Val Thr Ser Glu Lys Lys Met Ile
                100                 105                 110
Ser Arg Thr Glu Ser Arg Ser Leu Phe Glu Phe Lys Ser Val Pro Leu
         115                 120                 125
Tyr Gly Phe Thr Ser Ile Cys Gly Arg Arg Pro Glu Met Glu Asp Ala
     130                 135                 140
Val Ser Thr Ile Pro Arg Phe Leu Gln Ser Ser Ser Gly Ser Met Leu
145                 150                 155                 160
Asp Gly Arg Phe Asp Pro Gln Ser Ala Ala His Phe Phe Gly Val Tyr
                165                 170                 175
Asp Gly His Gly Gly Ser Gln Val Ala Asn Tyr Cys Arg Glu Arg Met
            180                 185                 190
His Leu Ala Leu Ala Glu Glu Ile Ala Lys Glu Lys Pro Met Leu Cys
         195                 200                 205
Asp Gly Asp Thr Trp Leu Glu Lys Trp Lys Lys Ala Leu Phe Asn Ser
     210                 215                 220
Phe Leu Arg Val Asp Ser Glu Ile Glu Ser Val Ala Pro Glu Thr Val
225                 230                 235                 240
Gly Ser Thr Ser Val Val Ala Val Val Phe Pro Ser His Ile Phe Val
                245                 250                 255
Ala Asn Cys Gly Asp Ser Arg Ala Val Leu Cys Arg Gly Lys Thr Ala
            260                 265                 270
Leu Pro Leu Ser Val Asp His Lys Pro Asp Arg Glu Asp Glu Ala Ala
         275                 280                 285
Arg Ile Glu Ala Ala Gly Gly Lys Val Ile Gln Trp Asn Gly Ala Arg
     290                 295                 300
Val Phe Gly Val Leu Ala Met Ser Arg Ser Ile Gly Asp Arg Tyr Leu
305                 310                 315                 320
Lys Pro Ser Ile Ile Pro Asp Pro Glu Val Thr Ala Val Lys Arg Val
                325                 330                 335
Lys Glu Asp Asp Cys Leu Ile Leu Ala Ser Asp Gly Val Trp Asp Val
            340                 345                 350
Met Thr Asp Glu Glu Ala Cys Glu Met Ala Arg Lys Arg Ile Leu Leu
         355                 360                 365
Trp His Lys Lys Asn Ala Val Ala Gly Asp Ala Ser Leu Leu Ala Asp
     370                 375                 380
Glu Arg Arg Lys Glu Gly Lys Asp Pro Ala Ala Met Ser Ala Ala Glu
385                 390                 395                 400
Tyr Leu Ser Lys Leu Ala Ile Gln Arg Gly Ser Lys Asp Asn Ile Ser
                405                 410                 415
Val Val Val Val Asp Leu Lys Pro Arg Arg Lys Leu Lys Ser Lys Pro
            420                 425                 430
Leu Asn
```

<210> SEQ ID NO 47
<211> LENGTH: 2466
<212> TYPE: DNA
<213> ORGANISM: Arabidopsis thaliana

<400> SEQUENCE: 47

| | | | | | |
|---|---|---|---|---|---|
| atggaaatgc | ccggtagaag | atctaattac | actttgctta | gtcaattttc | tgacgatcag | 60 |
| gtgtcagttt | ccgtcaccgg | agctcctccg | cctcactatg | attccttgtc | gagcgaaaac | 120 |
| aggagcaacc | ataacagcgg | gaacaccggg | aaagctaagg | cggagagagg | cggatttgat | 180 |
| tgggatccta | gcggtggtgg | tggtggtgat | cataggttga | ataatcaacc | gaatcgggtt | 240 |
| gggaataata | tgtatgcttc | gtctctaggg | ttgcaaaggc | aatccagtgg | gagtagtttc | 300 |
| ggtgagagct | cttttgtctgg | ggattattac | atgcctacgc | tttctgcggc | ggctaacgag | 360 |
| atcgaatctg | ttggatttcc | tcaagatgat | gggtttaggc | ttggatttgg | tggtggtgga | 420 |
| ggagatttga | ggatacagat | ggcggcggac | tccgctggag | ggtcttcatc | tgggaagagc | 480 |
| tgggcgcagc | agacggagga | gagttatcag | ctgcagcttg | cattggcgtt | aaggctttcg | 540 |
| tcggaggcta | cttgtgccga | cgatccgaac | tttctggatc | ctgtaccgga | cgagtctgct | 600 |
| ttacggactt | cgccaagttc | agccgaaacc | gtttcacatc | gtttctgggt | taatggctgc | 660 |
| ttatcgtact | atgataaagt | tcctgatggg | ttttatatga | tgaatggtct | ggatccctat | 720 |
| atttggacct | tatgcatcga | cctgcatgaa | agtggtcgca | tcccttcaat | tgaatcatta | 780 |
| agagctgttg | attctggtgt | tgattcttcg | cttgaagcga | tcatagttga | taggcgtagt | 840 |
| gatccagcct | tcaaggaact | tcacaataga | gtccacgaca | tatcttgtag | ctgcattacc | 900 |
| acaaaagagg | ttgttgatca | gctggcaaag | cttatctgca | atcgtatggg | gggtccagtt | 960 |
| atcatggggg | aagatgagtt | ggttcccatg | tggaaggagt | gcattgatgg | tctaaaagaa | 1020 |
| atctttaaag | tggtggttcc | cataggtagc | ctctctgttg | gactctgcag | acatcgagct | 1080 |
| ttactcttca | agtactggc | tgacataatt | gatttaccct | gtcgaattgc | caaggatgt | 1140 |
| aaatattgta | atagagacga | tgccgcttcg | tgccttgtca | ggtttgggct | tgatagggag | 1200 |
| tacctggttg | atttagtagg | aaagccaggt | cacttatggg | agcctgattc | cttgctaaat | 1260 |
| ggtccttcat | ctatctcaat | ttcttctcct | ctgcggtttc | cacgaccaaa | gccagttgaa | 1320 |
| cccgcagtcg | attttaggtt | actagccaaa | caatatttct | ccgatagcca | gtctcttaat | 1380 |
| cttgttttcg | atcctgcatc | agatgatatg | ggattctcaa | tgtttcatag | gcaatatgat | 1440 |
| aatccgggtg | gagagaatga | cgcattggca | gaaaatggtg | gtgggtcttt | gccacccagt | 1500 |
| gctaatatgc | ctccacagaa | catgatgcgt | gcgtcaaatc | aaattgaagc | agcacctatg | 1560 |
| aatgccccac | caatcagtca | gccagttcca | aacagggcaa | ataagggaact | tggacttgat | 1620 |
| ggtgatgata | tggacatccc | gtggtgtgat | cttaatataa | agaaaagat | tggagcaggt | 1680 |
| tcctttggca | ctgtccaccg | tgctgagtgg | catggctcgg | atgttgctgt | gaaaattctc | 1740 |
| atggagcaag | acttccatgc | tgagcgtgtt | aatgagttct | taagagaggt | tgcgataatg | 1800 |
| aaacgccttc | gccaccctaa | cattgttctc | ttcatgggtg | cggtcactca | acctccaaat | 1860 |
| ttgtcaatag | tgcacagaata | tttgtcaaga | ggtagtttat | acagactttt | gcataaaagt | 1920 |
| ggagcaaggg | agcaattaga | tgagagacgt | cgcctgagta | tggcttatga | tgtggctaag | 1980 |
| ggaatgaatt | atcttcacaa | tcgcaatcct | ccaattgtgc | atagagatct | aaaatctcca | 2040 |
| aacttattgg | ttgacaaaaa | atatacagtc | aaggtttgtg | attttggtct | ctcgcgattg | 2100 |

-continued

```
aaggccagca cgtttctttc ctcgaagtca gcagctggaa cccccgagtg gatggcacca      2160
gaagtcctgc gagatgagcc gtctaatgaa aagtcagatg tgtacagctt cggggtcatc      2220
ttgtgggagc ttgctacatt gcaacaacca tggggtaact taaatccggc tcaggttgta      2280
gctgcggttg gtttcaagtg taaacggctg gagatcccgc gtaatctgaa tcctcaggtt      2340
gcagccataa tcgagggttg ttggaccaat gagccatgga agcgtccatc atttgcaact      2400
ataatggact tgctaagacc attgatcaaa tcagcggttc ctccgcccaa ccgctcggat      2460
ttgtaa                                                                 2466

<210> SEQ ID NO 48
<211> LENGTH: 821
<212> TYPE: PRT
<213> ORGANISM: Arabidopsis thaliana

<400> SEQUENCE: 48

Met Glu Met Pro Gly Arg Arg Ser Asn Tyr Thr Leu Leu Ser Gln Phe
  1               5                  10                  15

Ser Asp Asp Gln Val Ser Val Ser Val Thr Gly Ala Pro Pro Pro His
                 20                  25                  30

Tyr Asp Ser Leu Ser Ser Glu Asn Arg Ser Asn His Asn Ser Gly Asn
             35                  40                  45

Thr Gly Lys Ala Lys Ala Glu Arg Gly Gly Phe Asp Trp Asp Pro Ser
         50                  55                  60

Gly Gly Gly Gly Gly Asp His Arg Leu Asn Asn Gln Pro Asn Arg Val
 65                  70                  75                  80

Gly Asn Asn Met Tyr Ala Ser Ser Leu Gly Leu Gln Arg Gln Ser Ser
                 85                  90                  95

Gly Ser Ser Phe Gly Glu Ser Ser Leu Ser Gly Asp Tyr Tyr Met Pro
            100                 105                 110

Thr Leu Ser Ala Ala Ala Asn Glu Ile Glu Ser Val Gly Phe Pro Gln
        115                 120                 125

Asp Asp Gly Phe Arg Leu Gly Phe Gly Gly Gly Gly Gly Asp Leu Arg
    130                 135                 140

Ile Gln Met Ala Ala Asp Ser Ala Gly Gly Ser Ser Ser Gly Lys Ser
145                 150                 155                 160

Trp Ala Gln Gln Thr Glu Glu Ser Tyr Gln Leu Gln Leu Ala Leu Ala
                165                 170                 175

Leu Arg Leu Ser Ser Glu Ala Thr Cys Ala Asp Asp Pro Asn Phe Leu
            180                 185                 190

Asp Pro Val Pro Asp Glu Ser Ala Leu Arg Thr Ser Pro Ser Ser Ala
        195                 200                 205

Glu Thr Val Ser His Arg Phe Trp Val Asn Gly Cys Leu Ser Tyr Tyr
    210                 215                 220

Asp Lys Val Pro Asp Gly Phe Tyr Met Met Asn Gly Leu Asp Pro Tyr
225                 230                 235                 240

Ile Trp Thr Leu Cys Ile Asp Leu His Glu Ser Gly Arg Ile Pro Ser
                245                 250                 255

Ile Glu Ser Leu Arg Ala Val Asp Ser Gly Val Asp Ser Ser Leu Glu
            260                 265                 270

Ala Ile Ile Val Asp Arg Arg Ser Asp Pro Ala Phe Lys Glu Leu His
        275                 280                 285

Asn Arg Val His Asp Ile Ser Cys Ser Cys Ile Thr Thr Lys Glu Val
    290                 295                 300
```

-continued

```
Val Asp Gln Leu Ala Lys Leu Ile Cys Asn Arg Met Gly Gly Pro Val
305                 310                 315                 320

Ile Met Gly Glu Asp Glu Leu Val Pro Met Trp Lys Glu Cys Ile Asp
            325                 330                 335

Gly Leu Lys Glu Ile Phe Lys Val Val Pro Ile Gly Ser Leu Ser
        340                 345                 350

Val Gly Leu Cys Arg His Arg Ala Leu Leu Phe Lys Val Leu Ala Asp
        355                 360                 365

Ile Ile Asp Leu Pro Cys Arg Ile Ala Lys Gly Cys Lys Tyr Cys Asn
    370                 375                 380

Arg Asp Asp Ala Ala Ser Cys Leu Val Arg Phe Gly Leu Asp Arg Glu
385                 390                 395                 400

Tyr Leu Val Asp Leu Val Gly Lys Pro Gly His Leu Trp Glu Pro Asp
                405                 410                 415

Ser Leu Leu Asn Gly Pro Ser Ser Ile Ser Ile Ser Ser Pro Leu Arg
                420                 425                 430

Phe Pro Arg Pro Lys Pro Val Glu Pro Ala Val Asp Phe Arg Leu Leu
            435                 440                 445

Ala Lys Gln Tyr Phe Ser Asp Ser Gln Ser Leu Asn Leu Val Phe Asp
    450                 455                 460

Pro Ala Ser Asp Asp Met Gly Phe Ser Met Phe His Arg Gln Tyr Asp
465                 470                 475                 480

Asn Pro Gly Gly Glu Asn Asp Ala Leu Ala Glu Asn Gly Gly Gly Ser
                485                 490                 495

Leu Pro Pro Ser Ala Asn Met Pro Pro Gln Asn Met Met Arg Ala Ser
                500                 505                 510

Asn Gln Ile Glu Ala Ala Pro Met Asn Ala Pro Pro Ile Ser Gln Pro
    515                 520                 525

Val Pro Asn Arg Ala Asn Arg Glu Leu Gly Leu Asp Gly Asp Asp Met
530                 535                 540

Asp Ile Pro Trp Cys Asp Leu Asn Ile Lys Glu Lys Ile Gly Ala Gly
545                 550                 555                 560

Ser Phe Gly Thr Val His Arg Ala Glu Trp His Gly Ser Asp Val Ala
                565                 570                 575

Val Lys Ile Leu Met Glu Gln Asp Phe His Ala Glu Arg Val Asn Glu
            580                 585                 590

Phe Leu Arg Glu Val Ala Ile Met Lys Arg Leu Arg His Pro Asn Ile
        595                 600                 605

Val Leu Phe Met Gly Ala Val Thr Gln Pro Pro Asn Leu Ser Ile Val
    610                 615                 620

Thr Glu Tyr Leu Ser Arg Gly Ser Leu Tyr Arg Leu Leu His Lys Ser
625                 630                 635                 640

Gly Ala Arg Glu Gln Leu Asp Glu Arg Arg Leu Ser Met Ala Tyr
                645                 650                 655

Asp Val Ala Lys Gly Met Asn Tyr Leu His Asn Arg Asn Pro Pro Ile
            660                 665                 670

Val His Arg Asp Leu Lys Ser Pro Asn Leu Leu Val Asp Lys Lys Tyr
        675                 680                 685

Thr Val Lys Val Cys Asp Phe Gly Leu Ser Arg Leu Lys Ala Ser Thr
    690                 695                 700

Phe Leu Ser Ser Lys Ser Ala Ala Gly Thr Pro Glu Trp Met Ala Pro
705                 710                 715                 720

Glu Val Leu Arg Asp Glu Pro Ser Asn Glu Lys Ser Asp Val Tyr Ser
```

```
                725                 730                 735
Phe Gly Val Ile Leu Trp Glu Leu Ala Thr Leu Gln Gln Pro Trp Gly
        740                 745                 750

Asn Leu Asn Pro Ala Gln Val Val Ala Val Gly Phe Lys Cys Lys
        755                 760                 765

Arg Leu Glu Ile Pro Arg Asn Leu Asn Pro Gln Val Ala Ala Ile Ile
        770                 775                 780

Glu Gly Cys Trp Thr Asn Glu Pro Trp Lys Arg Pro Ser Phe Ala Thr
785                 790                 795                 800

Ile Met Asp Leu Leu Arg Pro Leu Ile Lys Ser Ala Val Pro Pro Pro
                805                 810                 815

Asn Arg Ser Asp Leu
        820

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 49
atggcgcgcc atggttcgtc ctggattcat tatgc                              35

<210> SEQ ID NO 50
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 50
gcttaattaa tcaggctttg gattttaccg ggac                               34

<210> SEQ ID NO 51
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 51
atggcgcgcc ggggaggcca ccaagaaagt gctg                               34

<210> SEQ ID NO 52
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 52
tcttaattaa gctacattta tcattgccgg cctc                               34

<210> SEQ ID NO 53
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 53
atggcgcgcc gagccgttat tagtttttcat tcaaggg                           37
```

```
<210> SEQ ID NO 54
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 54
agttaattaa tcttaactta ccaaggagcc gacaaa                                 36

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 55
attggcgcgc ctggtgttgc agtgatttga ttc                                    33

<210> SEQ ID NO 56
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 56
gcgttaatta agcagttcat agccagcaac caa                                    33

<210> SEQ ID NO 57
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 57
atggcgcgcc atgaccacgt tattcctcct tattgc                                 36

<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 58
gcttaattaa catcactcaa ccgccgtacc gtc                                    33

<210> SEQ ID NO 59
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 59
atggcgcgcc gggcaaaggc cattgtcgag t                                      31

<210> SEQ ID NO 60
<211> LENGTH: 34
<212> TYPE: DNA
<213> ORGANISM: Artificial Sequence
<220> FEATURE:
```

<223> OTHER INFORMATION: Description of Artificial Sequence: Primer

<400> SEQUENCE: 60
gcttaattaa ccggtactcg gtttagttca attt          34

<210> SEQ ID NO 61
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 61
atggcgcgcc catggatgtc ttgtttctcg atctg          35

<210> SEQ ID NO 62
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 62
gcttaattaa gatttctgac tttgaatgga aatgg          35

<210> SEQ ID NO 63
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 63
atggcgcgcc gaatcagaaa ttgggcgaag aag          33

<210> SEQ ID NO 64
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 64
gcttaattaa cacaacaatc actagctcag aagagc          36

<210> SEQ ID NO 65
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 65
atggcgcgcc atggagaaag tgaccaactc agact          35

<210> SEQ ID NO 66
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 66
gcttaattaa ttcaacggta gagacggtat gtggg          35

<210> SEQ ID NO 67
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 67
atggcgcgcc agaaaaaagc aatggcgtca gac                               33

<210> SEQ ID NO 68
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 68
gcttaattaa ctcacagctt tcccttatct ttcc                              34

<210> SEQ ID NO 69
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 69
atggcgcgcc gccagaggac gagacaaggg g                                 31

<210> SEQ ID NO 70
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 70
gcttaattaa ccattgggga tggtctaagt ttcc                              34

<210> SEQ ID NO 71
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 71
atggcgcgcc atggaaggtg gagctgctct c                                 31

<210> SEQ ID NO 72
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 72
gcttaattaa gccaaataaa gacagatcga ggg                               33

<210> SEQ ID NO 73
<211> LENGTH: 32
<212> TYPE: DNA
<213> ORGANISM: Artificial Sequence
<220> FEATURE:
<223> OTHER INFORMATION: Description of Artificial Sequence: Primer

```
<400> SEQUENCE: 73
atggcgcgcc atgggtcat cacagtcttc gc                                32

<210> SEQ ID NO 74
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 74
gcttaattaa tcaatagtgt agaaacctaa caagtattgg                        40

<210> SEQ ID NO 75
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 75
atggcgcgcc caaggggggt ctctgtcggt tc                                32

<210> SEQ ID NO 76
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 76
gcttaattaa catcatcatt gctctccaaa ccc                               33

<210> SEQ ID NO 77
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 77
atggcgcgcc gagaagaaga atcaaaatcc cacaca                            36

<210> SEQ ID NO 78
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 78
gcttaattaa gcgatagatc gaataaaagg acca                              34

<210> SEQ ID NO 79
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 79
atggcgcgcc ccttcttgat tcgtcctctc cact                              34

<210> SEQ ID NO 80
<211> LENGTH: 34
```

```
<210> SEQ ID NO 80
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 80
gcttaattaa ccaccatctc ctccgattct cttc                              34

<210> SEQ ID NO 81
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 81
atggcgcgcc atggttaaag aaatagcttc ttggtt                            36

<210> SEQ ID NO 82
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 82
gcttaattaa ttagagaagt tggtcagctt gcaac                             35

<210> SEQ ID NO 83
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 83
atggcgcgcc atggaagtct gcaattgtat tgaacc                            36

<210> SEQ ID NO 84
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 84
gcttaattaa ttacatgccc tcgtacagta cccg                              34

<210> SEQ ID NO 85
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 85
atggcgcgcc atggaagtct gcaattgtat tgaacc                            36

<210> SEQ ID NO 86
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 86
```
gcttaattaa ttacatgccc tcgtacagta cccg        34

<210> SEQ ID NO 87
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 87
atggcgcgcc atgatgggca gtgtcgagct g        31

<210> SEQ ID NO 88
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 88
gcttaattaa tcaagctctg ctcttgcact tct        33

<210> SEQ ID NO 89
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 89
atggcgcgcc atgatcggcc aacttatgaa cct        33

<210> SEQ ID NO 90
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 90
gcttaattaa tcaagatctg ttcttgcagt acttctc        37

<210> SEQ ID NO 91
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 91
atggcgcgcc ggagaaaata gttagctttg gtcgg        35

<210> SEQ ID NO 92
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 92
gcttaattaa ccaaacgagt ggtgcaatta cac        33

<210> SEQ ID NO 93
<211> LENGTH: 34
<212> TYPE: DNA
<213> ORGANISM: Artificial Sequence

```
<220> FEATURE:
<223> OTHER INFORMATION: Description of Artificial Sequence: Primer

<400> SEQUENCE: 93
atggcgcgcc atggaggaag tatctccggc gatc                          34

<210> SEQ ID NO 94
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 94
gcttaattaa tcagttcaag ggtttgctct tgag                          34

<210> SEQ ID NO 95
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 95
atggcgcgcc atggaaatgc ccggtagaag atc                           33

<210> SEQ ID NO 96
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 96
gcttaattaa ttacaaatcc gagcggttgg gcg                           33

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 97
caggaaacag ctatgacc                                            18

<210> SEQ ID NO 98
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 98
ctaaagggaa caaaagctg                                           19

<210> SEQ ID NO 99
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 99
tgtaaaacga cggccagt                                            18
```

SUGAR AND LIPID METABOLISM REGULATORS IN PLANTS II

CROSS REFERENCE TO RELATED APPLICATIONS

The present invention claims the priority benefit of U.S. Provisional Patent Application Ser. No. 60/295,680 filed Jun. 4, 2001, the entire contents of which are hereby incorporated by reference.

BACKGROUND OF THE INVENTION

1. Field of the Invention

This invention relates generally to nucleic acid sequences encoding proteins that are related to the presence of seed storage compounds in plants. More specifically, the present invention relates to nucleic acid sequences encoding sugar and lipid metabolism regulator proteins and the use of these sequences in transgenic plants.

2. Background Art

The study and genetic manipulation of plants has a long history that began even before the famed studies of Gregor Mendel. In perfecting this science, scientists have accomplished modification of particular traits in plants ranging from potato tubers having increased starch content to oilseed plants such as canola and sunflower having increased or altered fatty acid content. With the increased consumption and use of plant oils, the modification of seed oil content and seed oil levels has become increasingly widespread (e.g. Töpfer et al. 1995, Science 268:681-686). Manipulation of biosynthetic pathways in transgenic plants provides a number of opportunities for molecular biologists and plant biochemists to affect plant metabolism giving rise to the production of specific higher-value products. The seed oil production or composition has been altered in numerous traditional oilseed plants such as soybean (U.S. Pat. No. 5,955,650), canola (U.S. Pat. No. 5,955,650), sunflower (U.S. Pat. No. 6,084,164) and rapeseed (Töpfer et al. 1995, Science 268:681-686), and non-traditional oil seed plants such as tobacco (Cahoon et al. 1992, Proc. Natl. Acad. Sci. USA 89:11184-11188).

Plant seed oils comprise both neutral and polar lipids (see Table 1). The neutral lipids contain primarily triacylglycerol, which is the main storage lipid that accumulates in oil bodies in seeds. The polar lipids are mainly found in the various membranes of the seed cells, e.g. the endoplasmic reticulum, microsomal membranes and the cell membrane. The neutral and polar lipids contain several common fatty acids (see Table 2) and a range of less common fatty acids. The fatty acid composition of membrane lipids is highly regulated and only a select number of fatty acids are found in membrane lipids. On the other hand, a large number of unusual fatty acids can be incorporated into the neutral storage lipids in seeds of many plant species (Van de Loo F. J. et al. 1993, Unusual Fatty Acids in Lipid Metabolism in Plants pp. 91-126, editor T S Moore Jr. CRC Press; Millar et al. 2000, Trends Plant Sci. 5:95-101).

TABLE 1

| Plant Lipid Classes | |
|---|---|
| Neutral Lipids | Triacylglycerol (TAG) |
|  | Diacylglycerol (DAG) |
|  | Monoacylglycerol (MAG) |

TABLE 1-continued

| Plant Lipid Classes | |
|---|---|
| Polar Lipids | Monogalactosyldiacylglycerol (MGDG) |
|  | Digalactosyldiacylglycerol (DGDG) |
|  | Phosphatidylglycerol (PG) |
|  | Phosphatidylcholine (PC) |
|  | Phosphatidylethanolamine (PE) |
|  | Phosphatidylinositol (PI) |
|  | Phosphatidylserine (PS) |
|  | Sulfoquinovosyldiacylglycerol |

TABLE 2

| Common Plant Fatty Acids | |
|---|---|
| 16:0 | Palmitic acid |
| 16:1 | Palmitoleic acid |
| 16:3 | Palmitolenic acid |
| 18:0 | Stearic acid |
| 18:1 | Oleic acid |
| 18:2 | Linoleic acid |
| 18:3 | Linolenic acid |
| γ-18:3 | Gamma-linolenic acid* |
| 20:0 | Arachidic acid |
| 22:6 | Docosahexanoic acid (DHA)* |
| 20:2 | Eicosadienoic acid |
| 20:4 | Arachidonic acid (AA)* |
| 20:5 | Eicosapentaenoic acid (EPA)* |
| 22:1 | Erucic acid |

*These fatty acids do not normally occur in plant seed oils, but their production in transgenic plant seed oil is of importance in plant biotechnology.

Lipids are synthesized from fatty acids and their synthesis may be divided into two parts: the prokaryotic pathway and the eukaryotic pathway (Browse et al. 1986, Biochemical J. 235:25-31; Ohlrogge & Browse 1995, Plant Cell 7:957-970). The prokaryotic pathway is located in plastids that are the primary site of fatty acid biosynthesis. Fatty acid synthesis begins with the conversion of acetyl-CoA to malonyl-CoA by acetyl-CoA carboxylase (ACCase). Malonyl-CoA is converted to malonyl-acyl carrier protein (ACP) by the malonyl-CoA:ACP transacylase. The enzyme beta-ketoacyl-ACP-synthase III (KAS III) catalyzes a condensation reaction in which the acyl group from acetyl-CoA is transferred to malonyl-ACP to form 3-ketobutyryl-ACP. In a subsequent series of condensation, reduction and dehydration reactions the nascent fatty acid chain on the ACP cofactor is elongated by the step-by-step addition (condensation) of two carbon atoms donated by malonyl-ACP until a 16- or 18-carbon saturated fatty acid chain is formed. The plastidial delta-9 acyl-ACP desaturase introduces the first unsaturated double bond into the fatty acid. Thioesterases cleave the fatty acids from the ACP cofactor and free fatty acids are exported to the cytoplasm where they participate as fatty acyl-CoA esters in the eukaryotic pathway. In this pathway the fatty acids are esterified by glycerol-3-phosphate acyltransferase and lysophosphatidic acid acyltransferase to the sn-1 and sn-2 positions of glycerol-3-phosphate, respectively, to yield phosphatidic acid (PA). The PA is the precursor for other polar and neutral lipids, the latter being formed in the Kennedy pathway (Voelker 1996, Genetic Engineering ed.: Setlow 18:111-113; Shanklin & Cahoon 1998, Annu. Rev. Plant Physiol. Plant Mol. Biol. 49:611-641; Frentzen 1998, Lipids 100:161-166; Millar et al. 2000, Trends Plant Sci. 5:95-101).

Storage lipids in seeds are synthesized from carbohydrate-derived precursors. Plants have a complete glycolytic pathway in the cytosol (Plaxton 1996, Annu. Rev. Plant Physiol.

Plant Mol. Biol. 47:185-214) and it has been shown that a complete pathway also exists in the plastids of rapeseeds (Kang & Rawsthorne 1994, Plant J. 6:795-805). Sucrose is the primary source of carbon and energy, transported from the leaves into the developing seeds. During the storage phase of seeds, sucrose is converted in the cytosol to provide the metabolic precursors glucose-6-phosphate and pyruvate. These are transported into the plastids and converted into acetyl-CoA that serves as the primary precursor for the synthesis of fatty acids. Acetyl-CoA in the plastids is the central precursor for lipid biosynthesis. Acetyl-CoA can be formed in the plastids by different reactions and the exact contribution of each reaction is still being debated (Ohlrogge & Browse 1995, Plant Cell 7:957-970). It is however accepted that a large part of the acetyl-CoA is derived from glucose-6-phospate and pyruvate that are imported from the cytoplasm into the plastids. Sucrose is produced in the source organs (leaves, or anywhere that photosynthesis occurs) and is transported to the developing seeds that are also termed sink organs. In the developing seeds, the sucrose is the precursor for all the storage compounds, i.e. starch, lipids and partly the seed storage proteins. Therefore, it is clear that carbohydrate metabolism in which sucrose plays a central role is very important to the accumulation of seed storage compounds.

Although lipid and fatty acid content of seed oil can be modified by the traditional methods of plant breeding, the advent of recombinant DNA technology has allowed for easier manipulation of the seed oil content of a plant, and in some cases, has allowed for the alteration of seed oils in ways that could not be accomplished by breeding alone (see, e.g., Töpfer et al. 1995, Science 268:681-686). For example, introduction of a $\Delta^{12}$-hydroxylase nucleic acid sequence into transgenic tobacco resulted in the introduction of a novel fatty acid, ricinoleic acid, into the tobacco seed oil (Van de Loo et al. 1995, Proc. Natl. Acad. Sci USA 92:6743-6747). Tobacco plants have also been engineered to produce low levels of petroselinic acid by the introduction and expression of an acyl-ACP desaturase from coriander (Cahoon et al. 1992, Proc. Natl. Acad. Sci USA 89:11184-11188).

The modification of seed oil content in plants has significant medical, nutritional and economic ramifications. With regard to the medical ramifications, the long chain fatty acids (C18 and longer) found in many seed oils have been linked to reductions in hypercholesterolemia and other clinical disorders related to coronary heart disease (Brenner 1976, Adv. Exp. Med. Biol. 83:85-101). Therefore, consumption of a plant having increased levels of these types of fatty acids may reduce the risk of heart disease. Enhanced levels of seed oil content also increase large-scale production of seed oils and thereby reduce the cost of these oils.

In order to increase or alter the levels of compounds such as seed oils in plants, nucleic acid sequences and proteins regulating lipid and fatty acid metabolism must be identified. As mentioned earlier, several desaturase nucleic acids such as the $\Delta^6$-desaturase nucleic acid, $\Delta^{12}$-desaturase nucleic acid and acyl-ACP desaturase nucleic acid have been cloned and demonstrated to encode enzymes required for fatty acid synthesis in various plant species. Oleosin nucleic acid sequences from such different species as Brassica, soybean, carrot, pine and Arabidopsis thaliana have also been cloned and determined to encode proteins associated with the phospholipid monolayer membrane of oil bodies in those plants.

It has also been determined that two phytohormones, gibberellic acid (GA) and absisic acid (ABA), are involved in overall regulatory processes in seed development (e.g. Ritchie & Gilroy 1998, Plant Physiol. 116:765-776; Arenas-Huertero et al. 2000, Genes Dev. 14:2085-2096). Both the GA and ABA pathways are affected by okadaic acid, a protein phosphatase inhibitor (Kuo et al. 1996, Plant Cell. 8:259-269). The regulation of protein phosphorylation by kinases and phosphatases is accepted as a universal mechanism of cellular control (Cohen 1992, Trends Biochem. Sci. 17:408-413. Likewise, the plant hormones ethylene (e.g. Zhou et al. 1998, Proc. Natl. Acad. Sci. USA 95:10294-10299; Beaudoin et al. 2000, Plant Cell 2000:1103-1115) and auxin (e.g. Colon-Carmona et al. 2000, Plant Physiol. 124:1728-1738) are involved in controlling plant development as well.

Although several compounds are known that generally affect plant and seed development, there is a clear need to specifically identify factors that are more specific for the developmental regulation of storage compound accumulation and to identify genes which have the capacity to confer altered or increased oil production to its host plant and to other plant species. This invention discloses a large number of nucleic acid sequences from Arabidopsis thaliana. These nucleic acid sequences can be used to alter or increase the levels of seed storage compounds such as proteins, sugars and oils, in plants, including transgenic plants, such as rapeseed, canola, linseed, soybean, sunflower maize, oat, rye, barley, wheat, pepper, tagetes, cotton, oil palm, coconut palm, flax, castor and peanut, which are oilseed plants containing high amounts of lipid compounds.

SUMMARY OF THE INVENTION

The present invention provides novel isolated nucleic acid and amino acid sequences associated with the metabolism of seed storage compounds in plants.

The present invention also provides an isolated nucleic acid from Arabidopsis encoding a Lipid Metabolism Protein (LMP), or a portion thereof. These sequences may be used to modify or increase lipids and fatty acids, cofactors and enzymes in microorganisms and plants.

Arabidopsis plants are known to produce considerable amounts of fatty acids like linoleic and linolenic acid (see, e.g., Table 2) and for their close similarity in many aspects (gene homology etc.) to the oil crop plant Brassica. Therefore nucleic acid molecules originating from a plant like Arabidopsis thaliana are especially suited to modify the lipid and fatty acid metabolism in a host, especially in microorganisms and plants. Furthermore, nucleic acids from the plant Arabidopsis thaliana can be used to identify those DNA sequences and enzymes in other species which are useful to modify the biosynthesis of precursor molecules of fatty acids in the respective organisms.

The present invention further provides an isolated nucleic acid comprising a fragment of at least 15 nucleotides of a nucleic acid from a plant (Arabidopsis thaliana) encoding a Lipid Metabolism Protein (LMP), or a portion thereof.

Also provided by the present invention are polypeptides encoded by the nucleic acids, and heterologous polypeptides comprising polypeptides encoded by the nucleic acids, and antibodies to those polypeptides.

Additionally, the present invention relates to and provides the use of LMP nucleic acids in the production of transgenic plants having a modified level of a seed storage compound. A method of producing a transgenic plant with a modified level of a seed storage compound includes the steps of transforming a plant cell with an expression vector comprising a LMP nucleic acid, and generating a plant with a modified level of the seed storage compound from the plant cell. In a preferred embodiment, the plant is an oil producing species selected from the group consisting of rapeseed, canola, linseed, soybean, sunflower, maize, oat, rye, barley, wheat, pepper, tagetes, cotton, oil palm, coconut palm, flax, castor and peanut, for example.

According to the present invention, the compositions and methods described herein can be used to increase or decrease the level of a LMP in a transgenic plant comprising increasing or decreasing the expression of a LMP nucleic acid in the plant. Increased or decreased expression of the LMP nucleic acid can be achieved through in vivo mutagenesis of the LMP nucleic acid. The present invention can also be used to increase or decrease the level of a lipid in a seed oil, to increase or decrease the level of a fatty acid in a seed oil, or to increase or decrease the level of a starch in a seed or plant.

Also included herein is a seed produced by a transgenic plant transformed by a LMP DNA sequence, wherein the seed contains the LMP DNA sequence and wherein the plant is true breeding for a modified level of a seed storage compound. The present invention additionally includes a seed oil produced by the aforementioned seed.

Further provided by the present invention are vectors comprising the nucleic acids, host cells containing the vectors, and descendent plant materials produced by transforming a plant cell with the nucleic acids and/or vectors.

According to the present invention, the compounds, compositions, and methods described herein can be used to increase or decrease the level of a lipid in a seed oil, or to increase or decrease the level of a fatty acid in a seed oil, or to increase or decrease the level of a starch or other carbohydrate in a seed or plant. A method of producing a higher or lower than normal or typical level of storage compound in a transgenic plant, comprises expressing a LMP nucleic acid from *Arabidopsis thaliana* in the transgenic plant, wherein the transgenic plant is *Arabidopsis thaliana* or a species different from *Arabidopsis thaliana*. Also included herein are compositions and methods of the modification of the efficiency of production of a seed storage compound.

Accordingly, it is an object of the present invention to provide novel isolated LMP nucleic acids and isolated LMP amino acid sequences from *Arabidopsis thaliana*, as well as active fragments, analogs and orthologs thereof.

It is another object of the present invention to provide transgenic plants having modified levels of seed storage compounds, and in particular, modified levels of a lipid, a fatty acid or a sugar.

It is a further object of the present invention to provide methods for producing such aforementioned transgenic plants.

It is another object of the present invention to provide seeds and seed oils from such aforementioned transgenic plants.

These and other objects, features and advantages of the present invention will become apparent after a review of the following detailed description of the disclosed embodiments and the appended claims.

BRIEF DESCRIPTION OF THE FIGURES

FIGS. 1A-B: FIG. 1A shows the polynucleotide sequences of the open reading frame of Clone ID NO: pk002b from *Arabidopsis thaliana* (SEQ ID NO:1) of the present invention. The polynucleotide sequence contains 2253 nucleotides. FIG. 1B shows the deduced amino acid sequence of SEQ ID NO:1 (SEQ ID NO:2) (Clone ID NO: pk002b) of the present invention. The polypeptide sequence contains 750 amino acids. The standard one-letter abbreviation for amino acids is used to illustrate the deduced amino acid sequence.

FIGS. 2A-B: FIG. 2A shows the polynucleotide sequences of the open reading frame of Clone ID NO: pk020b from *Arabidopsis thaliana* (SEQ ID NO:3) of the present invention. The polynucleotide sequence contains 681 nucleotides. FIG. 2B shows the deduced amino acid sequence of SEQ ID NO:3 (SEQ ID NO:4) (Clone ID NO: pk020b) of the present invention. The polypeptide sequence contains 226 amino acids. The standard one-letter abbreviation for amino acids is used to illustrate the deduced amino acid sequence.

FIGS. 3A-B: FIG. 3A shows the polynucleotide sequences of the open reading frame of Clone ID NO: pk033 from *Arabidopsis thaliana* (SEQ ID NO:5) of the present invention. The polynucleotide sequence contains 1815 nucleotides. FIG. 3B shows the deduced amino acid sequence of SEQ ID NO:5 (SEQ ID NO:6) (Clone ID NO: pk033) of the present invention. The polypeptide sequence contains 604 amino acids. The standard one-letter abbreviation for amino acids is used to illustrate the deduced amino acid sequence.

FIGS. 4A-B: FIG. 4A shows the polynucleotide sequences of the open reading frame of Clone ID NO: pk037 from *Arabidopsis thaliana* (SEQ ID NO:7) of the present invention. The polynucleotide sequence contains 1773 nucleotides. FIG. 4B shows the deduced amino acid sequence of SEQ ID NO:7 (SEQ ID NO:8) (Clone ID NO: pk037) of the present invention. The polypeptide sequence contains 590 amino acids. The standard one-letter abbreviation for amino acids is used to illustrate the deduced amino acid sequence.

FIGS. 5A-B: FIG. 5A shows the polynucleotide sequences of the open reading frame of Clone ID NO: pk038 from *Arabidopsis thaliana* (SEQ ID NO:9) of the present invention. The polynucleotide sequence contains 1035 nucleotides. FIG. 5B shows the deduced amino acid sequence of SEQ ID NO:9 (SEQ ID NO:10) (Clone ID NO: pk038) of the present invention. The polypeptide sequence contains 344 amino acids. The standard one-letter abbreviation for amino acids is used to illustrate the deduced amino acid sequence.

FIGS. 6A-B: FIG. 6A shows the polynucleotide sequences of the open reading frame of Clone ID NO: pk042a from *Arabidopsis thaliana* (SEQ ID NO:11) of the present invention. The polynucleotide sequence contains 804 nucleotides. FIG. 6B shows the deduced amino acid sequence of SEQ ID NO:11 (SEQ ID NO:12) (Clone ID NO: pk042a) of the present invention. The polypeptide sequence contains 267 amino acids. The standard one-letter abbreviation for amino acids is used to illustrate the deduced amino acid sequence.

FIGS. 7A-B: FIG. 7A shows the polynucleotide sequences of the open reading frame of Clone ID NO: pk053b from *Arabidopsis thaliana* (SEQ ID NO:13) of the present invention. The polynucleotide sequence contains 272 nucleotides. FIG. 7B shows the deduced amino acid sequence of SEQ ID NO:13 (SEQ ID NO:14) (Clone ID NO: pk053b) of the present invention. The polypeptide sequence contains 90 amino acids. The standard one-letter abbreviation for amino acids is used to illustrate the deduced amino acid sequence.

FIGS. 8A-B: FIG. 8A shows the polynucleotide sequences of the open reading frame of Clone ID NO: pk060 from *Arabidopsis thaliana* (SEQ ID NO:15) of the present invention. The polynucleotide sequence contains 603 nucleotides. FIG. 8B shows the deduced amino acid sequence of SEQ ID NO:15 (SEQ ID NO:16) (Clone ID NO: pk060) of the present invention. The polypeptide sequence contains 200 amino acids. The standard one-letter abbreviation for amino acids is used to illustrate the deduced amino acid sequence.

FIGS. 9A-B: FIG. 9A shows the polynucleotide sequences of the open reading frame of Clone ID NO: pk063b from *Arabidopsis thaliana* (SEQ ID NO:17) of the present invention. The polynucleotide sequence contains 1746 nucleotides. FIG. 9B shows the deduced amino acid sequence of SEQ ID NO:17 (SEQ ID NO:18) (Clone ID NO: pk063b) of the present invention. The polypeptide sequence contains 581 amino acids. The standard one-letter abbreviation for amino acids is used to illustrate the deduced amino acid sequence.

FIGS. 10A-B: FIG. 10A shows the polynucleotide sequences of the open reading frame of Clone ID NO: pk064 from *Arabidopsis thaliana* (SEQ ID NO:19) of the present invention. The polynucleotide sequence contains 1347 nucleotides. FIG. 10B shows the deduced amino acid sequence of SEQ ID NO:19 (SEQ ID NO:20) (Clone ID NO: pk064) of the present invention. The polypeptide sequence contains 448 amino acids. The standard one-letter abbreviation for amino acids is used to illustrate the deduced amino acid sequence.

FIGS. 11A-B. FIG. 11A shows the polynucleotide sequences of the open reading frame of Clone ID NO: pk073 from *Arabidopsis thaliana* (SEQ ID NO:21) of the present invention. The polynucleotide sequence contains 564 nucleotides. FIG. 11B shows the deduced amino acid sequence of SEQ ID NO:21 (SEQ ID NO:22) (Clone ID NO: pk073) of the present invention. The polypeptide sequence contains 187 amino acids. The standard one-letter abbreviation for amino acids is used to illustrate the deduced amino acid sequence.

FIGS. 12A-B. FIG. 12A shows the polynucleotide sequences of the open reading frame of Clone ID NO: pk082 from *Arabidopsis thaliana* (SEQ ID NO:23) of the present invention. The polynucleotide sequence contains 753 nucleotides. FIG. 12B shows the deduced amino acid sequence of SEQ ID NO:23 (SEQ ID NO:24) (Clone ID NO: pk082) of the present invention. The polypeptide sequence contains 250 amino acids. The standard one-letter abbreviation for amino acids is used to illustrate the deduced amino acid sequence.

FIGS. 13A-B. FIG. 13A shows the polynucleotide sequences of the open reading frame of Clone ID NO: pk084 from *Arabidopsis thaliana* (SEQ ID NO:25) of the present invention. The polynucleotide sequence contains 1218 nucleotides. FIG. 13B shows the deduced amino acid sequence of SEQ ID NO:25 (SEQ ID NO:26) (Clone ID NO: pk084) of the present invention. The polypeptide sequence contains 405 amino acids. The standard one-letter abbreviation for amino acids is used to illustrate the deduced amino acid sequence.

FIGS. 14A-B. FIG. 14A shows the polynucleotide sequences of the open reading frame of Clone ID NO: pk086 from *Arabidopsis thaliana* (SEQ ID NO:27) of the present invention. The polynucleotide sequence contains 420 nucleotides. FIG. 14B shows the deduced amino acid sequence of SEQ ID NO:27 (SEQ ID NO:28) (Clone ID NO: pk086) of the present invention. The polypeptide sequence contains 139 amino acids. The standard one-letter abbreviation for amino acids is used to illustrate the deduced amino acid sequence.

FIGS. 15A-B. FIG. 15A shows the polynucleotide sequences of the open reading frame of Clone ID NO: pk088 from *Arabidopsis thaliana* (SEQ ID NO:29) of the present invention. The polynucleotide sequence contains 549 nucleotides. FIG. 15B shows the deduced amino acid sequence of SEQ ID NO:29 (SEQ ID NO:30) (Clone ID NO: pk088) of the present invention. The polypeptide sequence contains 182 amino acids. The standard one-letter abbreviation for amino acids is used to illustrate the deduced amino acid sequence.

FIGS. 16A-B. FIG. 16A shows the polynucleotide sequences of the open reading frame of Clone ID NO: pk095 from *Arabidopsis thaliana* (SEQ ID NO:31) of the present invention. The polynucleotide sequence contains 987 nucleotides. FIG. 16B shows the deduced amino acid sequence of SEQ ID NO:31 (SEQ ID NO:32) (Clone ID NO: pk095) of the present invention. The polypeptide sequence contains 328 amino acids. The standard one-letter abbreviation for amino acids is used to illustrate the deduced amino acid sequence.

FIGS. 17A-B. FIG. 17A shows the polynucleotide sequences of the open reading frame of Clone ID NO: pk096 from *Arabidopsis thaliana* (SEQ ID NO:33) of the present invention. The polynucleotide sequence contains 2322 nucleotides. FIG. 17B shows the deduced amino acid sequence of SEQ ID NO:33 (SEQ ID NO:34) (Clone ID NO: pk096) of the present invention. The polypeptide sequence contains 773 amino acids. The standard one-letter abbreviation for amino acids is used to illustrate the deduced amino acid sequence.

FIGS. 18A-D. FIG. 18A shows the polynucleotide sequences of the open reading frame of Clone ID NO: pk097a from *Arabidopsis thaliana* (SEQ ID NO:35) of the present invention. The polynucleotide sequence contains 2217 nucleotides. FIG. 18B shows the deduced amino acid sequence of SEQ ID NO:35 (SEQ ID NO:36) (Clone ID NO: pk097a) of the present invention. The polypeptide sequence contains 738 amino acids. The standard one-letter abbreviation for amino acids is used to illustrate the deduced amino acid sequence. FIG. 18C shows the polynucleotide sequences of the open reading frame of Clone ID NO: pk097b from *Arabidopsis thaliana* (SEQ ID NO:37) of the present invention. The polynucleotide sequence contains 2154 nucleotides. FIG. 18D shows the deduced amino acid sequence of SEQ ID NO:37 (SEQ ID NO:38) (Clone ID NO: pk097b) of the present invention. The polypeptide sequence contains 717 amino acids. The standard one-letter abbreviation for amino acids is used to illustrate the deduced amino acid sequence.

FIGS. 19A-B. FIG. 19A shows the polynucleotide sequences of the open reading frame of Clone ID NO: pk098 from *Arabidopsis thaliana* (SEQ ID NO:39) of the present invention. The polynucleotide sequence contains 690 nucleotides. FIG. 19B shows the deduced amino acid sequence of SEQ ID NO:39 (SEQ ID NO:40) (Clone ID NO: pk098) of the present invention. The polypeptide sequence contains 229 amino acids. The standard one-letter abbreviation for amino acids is used to illustrate the deduced amino acid sequence.

FIGS. 20A-B. FIG. 20A shows the polynucleotide sequences of the open reading frame of Clone ID NO: pk099 from *Arabidopsis thaliana* (SEQ ID NO:41) of the present invention. The polynucleotide sequence contains 732 nucleotides. FIG. 20B shows the deduced amino acid sequence of SEQ ID NO:41 (SEQ ID NO:42) (Clone ID NO: pk099) of the present invention. The polypeptide sequence contains 243 amino acids. The standard one-letter abbreviation for amino acids is used to illustrate the deduced amino acid sequence.

FIGS. 21A-B. FIG. 21A shows the polynucleotide sequences of the open reading frame of Clone ID NO: pk100 from *Arabidopsis thaliana* (SEQ ID NO:43) of the present invention. The polynucleotide sequence contains 2148 nucleotides. FIG. 21B shows the deduced amino acid sequence of SEQ ID NO:43 (SEQ ID NO:44) (Clone ID NO: pk100) of the present invention. The polypeptide sequence contains 715 amino acids. The standard one-letter abbreviation for amino acids is used to illustrate the deduced amino acid sequence.

FIGS. 22A-B. FIG. 22A shows the polynucleotide sequences of the open reading frame of Clone ID NO: pk105 from *Arabidopsis thaliana* (SEQ ID NO:45) of the present invention. The polynucleotide sequence contains 1305 nucleotides. FIG. 22B shows the deduced amino acid sequence of SEQ ID NO:45 (SEQ ID NO:46) (Clone ID NO: pk105) of the present invention. The polypeptide sequence contains 434 amino acids. The standard one-letter abbreviation for amino acids is used to illustrate the deduced amino acid sequence.

FIGS. 23A-B. FIG. 23A shows the polynucleotide sequences of the open reading frame of Clone ID NO: pk107 from *Arabidopsis thaliana* (SEQ ID NO:47) of the present invention. The polynucleotide sequence contains 2466 nucleotides. FIG. 23B shows the deduced amino acid sequence of SEQ ID NO:47 (SEQ ID NO:48) (Clone ID NO: pk107) of the present invention. The polypeptide sequence contains 821 amino acids. The standard one-letter abbreviation for amino acids is used to illustrate the deduced amino acid sequence.

DETAILED DESCRIPTION OF THE INVENTION

The present invention may be understood more readily by reference to the following detailed description of the preferred embodiments of the invention and the Examples included therein.

Before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing particular embodiments only and is not intended to be limiting. As used in the specification and in the claims, "a" or "an" can mean one or more, depending upon the context in which it is used. Thus, for example, reference to "a cell" can mean that at least one cell can be utilized.

In accordance with the purpose(s) of this invention, as embodied and broadly described herein, this invention, in one aspect, provides an isolated nucleic acid from a plant (*Arabidopsis thaliana*) encoding a Lipid Metabolism Protein (LMP), or a portion thereof.

One aspect of the invention pertains to isolated nucleic acid molecules that encode LMP polypeptides or biologically active portions thereof, as well as nucleic acid fragments sufficient for use as hybridization probes or primers for the identification or amplification of an LMP-encoding nucleic acid (e.g., LMP DNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of a gene: at least about 1000 nucleotides of sequence upstream from the 5' end of the coding region and at least about 200 nucleotides of sequence downstream from the 3' end of the coding region of the gene. The nucleic acid molecule can be single-stranded or double-stranded, but preferably is double-stranded DNA. An "isolated" nucleic acid molecule is one which is substantially separated from other nucleic acid molecules which are present in the natural source of the nucleic acid. Preferably, an "isolated" nucleic acid is substantially free of sequences which naturally flank the nucleic acid (i.e., sequences located at the 5' and 3' ends of the nucleic acid) in the genomic DNA of the organism from which the nucleic acid is derived. For example, in various embodiments, the isolated LMP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a *Arabidopsis thaliana* cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having a nucleotide sequence of the Figures, or a portion thereof, can be isolated using standard molecular biology techniques and the sequence information provided herein. For example, an *Arabidopsis thaliana* LMP cDNA can be isolated from an *Arabidopsis thaliana* library using all or portion of one of the sequences of the Figures as a hybridization probe and standard hybridization techniques (e.g., as described in Sambrook et al. 1989, *Molecular Cloning: A Laboratory Manual. 2nd, ed., Cold Spring Harbor Laboratory*, Cold Spring Harbor Laboratory Press, Cold Spring Harbor, N.Y.). Moreover, a nucleic acid molecule encompassing all or a portion of one of the sequences of the Figures can be isolated by the polymerase chain reaction using oligonucleotide primers designed based upon this sequence (e.g., a nucleic acid molecule encompassing all or a portion of one of the sequences of the Figures can be isolated by the polymerase chain reaction using oligonucleotide primers designed based upon this same sequence the Figures). For example, mRNA can be isolated from plant cells (e.g., by the guanidinium-thiocyanate extraction procedure of Chirgwin et al. 1979, Biochemistry 18:5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in the Figures. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a LMP nucleotide sequence can be prepared by standard synthetic techniques, e.g., using an automated DNA synthesizer.

In a preferred embodiment, an isolated nucleic acid of the invention comprises one of the polynucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45 or SEQ ID NO:47. These polynucleotide correspond to the *Arabidopsis thaliana* LMP cDNAs of the invention. These cDNAs comprise sequences encoding LMPs (i.e., the "coding region"), as well as 5' untranslated sequences and 3' untranslated sequences. Alternatively, the nucleic acid molecules can comprise only the coding region of any of the polynucleotide sequences described herein. Examples of polynucleotides comprising only the coding region or open reading frame (ORF) are shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45 or SEQ ID NO:47.

For the purposes of this application, it will be understood that each of the polynucleotide sequences set forth in the Figures has an identifying entry number (e.g., pk002b). Each of these sequences may generally comprise three parts: a 5' upstream region, a coding region, and a downstream region. The particular sequences shown in the figures represent the open reading frames. The putative functions of these proteins are indicated in Table 4.

In another preferred embodiment, an isolated nucleic acid molecule of the present invention encodes a polypeptide that is able to participate in the metabolism of seed storage compounds such as lipids, starch and seed storage proteins and that contains a DNA-binding (or transcription factor) domain, a protein kinase domain, a signal transduction domain, a protease domain, or a carbohydrate metabolism domain. Examples of isolated LMPs that contain such domains can be found in Table 5. LMPs containing a DNA-binding domain include those shown in SEQ ID NO:4, SEQ ID NO:8, SEQ ID NO:20, SEQ ID NO:24, SEQ ID NO:26, SEQ ID NO:28, SEQ ID NO:32, or SEQ ID NO:44. LMPs containing a protein kinase domain include those shown in SEQ ID NO:36, SEQ ID NO:38, SEQ ID NO:48, SEQ ID NO:22 or SEQ ID NO:16. LMPs containing a signal transduction domain include those shown in SEQ ID NO:2, SEQ ID NO:14, SEQ ID NO:34, SEQ ID NO:40, SEQ ID NO:42 or SEQ ID NO:46. LMPs containing a protease domain include those shown in SEQ ID NO:6 or SEQ ID NO:12. LMPs containing a carbohydrate metabolism domain include those shown in SEQ ID NO:10, SEQ ID NO:18 or SEQ ID NO:30.

In another preferred embodiment, an isolated nucleic acid molecule of the invention comprises a nucleic acid molecule which is a complement of any of the nucleic acid sequences disclosed herein, including one of the nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45 or SEQ ID NO:47, or a portion thereof. As used herein, the term "complementary" refers to a nucleotide sequence that can hybridize to one of the nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45 or SEQ ID NO:47, thereby forming a stable duplex.

In another preferred embodiment, an isolated nucleic acid of the invention comprises a polynucleotide sequence encoding a polypeptide selected from the group consisting of: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46 or SEQ ID NO:48.

In still another preferred embodiment, an isolated nucleic acid molecule of the invention comprises a nucleotide sequence which is at least about 50-60%, preferably at least about 60-70%, more preferably at least about 70-80%, 80-90%, or 90-95%, and even more preferably at least about 95%, 96%, 97%, 98%, 99% or more homologous to a nucleotide sequence shown in the Figures, or a portion thereof. In an additional preferred embodiment, an isolated nucleic acid molecule of the invention comprises a nucleotide sequence which hybridizes, e.g., hybridizes under stringent conditions, to one of the nucleotide sequences shown in the Figures, or a portion thereof. These hybridization conditions include washing with a solution having a salt concentration of about 0.02 molar at pH 7 at about 60° C.

Moreover, the nucleic acid molecule of the invention can comprise only a portion of the coding region of one of the sequences in the Figures, for example a fragment which can be used as a probe or primer or a fragment encoding a biologically active portion of a LMP. The nucleotide sequences determined from the cloning of the LMP genes from *Arabidopsis thaliana* allows for the generation of probes and primers designed for use in identifying and/or cloning LMP homologues in other cell types and organisms, as well as LMP homologues from other plants or related species. Therefore this invention also provides compounds comprising the nucleic acids disclosed herein, or fragments thereof. These compounds include the nucleic acids attached to a moiety. These moieties include, but are not limited to, detection moieties, hybridization moieties, purification moieties, delivery moieties, reaction moieties, binding moieties, and the like. The probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of one of the sequences set forth in the Figures, an anti-sense sequence of one of the sequences set forth in the Figures, or naturally occurring mutants thereof. Primers based on a nucleotide sequence of the Figures can be used in PCR reactions to clone LMP homologues. Probes based on the LMP nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a LMP, such as by measuring a level of a LMP-encoding nucleic acid in a sample of cells, e.g., detecting LMP mRNA levels or determining whether a genomic LMP gene has been mutated or deleted.

In one embodiment, the nucleic acid molecule of the invention encodes a protein or portion thereof which includes an amino acid sequence which is sufficiently homologous to an amino acid encoded by a sequence of the Figures such that the protein or portion thereof maintains the same or a similar function as the wild-type protein. As used herein, the language "sufficiently homologous" refers to proteins or portions thereof which have amino acid sequences which include a minimum number of identical or equivalent (e.g., an amino acid residue which has a similar side chain as an amino acid residue in one of the ORFs of a sequence of the Figures) amino acid residues to an amino acid sequence such that the protein or portion thereof is able to participate in the metabolism of compounds necessary for the production of seed storage compounds in plants, construction of cellular membranes in microorganisms or plants, or in the transport of molecules across these membranes. Regulatory proteins, such as DNA binding proteins, transcription factors, kinases, phosphatases, or protein members of metabolic pathways such as the lipid, starch and protein biosynthetic pathways, or membrane transport systems, may play a role in the biosynthesis of seed storage compounds. Examples of such activities are described herein (see putative annotations in Table 4). Examples of LMP-encoding nucleic acid sequences are set forth in the Figures.

As altered or increased sugar and/or fatty acid production is a general trait wished to be inherited into a wide variety of plants like maize, wheat, rye, oat, triticale, rice, barley, soybean, peanut, cotton, rapeseed, canola, manihot, pepper, sunflower and tagetes, solanaceous plants like potato, tobacco, eggplant, and tomato, Vicia species, pea, alfalfa, bushy plants (coffee, cacao, tea), Salix species, trees (oil palm, coconut) and perennial grasses and forage crops, these crop plants are also preferred target plants for genetic engineering as one further embodiment of the present invention.

Portions of proteins encoded by the LMP nucleic acid molecules of the invention are preferably biologically active portions of one of the LMPs. As used herein, the term "biologically active portion of a LMP" is intended to include a portion, e.g., a domain/motif, of a LMP that participates in the metabolism of compounds necessary for the biosynthesis of seed storage lipids, or the construction of cellular membranes in microorganisms or plants, or in the transport of molecules across these membranes, or has an activity as set forth in Table 3. To determine whether a LMP or a biologically active portion thereof can participate in the metabolism of compounds necessary for the production of seed storage compounds and cellular membranes, an assay of enzymatic activity may be performed. Such assay methods are well known to those skilled in the art, and as described in Example 14 of the Exemplification.

Biologically active portions of a LMP include peptides comprising amino acid sequences derived from the amino acid sequence of a LMP (e.g., an amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46 or SEQ ID NO:48 or the amino acid sequence of a protein homologous to a LMP, which include fewer amino acids than a full length LMP or the full length protein which is homologous to a LMP) and exhibit at least one activity of a LMP. Typically, biologically active portions (peptides, e.g., peptides which are, for example, 5, 10, 15, 20, 25, 30, 35, 36, 37, 38, 39, 40, 50, 100 or more amino acids in length) comprise a domain or motif with at least one activity of a LMP. Moreover, other biologically active portions, in which other regions of the protein are deleted, can be prepared by recombinant techniques and evaluated for one or more of the activities described herein. Preferably, the biologically active portions of a LMP include one or more selected domains/motifs or portions thereof having biological activity.

Additional nucleic acid fragments encoding biologically active portions of a LMP can be prepared by isolating a portion of one of the sequences, expressing the encoded portion of the LMP or peptide (e.g., by recombinant expression in vitro) and assessing the activity of the encoded portion of the LMP or peptide.

The invention further encompasses nucleic acid molecules that differ from one of the polynucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45 or SEQ ID NO:47 (and portions thereof) due to degeneracy of the genetic code and thus encode the same LMP as that encoded by the nucleotide sequences shown in the Figures. In a further embodiment, the nucleic acid molecule of the invention encodes a full length protein which is substantially homologous to an amino acid sequence of a polypeptide encoded by an open reading frame shown in the Figures. In one embodiment, the full-length nucleic acid or protein or fragment of the nucleic acid or protein is from *Arabidopsis thaliana*.

In addition to the *Arabidopsis thaliana* LMP nucleotide sequences described herein, it will be appreciated by those skilled in the art that DNA sequence polymorphisms that lead to changes in the amino acid sequences of LMPs may exist within a population (e.g., the *Arabidopsis thaliana* population). Such genetic polymorphism in the LMP gene may exist among individuals within a population due to natural variation. As used herein, the terms "gene" and "recombinant gene" refer to nucleic acid molecules comprising an open reading frame encoding a LMP, preferably a *Arabidopsis thaliana* LMP. Such natural variations can typically result in 1-40% variance in the nucleotide sequence of the LMP gene. Any and all such nucleotide variations and resulting amino acid polymorphisms in LMP that are the result of natural variation and that do not alter the functional activity of LMPs are intended to be within the scope of the invention.

Nucleic acid molecules corresponding to natural variants and non-*Arabidopsis thaliana* orthologs of the *Arabidopsis thaliana* LMP cDNA of the invention can be isolated based on their homology to *Arabidopsis thaliana* LMP nucleic acid disclosed herein using the *Arabidopsis thaliana* cDNA, or a portion thereof, as a hybridization probe according to standard hybridization techniques under stringent hybridization conditions. As used herein, the term "orthologs" refers to two nucleic acids from different species, but that have evolved from a common ancestral gene by speciation. Normally, orthologs encode proteins having the same or similar functions. Accordingly, in another embodiment, an isolated nucleic acid molecule of the invention is at least 15 nucleotides in length and hybridizes under stringent conditions to the nucleic acid molecule comprising a nucleotide sequence of the Figures. In other embodiments, the nucleic acid is at least 30, 50, 100, 250 or more nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, John Wiley & Sons, N.Y. (1989) 6.3.1-6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to a polynucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45 or SEQ ID NO:47 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural *Arabidopsis thaliana* LMP.

In addition to naturally-occurring variants of the LMP sequence that may exist in the population, the skilled artisan will further appreciate that changes can be introduced by mutation into a nucleotide sequence of the Figures, thereby leading to changes in the amino acid sequence of the encoded LMP, without altering the functional ability of the LMP. For example, nucleotide substitutions leading to amino acid substitutions at "non-essential" amino acid residues can be made in a a LMP polynucleotide sequence. A "non-essential" amino acid residue is a residue that can be altered from the wild-type sequence of one of the LMPs provided herein without altering the activity of said LMP, whereas an "essential" amino acid residue is required for LMP activity. Other amino acid residues, however, (e.g., those that are not conserved or only semi-conserved in the domain having LMP activity) may not be essential for activity and thus are likely to be amenable to alteration without altering LMP activity.

Accordingly, another aspect of the invention pertains to nucleic acid molecules encoding LMPs that contain changes in amino acid residues that are not essential for LMP activity. Such LMPs differ in amino acid sequence from a sequence yet retain at least one of the LMP activities described herein. In one embodiment, the isolated nucleic acid molecule comprises a nucleotide sequence encoding a protein, wherein the protein comprises an amino acid sequence at least about 50% homologous to an amino acid sequence encoded by a nucleic acid of the Figures and is capable of participation in the metabolism of compounds necessary for the production of seed storage compounds in *Arabidopsis thaliana*, or cellular membranes, or has one or more activities set forth in Table 4. Preferably, the protein encoded by the nucleic acid molecule is at least about 50-60% homologous as shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46 or SEQ ID NO:48, more preferably at least about 60-70% homologous as shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46 or SEQ ID NO:48, even more preferably at least about 70-80%, 80-90%, 90-95% homologous as shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46 or SEQ ID NO:48, and most preferably at least about 96%, 97%, 98%, or 99% homologous as shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46 or SEQ ID NO:48.

To determine the percent homology of two amino acid sequences (e.g., the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46 or SEQ ID NO:48 and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46 or SEQ ID NO:48) is occupied by the same amino acid residue or nucleotide as the corresponding position in the other sequence (e.g., a mutant or homolog of the sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46 or SEQ ID NO:48), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=numbers of identical positions/total numbers of positions×100).

An isolated nucleic acid molecule encoding a LMP homologous to a protein sequence encoded by a nucleic acid of the Figures can be created by introducing one or more nucleotide substitutions, additions or deletions into a nucleotide sequence of the Figures such that one or more amino acid substitutions, additions or deletions are introduced into the encoded protein. Mutations can be introduced into one of the sequences of the Figures by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a LMP is preferably replaced with another amino acid residue from the same side chain family. Alternatively, in another embodiment, mutations can be introduced randomly along all or part of a LMP coding sequence, such as by saturation mutagenesis, and the resultant mutants can be screened for a LMP activity described herein to identify mutants that retain LMP activity. Following mutagenesis of one of the sequences of the Figures, the encoded protein can be expressed recombinantly and the activity of the protein can be determined using, for example, assays described herein (see Examples 9, 13,-14 of the Exemplification).

LMPs are preferably produced by recombinant DNA techniques. For example, a nucleic acid molecule encoding the protein is cloned into an expression vector (as described above), the expression vector is introduced into a host cell (as described herein) and the LMP is expressed in the host cell. The LMP can then be isolated from the cells by an appropriate purification scheme using standard protein purification techniques. Alternative to recombinant expression, a LMP or peptide thereof can be synthesized chemically using standard peptide synthesis techniques. Moreover, native LMP can be isolated from cells, for example using an anti-LMP antibody, which can be produced by standard techniques utilizing a LMP or fragment thereof of this invention.

The invention also provides LMP chimeric or fusion proteins. As used herein, a LMP "chimeric protein" or "fusion protein" comprises a LMP polypeptide operatively linked to a non-LMP polypeptide. An "LMP polypeptide" refers to a polypeptide having an amino acid sequence corresponding to a LMP, whereas a "non-LMP polypeptide" refers to a polypeptide having an amino acid sequence corresponding to a protein which is not substantially homologous to the LMP, e.g., a protein which is different from the LMP and which is derived from the same or a different organism. Within the fusion protein, the term "operatively linked" is intended to indicate that the LMP polypeptide and the non-LMP polypeptide are fused to each other so that both sequences fulfill the proposed function attributed to the sequence used. The non-LMP polypeptide can be fused to the N-terminus or C-terminus of the LMP polypeptide. For example, in one embodiment, the fusion protein is a GST-LMP (glutathione S-transferase) fusion protein in which the LMP sequences are fused to the C-terminus of the GST sequences. Such fusion proteins can facilitate the purification of recombinant LMPs. In another embodiment, the fusion protein is a LMP containing a heterologous signal sequence at its N-terminus. In certain host cells (e.g., mammalian host cells), expression and/or secretion of a LMP can be increased through use of a heterologous signal sequence.

Preferably, a LMP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al., John Wiley & Sons: 1992). Moreover, many expression vectors are commercially available that already encode a fusion moiety (e.g., a GST polypeptide). An LMP-encoding nucleic acid can be cloned into such an expression vector such that the fusion moiety is linked in-frame to the LMP.

In addition to the nucleic acid molecules encoding LMPs described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire LMP coding strand, or to only a portion thereof. In one embodiment, an antisense nucleic acid molecule is antisense to a "coding region" of the coding strand of a nucleotide sequence encoding a LMP. The term "coding region" refers to the region of the nucleotide sequence comprising codons which are translated into amino acid residues (e.g., the entire coding region of Pk002b comprises nucleotides 1 to 2050). In another embodiment, the antisense nucleic acid molecule is antisense to a "noncoding region" of the coding strand of a nucleotide sequence encoding LMP. The term "noncoding region" refers to 5' and 3' sequences which flank the coding region that are not translated into amino acids (i.e., also referred to as 5' and 3' untranslated regions).

Given the coding strand sequences encoding LMP disclosed herein (e.g., the sequences set forth in the Figures), antisense nucleic acids of the invention can be designed according to the rules of Watson and Crick base pairing. The antisense nucleic acid molecule can be complementary to the entire coding region of LMP mRNA, but more preferably is an oligonucleotide which is antisense to only a portion of the coding or noncoding region of LMP mRNA. For example, the antisense oligonucleotide can be complementary to the region surrounding the translation start site of LMP mRNA. An antisense oligonucleotide can be, for example, about 5, 10, 15, 20, 25, 30, 35, 40, 45 or 50 nucleotides in length. An antisense or sense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylamino-methyl-2-thiouridine, 5-carboxymethylaminomethyluracil, dihydro-uracil, beta-D-galactosylqueosine, inosine, N-6-isopentenyladenine, 1-methylguanine, 1-methylinosine, 2,2-dimethylguanine, 2-methyladenine, 2-methylguanine, 3-methylcytosine, 5-methyl-cytosine, N-6-adenine, 7-methylguanine, 5-methylaminomethyluracil, 5-methoxyamino-methyl-2-thiouracil, beta-D-mannosylqueosine, 5'-methoxycarboxymethyl-uracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diamino-purine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another variation of the antisense technology, a double-strand interfering RNA construct can be used to cause a down-regulation of the LMP mRNA level and LMP activity in transgenic plants. This requires transforming the plants with a chimeric construct containing a portion of the LMP sequence in the sense orientation fused to the antisense sequence of the same portion of the LMP sequence. A DNA linker region of variable length can be used to separate the sense and antisense fragments of LMP sequences in the construct.

The antisense nucleic acid molecules of the invention are typically administered to a cell or generated in situ such that they hybridize with or bind to cellular mRNA and/or genomic DNA encoding a LMP to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic including plant promoters are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. 1987, Nucleic Acids Res. 15:6625-6641). The antisense nucleic acid molecule can also comprise a 2'-o-methylribonucleotide (Inoue et al. 1987, Nucleic Acids Res. 15:6131-6148) or a chimeric RNA-DNA analogue (Inoue et al. 1987, FEBS Lett. 215: 327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff & Gerlach 1988, Nature 334:585-591)) can be used to catalytically cleave LMP mRNA transcripts to thereby inhibit translation of LMP mRNA. A ribozyme having specificity for a LMP-encoding nucleic acid can be designed based upon the nucleotide sequence of a LMP cDNA disclosed herein (i.e., Pk002b in the Figures) or on the basis of a heterologous sequence to be isolated according to methods taught in this invention. For example, a derivative of a *Tetrahymena* L-19 IVS RNA can be constructed in which the nucleotide sequence of the active site is complementary to the nucleotide sequence to be cleaved in a LMP-encoding mRNA (see, e.g., Cech et al., U.S. Pat. No. 4,987,071 and Cech et al., U.S. Pat. No. 5,116,742). Alternatively, LMP mRNA can be used to select a catalytic RNA having a specific ribonuclease activity from a pool of RNA molecules (see, e.g., Bartel, D. & Szostak J. W. 1993, Science 261:1411-1418).

Alternatively, LMP gene expression can be inhibited by targeting nucleotide sequences complementary to the regulatory region of a LMP nucleotide sequence (e.g., a LMP promoter and/or enhancers) to form triple helical structures that prevent transcription of a LMP gene in target cells (See generally, Helene C. 1991, Anticancer Drug Des. 6:569-84; Helene C. et al. 1992, Ann. N.Y. Acad. Sci. 660:27-36; and Maher, L. J. 1992, Bioassays 14:807-15).

Another aspect of the invention pertains to vectors, preferably expression vectors, containing a nucleic acid encoding a LMP (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence and both sequences are fused to each other so that each fulfills its proposed function (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990) or see: Gruber and Crosby, in: Methods in Plant Molecular Biology and Biotechnolgy, CRC Press, Boca Raton, Fla., eds.: Glick & Thompson, Chapter 7, 89-108 including the references therein. Regulatory sequences include those which direct constitutive expression of a nucleotide sequence in many types of host cell and those which direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., LMPs, mutant forms of LMPs, fusion proteins, etc.).

The recombinant expression vectors of the invention can be designed for expression of LMPs in prokaryotic or eukaryotic cells. For example, LMP genes can be expressed in bacterial cells, insect cells (using baculovirus expression vectors), yeast and other fungal cells (see Romanos M. A. et al. 1992, Foreign gene expression in yeast: a review, Yeast 8:423-488; van den Hondel, C. A. M. J. J. et al. 1991, Heterologous gene expression in filamentous fungi, in: More Gene Manipulations in Fungi, Bennet & Lasure, eds., p. 396-428:Academic Press: an Diego; and van den Hondel & Punt 1991, Gene transfer systems and vector development for filamentous fungi, in: Applied Molecular Genetics of Fungi, Peberdy et al., eds., p. 1-28, Cambridge University Press: Cambridge), algae (Falciatore et al. 1999, Marine Biotechnology 1:239-251), ciliates of the types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella*, and *Stylonychia*, especially of the genus *Stylonychia lemnae* with vectors following a transformation method as described in WO 98/01572 and multicellular plant cells (see Schmidt & Willmitzer 1988, High efficiency *Agrobacterium tumefaciens*-mediated transformation of *Arabidopsis thaliana* leaf and cotyledon plants, Plant Cell Rep.:583-586); Plant Molecular Biology and Biotechnology, C Press, Boca Raton, Fla., chapter 6/7, S.71-119 (1993); White, Jenes et al., Techniques for Gene Transfer, in: Transgenic Plants, Vol. 1, Engineering and Utilization, eds.: Kung and Wu, Academic Press 1993, 128-43; Potrykus 1991, Annu. Rev. Plant Physiol. Plant Mol. Biol. 42:205-225 (and references cited therein) or mammalian cells. Suitable host cells are discussed further in Goeddel, Gene Expression Technology: Methods in Enzymology 185, Academic Press, San Diego, Calif. 1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve one or more of the following purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith & Johnson 1988, Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the LMP is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant LMP unfused to GST can be recovered by cleavage of the fusion protein with thrombin.

Examples of suitable inducible non-fusion *E. coli* expression vectors include pTrc (Amann et al. 1988, Gene 69:301-315) and pET 11d (Studier et al. 1990, Gene Expression Technology: Methods in Enzymology 185, Academic Press, San Diego, Calif. 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression is to express the protein in a host bacteria with an impaired capacity to proteolytically cleave the recombinant protein (Gottesman S. 1990, Gene Expression Technology: Methods in Enzymology 185:119-128, Academic Press, San Diego, Calif.). Another strategy is to alter the nucleic acid sequence of the nucleic acid to be inserted into an expression vector so that the individual codons for each amino acid are those preferentially utilized in the bacterium chosen for expression (Wada et al. 1992, Nucleic Acids Res. 20:2111-2118). Such alteration of nucleic acid sequences of the invention can be carried out by standard DNA synthesis techniques.

In another embodiment, the LMP expression vector is a yeast expression vector. Examples of vectors for expression in yeast *S. cerevisiae* include pYepSec1 (Baldari et al. 1987, EMBO J. 6:229-234), pMFa (Kurjan & Herskowitz 1982, Cell 30:933-943), pJRY88 (Schultz et al. 1987, Gene 54:113-123), and pYES2 (Invitrogen Corporation, San Diego, Calif.). Vectors and methods for the construction of vectors appropriate for use in other fungi, such as the filamentous fungi, include those detailed in: van den Hondel & Punt 1991, "Gene transfer systems and vector development for filamentous fungi, in: Applied Molecular Genetics of Fungi, Peberdy et al., eds., p. 1-28, Cambridge University Press: Cambridge.

Alternatively, the LMPs of the invention can be expressed in insect cells using baculovirus expression vectors. Baculovirus vectors available for expression of proteins in cultured insect cells (e.g., Sf9 cells) include the pAc series (Smith et al. 1983, Mol. Cell Biol. 3:2156-2165) and the pVL series (Lucklow & Summers 1989, Virology 170:31-39).

In yet another embodiment, a nucleic acid of the invention is expressed in mammalian cells using a mammalian expression vector. Examples of mammalian expression vectors include pCDM8 (Seed 1987, Nature 329:840) and pMT2PC (Kaufman et al. 1987, EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, Fritsh and Maniatis, *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the LMPs of the invention may be expressed in uni-cellular plant cells (such as algae, see Falciatore et al. (1999, Marine Biotechnology 1:239-251 and references therein) and plant cells from higher plants (e.g., the spermatophytes, such as crop plants)). Examples of plant expression vectors include those detailed in: Becker, Kemper, Schell and Masterson (1992, "New plant binary vectors with selectable markers located proximal to the left border", Plant Mol. Biol. 20:1195-1197) and Bevan (1984, "Binary *Agrobacterium* vectors for plant transformation, Nucleic Acids Res. 12:8711-8721; Vectors for Gene Transfer in Higher Plants; in: Transgenic Plants, Vol. 1, Engineering and Utilization, eds.: Kung und R. Wu, Academic Press, 1993, S. 15-38).

A plant expression cassette preferably contains regulatory sequences capable to drive gene expression in plant cells and which are operably linked so that each sequence can fulfill its function such as termination of transcription such as polyadenylation signals. Preferred polyadenylation signals are those originating from *Agrobacterium tumefaciens* t-DNA such as the gene 3 known as octopine synthase of the Ti-plasmid pTiACH5 (Gielen et al. 1984, EMBO J. 3:835) or functional equivalents thereof but also all other terminators functionally active in plants are suitable.

As plant gene expression is very often not limited on transcriptional levels a plant expression cassette preferably contains other operably linked sequences like translational enhancers such as the overdrive-sequence containing the 5'-untranslated leader sequence from tobacco mosaic virus enhancing the protein per RNA ratio (Gallie et al. 1987, Nucleic Acids Res. 15:8693-8711).

Plant gene expression has to be operably linked to an appropriate promoter conferring gene expression in a timely, cell or tissue specific manner. Preferred are promoters driving constitutive expression (Benfey et al. 1989, EMBO J. 8:2195-2202) like those derived from plant viruses like the 35S CAMV (Franck et al. 1980, Cell 21:285-294), the 19S CaMV (see also U.S. Pat. No. 5,352,605 and WO 84/02913) or plant promoters like those from Rubisco small subunit described in U.S. Pat. No. 4,962,028. Even more preferred are seed-specific promoters driving expression of LMP proteins during all or selected stages of seed development. Seed-specific plant promoters are known to those of ordinary skill in the art and are identified and characterized using seed-specific mRNA libraries and expression profiling techniques. Seed-specific promoters include the napin-gene promoter from rapeseed (U.S. Pat. No. 5,608,152), the USP-promoter from *Vicia faba* (Baeumlein et al. 1991, Mol. Gen. Genetics 225:459-67), the oleosin-promoter from *Arabidopsis* (WO 98/45461), the phaseolin-promoter from *Phaseolus vulgaris* (U.S. Pat. No. 5,504,200), the Bce4-promoter from *Brassica* (WO9113980) or the legumin B4 promoter (LeB4; Baeumlein et al. 1992, Plant J. 2:233-239) as well as promoters conferring seed specific expression in monocot plants like maize, barley, wheat, rye, rice etc. Suitable promoters to note are the 1pt2 or 1pt1-gene promoter from barley (WO 95/15389 and WO 95/23230) or those described in WO 99/16890 (promoters from the barley hordein-gene, the rice glutelin gene, the rice oryzin gene, the rice prolamin gene, the wheat gliadin gene, wheat glutelin gene, the maize zein gene, the oat glutelin gene, the Sorghum kasirin-gene, the rye secalin gene).

Plant gene expression can also be facilitated via an inducible promoter (for review see Gatz 1997, Annu. Rev. Plant Physiol. Plant Mol. Biol. 48:89-108). Chemically inducible promoters are especially suitable if gene expression is desired in a time specific manner. Examples for such promoters are a salicylic acid inducible promoter (WO 95/19443), a tetracycline inducible promoter (Gatz et al. 1992, Plant J. 2:397-404) and an ethanol inducible promoter (WO 93/21334).

Promoters responding to biotic or abiotic stress conditions are also suitable promoters such as the pathogen inducible PRP1-gene promoter (Ward et al., 1993, Plant. Mol. Biol. 22:361-366), the heat inducible hsp80-promoter from tomato (U.S. Pat. No. 5,187,267), cold inducible alpha-amylase promoter from potato (WO 96/12814) or the wound-inducible pinII-promoter (EP 375091).

Other preferred sequences for use in plant gene expression cassettes are targeting-sequences necessary to direct the gene-product in its appropriate cell compartment (for review see Kermode 1996, Crit. Rev. Plant Sci. 15:285-423 and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells. Also especially suited are promoters that confer plastid-specific gene expression, as plastids are the compartment where precursors and some end products of lipid biosynthesis are synthesized. Suitable promoters such as the viral RNA-polymerase promoter are described in WO 95/16783 and WO 97/06250 and the clpP-promoter from *Arabidopsis* described in WO 99/46394.

The invention further provides a recombinant expression vector comprising a DNA molecule of the invention cloned into the expression vector in an antisense orientation. That is, the DNA molecule is operatively linked to a regulatory sequence in a manner, which allows for expression (by transcription of the DNA molecule) of an RNA molecule, which is antisense to LMP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986, Antisense RNA as a molecular tool for genetic analysis, Reviews—Trends in Genetics, Vol. 1) and Mol et al. (1990, FEBS Lett. 268:427-430).

Another aspect of the invention pertains to host cells into which a recombinant expression vector of the invention has been introduced. The terms "host cell" and "recombinant host cell" are used interchangeably herein. It is to be understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a LMP can be expressed in bacterial cells, insect cells, fungal cells, mammalian cells (such as Chinese hamster ovary cells (CHO) or COS cells), algae, ciliates or plant cells. Other suitable host cells are known to those skilled in the art.

Vector DNA can be introduced into prokaryotic or eukaryotic cells via conventional transformation or transfection techniques. As used herein, the terms "transformation" and "transfection", "conjugation" and "transduction" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells including plant cells can be found in Sambrook et al. (1989, *Molecular Cloning: A Laboratory Manual. 2nd, ed., Cold Spring Harbor Laboratory*, Cold Spring Harbor Laboratory Press, Cold Spring Harbor, N.Y.) and other laboratory manuals such as Methods in Molecular Biology 1995, Vol. 44, *Agrobacterium* protocols, ed: Gartland and Davey, Humana Press, Totowa, N.J.

For stable transfection of mammalian and plant cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin, kanamycin and methotrexate or in plants that confer resistance towards an herbicide such as glyphosate or glufosinate. A nucleic acid encoding a selectable marker can be introduced into a host cell on the same vector as that encoding a LMP or can be introduced on a separate vector. Cells stably transfected with the introduced nucleic acid can be identified by, for example, drug selection (e.g., cells that have incorporated the selectable marker gene will survive, while the other cells die).

To create a homologous recombinant microorganism, a vector is prepared which contains at least a portion of a LMP gene into which a deletion, addition or substitution has been introduced to thereby alter, e.g., functionally disrupt, the LMP gene. Preferably, this LMP gene is an *Arabidopsis thaliana* LMP gene, but it can be a homologue from a related plant or even from a mammalian, yeast, or insect source. In a preferred embodiment, the vector is designed such that, upon homologous recombination, the endogenous LMP gene is functionally disrupted (i.e., no longer encodes a functional protein; also referred to as a knock-out vector). Alternatively, the vector can be designed such that, upon homologous recombination, the endogenous LMP gene is mutated or otherwise altered but still encodes functional protein (e.g., the upstream regulatory region can be altered to thereby alter the expression of the endogenous LMP). To create a point mutation via homologous recombination, DNA-RNA hybrids can be used in a technique known as chimeraplasty (Cole-Strauss et al. 1999, Nucleic Acids Res. 27:1323-1330 and Kmiec 1999, American Scientist 87:240-247). Homologous recombination procedures in *Arabidopsis thaliana* are also well known in the art and are contemplated for use herein.

In a homologous recombination vector, the altered portion of the LMP gene is flanked at its 5' and 3' ends by additional nucleic acid of the LMP gene to allow for homologous recombination to occur between the exogenous LMP gene carried by the vector and an endogenous LMP gene in a microorganism or plant. The additional flankinLMP nucleic acid is of sufficient length for successful homologous recombination with the endogenous gene. Typically, several hundreds of base pairs up to kilobases of flanking DNA (both at the 5' and 3' ends) are included in the vector (see e.g., Thomas & Capecchi 1987, Cell 51:503, for a description of homologous recombination vectors). The vector is introduced into a microorganism or plant cell (e.g., via polyethyleneglycol mediated DNA). Cells in which the introduced LMP gene has homologously recombined with the endogenous LMP gene are selected using art-known techniques.

In another embodiment, recombinant microorganisms can be produced which contain selected systems which allow for regulated expression of the introduced gene. For example, inclusion of a LMP gene on a vector placing it under control of the lac operon permits expression of the LMP gene only in the presence of IPTG. Such regulatory systems are well known in the art.

A host cell of the invention, such as a prokaryotic or eukaryotic host cell in culture can be used to produce (i.e., express) a LMP. Accordingly, the invention further provides methods for producing LMPs using the host cells of the invention. In one embodiment, the method comprises culturing a host cell of the invention (into which a recombinant expression vector encoding a LMP has been introduced, or which contains a wild-type or altered LMP gene in it's genome) in a suitable medium until LMP is produced. In another embodiment, the method further comprises isolating LMPs from the medium or the host cell.

Another aspect of the invention pertains to isolated LMPs, and biologically active portions thereof. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of LMP in which the protein is separated from cellular components of the cells in which it is naturally or recombinantly produced. In one embodiment, the language "substantially free of cellular material" includes preparations of LMP having less than about 30% (by dry weight) of non-LMP (also referred to herein as a "contaminating protein"), more preferably less than about 20% of non-LMP, still more preferably less than about 10% of non-LMP, and most preferably less than about 5% non-LMP. When the LMP or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of LMP in which the protein is separated from chemical precursors or other chemicals which are involved in the synthesis of the protein. In one embodiment, the language "substantially free of chemical precursors or other chemicals" includes preparations of LMP having less than about 30% (by dry weight) of chemical precursors or non-LMP chemicals, more preferably less than about 20% chemical precursors or non-LMP chemicals, still more preferably less than about 10% chemical precursors or non-LMP chemicals, and most preferably less than about 5% chemical precursors or non-LMP chemicals. In preferred embodiments, isolated proteins or biologically active portions thereof lack contaminating proteins from the same organism from which the LMP is derived. Typically, such proteins are produced by recombinant expression of, for example, an *Arabidopsis thaliana* LMP in other plants than *Arabidopsis thaliana* or microorganisms, algae or fungi.

An isolated LMP or a portion thereof of the invention can participate in the metabolism of compounds necessary for the production of seed storage compounds in *Arabidopsis thaliana*, or of cellular membranes, or has one or more of the activities set forth in Table 4. In preferred embodiments, the protein or portion thereof comprises an amino acid sequence which is sufficiently homologous to an amino acid sequence encoded by a nucleic acid of the Figures such that the protein or portion thereof maintains the ability to participate in the metabolism of compounds necessary for the construction of cellular membranes in *Arabidopsis thaliana*, or in the transport of molecules across these membranes. The portion of the protein is preferably a biologically active portion as described herein. In another preferred embodiment, a LMP of the invention has an amino acid sequence encoded by a nucleic acid of the Figures. In yet another preferred embodiment, the LMP has an amino acid sequence which is encoded by a nucleotide sequence which hybridizes, e.g., hybridizes under stringent conditions, to a nucleotide sequence of the Figures. In still another preferred embodiment, the LMP has an amino acid sequence which is encoded by a nucleotide sequence that is at least about 50-60%, preferably at least about 60-70%, more preferably at least about 70-80, 80-90%, 90-95%, and even more preferably at least about 96%, 97%, 98%, 99% or more homologous to one of the amino acid sequences encoded by a nucleic acid of the Figures. The preferred LMPs of the present invention also preferably possess at least one of the LMP activities described herein. For example, a preferred LMP of the present invention includes an amino acid sequence encoded by a nucleotide sequence which hybridizes, e.g., hybridizes under stringent conditions, to a nucleotide sequence of the Figures, and which can participate in the metabolism of compounds necessary for the construction of cellular membranes in *Arabidopsis thaliana*, or in the transport of molecules across these membranes, or which has one or more of the activities set forth in Table 4.

In other embodiments, the LMP is substantially homologous to an amino acid sequence encoded by a nucleic acid of the Figures and retains the functional activity of the protein of one of the sequences encoded by a nucleic acid of the Figures yet differs in amino acid sequence due to natural variation or mutagenesis, as described in detail above. Accordingly, in another embodiment, the LMP is a protein which comprises an amino acid sequence which is at least about 50-60%, preferably at least about 60-70%, and more preferably at least about 70-80, 80-90, 90-95%, and most preferably at least about 96%, 97%, 98%, 99% or more homologous to an entire amino acid sequence and which has at least one of the LMP activities described herein. In another embodiment, the invention pertains to a full *Arabidopsis thaliana* protein which is substantially homologous to an entire amino acid sequence encoded by a nucleic acid of the Figures.

Homologues of the LMP can be generated by mutagenesis, e.g., discrete point mutation or truncation of the LMP. As used herein, the term "homologue" refers to a variant form of the LMP which acts as an agonist or antagonist of the activity of the LMP. An agonist of the LMP can retain substantially the same, or a subset, of the biological activities of the LMP. An antagonist of the LMP can inhibit one or more of the activities of the naturally occurring form of the LMP, by, for example, competitively binding to a downstream or upstream member of the cell membrane component metabolic cascade which includes the LMP, or by binding to a LMP which mediates transport of compounds across such membranes, thereby preventing translocation from taking place.

In an alternative embodiment, homologues of the LMP can be identified by screening combinatorial libraries of mutants, e.g., truncation mutants, of the LMP for LMP agonist or antagonist activity. In one embodiment, a variegated library of LMP variants is generated by combinatorial mutagenesis at the nucleic acid level and is encoded by a variegated gene library. A variegated library of LMP variants can be produced by, for example, enzymatically ligating a mixture of synthetic oligonucleotides into gene sequences such that a degenerate set of potential LMP sequences is expressible as individual polypeptides, or alternatively, as a set of larger fusion proteins (e.g., for phage display) containing the set of LMP sequences therein. There are a variety of methods which can be used to produce libraries of potential LMP homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential LMP sequences. Methods for synthesizing degenerate oligonucleotides are known in the art (see, e.g., Narang 1983, Tetrahedron 39:3; Itakura et al. 1984, Annu. Rev. Biochem. 53:323; Itakura et al. 1984, Science 198:1056; Ike et al. 1983, Nucleic Acids Res. 11:477).

In addition, libraries of fragments of the LMP coding sequences can be used to generate a variegated population of LMP fragments for screening and subsequent selection of homologues of a LMP. In one embodiment, a library of coding sequence fragments can be generated by treating a double stranded PCR fragment of a LMP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the LMP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of LMP homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify LMP homologues (Arkin & Yourvan 1992, Proc. Natl. Acad. Sci. USA 89:7811-7815; Delgrave et al. 1993, Protein Engineering 6:327-331).

In another embodiment, cell based assays can be exploited to analyze a variegated LMP library, using methods well known in the art.

The nucleic acid molecules, proteins, protein homologues, fusion proteins, primers, vectors, and host cells described herein can be used in one or more of the following methods: identification of *Arabidopsis thaliana* and related organisms; mapping of genomes of organisms related to *Arabidopsis thaliana*; identification and localization of *Arabidopsis thaliana* sequences of interest; evolutionary studies; determination of LMP regions required for function; modulation of a LMP activity; modulation of the metabolism of one or more cell functions; modulation of the transmembrane transport of one or more compounds; and modulation of seed storage compound accumulation.

The plant *Arabidopsis thaliana* represents one member of higher (or seed) plants. It is related to other plants such as *Brassica napus* or soybean which require light to drive photosynthesis and growth. Plants like *Arabidopsis thaliana* and *Brassica napus* share a high degree of homology on the DNA sequence and polypeptide level, allowing the use of heterologous screening of DNA molecules with probes evolving from other plants or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of *Arabidopsis* genomes, or of genomes of related organisms.

The LMP nucleic acid molecules of the invention have a variety of uses. First, they may be used to identify an organism as being *Arabidopsis thaliana* or a close relative thereof. Also, they may be used to identify the presence of *Arabidopsis thaliana* or a relative thereof in a mixed population of microorganisms. The invention provides the nucleic acid sequences of a number of *Arabidopsis thaliana* genes; by probing the extracted genomic DNA of a culture of a unique or mixed population of microorganisms under stringent conditions with a probe spanning a region of an *Arabidopsis thaliana* gene which is unique to this organism, one can ascertain whether this organism is present.

Further, the nucleic acid and protein molecules of the invention may serve as markers for specific regions of the genome. This has utility not only in the mapping of the genome, but also for functional studies of *Arabidopsis thaliana* proteins. For example, to identify the region of the genome to which a particular *Arabidopsis thaliana* DNA-binding protein binds, the *Arabidopsis thaliana* genome could be digested, and the fragments incubated with the DNA-binding protein. Those which bind the protein may be additionally probed with the nucleic acid molecules of the invention, preferably with readily detectable labels; binding of such a nucleic acid molecule to the genome fragment enables the localization of the fragment to the genome map of *Arabidopsis thaliana*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related plants.

The LMP nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein which are essential for the functioning of the enzyme. This type of determination is of value for protein engineering studies and may give an indication of what the protein can tolerate in terms of mutagenesis without losing function.

Manipulation of the LMP nucleic acid molecules of the invention may result in the production of LMPs having functional differences from the wild-type LMPs. These proteins may be improved in efficiency or activity, may be present in greater numbers in the cell than is usual, or may be decreased in efficiency or activity.

There are a number of mechanisms by which the alteration of a LMP of the invention may directly affect the accumulation of seed storage compounds. In the case of plants expressing LMPs, increased transport can lead to altered accumulation of compounds and/or solute partitioning within the plant tissue and organs which ultimately could be used to affect the accumulation of one or more seed storage compounds during seed development. An example is provided by Mitsukawa et al. (1997, Proc. Natl. Acad. Sci. USA 94:7098-7102), where over expression of an *Arabidopsis* high-affinity phosphate transporter gene in tobacco cultured cells enhanced cell growth under phosphate-limited conditions. Phosphate availability also affects significantly the production of sugars and metabolic intermediates (Hurry et al. 2000, Plant J. 24:383-396) and the lipid composition in leaves and roots (Härtel et al. 2000, Proc. Natl. Acad. Sci. USA 97:10649-10654). Likewise, the activity of the plant ACCase has been demonstrated to be regulated by phosphorylation (Savage & Ohlrogge 1999, Plant J. 18:521-527) and alterations in the activity of the kinases and phosphatases (LMPs) that act on the ACCase could lead to increased or decreased levels of seed lipid accumulation. Moreover, the presence of lipid kinase activities in chloroplast envelope membranes suggests that signal transduction pathways and/or membrane protein regulation occur in envelopes (see, e.g., Müller et al. 2000, J. Biol. Chem. 275:19475-19481 and literature cited therein). The ABI1 and ABI2 genes encode two protein serine/threonine phosphatases 2C, which are regulators in abscisic acid signaling pathway, and thereby in early and late seed development (e.g. Merlot et al. 2001, Plant J. 25:295-303). For more examples see also the section 'background of the invention'.

The present invention also provides antibodies which specifically binds to an LMP-polypeptide, or a portion thereof, as encoded by a nucleic acid disclosed herein or as described herein.

Antibodies can be made by many well-known methods (see, e.g. Harlow and Lane, "Antibodies; A Laboratory Manual" Cold Spring Harbor Laboratory, Cold Spring Harbor, N.Y., 1988). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced (see, for example, Kelly et al. 1992, Bio/Technology 10:163-167; Bebbington et al. 1992, Bio/Technology 10: 169-175).

The phrase "selectively binds" with the polypeptide refers to a binding reaction which is determinative of the presence of the protein in a heterogeneous population of proteins and other biologics. Thus, under designated immunoassay conditions, the specified antibodies bound to a particular protein do not bind in a significant amount to other proteins present in the sample. Selective binding to an antibody under such conditions may require an antibody that is selected for its specificity for a particular protein. A variety of immunoassay formats may be used to select antibodies that selectively bind with a particular protein. For example, solid-phase ELISA immunoassays are routinely used to select antibodies selectively immunoreactive with a protein. See Harlow and Lane "Antibodies, A Laboratory Manual" Cold Spring Harbor Publications, New York (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "Basic and Clinical Immunology," (Lange Medical Publications, Los Altos, Calif., Fourth Edition) and references cited therein, and in Harlow and Lane ("Antibodies, A Laboratory Manual" Cold Spring Harbor Publications, New York, 1988).

Throughout this application, various publications are referenced. The disclosures of all of these publications and those references cited within those publications in their entireties are hereby incorporated by reference into this application in order to more filly describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and Examples be considered as exemplary only, with a true scope and spirit of the invention being indicated by the claims included herein.

EXAMPLES

Example 1

General Processes a) General Cloning Processes:

Cloning processes such as, for example, restriction cleavages, agarose gel electrophoresis, purification of DNA fragments, transfer of nucleic acids to nitrocellulose and nylon membranes, linkage of DNA fragments, transformation of *Escherichia coli* and yeast cells, growth of bacteria and sequence analysis of recombinant DNA were carried out as described in Sambrook et al. (1989, Cold Spring Harbor Laboratory Press: ISBN 0-87969-309-6) or Kaiser, Michaelis and Mitchell (1994, "Methods in Yeast Genetics", Cold Spring Harbor Laboratory Press: ISBN 0-87969-451-3).

b) Chemicals:

The chemicals used were obtained, if not mentioned otherwise in the text, in p.a. quality from the companies Fluka (Neu-Ulm), Merck (Darmstadt), Roth (Karlsruhe), Serva (Heidelberg) and Sigma (Deisenhofen). Solutions were prepared using purified, pyrogen-free water, designated as $H_2O$ in the following text, from a Milli-Q water system water purification plant (Millipore, eschborn). Restriction endonucleases, DNA-modifying enzymes and molecular biology kits were obtained from the companies AGS (Heidelberg), Amersham (Braunschweig), Biometra (Göttingen), Boehringer (Mannheim), Genomed (Bad Oeynhausen), New England Biolabs (Schwalbach/Taunus), Novagen (Madison, Wis., USA), Perkin-Elmer (Weiterstadt), Pharmacia (Freiburg), Qiagen (Hilden) and Stratagene (Amsterdam, Netherlands). They were used, if not mentioned otherwise, according to the manufacturer's instructions.

c) Plant Material:

For this study, in one series of experiments, root material of wild-type and pickle mutant plants of *Arabidopsis thaliana* were used. The pkl mutation was isolated from an ethyl methanesulfonate-mutagenized population of the Columbia ecotype as described (Ogas et al. 1997, Science 277:91-94; Ogas et al. 1999, Proc. Natl. Acad. Sci. USA 96:13839-13844). In other series of experiments, siliques of individual ecotypes of *Arabidopsis thaliana* and of selected *Arabidopsis* phytohormone mutants were used. Seeds were obtained from the *Arabidopsis* stock center.

d) Plant Growth:

Plants were either grown on Murashige-Skoog medium as described in Ogas et al. (1997, Science 277:91-94; 1999, Proc. Natl. Acad. Sci. USA 96:13839-13844) or on soil under standard conditions as described in Focks & Benning (1998, Plant Physiol. 118:91-101).

Example 2

Total DNA Isolation from Plants

The details for the isolation of total DNA relate to the working up of one gram fresh weight of plant material.

CTAB buffer: 2% (w/v) N-cethyl-N,N,N-trimethylammonium bromide (CTAB); 100 mM Tris HCl pH 8.0; 1.4 M NaCl; 20 mM EDTA. N-Laurylsarcosine buffer:10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 1 of N-laurylsarcosine buffer, 20 1 of -mercaptoethanol and 10 1 of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000 g and RT for 15 min in each case. The DNA was then precipitated at −70° C. for 30 min using ice-cold isopropanol. The precipitated DNA was sedimented at 4° C. and 10,000 g for 30 min and resuspended in 180 1 of TE buffer (Sambrook et al. 1989, Cold Spring Harbor Laboratory Press: ISBN 0-87969-309-6). For further purification, the DNA was treated with NaCl (1.2 M final concentration) and precipitated again at −70° C. for 30 min using twice the volume of absolute ethanol. After a washing step with 70% ethanol, the DNA was dried and subsequently taken up in 50 1 of $H_2O$+RNAse (50 mg/ml final concentration). The DNA was dissolved overnight at 4° C. and the RNAse digestion was subsequently carried out at 37° C. for 1 h. Storage of the DNA took place at 4° C.

Example 3

Isolation of Total RNA and poly-(A)+ RNA from Plants

For the investigation of transcripts, both total RNA and poly-(A)$^+$ RNA were isolated. RNA is isolated from siliques of *Arabidopsis* plants according to the following procedure:

RNA Preparation from *Arabidopsis* Seeds—"Hot" Extraction:

1. Buffers, Enzymes and Solution
   2M KCl
   Proteinase K
   Phenol (for RNA)
   Chloroform:Isoamylalcohol
      (Phenol:choloroform 1:1; pH adjusted for RNA)
   4 M LiCl, DEPC-treated
   DEPC-treated water
   3M NaOAc, pH 5, DEPC-treated
   Isopropanol
   70% ethanol (made up with DEPC-treated water)
   Resuspension buffer: 0.5% SDS, 10 mM Tris pH 7.5, 1 mM EDTA made up with DEPC-treated water as this solution can not be DEPC-treated
   Extraction Buffer:
      0.2M Na Borate
      30 mM EDTA
      30 mM EGTA
      1% SDS (250 µl of 10% SDS-solution for 2.5 ml buffer)
      1% Deoxycholate (25 mg for 2,5 ml buffer)
      2% PVPP (insoluble—50 mg for 2.5 ml buffer)
      2% PVP 40K (50 mg for 2.5 ml buffer)
      10 mM DTT
      100 mM β-Mercaptoethanol (fresh, handle under fume hood—use 35 µl of 14.3M solution for 5 ml buffer)

2. Extraction
   Heat extraction buffer up to 80° C. Grind tissue in liquid nitrogen-cooled mortar, transfer tissue powder to 1.5 ml tube. Tissue should kept frozen until buffer is added so transfer the sample with pre-cooled spatula and keep the tube in liquid nitrogen all time. Add 350 µl preheated extraction buffer (here for 100 mg tissue, buffer volume can be as much as 500 µl for bigger samples) to tube, vortex and heat tube to 80° C. for ~1 min. Keep then on ice. Vortex sample, grind additionally with electric mortar.

3. Digestion
   Add Proteinase K (0.15 mg/100 mg tissue), vortex and keep at 37° C. for one hour.

4. First Purification
   Add 27 µl 2M KCl. Chill on ice for 10 min. Centrifuge at 12.000 rpm for 10 minutes at room temperature. Transfer supernatant to fresh, RNAase-free tube and do one phenol extraction, followed by a choloroform:isoamylalcohol extraction. Add 1 vol. isopropanol to supernatant and chill on ice for 10 min. Pellet RNA by centrifugation (7000 rpm for 10 min at RT). Resolve pellet in 1 ml 4M LiCl by 10 to 15 min vortexing. Pellet RNA by 5 min centrifugation.

5. Second Purification
   Resuspend pellet in 500 µl Resuspension buffer. Add 500 µl phenol and vortex. Add 250 µl chloroform:isoamylalcohol and vortex. Spin for 5 min. and transfer supernatant to fresh tube. Repeat choloform:isoamylalcohol extraction until interface is clear. Transfer supernatant to fresh tube and add 1/10 vol 3M NaOAc, pH 5 and 600 µl isopropanol. Keep at −20 for 20 min or longer. Pellet RNA by 10 min centrifugation. Wash pellet once with 70% ethanol. Remove all remaining alcohol before resolving pellet with 15 to 20 µl DEPC-water. Determine quantity and quality by measuring the absorbance of a 1:200 dilution at 260 and 280 nm. 40 µg RNA/ml=1$OD_{260}$ RNA from roots of wild-type and the pickle mutant of *Arabidopsis* is isolated as described (Ogas et al. 1997, Science 277:91-94; Ogas et al. 1999, Proc. Natl. Acad. Sci. USA 96:13839-13844).

The mRNA is prepared from total RNA, using the Amersham Pharmacia Biotech mRNA purification kit, which utilizes oligo(dT)-cellulose columns.

Isolation of Poly-(A)+ RNA was isolated using Dyna Beads® (Dynal, Oslo, Norway) following the instructions of the manufacturer's protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

Example 4 cDNA Library Construction

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 h), 16° C. (1 h) and 22° C. (1 h). The reaction was stopped by incubation at 65° C. (10 min) and subsequently transferred to ice. Double stranded DNA molecules were blunted by T4-DNA-polymerase (Roche, Mannheim) at 37° C. (30 min). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 min). This mixture was subjected to separation on a low melting agarose gel. DNA molecules larger than 300 base pairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 5

Identification of LMP Genes of Interest

The pickle *Arabidopsis* mutant was used to identify LMP-encoding genes. The pickle mutant accumulates seed storage compounds, such as seed storage lipids and seed storage proteins, in the root tips (Ogas et al. 1997, Science 277:91-94; Ogas et al. 1999, Proc. Natl. Acad. Sci. USA 96:13839-13844). mRNA isolated from roots of wild-type and pickle plants was used to create a subtracted and normalized cDNA library (SSH library) containing cDNAs that are only present in the pickle roots, but not in the wild-type roots. Clones from the SSH library were spotted onto nylon membranes and hybridized with radio-labeled pickle or wild-type root mRNA to ascertain that the SSH clones were more abundant in pickle roots compared to wild-type roots. These SSH clones were randomly sequenced and the sequences were annotated (see Example 9). Based on the expression levels and on these initial functional annotations (see Table 4), clones from the SSH library were identified as potential LMP-encoding genes.

Other LMP candidate genes were identified by selecting various *Arabidopsis* phytohormone mutants (e.g. obtained from EMS treatment) from the *Arabidopsis* stock center. These mutants and control wild-type plants were grown under standard conditions in growth chambers and screened for the accumulation of seed storage compounds. Mutants showing altered levels of seed storage lipids were considered as having a mutation in a LMP candidate gene and were investigated further. Table 3 contains the phytohormone mutants that showed the largest decrease in seed storage lipids. Based on our finding that some mutants had significantly decreased seed oil content we selected the respective wild-type allele or other enzymes in the same pathway as LMP-encoding genes (see table 4, sequence codes pk095, pk096, pk097, pk098, pk099, pk199, pk105 and pk107).

TABLE 3

Total fatty acid content in seeds of selected phytohormone mutants

| Allele | Phenotype | FA (g/g) Analysis of the first generation of seeds | FA (g/g) Analysis of the next generation of seeds |
| --- | --- | --- | --- |
| Ler-0 wild type | | 0.35 ± 0.02 | 0.35 ± 0.02 |
| abi1-1 (in Ler background) | ABA-insensitive | 0.33 ± 0.01 | 0.34 ± 0.02 |
| abi2-1 (in Ler background) | ABA-insensitive | 0.34 ± 0.03 | 0.37 ± 0.02 |
| abi3-1 (in Ler background) | ABA-insensitive | 0.29 ± 0.02 | 0.29 ± 0.02 |
| Col wild type | | 0.35 ± 0.02 | 0.35 ± 0.01 |
| axr2 (in Col background) | Auxin-resistant | 0.28 ± 0.02 | 0.28 ± 0.02 |
| etr1-1 (in Col background) | Ethylene-insensitive | 0.27 ± 0.03 | 0.29 ± 0.02 |
| ein5-1 (in Col background) | Ethylene-insensitive | 0.29 ± 0.03 | 0.30 ± 0.03 |
| Ein7 (in Col background) | Ethylene-insensitive | 0.29 ± 0.02 | 0.30 ± 0.01 |

TABLE 4

Putative LMP Functions

| Sequence code | Function | SEQ ID NO: |
| --- | --- | --- |
| Pk002b | Hypothetical protein - *Arabidopsis thaliana* | 1 |
| Pk020b | Unknown protein - conserved hypothetical protein SPCG330.09 *Schizosaccharomyces pombe* | 3 |
| Pk033 | Hypothetical protein- *A. thaliana* chromosome II BAC T08I13 genomic | 5 |
| Pk037 | 65 kDa regulatory subunit of protein phosphatase 2A, PP2A-A | 7 |
| Pk038 | Beta-1,3-glucanase class I precursor | 9 |
| Pk042a | ATP dependent copper transporter - Arabidopsis | 11 |
| Pk053b | unknown protein - *Arabidopsis thaliana* | 13 |
| Pk060 | Sequence of BAC T22H22 from *Arabidopsis thaliana* | 15 |
| Pk063b | putative malate dehydrogenase - *Arabidopsis thaliana* | 17 |

TABLE 4-continued

Putative LMP Functions

| Sequence code | Function | SEQ ID NO: |
|---|---|---|
| Pk064 | late embryogenesis abundant protein - Arabidopsis | 19 |
| Pk073 | gene: "T18B16.210"; product: "putative protein" | 21 |
| Pk082 | Nucleic acid binding protein-like - *Arabidopsis thaliana* | 23 |
| Pk084a | *A. thaliana*, BAC F13K23.10, chromosome 1, | 25 |
| Pk086 | hypothetical protein A_IG002P16.9 - *Arabidopsis thaliana* | 27 |
| Pk088b | putative nonspecific lipid-transfer protein precursor | 29 |
| Pk095 | *A. thaliana* AP2 domain family transcription factor homolog (ABI4) | 31 |
| Pk096 | *Arabidopsis thaliana* putative ethylene receptor (ETR2) | 33 |
| Pk097a | Arabidopsis ethylene-response gene ETR1 | 35 |
| Pk097b | Arabidopsis ethylene-response gene ETR1 like | 37 |
| Pk098 | *Arabidopsis thaliana* IAA17 (F19P19.31), auxin response gene | 39 |
| Pk099 | *A. thaliana* IAA7 (IAA7) gene, primary auxin-responsive genes | 41 |
| Pk100 | ABI3 gene; abscisic acid insensitive gene | 43 |
| Pk105 | protein phosphatase 2C involved in ABA signal (abi1) | 45 |
| Pk107 | regulation of ethylene response pathway (ctr1) | 47 |

TABLE 5

Grouping of LMPs based on Functional protein domains

| Functional cateory | SEQ ID: | SEQ Code: | Functional domain | Domain position |
|---|---|---|---|---|
| DNA-binding proteins | 4 | pk020b | HMG-I and HMG-Y DNA-binding domain (A + T-hook) | 206-226 |
| | 8 | pk037 | LexA DNA binding domain | 127-141 |
| | 8 | pk037 | STE-like transcription factor | 7-12 |
| | 20 | pk064 | DM DNA-binding domain | 201-240 |
| | 20 | pk064 | Histone H2B | 209-253 |
| | 24 | pk082 | HMG-I and HMG-Y DNA-binding domain (A + T-hook) | 174-192 |
| | 24 | pk082 | B-box zinc finger superfamily | 212-225 |
| | 26 | pk084a | HMG-I and HMG-Y DNA-binding domain (A + T-hook) | 8-30 |
| | 26 | pk084a | High mobility group proteins HMG1 and HMG2 | 11-35 |
| | 28 | pk086 | GATA-type zinc finger | 38-70 |
| | 32 | pk095 | Ethylene responsive element binding protein | 55-66<br>77-93<br>93-113<br>119-140 |
| | 44 | pk100 | B3 DNA-binding domain | 37-47<br>270-312<br>457-473<br>533-549<br>565-598<br>617-631 |
| Kinases | 36, 38 | pk097a, pk097b | His-kinase A | 351-360,<br>466-475,<br>511-519 |
| | 48 | pk107 | Protein kinase C-terminal domain | 666-700 |
| | 48 | pk107 | Tyrosine kinase catalytic domain | 714-752 |
| | 22 | pk073 | Shikimate kinase | 165-161 |
| | 22 | pk073 | Diacylglycerol kinase accessory domain | 138-161 |
| | 16 | pk060 | Glycerate kinase | 156-181 |

TABLE 5-continued

Grouping of LMPs based on Functional protein domains

| Functional cateory | SEQ ID: | SEQ Code: | Functional domain | Domain position |
|---|---|---|---|---|
| Signal Transduction | 2 | pk002b | Troponin Ca2+ sensitive switch | 336-371 |
| | 2 | pk002b | HMG1 and HMG2 domain | 352-376 |
| | 14 | pk053b | Developmental signaling protein Wnt-1 family | 8-69 |
| | 34 | pk096 | Response regulator receiver domain | 697-710 |
| | 34 | pk096 | Inositol 1,4,5-triphosphate-binding protein receptor | 645-669 |
| | 40 | pk098 | AUX/IAA family domain | 7-22 |
| | | | | 82-95 |
| | | | | 112-143 |
| | | | | 181-210 |
| | 42 | pk099 | AUX/IAA family domain | 6-21 |
| | | | | 82-95 |
| | | | | 126-157 |
| | | | | 194-223 |
| | 46 | Pk105 | Protein phosphatase 2C family | 135-420 |
| Proteases | 6 | pk033 | DnaJ chaperonin central domain | 6-38 |
| | 6 | pk033 | ATP-dependent protease La (LON) domain | 535-569 |
| | 6 | pk033 | Protease-associated (PA) domain | 375-405 |
| | 12 | pk042a | Carboxypeptidase Taq metalloprotease signature | 176-196 |
| | 12 | pk042a | Gamma-glutamyltranspeptidase | 110-164 |
| | 12 | pk042a | E1-E2 ATPase | 127-156 |
| | 12 | pk042a | X-His dipeptidase (M25) signature | 3-20 |
| Carbohydrate metabolism | 10 | pk038 | Beta-1,3-glucanase, Glycoside hydrolase family 17 | 24-334 |
| | 18 | pk063b | Malic enzyme | 45-555 |
| | 30 | pk088b | Lipid transfer protein | 42-56 |
| | | | | 70-95 |
| | 30 | pk088b | Cellulose-binding domain | 56-86 |
| | 30 | pk088b | Mannose-6-phosphate isomerase type II | 150-174 |
| | 30 | pk088b | Glyceraldehyde 3-phosphate dehydrogenase | 137-171 |

Classification of the proteins was done by Blasting against the BLOCKS database (S. Henikoff & J. G. Henikoff, "Protein family classification based on searching a database of blocks", Genomics 19:97-107 (1994)).

Example 6

Cloning of Full-length cDNAs and Binary Plasmids for Plant Transformation

RACE-PCR to Determine Full-length Sequences

Full-length sequences of the *Arabidopsis thaliana* partial cDNAs (ESTs) that were identified in the SSH library and from MegaSort and MPSS EST sequencing in the *Arabidopsis thaliana* EST sequencing program using the annotation program EST-Max were isolated by RACE PCR using the SMART RACE cDNA amplification kit from Clontech allowing both 5'- and 3' rapid amplification of cDNA ends (RACE). The isolation of cDNAs and the RACE PCR protocol used were based on the manufacturer's conditions. The RACE product fragments were extracted from agarose gels with a QIAquick® Gel Extraction Kit (Qiagen) and ligated into the TOPO® pCR 2.1 vector (Invitrogen) following manufacturer's instructions. Recombinant vectors were transformed into TOP10 cells (Invitrogen) using standard conditions (Sambrook et al. 1989). Transformed cells are grown overnight at 37° C. on LB agar containing 50 µg/ml kanamycin and spread with 40 µl of a 40 mg/ml stock solution of X-gal in dimethylformamide for blue-white selection. Single white colonies are selected and used to inoculate 3 ml of liquid LB containing 50 µg/ml kanamycin and grown overnight at 37° C. Plasmid DNA was extracted using the QIAprep® Spin Miniprep Kit (Qiagen) following manufacturer's instructions. Subsequent analyses of clones and restriction mapping was performed according to standard molecular biology techniques (Sambrook et al. 1989). The sequences obtained from the RACE reactions were compiled to give the nucleotide sequences for the LMP genes (SEQ ID NOs: 1, 3, 5, 7, 9, 11, 13, 15, 17, 19, 21, 23, 25, 27, 29, 31, 33, 35, 37, 39, 41, 43, 45 and 47).

RT-PCR and Cloning of *Arabidopsis thaliana* LMP Genes

Full-length LMP cDNAs were isolated by RT-PCR from *Arabidopsis thaliana* RNA. The synthesis of the first strand cDNA was achieved using AMV Reverse Transcriptase (Roche, Mannheim, Germany). The resulting single-stranded cDNA was amplified via Polymerase Chain Reaction (PCR) utilizing two gene-specific primers. The conditions for the reaction were standard conditions with Expand High Fidelity PCR system (Roche). The parameters for the reaction were: five minutes at 94° C. followed by five cycles of 40 seconds at 94° C., 40 seconds at 50° C. and 1.5 minutes at 72° C. This was followed by thirty cycles of 40 seconds at 94° C., 40 seconds at 65° C. and 1.5 minutes at 72° C. The fragments generated under these RT-PCR conditions were analyzed by agarose gel electrophoresis to make sure that PCR products of the expected length had been obtained.

Full-length LMP cDNA were isolated by using synthetic oligonucleotide primers (MWG-Biotech) designed based on the LMP gene specific DNA sequence that was determined by EST sequencing and by sequencing of RACE PCR products. All 5' PCR primers ("forward primer", F) contained an AscI restriction site 5' upstream of the ATG start codon. All 3' PCR primers ("reverse primers", R) contained a PacI restriction site 3' downstream of the stop codon. The restriction sites were added so that the RT-PCR amplification products could be cloned into the AscI and PacI restriction sites located in the multiple cloning site of the binary vector pBPS-GB1. The first 2 nucleotides are used as spacers so the restriction enzymes cut properly. The following "forward" (F) and "reverse" (R) primers were used to amplify the full-length *Arabidopsis thaliana* cDNAs by RT-PCR using RNA from Physcomitrella as original template:

```
For amplification of SEQ ID NO:1
Pk002F (5'-ATGGCGCGCCATGGTTCGTCCTGGATTCATTATGC-3')     (SEQ ID NO:49)
pk002R (5'-GCTTAATTAATCAGGCTTTGGATTTTACCGGGAC-3')      (SEQ ID NO:50)

For amplification of SEQ ID NO:3
pk020F (5'-ATGGCGCGCCGGGGAGGCCACCAAGAAAGTGCTG-3')      (SEQ ID NO:51)
pk020R (5'-TCTTAATTAAGCTACATTTATCATTGCCGGCCTC-3')      (SEQ ID NO:52)

For amplification of SEQ ID NO:5
pk033F (5'-ATGGCGCGCCGAGCCGTTATTAGTTTTCATTCAAGGG-3')   (SEQ ID NO:53)
pk033R (5'-AGTTAATTAATCTTAACTTACCAAGGAGCCGACAAA-3')    (SEQ ID NO:54)

For amplification of SEQ ID NO:7
pk037F (5'-ATTGGCGCGCCTGGTGTTGCAGTGATTTGATTC-3')       (SEQ ID NO:55)
pk037R (3'-GCGTTAATTAAGCAGTTCATAGCCAGCAACCAA-5')       (SEQ ID NO:56)

For amplification of SEQ ID NO:9
pk038F (5'-ATGGCGCGCCATGACCACGTTATTCCTCCTTATTGC-3')    (SEQ ID NO:57)
pk038R (5'-GCTTAATTAACATCACTCAACCGCCGTACCGTC-3')       (SEQ ID NO:58)

For amplification of SEQ ID NO:11
pk042F (5'-ATGGCGCGCCGGGCAAAGGCCATTGTCGAGT-3')         (SEQ ID NO:59)
pk042R (5'-GCTTAATTAACCGGTACTCGGTTTAGTTCAATTT-3')      (SEQ ID NO:60)

For amplification of SEQ ID NO:13
pk053F (5'-ATGGCGCGCCCATGGATGTCTTGTTTCTCGATCTG-3')     (SEQ ID NO:61)
pk053R (5'-GCTTAATTAAGATTTCTGACTTTGAATGGAAATGG-3')     (SEQ ID NO:62)

For amplification of SEQ ID NO:15
pk060F (5'-ATGGCGCGCCGAATCAGAAATTGGGCGAAGAAG-3')       (SEQ ID NO:63)
pk060R (5'-GCTTAATTAACACAACAATCACTAGCTCAGAAGAGC-3')    (SEQ ID NO:64)

For amplification of SEQ ID NO:17
pk063F (5'-ATGGCGCGCCATGGAGAAAGTGACCAACTCAGACT-3')     (SEQ ID NO:65)
pk063R (5'-GCTTAATTAATTCAACGGTAGAGACGGTATGTGGG-3')     (SEQ ID NO:66)

For amplification of SEQ ID NO:19
pk064F (5'-ATGGCGCGCCAGAAAAAAGCAATGGCGTCAGAC-3')       (SEQ ID NO:67)
pk064R (5'-GCTTAATTAACTCACAGCTTTCCCTTATCTTTCC-3')      (SEQ ID NO:68)

For amplification of SEQ ID NO:21
pk073F (5'-ATGGCGCGCCGCCAGAGGACGAGACAAGGGG-3')         (SEQ ID NO:69)
pk073R (5'-GCTTAATTAACCATTGGGGATGGTCTAAGTTTCC-3')      (SEQ ID NO:70)

For amplification of SEQ ID NO:23
pk082F (5'-ATGGCGCGCCATGGAAGGTGGAGCTGCTCTC-3')         (SEQ ID NO:71)
pk082R (5'-GCTTAATTAAGCCAAATAAAGACAGATCGAGGG-3')       (SEQ ID NO:72)

For amplification of SEQ ID NO:25
pk084F (5'-ATGGCGCGCCATGGGTCATCACAGTCTTCGC-3')         (SEQ ID NO:73)
pk084R (5'-GCTTAATTAATCAATAGTGTAGAAACCTAACAAGTATTGG-3')(SEQ ID NO:74)

For amplification of SEQ ID NO:27
pk086F (5'-ATGGCGCGCCCAAGGGGGTCTCTGTCGGTTC-3')         (SEQ ID NO:75)
pk086R (5'-GCTTAATTAACATCATCATTGCTCTCCAAACCC-3')       (SEQ ID NO:76)

For amplification of SEQ ID NO:29
pk088F (5'-ATGGCGCGCCGAGAAGAAGAATCAAAATCCCACACA-3')    (SEQ ID NO:77)
pk088R (5'-GCTTAATTAAGCGATAGATCGAATAAAAGGACCA-3')      (SEQ ID NO:78)

For amplification of SEQ ID NO:31
pk095F (5'-ATGGCGCGCCCCTTCTTGATTCGTCCTCTCCACT-3')      (SEQ ID NO:79)
pk095R (5'-GCTTAATTAACCACCATCTCCTCCGATTCTCTTC-3')      (SEQ ID NO:80)

For amplification of SEQ ID NO:33
pk096F (5'-ATGGCGCGCCATGGTTAAAGAAATAGCTTCTTGGTT-3')    (SEQ ID NO:81)
pk096R (5'-GCTTAATTAATTAGAGAAGTTGGTCAGCTTGCAAC-3')     (SEQ ID NO:82)
```

```
-continued

For amplification of SEQ ID NO:35
pk097F (5'-ATGGCGCGCCATGGAAGTCTGCAATTGTATTGAACC-3')          (SEQ ID NO:83)
pk097R (5'-GCTTAATTAATTACATGCCCTCGTACAGTACCCG-3')           (SEQ ID NO:84)

For amplification of SEQ ID NO:37
pk097F (5'-ATGGCGCGCCATGGAAGTCTGCAATTGTATTGAACC-3')          (SEQ ID NO:85)
pk097R (5'-GCTTAATTAATTACATGCCCTCGTACAGTACCCG-3')           (SEQ ID NO:86)

For amplification of SEQ ID NO:39
pk098F (5'-ATGGCGCGCCATGATGGGCAGTGTCGAGCTG-3')              (SEQ ID NO:87)
pk098R (5'-GCTTAATTAATCAAGCTCTGCTCTTGCACTTCT-3')            (SEQ ID NO:88)

For amplification of SEQ ID NO:41
Pk099F (5'-ATGGCGCGCCATGATCGGCCAACTTATGAACCT-3')            (SEQ ID NO:89)
pk099R (5'-GCTTAATTAATCAAGATCTGTTCTTGCAGTACTTCTC-3')        (SEQ ID NO:90)

For amplification of SEQ ID NO:43
Pk100F (5'-ATGGCGCGCCGGAGAAAATAGTTAGCTTTGGTCGG-3')          (SEQ ID NO:91)
pk100R (5'-GCTTAATTAACCAAACGAGTGGTGCAATTACAC-3')            (SEQ ID NO:92)

For amplification of SEQ ID NO:45
Pk105F (5'-ATGGCGCGCCATGGAGGAAGTATCTCCGGCGATC-3')           (SEQ ID NO:93)
pk105R (5'-GCTTAATTAATCAGTTCAAGGGTTTGCTCTTGAG-3')           (SEQ ID NO:94)

For amplification of SEQ ID NO:47
Pk107F (5'-ATGGCGCGCCATGGAAATGCCCGGTAGAAGATC-3')            (SEQ ID NO:95)
pk107R (5'-GCTTAATTAATTACAAATCCGAGCGGTTGGGCG-3')            (SEQ ID NO:96)
```

Example 7

*Agrobacterium* Mediated Plant Transformation

For plant transformation, binary vectors such as pBinAR can be used (Höfgen & Willmitzer 1990, Plant Sci. 66: 221-230). Plant binary vectors encoding LMP genes were constructed with the aim to achieve the overexpression of functionally active proteins in transgenic plants. All LMP gene candidates were cloned into the plant binary vector pBPS-GB1 vector. The binary vector contains a selecta the AtAct2-I promoter (Ann Y-Q et al., 1996, Plant Journal 10:107-121) and a USP (unknown seed protein, Bäumlein et al., Mol Gen Genet 225: 459-467, 1991) seed-specific promoter driving the candidate LMP gene with the NOSpA terminator. Full-length LMP cDNA were cloned into AscI and PacI restriction sites in the multiple cloning site of pBPS-GB1 in sense orientation behind the USP seed-s vectors (based on pBPS-GB1) containing the genes of interest were transformed into *E. coli* Top10 cells (Invitrogen) using standard conditions. Transformed cells were selected for on LB agar containing an antibiotic and grown overnight at 37° C. Plasmid DNA was extracted using the QIAprep Spin Miniprep Kit (Qiagen) following manufacturer's instructions. Analysis of subsequent clones and restriction mapping was performed according to standard molecular biology techniques (Sambrook et al. 1989, Molecular Cloning, A Laboratory Manual. $2^{nd}$ Edition. Cold Spring Harbor Laboratory Press. Cold Spring Harbor, N.Y.). The nucleotide sequence of the inserted LMP genes was verified by "2+1" sequencing (the insert DNA was sequence by determining the nucleotide sequence of one DNA stand with two independent sequence reactions and the complementary DNA strand with on sequencing reaction according to the Bermuda convention). The full length sequences are shown as SEQ ID NOs: 1, 3, 5, 7, 9, 11, 13, 15, 17, 19, 21, 23, 25, 27, 29, 31, 33, 35, 37, 39, 41, 43, 45 and 47.

*Agrobacterium* mediated plant transformation with binary vectors encoding the LMP nucleic acids described herein was performed using standard transformation and regeneration techniques (Gelvin, Stanton B. & Schilperoort R. A, Plant Molecular Biology Manual, 2nd ed. Kluwer Academic Publ., Dordrecht 1995 in Sect., Ringbuc Zentrale Signatur: BT11-P; Glick, Bernard R. and Thompson, John E. Methods in Plant Molecular Biology and Biotechnology, S. 360, CRC Press, Boca Raton 1993).

The *Agrobacterium* mediated transformation of *Arabidopsis thaliana* was performed using the GV3 (pMP90) (Koncz & Schell, 1986, Mol. Gen. Genet. 204: 383-396) *Agrobacterium tumefaciens* strain. *Arabidopsis thaliana* ecotype Col-2 was grown and transformed according to standard conditions (Bechtold 1993, Acad. Sci. Paris. 316: 1194-1199; Bent et al. 1994, Scienc marker for *Agrobacterium* transformation. The presence and correct orientation of the LMP-encoding binary vectors in *Agrobacterium* cultures was verified by PCR using the LMP gene-specific primers described in example 6. For the plant transformation flowering *Arabidopsis* plants were dipped into the recombinant *Agrobacterium* cultures and allowed to go to seed. Transgenic *Arabidopsis* T1 plants were identified by growing the seeds on Petri plates containing the selection agent appropriate for the selection marker present on the T-DNA. Surviving healthy seedlings were transferred to soil and grown in a growth chamber under controlled conditions. T2 seeds were harvested from these T1 plants. The transgenic lines were propagated through successive generations and T2, T3 and T4 seeds were obtained. The segregation ratio of the presence or absence of the T-DNA was monitored in order to determine whether the lines contained single-locus or multi-locus insertions and whether the lines were homozygous or heterozygous for the T-DNA insertion. T2, T3 and T4 seeds were analyzed for seed oil content (see also example 8).

*Agrobacterium* mediated plant transformation is also applicable to *Brassica* and other crops. In particular, seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. The seed coats are removed and the seeds are air dried overnight in a half-open sterile Petri dish. During this period, the seeds lose approximately 85% of their water content. The seeds are then stored at room temperature in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature, and re-suspended in MS (Murashige & Skoog 1962, Physiol. Plant. 15: 473-497) medium supplemented with 100 µM acetosyringone. Bacteria cultures are incubated in this pre-induction medium for 2 hours at room temperature before use. The axis of soybean zygotic seed embryos at approximately 44% moisture content are imbibed for 2 hours at room temperature with the pre-induced *Agrobacterium* suspension culture. (The imbibition of dry embryos with a culture of *Agrobacterium* is also applicable to maize embryo axes). The embryos are removed from the imbibition culture and are transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/l carbenicillin or 300 mg/l cefotaxime to kill the agrobacteria. The liquid medium is used to moisten the sterile filter paper. The embryos are incubated during 4 weeks at 25° C., under 440 µmol $m^{-2}sec^{-1}$ and 12 hours photoperiod. Once the seedlings have produced roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 440 µmol $m^{-2}s^{-1}$ light intensity and 12 h photoperiod for about 80 days.

Samples of the primary transgenic plants ($T_0$) are analyzed by PCR to confirm the presence of T-DNA. These results are confirmed by Southern hybridization wherein DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labeled probe by PCR, and used as recommended by the manufacturer.

Transformation of soybean can be performed using for example a technique described in EP 424 047, U.S. Pat. No. 5,322,783 (Pioneer Hi-Bred International) or in EP 0397 687, U.S. Pat. No. 5,376,543 or U.S. Pat. No. 5,169,770 (University Toledo). Soybean seeds are surface sterilized with 70% ethanol for 4 minutes at room temperature with continuous shaking, followed by 20% (v/v) Clorox supplemented with 0.05% (v/v) Tween for 20 minutes with continuous shaking. Then the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

Example 8

Analysis of the Impact of Recombinant LMPs on the Production of a Desired Seed Storage Compound: Fatty Acid Production The total fatty acid content of *Arabidopsis* seeds was determined by saponification of seeds in 0.5 M KOH in methanol at 80° C. for 2 h followed by LC-MS analysis of the free fatty acids. Total fatty acid content of seeds of control and transgenic plants was measured with bulked seeds (usually 5 mg seed weight) of a single plant. Three different types of controls have been used: Col-2 (Columbia-2, the *Arabidopsis* ecotypes LMP gene of interest have been transformed in), C-24 (an *Arabidopsis* ecotype found to accumulate high amounts of total fatty acids in seeds) and BPS empty (without LMP gene of interest) binary vector construct. The controls indicated in the tables below have been grown side by side with the transgenic lines. Differences in the total values of the controls are explained either by differences in the growth conditions, which were found to be very sensitive to small variations in the plant cultivation, or by differences in the standards added to quantify the fatty acid content. Because of the seed bulking all values obtained with T2 seeds and in part also with T3 seeds are the result of a mixture of homozygous (for the gene of interest) and heterozygous events, implying that these data underestimate the LMP gene effect.

TABLE 6

Determination of the T2 seed total fatty acid content of transgenic lines of pk002b (containing SEQ ID NO: 1). Shown are the means (± standard deviation). (Average mean values are shown ± standard deviation, number of individual measurements per plant line: 12-18; Col-2 is the Arabidopsis ecotype the LMP gene has been transformed in, C-24 is a high-oil Arabidopsis ecotype used as another control)

| Genotype | g total fatty acids/ g seed weight |
|---|---|
| C-24 wild-type seeds | 0.513 ± 0.042 |
| Col-2 wild-type seeds | 0.462 ± 0.053 |
| pk002b transgenic seeds | 0.487 ± 0.047 |

TABLE 7

Determination of the T2 seed total fatty acid content of transgenic lines of pk020b (containing SEQ ID NO: 3). Shown are the means (± standard deviation) of 10 (Col-2) and - 9 (pk020b) individual plants, respectively.

| Genotype | g total fatty acids/ g seed weight |
|---|---|
| Col-2 wild-type seeds | 0.353 ± 0.045 |
| pk020b transgenic seeds | 0.402 ± 0.050 |

TABLE 8

Determination of the T2 seed total fatty acid content of transgenic lines of pk033 (containing SEQ ID NO: 5). Shown are the means (± standard deviation) of 9 (Col-2) and 18 (pk033) individual plants, respectively.

| Genotype | g total fatty acids/ g seed weight |
|---|---|
| Col-2 wild-type seeds | 0.481 ± 0.034 |
| Pk033 transgenic seeds | 0.507 ± 0.047 |

TABLE 9

Determination of the T2 seed total fatty acid content of transgenic lines of pk037 (containing SEQ ID NO: 7). Shown are the means (± standard deviation) of 10 (Col-2) and 19 (pk037) individual plants, respectively.

| Genotype | g total fatty acids/ g seed weight |
| --- | --- |
| Col-2 wild-type seeds | 0.301 ± 0.028 |
| pk037 transgenic seeds | 0.328 ± 0.026 |

TABLE 10

Determination of the T2 seed total fatty acid content of transgenic lines of pk038 (containing SEQ ID NO: 9). Shown are the means (± standard deviation) of 12-20 individual plants per line.

| Genotype | g total fatty acids/ g seed weight |
| --- | --- |
| C-24 wild-type seeds | 0.366 ± 0.025 |
| Col-2 wild-type seeds | 0.319 ± 0.026 |
| Pk038 transgenic seeds | 0.382 ± 0.028 |

TABLE 11

Determination of the T2 seed total fatty acid content of transgenic lines of pk053b (containing SEQ ID NO: 13). Shown are the means (± standard deviation) of 13-19 individual plants per line.

| Genotype | g total fatty acids/ g seed weight |
| --- | --- |
| Col-2 wild-type seeds | 0.483 ± 0.040 |
| C-24 wild-type seeds | 0.483 ± 0.040 |
| pk053b transgenic seeds | 0.472 ± 0.042 |

TABLE 12

Determination of the T2 seed total fatty acid content of transgenic lines of pk060 (containing SEQ ID NO: 15). Shown are the means (± standard deviation) of 14-18 individual plants per line.

| Genotype | g total fatty acids/ g seed weight |
| --- | --- |
| Col-2 wild-type seeds | 0.406 ± 0.047 |
| pk060 transgenic seeds | 0.435 ± 0.034 |

TABLE 13

Determination of the T2 seed total fatty acid content of transgenic lines of pk063b (containing SEQ ID NO: 17). Shown are the means (± standard deviation) of 16-19 individual plants per line.

| Genotype | g total fatty acids/ g seed weight |
| --- | --- |
| Col-2 wild-type seeds | 0.466 ± 0.036 |
| C-24 wild-type seeds | 0.485 ± 0.046 |
| pk063b transgenic seeds | 0.480 ± 0.064 |

TABLE 14

Determination of the T2 seed total fatty acid content of transgenic lines of pk064 (containing SEQ ID NO: 19). Shown are the means (± standard deviation) of 15-19 individual plants per line.

| Genotype | g total fatty acids/ g seed weight |
| --- | --- |
| Col-2 wild-type seeds | 0.466 ± 0.036 |
| C-24 wild-type seeds | 0.485 ± 0.046 |
| pk064 transgenic seeds | 0.480 ± 0.055 |

TABLE 15

Determination of the T2 seed total fatty acid content of transgenic lines of pk073 (containing SEQ ID NO: 21). Shown are the means (± standard deviation) of 13-17 individual plants per line.

| Genotype | g total fatty acids/ g seed weight |
| --- | --- |
| C-24 wild-type seeds | 0.513 ± 0.042 |
| Col-2 wild-type seeds | 0.462 ± 0.053 |
| pk073 transgenic seeds | 0.498 ± 0.035 |

TABLE 16a

Determination of the T2 seed total fatty acid content of transgenic lines of pk082 (containing SEQ ID NO: 23). Shown are the means (± standard deviation) of 14-19 individual plants per line.

| Genotype | g total fatty acids/ g seed weight |
| --- | --- |
| C-24 wild-type seeds | 0.377 ± 0.041 |
| Col-2 wild-type seeds | 0.358 ± 0.028 |
| pk082 transgenic seeds | 0.381 ± 0.029 |

TABLE 16b

Determination of the T3 seed total fatty acid content of transgenic lines of pk082 (containing SEQ ID NO: 23). Shown are the means (± standard deviation) of 14-19 individual plants per line.

| Genotype | g total fatty acids/ g seed weight |
| --- | --- |
| C-24 wild-type seeds | 0.351 ± 0.026 |
| Col-2 wild-type seeds | 0.326 ± 0.036 |
| pk082-4 transgenic seeds | 0.351 ± 0.021 |
| pk082-10 transgenic seeds | 0.361 ± 0.027 |
| pk082-11 transgenic seeds | 0.342 ± 0.032 |
| pk082-12 transgenic seeds | 0.335 ± 0.019 |

TABLE 17

Determination of the T2 seed total fatty acid content of transgenic lines of pk084 (containing SEQ ID NO: 25). Shown are the means (± standard deviation) of 12-18 individual plants per line.

| Genotype | g total fatty acids/ g seed weight |
|---|---|
| C-24 wild-type seeds | 0.377 ± 0.041 |
| Col-2 wild-type seeds | 0.358 ± 0.028 |
| pk084 transgenic seeds | 0.372 ± 0.042 |

TABLE 18

Determination of the T2 seed total fatty acid content of transgenic lines of pk086 (containing SEQ ID NO: 27). Shown are the means (± standard deviation) of 14-20 individual plants per line.

| Genotype | g total fatty acids/ g seed weight |
|---|---|
| C-24 wild-type seeds | 0.496 ± 0.049 |
| Col-2 wild-type seeds | 0.443 ± 0.036 |
| Pk086 transgenic seeds | 0.472 ± 0.049 |

TABLE 19

Determination of the T2 seed total fatty acid content of transgenic lines of pk088 (containing SEQ ID NO: 29). Shown are the means (± standard deviation) of 14-20 individual plants per line.

| Genotype | g total fatty acids/ g seed weight |
|---|---|
| C-24 wild-type seeds | 0.466 ± 0.033 |
| Col-2 wild-type seeds | 0.372 ± 0.045 |
| Pk088 transgenic seeds | 0.448 ± 0.015 |

TABLE 20

Determination of the T2 seed total fatty acid content of transgenic lines of pk095 (containing SEQ ID NO: 31). Shown are the means (± standard deviation) of 14-20 individual plants per line.

| Genotype | g total fatty acids/ g seed weight |
|---|---|
| C-24 wild-type seeds | 0.439 ± 0.036 |
| Col-2 wild-type seeds | 0.419 ± 0.034 |
| Pk095 transgenic seeds | 0.442 ± 0.037 |

TABLE 21

Determination of the T2 seed total fatty acid content of transgenic lines of pk096 (containing SEQ ID NO: 33). Shown are the means (± standard deviation) of 11-19 individual plants per line.

| Genotype | g total fatty acids/ g seed weight |
|---|---|
| C-24 wild-type seeds | 0.496 ± 0.049 |
| Col-2 wild-type seeds | 0.443 ± 0.036 |
| Pk096 transgenic seeds | 0.472 ± 0.039 |

TABLE 22

Determination of the T2 seed total fatty acid content of transgenic lines of pk097a (containing SEQ ID NO: 35). Shown are the means (± standard deviation) of 14-18 individual plants per line.

| Genotype | g total fatty acids/ g seed weight |
|---|---|
| C-24 wild-type seeds | 0.513 ± 0.042 |
| Col-2 wild-type seeds | 0.462 ± 0.053 |
| Pk097a transgenic seeds | 0.506 ± 0.034 |

TABLE 23

Determination of the T2 seed total fatty acid content of transgenic lines of pk097b (containing SEQ ID NO: 37). Shown are the means (± standard deviation) of 14-18 individual plants per line.

| Genotype | g total fatty acids/ g seed weight |
|---|---|
| C-24 wild-type seeds | 0.513 ± 0.042 |
| Col-2 wild-type seeds | 0.462 ± 0.053 |
| Pk097b transgenic seeds | 0.506 ± 0.034 |

TABLE 24

Determination of the T2 seed total fatty acid content of transgenic lines of pk098 (containing SEQ ID NO: 39). Shown are the means (± standard deviation) of 12-19 individual plants per line.

| Genotype | g total fatty acids/ g seed weight |
|---|---|
| C-24 wild-type seeds | 0.513 ± 0.042 |
| Col-2 wild-type seeds | 0.462 ± 0.053 |
| Pk098 transgenic seeds | 0.489 ± 0.027 |

TABLE 25

Determination of the T2 seed total fatty acid content of transgenic lines of pk099 (containing SEQ ID NO: 41). Shown are the means (± standard deviation) of 11-20 individual plants per line.

| Genotype | g total fatty acids/ g seed weight |
|---|---|
| C-24 wild-type seeds | 0.496 ± 0.049 |
| Col-2 wild-type seeds | 0.443 ± 0.036 |
| Pk099 transgenic seeds | 0.492 ± 0.034 |

TABLE 26

Determination of the T2 seed total fatty acid content of transgenic lines of pk105 (containing SEQ ID NO: 45). Shown are the means (± standard deviation) of 14-20 individual plants per line.

| Genotype | g total fatty acids/ g seed weight |
|---|---|
| C-24 wild-type seeds | 0.439 ± 0.036 |
| Col-2 wild-type seeds | 0.419 ± 0.034 |
| pp84 transgenic seeds | 0.442 ± 0.037 |

TABLE 27a

Determination of the T2 seed total fatty acid content of transgenic lines of pk107 (containing SEQ ID NO: 47). Shown are the means (± standard deviation) of 14-20 individual plants per line.

| Genotype | g total fatty acids/ g seed weight |
| --- | --- |
| C-24 wild-type seeds | 0.496 ± 0.049 |
| Col-2 wild-type seeds | 0.443 ± 0.036 |
| Pk107 transgenic seeds | 0.492 ± 0.059 |

TABLE 27b

Determination of the T3 seed total fatty acid content of transgenic lines of pk107 (containing SEQ ID NO: 47). Shown are the means (± standard deviation) of 18-30 individual plants per line.

| Genotype | g total fatty acids/ g seed weight |
| --- | --- |
| C-24 wild-type seeds | 0.371 ± 0.025 |
| Col-2 wild-type seeds | 0.321 ± 0.028 |
| Pk107-10 transgenic seeds | 0.375 ± 0.023 |
| Pk107-14 transgenic seeds | 0.383 ± 0.023 |
| Pk107-17 transgenic seeds | 0.399 ± 0.024 |

Example 9

Analysis of the Impact of Recombinant Proteins on the Production of a Desired Seed Storage Compound The effect of the genetic modification in plants on a desired seed storage compound (such as a sugar, lipid or fatty acid) can be assessed by growing the modified plant under suitable conditions and analyzing the seeds or any other plant organ for increased production of the desired product (i.e., a lipid or a fatty acid). Such analysis techniques are well known to one skilled in the art, and include spectroscopy, thin layer chromatography, staining methods of various kinds, enzymatic and microbiological methods, and analytical chromatography such as high performance liquid chromatography (see, for example, Ullman 1985, Encyclopedia of Industrial Chemistry, vol. A2, pp. 89-90 and 443-613, VCH: Weinheim; Fallon, A. et al. 1987, Applications of HPLC in Biochemistry in: Laboratory Techniques in Biochemistry and Molecular Biology, vol. 17; Rehm et al., 1993 Product recovery and purification, Biotechnology, vol. 3, Chapter III, pp. 469-714, VCH: Weinheim; Belter, P. A. et al., 1988 Bioseparations: downstream processing for biotechnology, John Wiley & Sons; Kennedy J. F. & Cabral J. M. S. 1992, Recovery processes for biological materials, John Wiley and Sons; Shaeiwitz J. A. & Henry J. D. 1988, Biochemical separations in: Ulmann's Encyclopedia of Industrial Chemistry, Separation and purification techniques in biotechnology, vol. B3, Chapter 11, pp. 1-27, VCH: Weinheim; and Dechow F. J. 1989).

Besides the above-mentioned methods, plant lipids are extracted from plant material as described by Cahoon et al. (1999, Proc. Natl. Acad. Sci. USA 96, 22:12935-12940) and Browse et al. (1986, Anal. Biochemistry 442:141-145). Qualitative and quantitative lipid or fatty acid analysis is described in Christie, William W., Advances in Lipid Methodology. Ayr/Scotland:Oily Press.—(Oily Press Lipid Library; Christie, William W., Gas Chromatography and Lipids. A Practical Guide—Ayr, Scotland:Oily Press, 1989 Repr. 1992.—IX,307 S.—(Oily Press Lipid Library; and "Progress in lipid Research, Oxford: Pergamon Press, 1 (1952)—16 (1977) Progress in the Chemistry of Fats and Other Lipids CODEN.

Unequivocal proof of the presence of fatty acid products can be obtained by the analysis of transgenic plants following standard analytical procedures: GC, GC-MS or TLC as variously described by Christie and references therein (1997 in: Advances on Lipid Methodology 4th ed.: Christie, Oily Press, Dundee, pp. 119-169; 1998). Detailed methods are described for leaves by Lemieux et al. (1990, Theor. Appl. Genet. 80:234-240) and for seeds by Focks & Benning (1998, Plant Physiol. 118:91-101)

Positional analysis of the fatty acid composition at the C-1, C-2 or C-3 positions of the glycerol backbone is determined by lipase digestion (see, e.g., Siebertz & Heinz 1977, Z. Naturforsch. 32c:193-205, and Christie 1987, Lipid Analysis $2^{nd}$ Edition, Pergamon Press, Exeter, ISBN 0-08-023791-6).

A typical way to gather information regarding the influence of increased or decreased protein activities on lipid and sugar biosynthetic pathways is for example via analyzing the carbon fluxes by labeling studies with leaves or seeds using $^{14}C$-acetate or $^{14}C$-pyruvate (see, e.g. Focks & Benning 1998, Plant Physiol. 118:91-101; Eccleston & Ohlrogge 1998, Plant Cell 10:613-621). The distribution of carbon-14 into lipids and aqueous soluble components can be determined by liquid scintillation counting after the respective separation (for example on TLC plates) including standards like $^{14}C$-sucrose and $^{14}C$-malate (Eccleston & Ohlrogge 1998, Plant Cell 10:613-621).

Material to be analyzed can be disintegrated via sonification, glass milling, liquid nitrogen and grinding or via other applicable methods. The material has to be centrifuged after disintegration. The sediment is re-suspended in distilled water, heated for 10 minutes at 100° C., cooled on ice and centrifuged again followed by extraction in 0.5 M sulfuric acid in methanol containing 2% dimethoxypropane for 1 hour at 90° C. leading to hydrolyzed oil and lipid compounds resulting in transmethylated lipids. These fatty acid methyl esters are extracted in petrolether and finally subjected to GC analysis using a capillary column (Chrompack, WCOT Fused Silica, CP-Wax-52 CB, 25 m, 0.32 mm) at a temperature gradient between 170° C. and 240° C. for 20 minutes and 5 min. at 240° C. The identity of resulting fatty acid methylesters is defined by the use of standards available form commercial sources (i.e., Sigma).

In case of fatty acids where standards are not available, molecule identity is shown via derivatization and subsequent GC-MS analysis. For example, the localization of triple bond fatty acids is shown via GC-MS after derivatization via 4,4-Dimethoxy-oxazolin-Derivaten (Christie, Oily Press, Dundee, 1998).

A common standard method for analyzing sugars, especially starch, is published by Stitt M., Lilley R. Mc. C., Gerhardt R. and Heldt M. W. (1989, "Determination of metabolite levels in specific cells and subcellular compartments of plant leaves" Methods Enzymol. 174:518-552; for other methods see also Härtel et al. 1998, Plant Physiol. Biochem. 36:407-417 and Focks & Benning 1989, Plant Physoil. 118:91-101).

For the extraction of soluble sugars and starch, 50 seeds are homogenized in 500 µl of 80% (v/v) ethanol in a 1.5-ml polypropylene test tube and incubated at 70° C. for 90 min.

Following centrifugation at 16,000 g for 5 min, the supernatant is transferred to a new test tube. The pellet is extracted twice with 500 µl of 80% ethanol. The solvent of the combined supernatants is evaporated at room temperature under a vacuum. The residue is dissolved in 50 µl of water, representing the soluble carbohydrate fraction. The pellet left from the ethanol extraction, which contains the insoluble carbohydrates including starch, is homogenized in 200 µl of 0.2 N KOH, and the suspension is incubated at 95° C. for 1 h to dissolve the starch. Following the addition of 35 µl of 1 N acetic acid and centrifugation for 5 min at 16,000 g, the supernatant is used for starch quantification.

To quantify soluble sugars, 10 µl of the sugar extract is added to 990 µl of reaction buffer containing 100 mM imidazole, pH 6.9, 5 mM $MgCl_2$, 2 mM NADP, 1 mM ATP, and 2 units 2 $ml^{-1}$ of Glucose-6-P-dehydrogenase. For enzymatic determination of glucose, fructose and sucrose, 4.5 units of hexokinase, 1 unit of phosphoglucoisomerase, and 2 µl of a saturated fructosidase solution are added in succession. The production of NADPH is photometrically monitored at a wavelength of 340 nm. Similarly, starch is assayed in 30 µl of the insoluble carbohydrate fraction with a kit from Boehringer Mannheim.

An example for analyzing the protein content in leaves and seeds can be found by Bradford M. M. (1976, "A rapid and sensitive method for the quantification of microgram quantities of protein using the principle of protein dye binding" Anal. Biochem. 72:248-254). For quantification of total seed protein, 15-20 seeds are homogenized in 250 µl of acetone in a 1.5-ml polypropylene test tube. Following centrifugation at 16,000 g, the supernatant is discarded and the vacuum-dried pellet is resuspended in 250 µl of extraction buffer containing 50 mM Tris-HCl, pH 8.0, 250 mM NaCl, 1 mM EDTA, and 1% (w/v) SDS. Following incubation for 2 h at 25° C., the homogenate is centrifuged at 16,000 g for 5 min and 200 ml of the supernatant will be used for protein measurements. In the assay, γ-globulin is used for calibration. For protein measurements, Lowry DC protein assay (Bio-Rad) or Bradford-assay (Bio-Rad) are used.

Enzymatic assays of hexokinase and fructokinase are performed spectrophotometrically according to Renz et al. (1993, Planta 190:156-165), of phosphoglucoisomerase, ATP-dependent 6-phosphofructokinase, pyrophosphate-dependent 6-phospho-fructokinase, Fructose-1,6-bisphosphate aldolase, triose phosphate isomerase, glyceral-3-P dehydrogenase, phosphoglycerate kinase, phosphoglycerate mutase, enolase and pyruvate kinase are performed according to Burrell et al. (1994, Planta 194:95-101) and of UDP-Glucose-pyrophosphorylase according to Zrenner et al. (1995, Plant J. 7:97-107).

Intermediates of the carbohydrate metabolism, like Glucose-1-phosphate, Glucose-6-phosphate, Fructose-6-phosphate, Phosphoenolpyruvate, Pyruvate, and ATP are measured as described in Härtel et al. (1998, Plant Physiol. Biochem. 36:407-417) and metabolites are measured as described in Jelitto et al. (1992, Planta 188:238-244).

In addition to the measurement of the final seed storage compound (i.e., lipid, starch or storage protein) it is also possible to analyze other components of the metabolic pathways utilized for the production of a desired seed storage compound, such as intermediates and side-products, to determine the overall efficiency of production of the compound (Fiehn et al. 2000, Nature Biotech. 18:1447-1161).

For example, yeast expression vectors comprising the nucleic acids disclosed herein, or fragments thereof, can be constructed and transformed into *Saccharomyces cerevisiae* using standard protocols. The resulting transgenic cells can then be assayed for alterations in sugar, oil, lipid or fatty acid contents.

Similarly, plant expression vectors comprising the nucleic acids disclosed herein, or fragments thereof, can be constructed and transformed into an appropriate plant cell such as *Arabidopsis*, soybean, rape, maize, wheat, *Medicago truncatula*, etc., using standard protocols. The resulting transgenic cells and/or plants derived therefrom can then be assayed for alterations in sugar, oil, lipid or fatty acid contents.

Additionally, the sequences disclosed herein, or fragments thereof, can be used to generate knockout mutations in the genomes of various organisms, such as bacteria, mammalian cells, yeast cells, and plant cells (Girke at al. 1998, Plant J. 15:39-48). The resultant knockout cells can then be evaluated for their composition and content in seed storage compounds, and the effect on the phenotype and/or genotype of the mutation. For other methods of gene inactivation include U.S. Pat. No. 6,004,804 "Non-Chimeric Mutational Vectors" and Puttaraju et al. (1999, "Spliceosome-mediated RNA trans-splicing as a tool for gene therapy" Nature Biotech. 17:246-252).

Example 10

Northern-Hybridization

For RNA hybridization, 20 g of total RNA or 1 g of poly-(A)+ RNA is separated by gel electrophoresis in 1.25% strength agarose gels using formaldehyde as described in Amasino (1986, Anal. Biochem. 152:304), transferred by capillary attraction using 10×SSC to positively charged nylon membranes (Hybond N+, Amersham, Braunschweig), immobilized by UV light and pre-hybridized for 3 hours at 68° C. using hybridization buffer (10% dextran sulfate w/v, 1 M NaCl, 1% SDS, 100 g/ml of herring sperm DNA). The labeling of the DNA probe with the Highprime DNA labeling kit (Roche, Mannheim, Germany) is carried out during the pre-hybridization using alpha-$^{32}$P dCTP (Amersham, Braunschweig, Germany). Hybridization is carried out after addition of the labeled DNA probe in the same buffer at 68° C. overnight. The washing steps are carried out twice for 15 min using 2×SSC and twice for 30 min using 1×SSC, 1% SDS at 68° C. The exposure of the sealed filters is carried out at −70° C. for a period of 1 day to 14 days.

Example 11

DNA Sequencing and Computational Functional Analysis of SSH Library

The SSH cDNA library as described in Examples 4 and 5 was used for DNA sequencing according to standard methods, in particular by the chain termination method using the ABI PRISM Big Dye Terminator Cycle Sequencing Ready Reaction Kit (Perkin-Elmer, Weiterstadt, Germany). Random sequencing was carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA was prepared from overnight grown *E. coli* cultures grown in Luria-Broth medium containing ampicillin (see Sambrook et al. (1989, Cold Spring Harbor Laboratory Press: ISBN 0-87969-309-6) on a Qiagene DNA preparation robot (Qiagen, Hilden) according to the manufacturer's protocols). Sequencing primers with the following nucleotide sequences were used:

5'-CAGGAAACAGCTATGACC-3' (SEQ ID NO:97)
5'-CTAAAGGGAACAAAAGCTG-3' (SEQ ID NO:98)
5'-TGTAAAACGACGGCCAGT-3' (SEQ ID NO:99)

Sequences were processed and annotated using the software package EST-MAX commercially provided by Bio-Max (Munich, Germany). The program incorporates practically all bioinformatics methods important for functional and structural characterization of protein sequences. For reference see http://pedant.mips.biochem.mpg.de.

The most important algorithms incorporated in EST-MAX are: FASTA: Very sensitive protein sequence database searches with estimates of statistical significance (Pearson W. R. 1990, Rapid and sensitive sequence comparison with FASTP and FASTA. Methods Enzymol. 183:63-98). BLAST: Very sensitive protein sequence database searches with estimates of statistical significance (Altschul S. F., Gish W., Miller W., Myers E. W. and Lipman D. J. Basic local alignment search tool. J. Mol. Biol. 215:403-410). PREDATOR: High-accuracy secondary structure prediction from single and multiple sequences. (Frishman & Argos 1997, 75% accuracy in protein secondary structure prediction. Proteins 27:329-335). CLUSTALW: Multiple sequence alignment (Thompson, J. D., Higgins, D. G. and Gibson, T. J. 1994, CLUSTAL W: improving the sensitivity of progressive multiple sequence alignment through sequence weighting, positions-specific gap penalties and weight matrix choice, Nucleic Acids Res. 22:4673-4680). TMAP: Transmembrane region prediction from multiply aligned sequences (Persson B. & Argos P. 1994, Prediction of transmembrane segments in proteins utilizing multiple sequence alignments, J. Mol. Biol. 237:182-192). ALOM2: Transmembrane region prediction from single sequences (Klein P., Kanehisa M., and DeLisi C. 1984, Prediction of protein function from sequence properties: A discriminant analysis of a database. Biochim. Biophys. Acta 787:221-226. Version 2 by Dr. K. Nakai). PROSEARCH: Detection of PROSITE protein sequence patterns. Kolakowski L. F. Jr., Leunissen J. A. M. and Smith J. E. 1992, ProSearch: fast searching of protein sequences with regular expression patterns related to protein structure and function. Biotechniques 13:919-921). BLIMPS: Similarity searches against a database of ungapped blocks (Wallace & Henikoff 1992, PATMAT:A searching and extraction program for sequence, pattern and block queries and databases, CABIOS 8:249-254. Written by Bill Alford).

Example 12

In vivo Mutagenesis

In vivo mutagenesis of microorganisms can be performed by incorporation and passage of the plasmid (or other vector) DNA through *E. coli* or other microorganisms (e.g. Bacillus spp. or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp W. D. 1996, DNA repair mechanisms, in: *Escherichia coli* and *Salmonella*, p. 2277-2294, ASM: Washington.) Such strains are well known to those skilled in the art. The use of such strains is illustrated, for example, in Greener and Callahan 1994, Strategies 7:32-34. Transfer of mutated DNA molecules into plants is preferably done after selection and testing in microorganisms. Transgenic plants are generated according to various examples within the exemplification of this document.

Example 13

Assessment of the mRNA Expression and Activity of a Recombinant Gene Product in the Transformed Organism The activity of a recombinant gene product in the transformed host organism can be measured on the transcriptional or/and on the translational level. A useful method to ascertain the level of transcription of the gene (an indicator of the amount of mRNA available for translation to the gene product) is to perform a Northern blot (for reference see, for example, Ausubel et al. 1988, Current Protocols in Molecular Biology, Wiley: New York), in which a primer designed to bind to the gene of interest is labeled with a detectable tag (usually radioactive or chemiluminescent), such that when the total RNA of a culture of the organism is extracted, run on gel, transferred to a stable matrix and incubated with this probe, the binding and quantity of binding of the probe indicates the presence and also the quantity of mRNA for this gene. This information at least partially demonstrates the degree of transcription of the transformed gene. Total cellular RNA can be prepared from plant cells, tissues or organs by several methods, all well-known in the art, such as that described in Bormann et al. (1992, Mol. Microbiol. 6:317-326).

To assess the presence or relative quantity of protein translated from this mRNA, standard techniques, such as a Western blot, may be employed (see, for example, Ausubel et al. 1988, Current Protocols in Molecular Biology, Wiley: New York). In this process, total cellular proteins are extracted, separated by gel electrophoresis, transferred to a matrix such as nitrocellulose, and incubated with a probe, such as an antibody, which specifically binds to the desired protein. This probe is generally tagged with a chemiluminescent or calorimetric label which may be readily detected. The presence and quantity of label observed indicates the presence and quantity of the desired mutant protein present in the cell.

The activity of LMPs that bind to DNA can be measured by several well-established methods, such as DNA band-shift assays (also called gel retardation assays). The effect of such LMP on the expression of other molecules can be measured using reporter gene assays (such as that described in Kolmar H. et al. 1995, EMBO J. 14:3895-3904 and references cited therein). Reporter gene test systems are well known and established for applications in both prokaryotic and eukaryotic cells, using enzymes such as beta-galactosidase, green fluorescent protein, and several others.

The determination of activity of lipid metabolism membrane-transport proteins can be performed according to techniques such as those described in Gennis R. B. (1989 Pores, Channels and Transporters, in Biomembranes, Molecular Structure and Function, Springer: Heidelberg, pp. 85-137, 199-234 and 270-322).

Example 14

In vitro Analysis of the Function of *Arabidopsis thaliana* Genes in Transgenic Plants The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon, M. & Webb, E. C. 1979, Enzymes. Longmans: London; Fersht, (1985) Enzyme Structure and Mechanism. Freeman: New York; Walsh (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, $3^{rd}$ ed. Academic Press: New York; Bisswanger, H., (1994) Enzymkinetik, $2^{nd}$ ed. VCH: Weinheim (ISBN 3527300325); Bergmeyer, H. U., Bergmeyer, J., Graβ1, M., eds. (1983-1986) Methods of Enzymatic Analysis, $3^{rd}$ ed., vol. I-XII, Verlag Chemie: Weinheim; and Ullmann's Encyclopedia of Industrial Chemistry (1987) vol. A9, Enzymes. VCH: Weinheim, p. 352-363.

Those skilled in the art will recognize, or will be able to ascertain using no more than routine experimentation, many equivalents to the specific embodiments of the invention described herein. Such equivalents are intended to be encompassed by the following claims.

We claim:

1. A method of producing a transgenic plant with an increased level of fatty acids comprising, transforming a plant cell with an expression vector comprising a lipid metabolism protein (LMP) nucleic acid, generating from the plant cell a transgenic plant, analyzing the production of fatty acids in seeds of the transgenic plant, and selecting a transgenic plant having an increased level of fatty acids as compared to an untransformed wild type variety of the plant, wherein the LMP nucleic acid is selected from the group consisting of:
   a) a full-length polynucleotide sequence as shown in SEQ ID NO: 47;
   b) a polynucleotide sequence encoding the full-length polypeptide as shown in SEQ ID NO: 48;
   c) a polynucleotide sequence having at least 90% sequence identity with the full-length polynucleotide sequence of a) or b) above, wherein said polynucleotide sequence encodes a polypeptide that has protein kinase activity; and
   d) a polynucleotide sequence that hybridizes under stringent conditions to the complement of the full-length polynucleotide sequence of a) or b) above, wherein said polynucleotide sequence encodes a polypeptide that has protein kinase activity.

2. The method of claim 1, wherein the LMP nucleic acid comprises a full-length polynucleotide sequence as shown in SEQ ID NO: 47.

3. The method of claim 1, wherein the LMP nucleic acid comprises a polynucleotide sequence encoding the full-length polypeptide sequence as shown in SEQ ID NO: 48.

4. The method of claim 1, wherein the plant is a dicotyledonous plant.

5. The method of claim 1, wherein the plant is a monocotyledonous plant.

6. The method of claim 1, wherein the plant is an oil producing species.

7. The method of claim 1, wherein the plant is selected from the group consisting of rapeseed, canola, linseed, soybean, sunflower, maize, oat, rye, barley, wheat, sugarbeet, tagetes, cotton, oil palm, coconut palm, flax, castor, and peanut.

8. A method of increasing the level of fatty acids in a plant comprising, transforming a plant cell with an expression vector comprising a lipid metabolism protein (LMP) nucleic acid, generating from the plant cell a transgenic plant, and selecting a transgenic plant having an increased level of fatty acids as compared to an untransformed wild type variety of the plant, wherein the LMP nucleic acid is selected from the group consisting of:
   a) a full-length polynucleotide sequence as shown in SEQ ID NO: 47;
   b) a polynucleotide sequence encoding the full-length polypeptide as shown in SEQ ID NO: 48;
   c) a polynucleotide sequence having at least 90% sequence identity with the full-length polynucleotide sequence of a) or b) above, wherein said polynucleotide sequence encodes a polypeptide that has protein kinase activity; and
   d) a polynucleotide sequence that hybridizes under stringent conditions to the complement of the full-length polynucleotide sequence of a) or b) above, wherein said polynucleotide sequence encodes a polypeptide that has protein kinase activity.

9. The method of claim 8, wherein the LMP nucleic acid comprises a polynucleotide having at least 95% sequence identity with an LMP nucleic acid selected from the group consisting of:
   a) a full-length polynucleotide sequence as shown in SEQ ID NO: 47; and
   b) a polynucleotide sequence encoding the full-length polypeptide as shown in SEQ ID NO: 48;
wherein said LMP nucleic acid encodes a polypeptide that has protein kinase activity.

10. The method of claim 8, wherein the LMP nucleic acid comprises a first nucleic acid that hybridizes under stringent conditions to the complement of a second nucleic acid nucleic acid selected from the group consisting of:
    a) a full-length polynucleotide sequence as shown in SEQ ID NO: 47; and
    b) a polynucleotide sequence encoding the full-length polypeptide as shown in SEQ ID NO: 48,
wherein said LMP nucleic acid encodes a polypeptide that has protein kinase activity.

11. The method of claim 8, wherein the LMP nucleic acid is selected from the group consisting of:
    a) a full-length polynucleotide sequence as shown in SEQ ID NO: 47; and
    b) a polynucleotide sequence encoding the full-length polypeptide as shown in SEQ ID NO: 48.

12. The method of claim 8, wherein the plant is a dicotyledonous plant.

13. The method of claim 8, wherein the plant is a monocotyledonous plant.

14. The method of claim 8, wherein the plant is an oil producing species.

15. A method of increasing seed oil content in a plant comprising, transforming a plant cell with an expression vector comprising a lipid metabolism protein (LMP) nucleic acid, generating from the plant cell a transgenic plant, selecting a transgenic plant having an increased level of fatty acids as compared to an untransformed wild type variety of the plant, and extracting oil from seed of the transgenic plant, wherein the LMP nucleic acid is selected from the group consisting of:
    a) a full-length polynucleotide sequence as shown in SEQ ID NO: 47;
    b) a polynucleotide sequence encoding the full-length polypeptide as shown in SEQ ID NO: 48;
    c) a polynucleotide sequence having at least 90% sequence identity with the full-length polynucleotide sequence of a) or b) above, wherein said polynucleotide sequence encodes a polypeptide that has protein kinase activity; and
    d) a polynucleotide sequence that hybridizes under stringent conditions to the complement of the full-length polynucleotide sequence of a) or b) above, wherein said polynucleotide sequence encodes a polypeptide that has protein kinase activity.

16. The method of claim 15, wherein the plant is an oil producing species.

17. The method of claim 15, wherein the plant is selected from the group consisting of rapeseed, canola, linseed, soybean, sunflower, maize, oat, rye, barley, wheat, sugarbeet, tagetes, cotton, oil palm, coconut palm, flax, castor, and peanut.

* * * * *